United States Patent
Larsen et al.

(10) Patent No.: US 8,846,684 B2
(45) Date of Patent: Sep. 30, 2014

(54) ARBOVIRUS INHIBITORS AND USES THEREOF

(75) Inventors: Scott Larsen, South Lyon, MI (US); Janice Sindac, Ann Arbor, MI (US); Scott Barraza, Ann Arbor, MI (US); David J. Miller, Chelsea, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 18 days.

(21) Appl. No.: 13/423,647

(22) Filed: Mar. 19, 2012

(65) Prior Publication Data

US 2012/0252807 A1 Oct. 4, 2012

Related U.S. Application Data

(60) Provisional application No. 61/470,038, filed on Mar. 31, 2011.

(51) Int. Cl.

| | | |
|---|---|---|
| *A61K 31/497* | (2006.01) | |
| *A01N 43/40* | (2006.01) | |
| *A61K 31/445* | (2006.01) | |
| *C07D 413/00* | (2006.01) | |
| *C07D 401/00* | (2006.01) | |
| *C07D 401/06* | (2006.01) | |
| *C07D 491/048* | (2006.01) | |
| *C07D 401/14* | (2006.01) | |
| *C07D 471/04* | (2006.01) | |

(52) U.S. Cl.
CPC .......... *C07D 401/06* (2013.01); *C07D 491/048* (2013.01); *C07D 401/14* (2013.01); *C07D 471/04* (2013.01)
USPC ...... 514/254.09; 514/323; 514/326; 544/130; 546/201

(58) Field of Classification Search
USPC ............... 514/254.09, 323, 326; 435/375; 544/130; 546/201
See application file for complete search history.

(56) References Cited

U.S. PATENT DOCUMENTS

| | | |
|---|---|---|
| 2007/0155761 A1 | 7/2007 | Bissantz et al. |
| 2008/0200491 A1 | 8/2008 | Tran et al. |

FOREIGN PATENT DOCUMENTS

| | | |
|---|---|---|
| WO | 2007115315 | 10/2007 |

OTHER PUBLICATIONS

Stella et al. "Prodrugs: the control of drug delivery via bioreversible chemical modification" Drug Delivery Systems Characteristics and Biomedical Applications, 1980, New York, Oxford University Press, Chapter 4, pp. 112-176.*

Sheridan, R.P. "The Most Common Chemical Replacements in Drug-Like Compounds" J. Chem. Inf. Comput. Sci., 2002, vol. 42, pp. 103-108.*

J. G. Cannon, Chapter Nineteen in Burger's Medicinal Chemistry and Drug Discovery, Fifth Edition, vol. I: Principles and Practice, Wiley-Interscience 1995, pp. 783-802, 784.*

Malinoski & Stollar, "Inhibitors of IMP dehydrogenase prevent sindbis virus replication and reduce GTP levels in *Aedes albopictus* cells." Virology. Apr. 30, 1981; 110(2):281-9.

Puig-Basagoiti F et al., "ryl pyrazoline compound inhibits flavivirus RNA replication." Antimicrob Agents Chemother. Apr. 2006; 50(4):1320-9.

Li Y et al., "Seco-pregnane steroids target the subgenomic RNA of alphavirus-like RNA viruses." Proc Natl Acad Sci USA. May 8, 2007; 104(19):8083-8.

Gomez et al., "RNA helicase activity of Semliki Forest virus replicase protein NSP2." FEBS Lett. Apr. 1, 1999;448 (1):19-22.

Ahola T et al., "Critical residues of Semliki Forest virus RNA capping enzyme involved in methyltransferase and guanylyltransferase-like activities." J Virol. Jan. 1997; 71(1):392-7.

Hardy & Strauss, Processing the nonstructural polyproteins of sindbis virus: nonstructural proteinase is in the C-terminal half of nsP2 and functions both in cis and in trans. J Virol. Nov. 1989;63(11):4653-64.

Poch et al., "Identification of four conserved motifs among the RNA-dependent polymerase encoding elements." EMBO J. Dec. 1, 1989; 8(12):3867-74.

Vasiljeva L et al., "Site-specific protease activity of the carboxyl-terminal domain of Semliki Forest virus replicase protein nsP2." J Biol Chem. Aug. 17, 2001; 276(33):30786-93.

Tomar S. et al., "Catalytic core of alphavirus nonstructural protein nsP4 possesses terminal adenylyltransferase activity." J Virol. Oct. 2006; 80(20):9962-9.

Li M. et al., "A mutant of Sindbis virus which is able to replicate in cells with reduced CTP makes a replicase/transcriptase with a decreased Km for CTP." J Virol. Sep. 2004; 78(18):9645-51.

Lin YH et al., "A mutant of Sindbis virus that is resistant to pyrazofurin encodes an altered RNA polymerase." Virology. Jun. 20, 2000; 272(1):61-71.

Scheidel & Stollar, "Mutations that confer resistance to mycophenolic acid and ribavirin on Sindbis virus map to the nonstructural protein nsP1." Virology. Apr. 1991; 181(2):490-9.

Pardridge, "The blood-brain barrier and neurotherapeutics." NeuroRx. Jan. 2005; 2(1):1-2.

Pajouhesh & Lenz, "Medicinal chemical properties of successful central nervous system drugs." NeuroRx. Oct. 2005; 2 (4):541-53.

van de Waterbeemd H, "Estimation of blood-brain barrier crossing of drugs using molecular size and shape, and H-bonding descriptors." J Drug Target. 1998; 6(2):151-65.

Kelder et al., "Polar molecular surface as a dominating determinant for oral absorption and brain penetration of drugs." Pharm Res. Oct. 1999; 16(10):1514-9.

Peng et al., "Identification of thieno[3,2-b]pyrrole derivatives as novel small molecule inhibitors of neurotropic alphaviruses." J Infect Dis. Apr. 1, 2009; 199(7):950-7.

(Continued)

*Primary Examiner* — Kendra D Carter
(74) *Attorney, Agent, or Firm* — Tanya A. Arenson; Casimir Jones, S.C.

(57) ABSTRACT

The present invention relates to chemical compounds, methods for their discovery, and their therapeutic use. In particular, the present invention provides compounds as inhibitors of arboviruses.

9 Claims, 3 Drawing Sheets

(56) References Cited

OTHER PUBLICATIONS

Jackson et al., "The pathogenesis of spinal cord involvement in the encephalomyelitis of mice caused by neuroadapted Sindbis virus infection." Lab Invest. Apr. 1987; 56(4):418-23.

Jackson et al., "Basis of neurovirulence in Sindbis virus encephalomyelitis of mice." Lab Invest. May 1988; 58 (5):503-9.

SciFinder Search, N-benzylindole-2-piperidine-4, Copyright American Chemical Society 2012, 3 pages.

SciFinder Search, 4-halobenzyl indole-2-piperidine carboxamide, Mar. 2012, Copyright American Chemical Society, 2 pages.

SciFinder Search, N-CC-indole-2-piperidine-4, Copyright American Chemical Society 2012, 3 pages.

SciFinder Search, p-halobenzyl_indole-2-pipderidine_amide, Copyright American Chemical Society 2012, 2 pages.

\* cited by examiner

Figure 1

ARBOVIRUS INHIBITORS AND USES THEREOF

This application claims priority to provisional application 61/470,038, filed Mar. 31, 2011, which is herein incorporated by reference in its entirety.

GOVERNMENT SUPPORT

This invention was made with government support under AI089417 awarded by the National Institutes of Health. The government has certain rights in the invention.

FIELD OF THE INVENTION

The present invention relates to chemical compounds, methods for their discovery, and their therapeutic use. In particular, the present invention provides compounds as inhibitors of arboviruses (e.g., alphaviruses, flaviviruses or bunyaviruses).

BACKGROUND OF THE INVENTION

The Alphavirus genus within the Togaviridae family contains about 30 mosquito-borne, enveloped, positive-stranded RNA viruses, one third of which cause significant diseases in human and animals worldwide. For example, neurotropic alphaviruses such as western, eastern, and Venezuelan equine encephalitis viruses (WEEV, EEEV, and VEEV, respectively) infect the central nervous system (CNS) and can lead to severe encephalitis in humans with fatality rates of up to 70%, and where survivors often bear long-term neurological sequelae (Deresiewicz et al., N Engl J Med 1997; 336:1867-74; Earnest et al., Neurology 1971; 21:969-74). Neurotropic alphaviruses are also important members of the growing list of emerging or resurging public health threats (Gubler, Arch Med Res 2002; 33:330-42) and are listed as CDC and NIAID category B bioterrorism agents, due in part to numerous characteristics that make them potential biological weapons: (i) high clinical morbidity and mortality; (ii) potential for aerosol transmission; (iii) lack of effective countermeasures for disease prevention or control; (iv) public anxiety elicited by CNS infections; (v) ease with which large volumes of infectious materials can be produced; and (vi) potential for malicious introduction of foreign genes designed to increase alphavirus virulence (Sidwell et al., Antiviral Res 2003; 57:101-11).

There are currently no licensed vaccines or antiviral drugs for alphaviruses. Formalin inactivated vaccines for WEEV or EEEV and a live attenuated VEEV vaccine (TC-83 strain) are available on an investigational drug basis, and are limited primarily to laboratory workers conducting research on these viruses (Sidwell et al., supra). However, these vaccines have poor immunogenicity, require annual boosters, and have a high frequency of adverse reactions. The development of alternative live attenuated, chimeric, and DNA-based alphavirus vaccines is being actively pursued, and several candidates have been tested in animal models (Barabe et al., Vaccine 2007; 25:6271-6; Wu et al., Vaccine 2007; 25:4368-75; Nagata et al., Vaccine 2005; 23:2280-3; Schoepp et al., Virology 2002; 302:299-309; Turell et al., Am J Trop Med Hyg 1999; 60:1041-4; Wang et al., Vaccine 2007; 25:7573-81; Fine et al., Vaccine 2008; 26:3497-506; Turell et al., Am J Trop Med Hyg 2008; 78:328-32). Nevertheless, the broad clinical application of these newer generation vaccines is likely years away. Furthermore, combined active vaccination and antiviral therapy may be a more effective response to an outbreak due to either natural transmission or intentional exposure to a viral pathogen (Bronze et al., Curr Opin Investig Drugs 2003; 4:172-8).

Several compounds have been reported to inhibit alphavirus replication, including the nucleoside analogs ribavirin and mycophenolic acid (Malinoski et al., Virology 1981; 110: 281-9), (−)-carbodine, triaryl pyrazoline (Puig-Basagoiti et al., Antimicrob Agents Chemother 2006; 50:1320-9), and seco-pregnane steroids from the Chinese herbs *Strobilanthes cusia* and *Cynanchum paniculatum* (Li et al., Proc Natl Acad Sci USA 2007; 104:8083-8).

Nevertheless, there is still a pressing need to identify new antiviral drugs to treat these virulent pathogens.

SUMMARY

The present invention relates to chemical compounds, methods for their discovery, and their therapeutic use. In particular, the present invention provides compounds as inhibitors of arboviruses (e.g., alphaviruses, flaviviruses or bunyaviruses).

For example, in some embodiments, the present invention provides a composition, comprising a compound of the formula I:

including pharmaceutically acceptable salts, prodrugs, and both R and S enantiomeric forms and racemic mixtures thereof.

In some embodiments, $R^1$ is H, a $C_1$-$C_8$ alkyl or cycloalkyl, a substituted $C_1$-$C_8$ alkyl or cycloalkyl, a $C_0$-$C_6$ alkyl-aryl, a substituted $C_0$-$C_6$ alkyl-aryl, or a $C_0$-$C_6$-alkyl-heteroaryl or a substituted $C_0$-$C_6$-alkyl-heteroaryl. In some embodiments, $R^1$ is phenyl. In some embodiments, alkyl-aryl together form a cyclic structure. Examples of $R^1$ include, but are not limited to, phenyl, aryl, substituted aryl, heteroaryl and substituted heteroaryl (wherein halogen can be, for example, chlorine, fluorine, bromine, iodine, etc.),

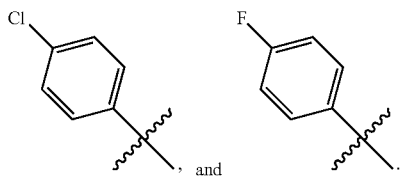 [SMILES: *c1ccc(Cl)cc1 ; *c1ccc(F)cc1 ; "," ; "and" ; "."]

, and

In some embodiments, X and Y may be identical, different, or together form a cyclic chemical moiety (e.g., an aromatic cyclic moiety) (e.g., a non-aromatic cyclic moiety). In some embodiments, X and/or Y are H. In some embodiments, X and Y are each H such that the resulting compound is

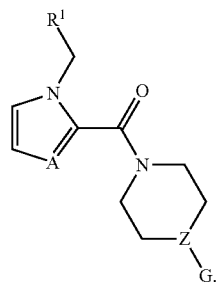

In some embodiments, X and Y together form a fused phenyl ring substituted with one or more R2 such that the resulting compound is

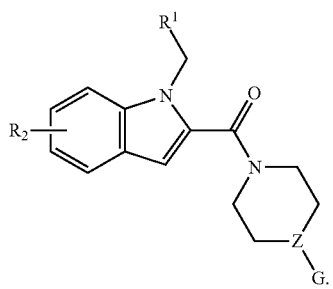

In some embodiments, there is only one R2. In some embodiments, there is more than one R2. In embodiments where there is more than one R2, each R2 may be the same or different. Examples of R2 include, but are not limited to, H, halogen, $OR^3$, $NR^3R^4$, $NHC(=O)R^3$, $NHSO_2R^3$, $C_1$-$C_6$ alkyl, $C_0$-$C_6$ alkyl-aryl or $C_0$-$C_6$-alkyl-heteroaryl.

In some embodiments, $R^3$ and $R^4$ are the same or different. Examples of $R^3$ and $R^4$ include, but are not limited to, H, $C_1$-$C_8$ alkyl, $C_0$-$C_6$ alkyl-aryl, or a $C_0$-$C_6$-alkyl-heteroaryl, all of which are optionally substituted. In some embodiments, $R^3$ and $R^4$ together with N form a substituted cyclic alkyl amine of 4-8 atoms or together form a piperazine ring substituted on the 4-nitrogen by $CH_2R^5$ or $C(=O)R^5$;

wherein $R^5$ is $C_0$-$C_6$ alkyl-aryl or $C_0$-$C_6$-alkyl-heteroaryl, which are optionally substituted.

In some embodiments, Z is CH or N.

In some embodiments, A is CH, C—CH3, or N.

In some embodiments, G is H, $CH_2$-aryl, $CH_2$-heteroaryl, $C(=O)NR^3R^4$, $CH(OH)R^3$, or $CH_2NR^3R^4$. Examples of G include, but are not limited to,

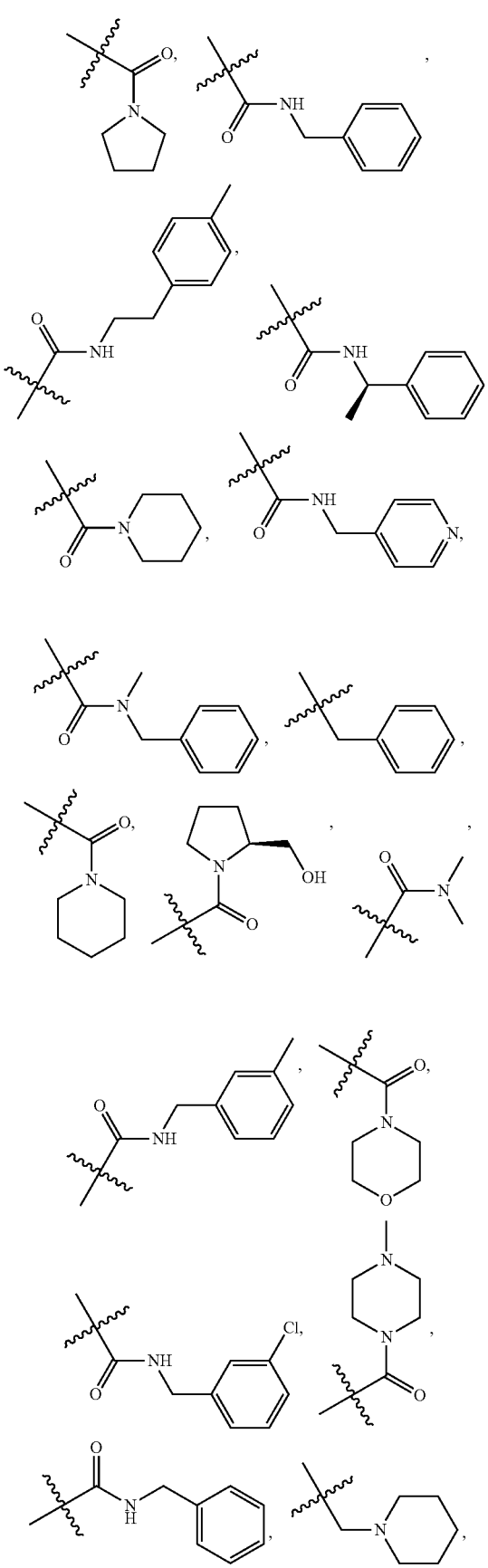

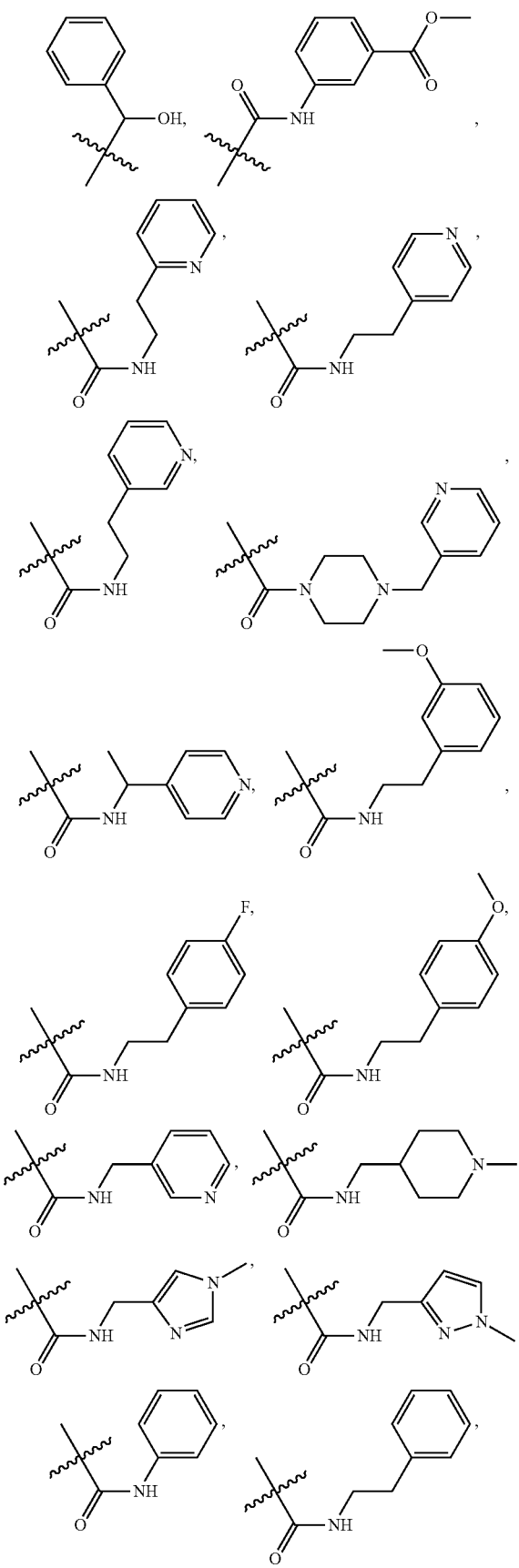
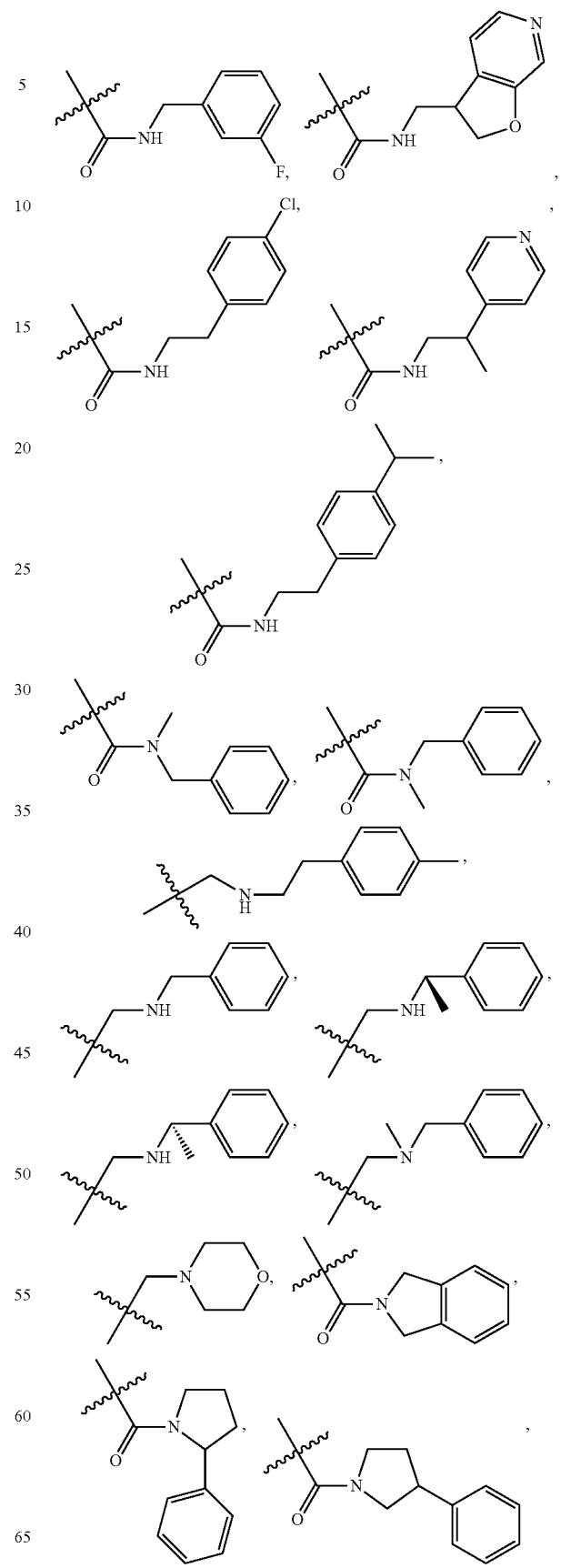

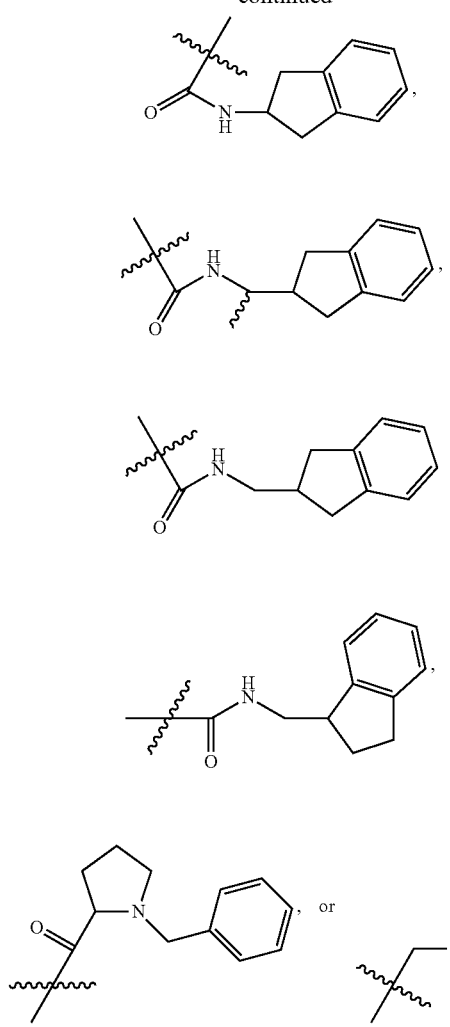
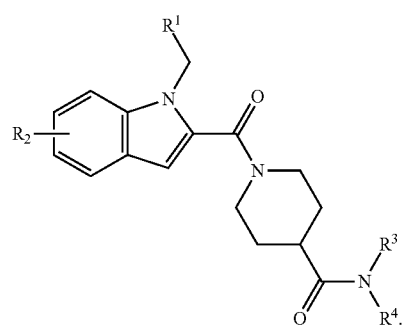
In some embodiments, the compound has the Formula II:
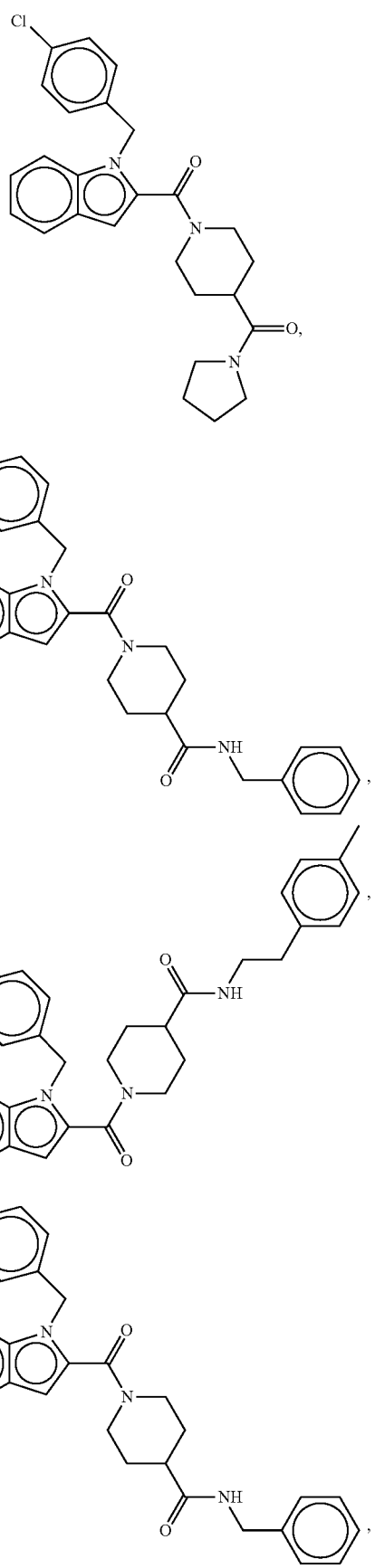
In some embodiments, the compounds is, for example, -continued
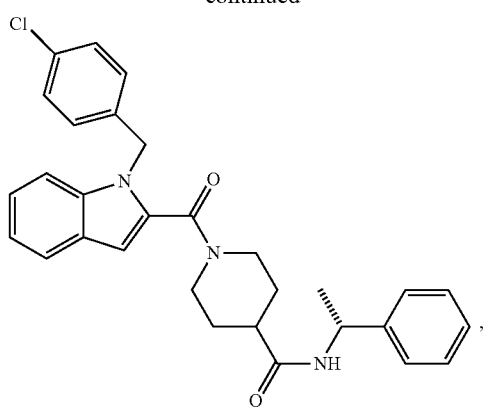
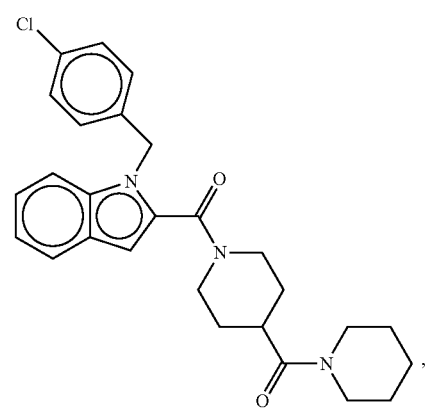
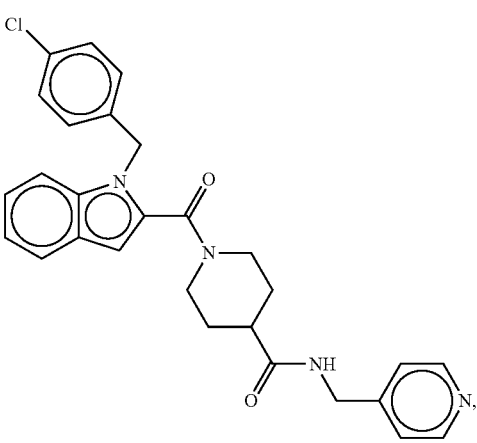
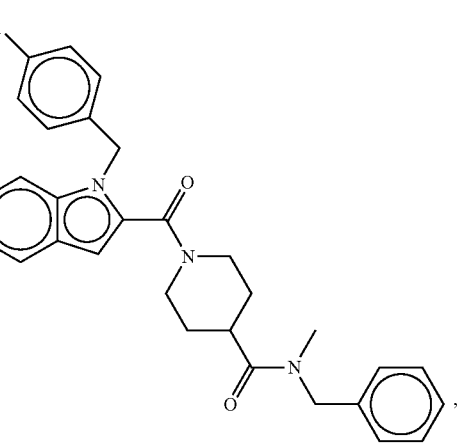
-continued
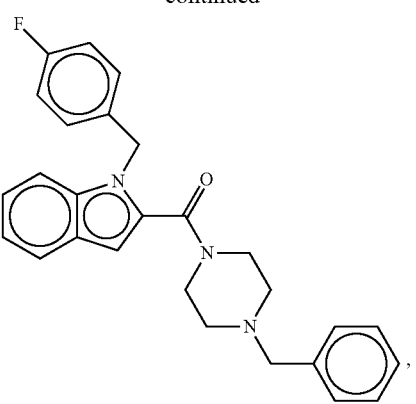
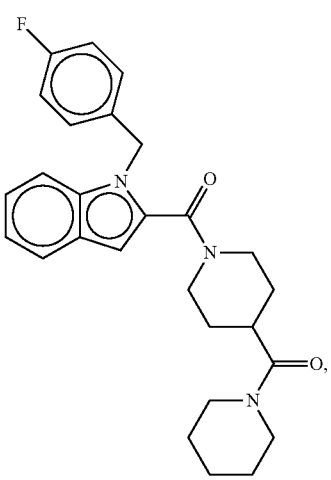
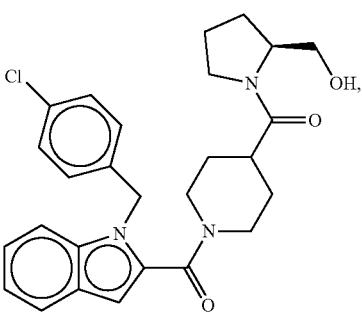
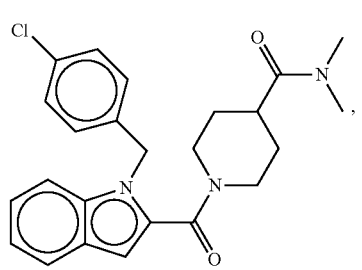

11
-continued
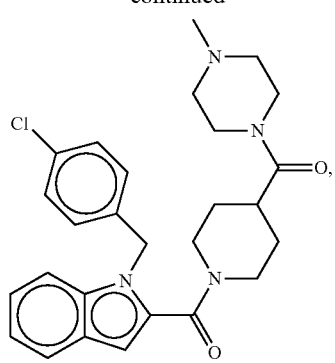
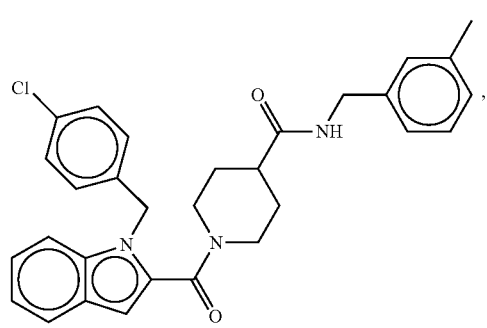
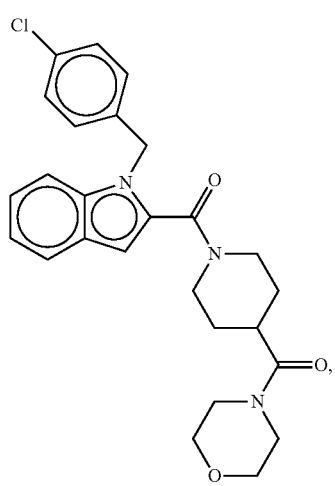
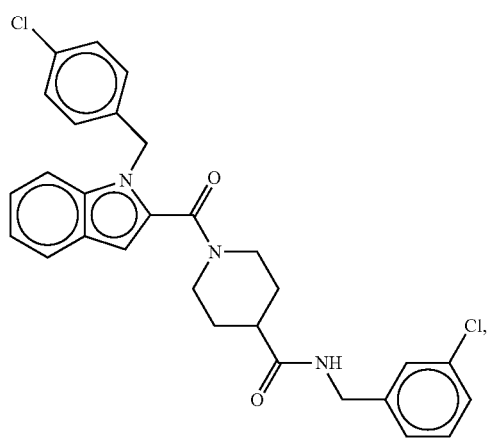
12
-continued
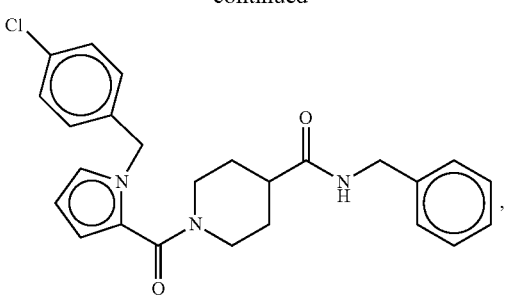
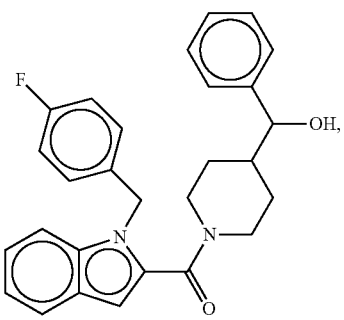
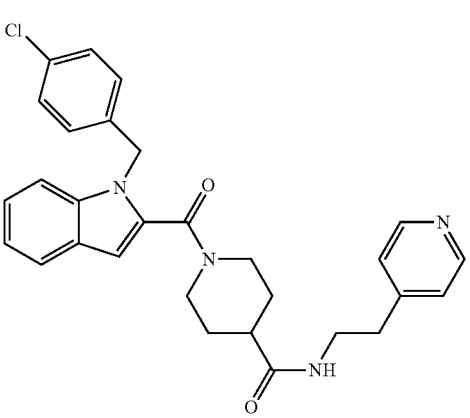

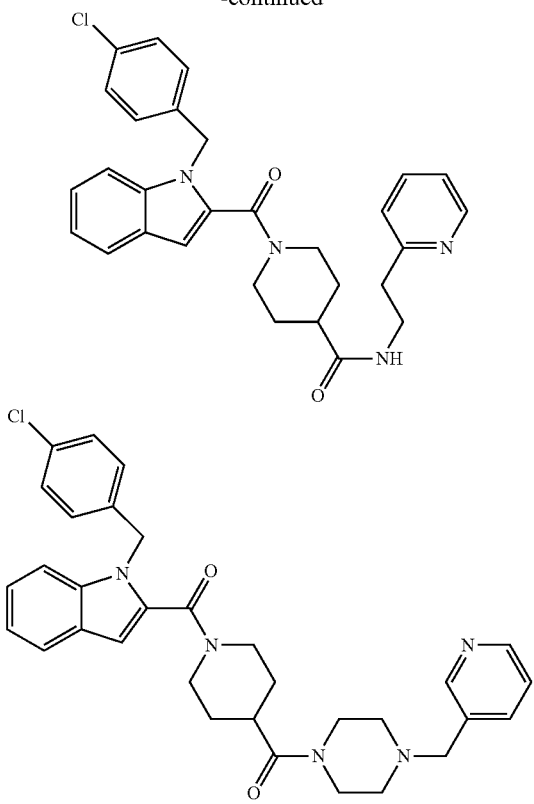
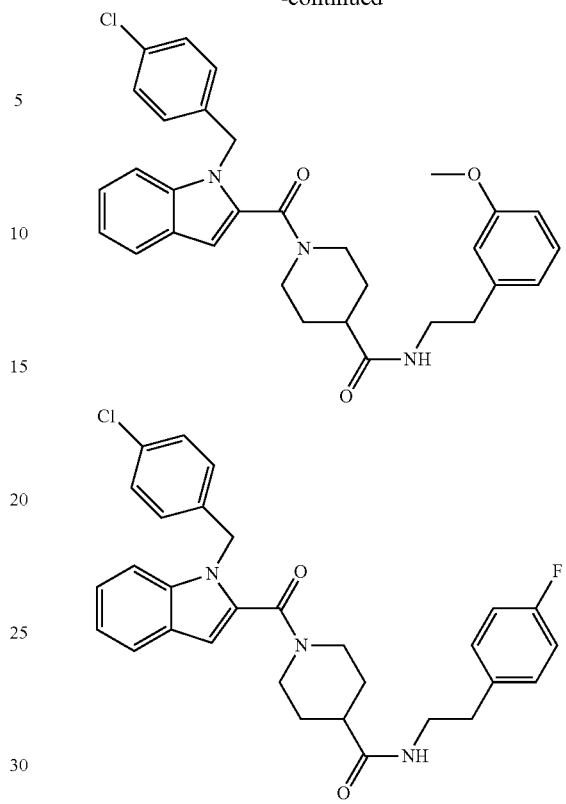
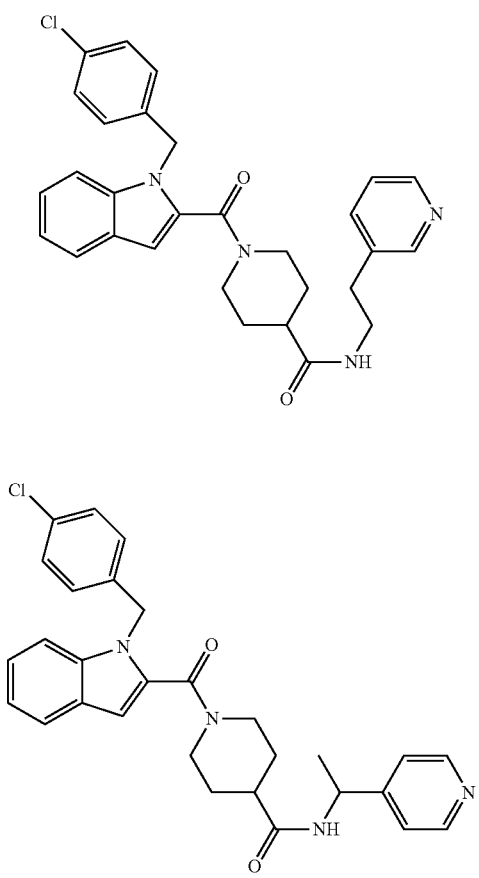
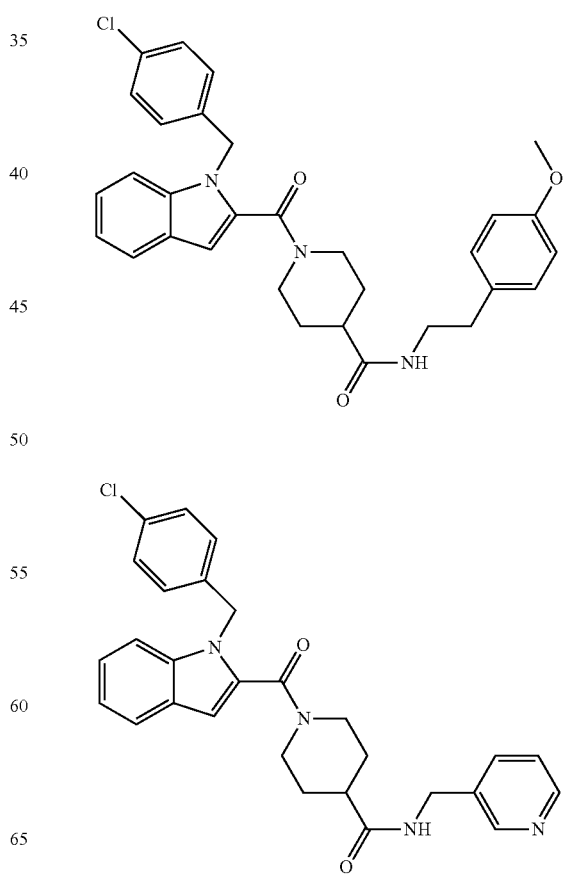

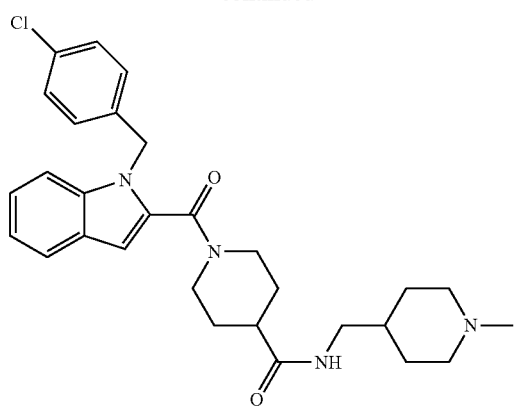
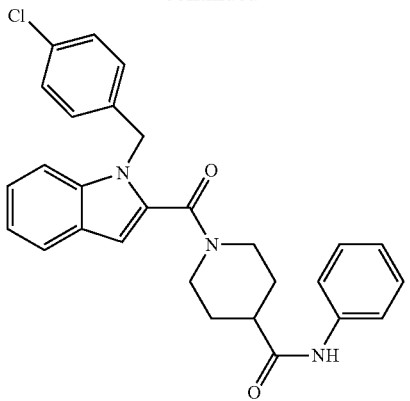
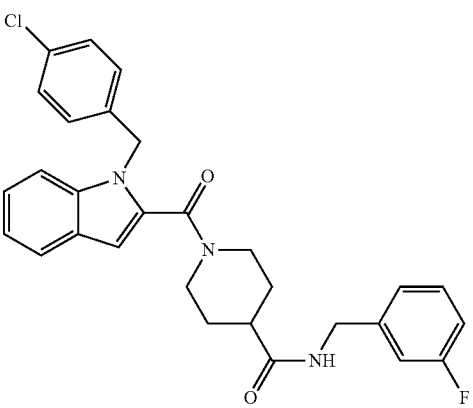
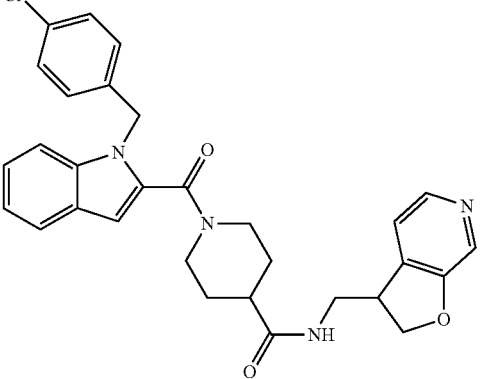

-continued
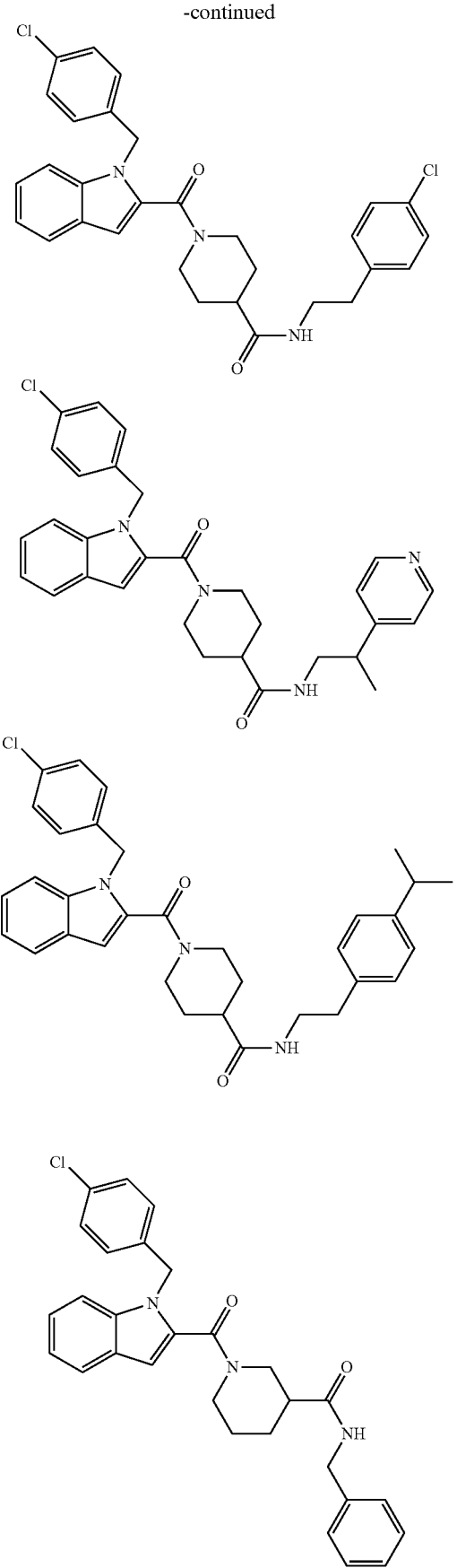
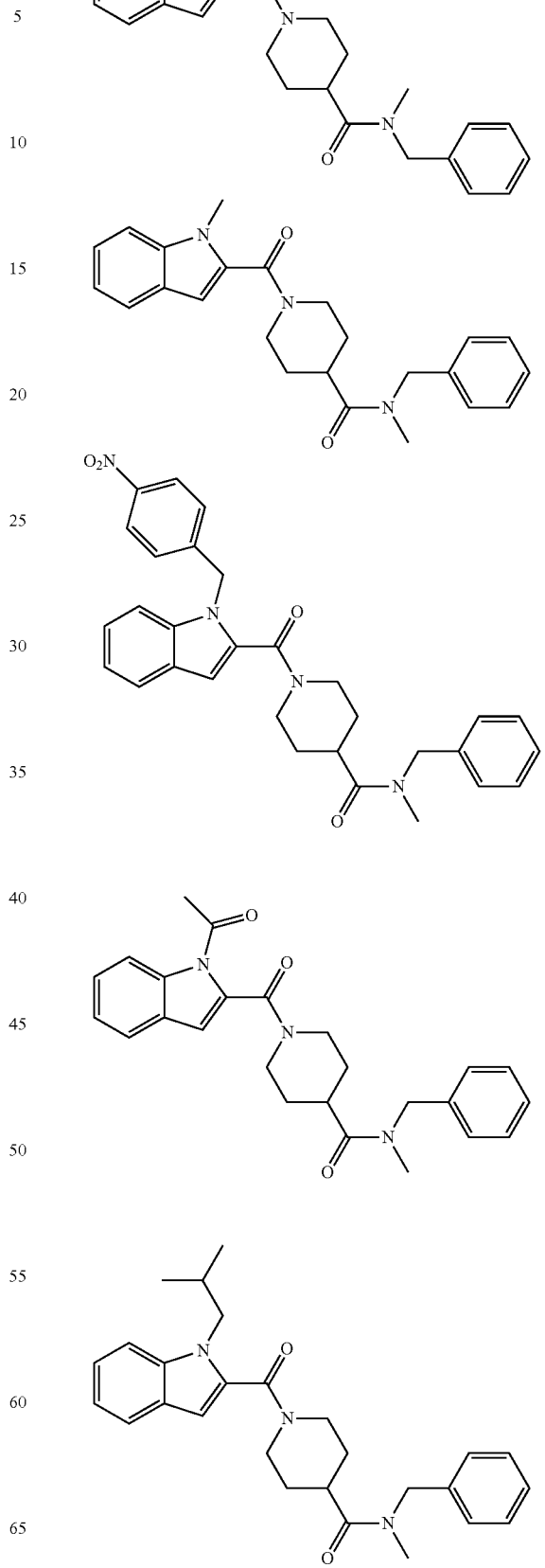

-continued
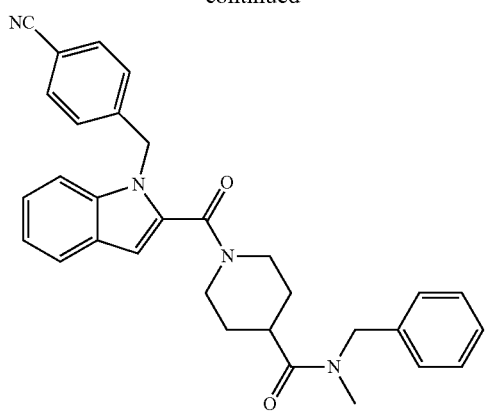
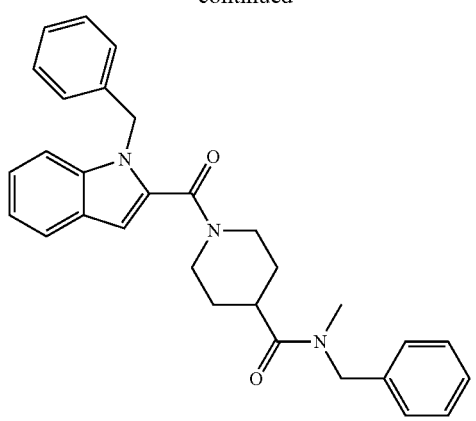
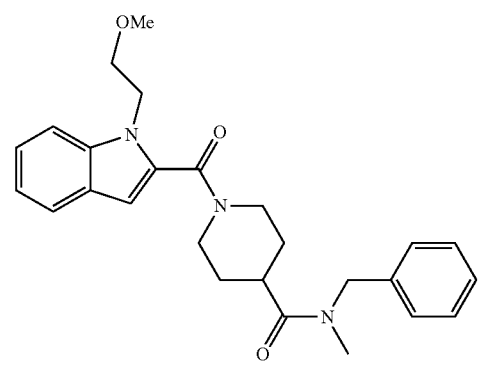
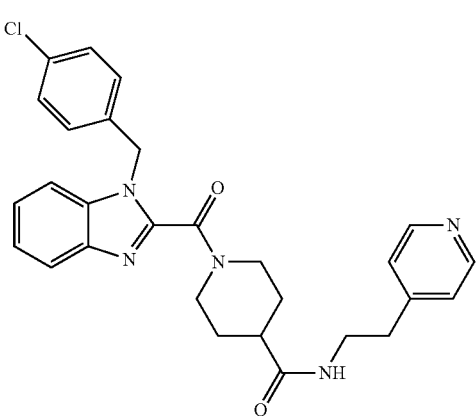
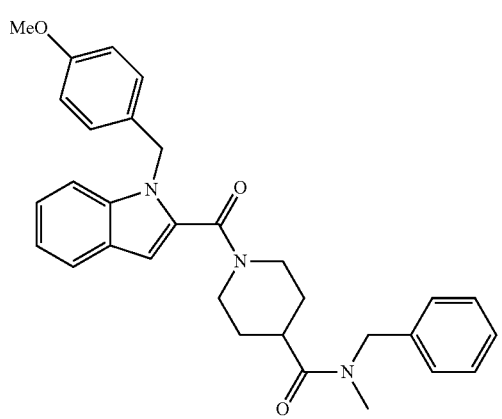
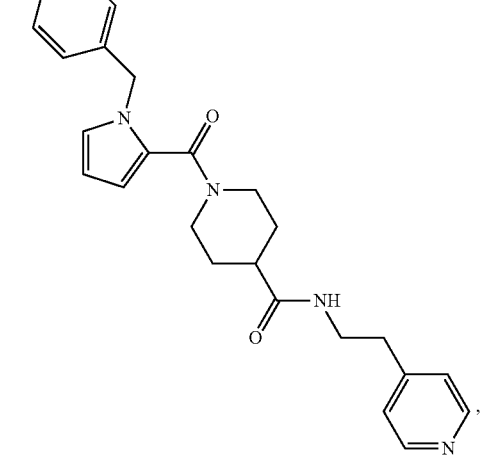

-continued
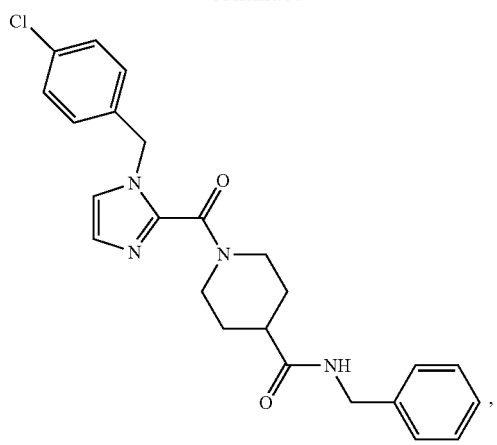
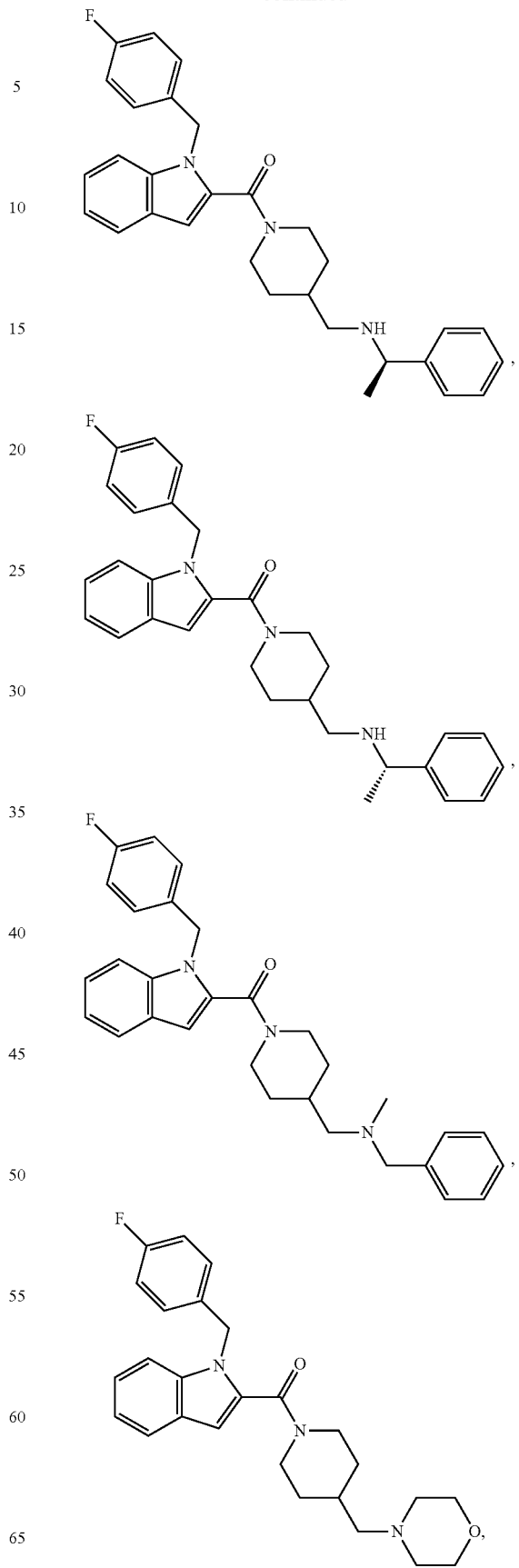

23
-continued
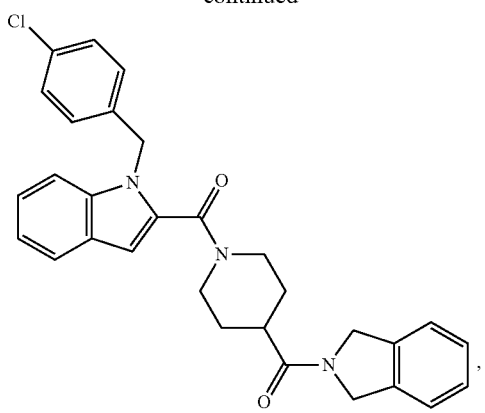
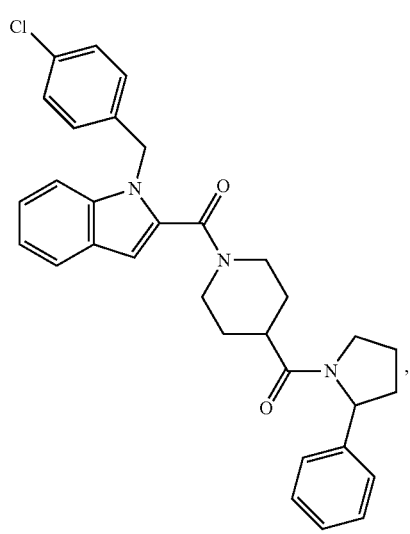
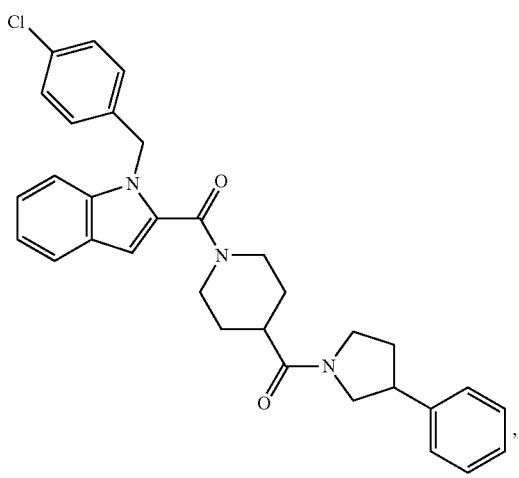
24
-continued
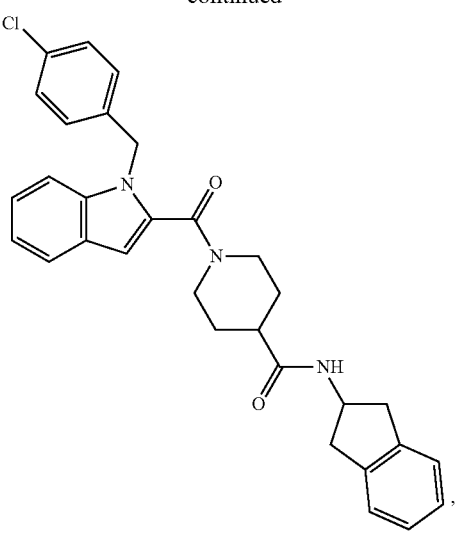
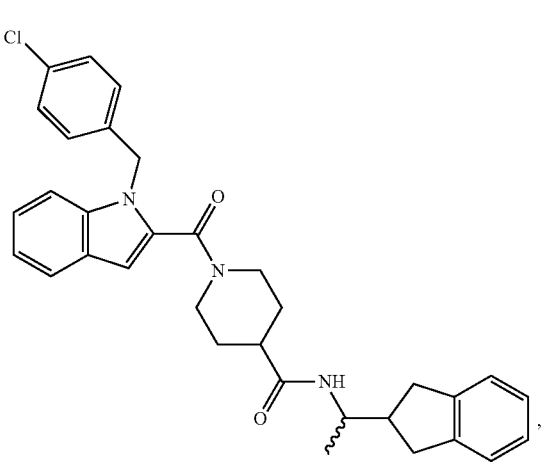

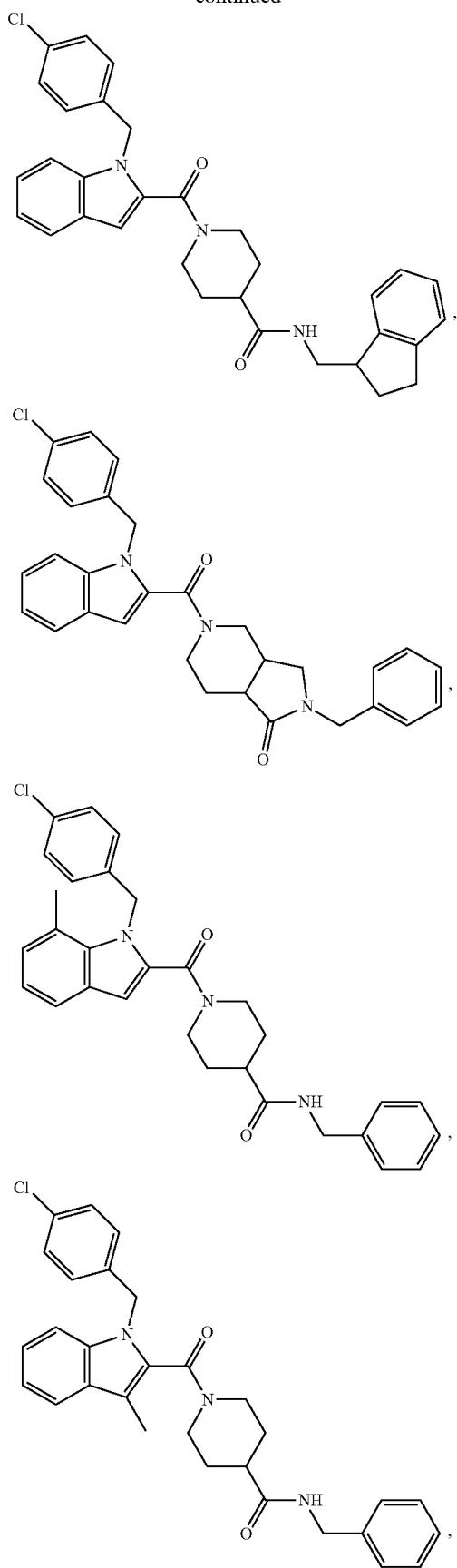

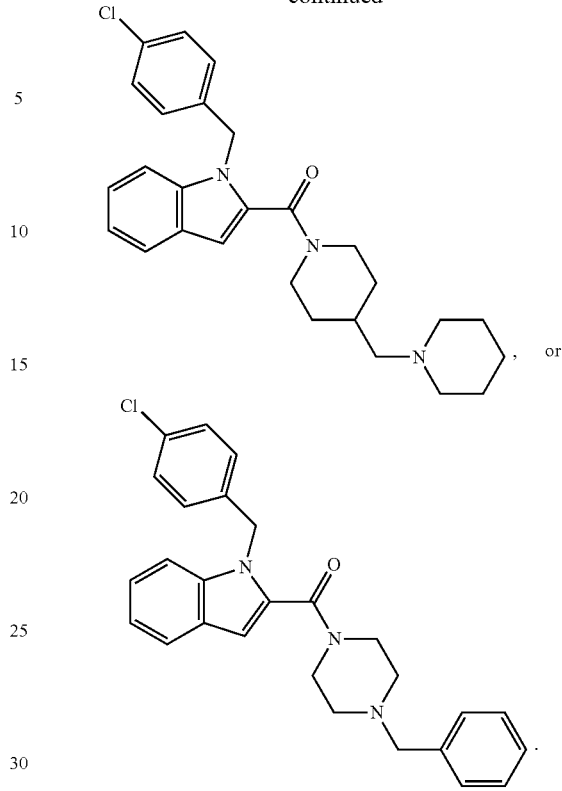

Embodiments of the present invention further provide derivatives, mimetics, stereoisomers, salts, etc. of the above named compounds.

Embodiments of the present invention further provide pharmaceutical preparations comprising the aforementioned compounds and a pharmaceutically acceptable carrier.

Additional embodiments of the present invention provide methods of using the aforementioned compounds to kill or inhibit the growth of an arbovirus. In some embodiments, the arbovirus is an alphavirus (e.g., Sindbis virus, Semliki forest virus, O'nyong'nyong virus, Chikungunya virus, Mayaro virus, Ross River virus, Barmah Forest virus, Eastern equine encephalitis virus, Western equine encephalitis virus, or Venezuelan equine encephalitis virus), flavivirus (e.g., West Nile virus, St. Louis encephalitis virus, Japanese encephalitis virus) or a bunyavirus (e.g., La Crosse encephalitis virus, California encephalitis virus). In some embodiments, the arbovirus is in a cell. In some embodiments, the cell is in an animal. In some embodiments, the animal exhibits symptoms of an arbovirus infection and contacting the cell with the compound results in a decrease or elimination of symptoms of an arbovirus infection.

DESCRIPTION OF THE FIGURES

FIG. 1 shows neuronal cell infection studies. Cell viability (A) and virus titers (B) were determined 24 h post-infection by MTT and plaque assays, respectively

DEFINITIONS

Figure 2:
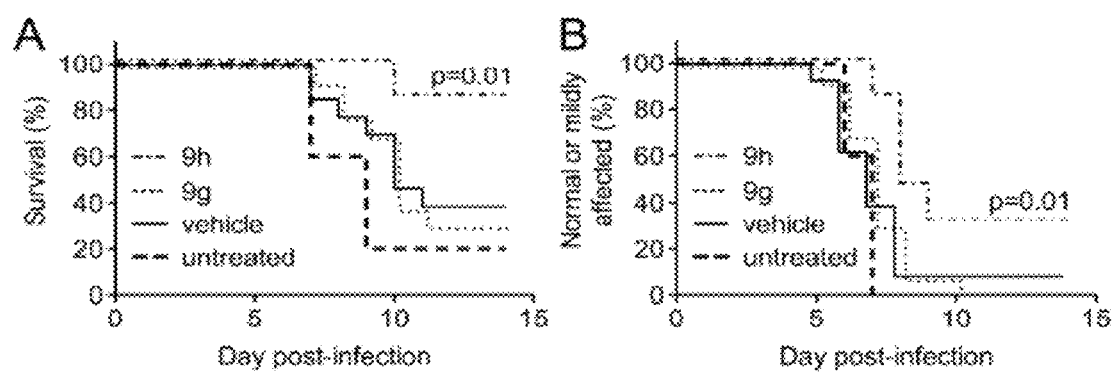
FIG. 2 shows clinical effects of indole enantiomers in mice with acute NSV encephalomyelitis. (A) Survival differences between drug- and vehicle-treated animals were measured using a log-rank (Mantel-Cox) test. (B) The proportion of mice that either developed mild or no hind limb paralysis following NSV challenge was determined in each group, and differences between drug- and vehicle-treated animals determined by a log-rank (Mantel-Cox) test.

To facilitate an understanding of the present invention, a number of terms and phrases are defined below.

As used herein, the term "aliphatic" represents the groups including, but not limited to, alkyl, alkenyl, alkynyl, alicyclic.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, chemical moieties comprising N, S, O, —$NH_2$, —$NHCOCH_3$, —OH, lower alkoxy ($C_1$-$C_4$), and halo (—F, —Cl, —Br, or —I).

As used herein, the term "substituted aliphatic" refers to an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" and "heteroaryl" refer to an aromatic ring or fused aromatic ring system consisting of no more than three fused rings at least one of which is aromatic, and where at least one of the hydrogen atoms on a ring carbon has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to a cycloalkane possessing less than 8 carbons or a fused ring system consisting of no more than three fused cycloaliphatic rings. Examples of such include, but are not limited to, decalin and the like.

As used herein, the term "substituted cycloaliphatic" refers to a cycloalkane possessing less than 10 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicycloheptanes, octanes, and nonanes (e.g., nonrbornyl) and the like.

As used herein, the term "heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such include, but are not limited to, morpholino and the like.

As used herein, the term "substituted heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "alkyl" refers to a saturated chain or ring of single-bonded carbon and hydrogen atoms. The term "alky'" includes "cycloalkyl (e.g., closed ring structures) and substituted or heteroalkyl (e.g., where one or more carbons are replaced by O or N).

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "bicyclic" refers to a structure comprising two or more fused rings. The rings may be all alkyl, all aryl, or a combination of alkyl and aryl. Bicyclic rings may be substituted or unsubstituted.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

The term "derivative" of a compound, as used herein, refers to a chemically modified compound wherein the chemical modification takes place at any location of the compound (e.g., at a functional group).

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by infection by arbovirus or risk of infection by arbovirus.

The term "diagnosed," as used herein, refers to the recognition of a disease by its signs and symptoms (e.g., resistance to conventional therapies), or genetic analysis, pathological analysis, histological analysis, diagnostic assay (e.g., for arbovirus infection) and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

As used herein, the term "co-administration" refers to the administration of at least two agent(s) (e.g., a compound of the present invention) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "sample" as used herein is used in its broadest sense. A sample suspected of indicating the presence of an arboavirus may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., a compound of the present invention) to affect (e.g., to kill or prevent the growth of) an arbovirus.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., infection by arbovirus). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that treat or prevent arbovirus infection.

DETAILED DESCRIPTION OF THE INVENTION

The present invention relates to chemical compounds, methods for their discovery, and their therapeutic use. In particular, the present invention provides compounds as inhibitors of arboviruses (e.g., alphaviruses, flaviviruses or bunyaviruses).

In some embodiments, the arbovirus is an alphavirus (e.g., Sindbis virus, Semliki forest virus, O'nyong'nyong virus, Chikungunya virus, Mayaro virus, Ross River virus, Barmah Forest virus, Eastern equine encephalitis virus, Western equine encephalitis virus, or Venezuelan equine encephalitis virus), flavivirus (e.g., West Nile virus, St. Louis encephalitis virus, Japanese encephalitis virus) or a bunyavirus (e.g., La Crosse encephalitis virus, California encephalitis virus).

The neurotropic alphaviruses represent emerging pathogens with the potential for widespread dissemination and the ability to cause substantial morbidity and mortality (Gubler, Arch Med Res 2002; 33:330-42; Sidwell et al., Antiviral Res 2003; 57:101-11), but for which no licensed therapies currently exist.

Alphaviruses, like all other group IV viruses, have a positive sense single stranded RNA genome. There are 27 alphaviruses, able to infect various vertebrates such as humans, rodents, birds, and larger mammals such as horses as well as invertebrates. Transmission between species and individuals occurs via mosquitoes, making the alphaviruses a contributor to the collection of Arboviruses—or Arthropod Borne Viruses. Alphaviruses particles are enveloped, have a 70 nm diameter, tend to be spherical (although slightly pleomorphic), and have a 40 nm isometric nucleocapsid. Table 1 shows medically important Alphaviruses and details of their human disease, vertebrate reservoir and distribution.

TABLE 1

Medically Important Alphaviruses

| Virus | Human Disease | Vertebrate Reservoir | Distribution |
|---|---|---|---|
| Sindbis virus | Rash, arthritis | Birds | Europe, Africa, Australia |
| Semliki forest virus | Rash | Birds | Africa |
| O'nyong'nyong virus | Rash | Primates | Africa |
| Chikungunya virus | Rash | Primates, humans | Africa, India, SE Asia |
| Mayaro virus | Rash | Primates, humans | South America |
| Ross River virus | Rash | Mammals, humans | Australia, South Pacific |
| Barmah Forest virus | Fever, malaise, rash, joint pain, muscle tenderness | Humans | Australia |
| Eastern equine encephalitis virus | Encephalitis | Birds | Americas |
| Western equine encephalitis virus | Encephalitis | Birds, mammals | North America |
| Venezuelan equine encephalitis virus | Encephalitis | Rodents, horses | Americas |

Alphavirus nsPs contain several distinct enzymatic activities, including methyltransferase (nsP1) (Ahola et al., J Virol 1997; 71:392-7) protease and helicase (nsP2) (Gomez et al., FEBS Lett 1999; 448:19-22; Hardy et al., J Virol 1989; 63:4653-64), and RNA polymerase (nsP4) (Poch et al., EMBO J. 1989; 8:3867-74). In vitro assays have been developed for several of these activities (Ahola et al., supra; Vasiljeva et al., J Biol Chem 2001; 276:30786-93; Tomar et al., J Virol 2006; 80:9962-9). Certain embodiments of the present invention utilize in vitro screening for target identification. An alternative approach that takes advantage of the intrinsically high error rate of viral RNA polymerases previously used successfully for antiviral target identification is the iso-lation and characterization of viral escape mutants (Li et al., J Virol 2004; 78:9645-51; Lin et al., Virology 2000; 272:61-71; Scheidel et al., Virology 1991; 181:490-9).

The treatment of CNS infections presents an additional hurdle to overcome, as the blood-brain-barrier (BBB) represents a formidable obstacle for drug penetration (Pardridge, NeuroRx 2005; 2:1-2). The BBB is a highly effective physiologic barrier whose primary function is to closely regulate access of blood stream components to the CNS. Although infectious and inflammatory CNS diseases often disrupt BBB function and increase permeability, drug penetration remains an important aspect to consider in the development of antiviral agents against neurotropic alphaviruses. Multiple physical and chemical factors influence CNS penetration of drugs, including lipophilicity, ionization properties, molecular flexibility, polar surface area (PSA), and size (Pajouhesh et al., NeuroRx 2005; 2:541-53). The latter two properties are particularly important, where studies of marketed CNS and non-CNS drugs indicate that PSA 20 values less than 60-90 Å2 and MW less than 450 Da are required for adequate penetration (Kelder et al., Pharm Res 1999; 16:1514-9; van de Waterbeemd et al., J Drug Target 1998; 6:151-65). In some embodiments, compounds are screened for their ability to cross the BBB.

I. Arbovirus Inhibitors

As described herein, embodiments of the present invention provide compounds for use in inhibiting the arbovirus replication, infectivity or ability to cause disease. In some embodiments, the compositions of the present invention have the structure of formula I:

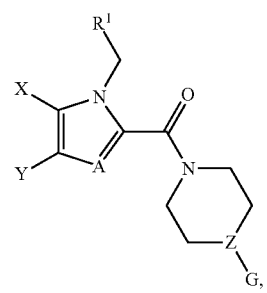

including pharmaceutically acceptable salts, prodrugs, and both R and S enantiomeric forms and racemic mixtures thereof.

In some embodiments, $R^1$ is H, a $C_1$-$C_8$ alkyl or cycloalkyl, a substituted $C_1$-$C_8$ alkyl or cycloalkyl, a $C_0$-$C_6$ alkyl-aryl, a substituted $C_0$-$C_6$ alkyl-aryl, or a $C_0$-$C_6$-alkyl-heteroaryl or a substituted $C_0$-$C_6$-alkyl-heteroaryl. In some embodiments, alkyl-aryl together form a cyclic structure (e.g., bicyclic structures such as, including but not limited to,

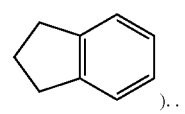

Examples of $R^1$ include, but are not limited to, phenyl, aryl, substituted aryl, heteroaryl, substituted heteroaryl,

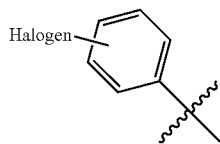

(wherein halogen can be, for example, chlorine, fluorine, bromine, iodine, etc.),

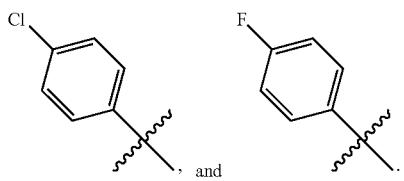 [SMILES: *c1ccc(Cl)cc1 ; *c1ccc(F)cc1 ; "," ; "and" ; "."]

In some embodiments, $R^1$ is phenyl.

In some embodiments, X and Y may be identical, different, or together form a cyclic chemical moiety (e.g., an aromatic cyclic moiety) (e.g., a non-aromatic cyclic moiety). In some embodiments, X and Y are each H. In some embodiments, X and Y are each H such that the resulting compound is

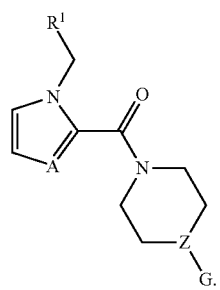

In some embodiments, X and Y together form a fused phenyl ring substituted with one or more R2 such that the resulting compound is

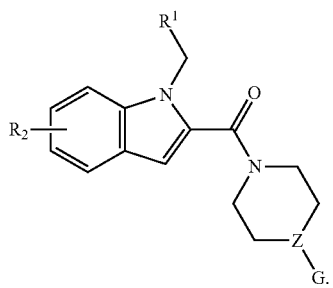

In some embodiments, there is only one R2. In some embodiments, there is more than one R2. In embodiments where there is more than one R2, each R2 may be the same or different. Examples of R2 include, but are not limited to, H, $OR^3$, $NR^3R^4$, $NHC(=O)R^3$, $NHSO_2R^3$, $C_1$-$C_6$ alkyl, $C_0$-$C_6$ alkyl-aryl or $C_0$-$C_6$-alkyl-heteroaryl.

In some embodiments, $R^3$ and $R^4$ are the same or different. Examples of $R^3$ and $R^4$ include, but are not limited to, H, $C_1$-$C_8$ alkyl, $C_0$-$C_6$ alkyl-aryl, or a $C_0$-$C_6$-alkyl-heteroaryl, all of which are optionally substituted. In some embodiments, $R^3$ and $R^4$ together with N form a substituted cyclic alkyl amine of 4-8 atoms or together form a piperazine ring substituted on the 4-nitrogen by $CH_2R^5$ or $C(=O)R^5$;

wherein $R^5$ is $C_0$-$C_6$ alkyl-aryl or $C_0$-$C_6$-alkyl-heteroaryl, which are optionally substituted.

In some embodiments, Z is CH or N.

In some embodiments, A is CH, C—$CH_3$ or N.

In some embodiments, G is H, $CH_2$-aryl, $CH_2$-heteroaryl, $C(=O)NR^3R^4$, $CH(OH)R^3$, or $CH_2NR^3R^4$. Examples of G include, but are not limited to,

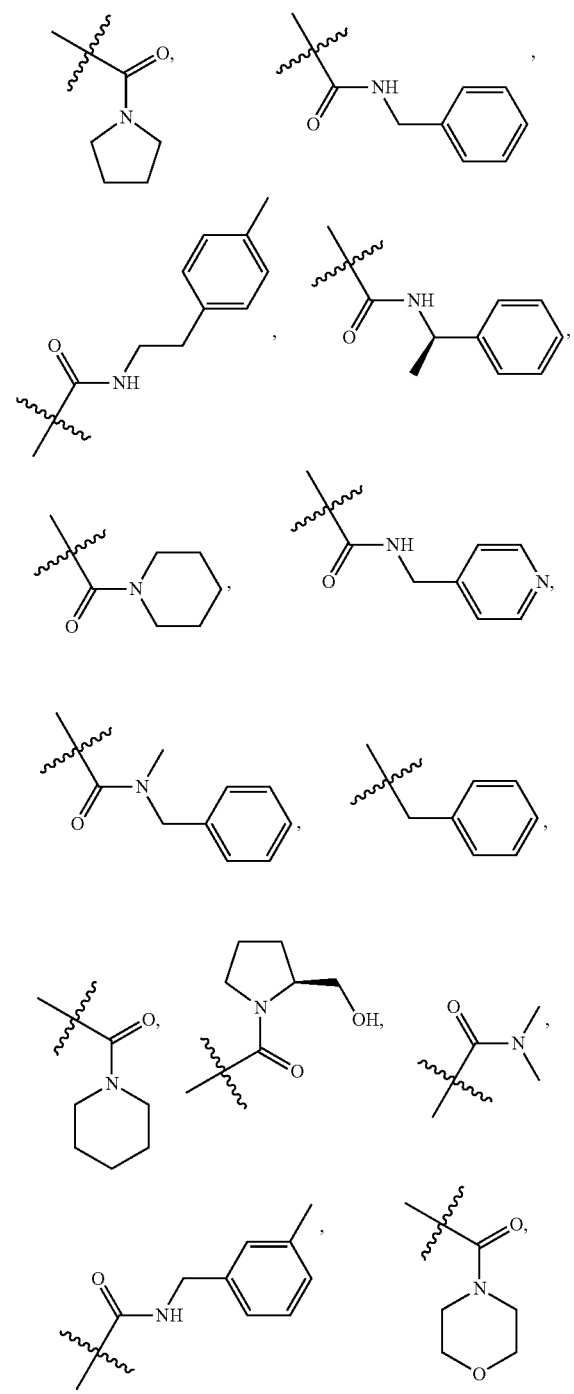

35
-continued
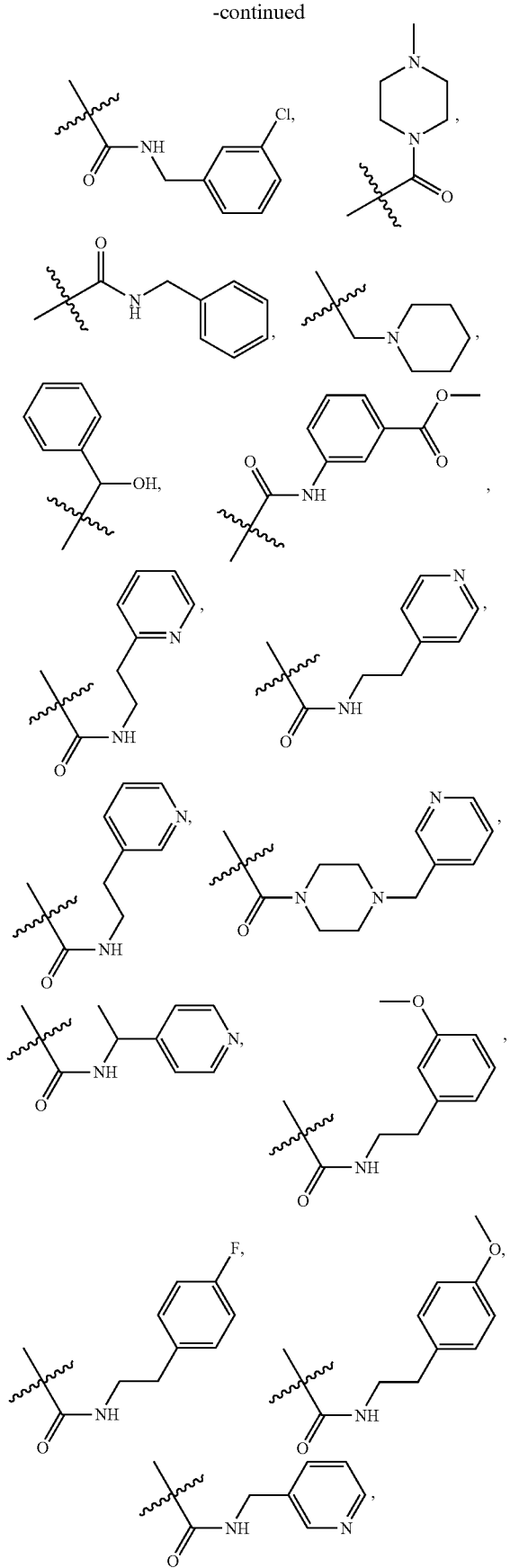
36
-continued
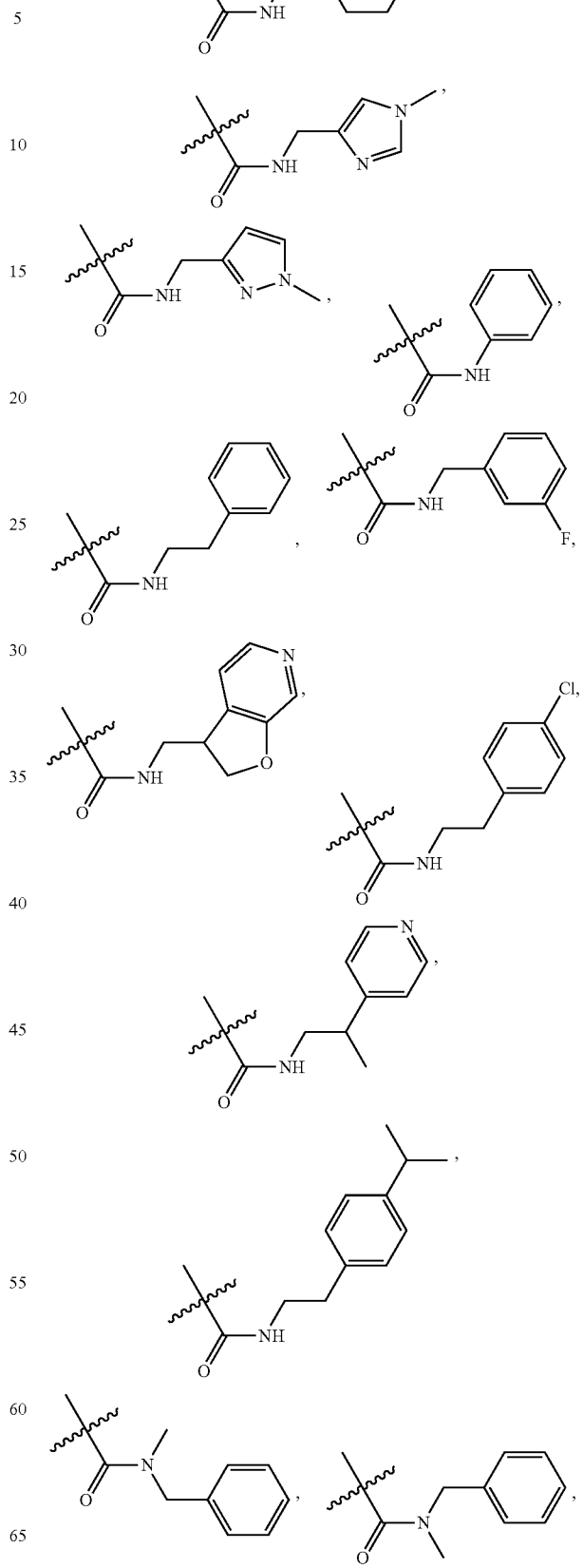

-continued
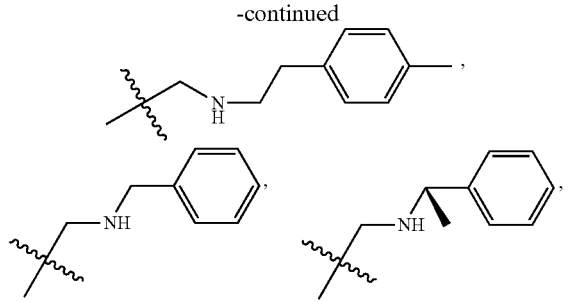
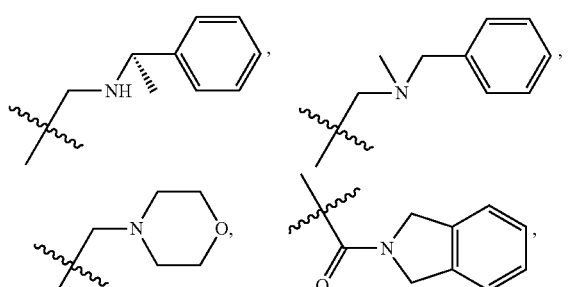
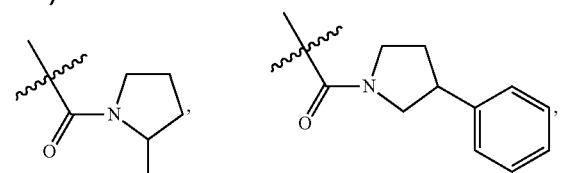
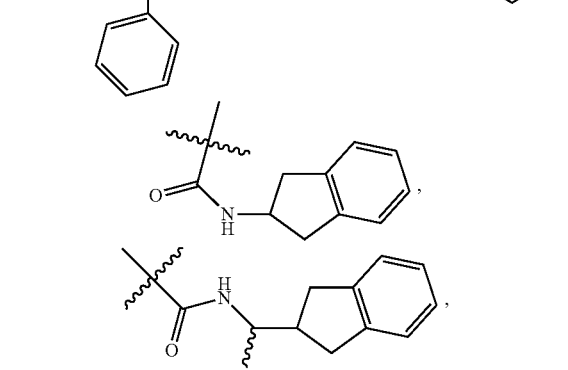
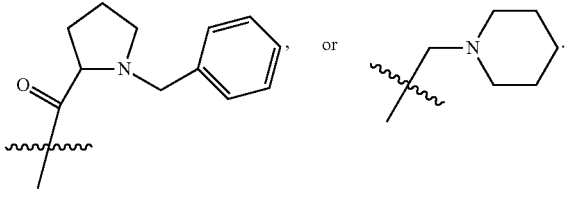
In some embodiments, the compound has the Formula II:
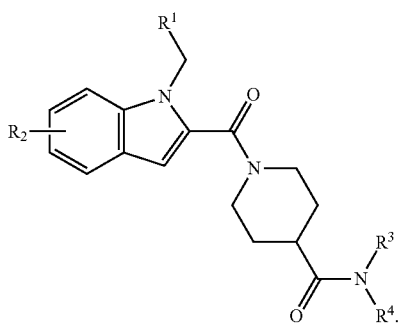
In some embodiments, the compounds is, for example,
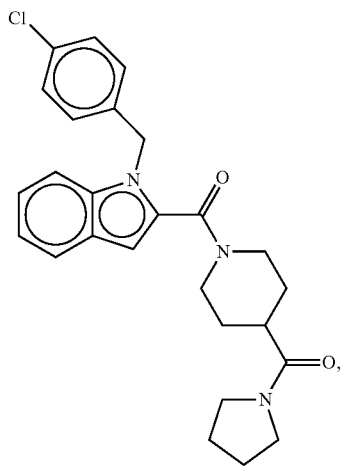
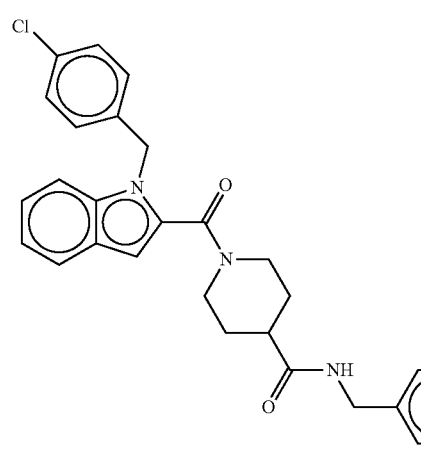

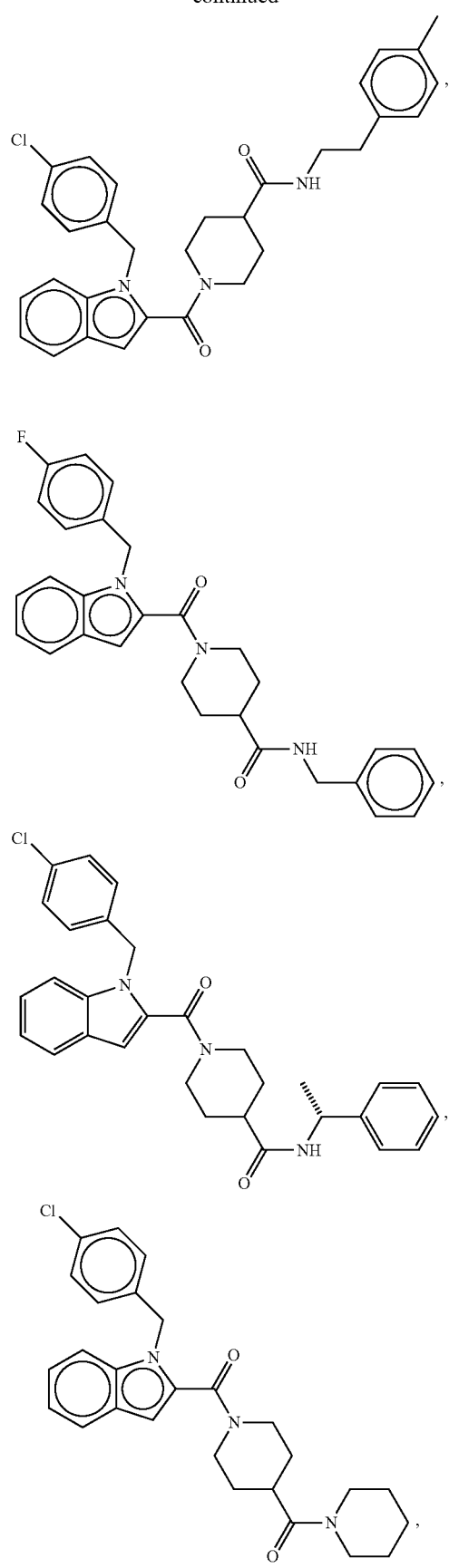
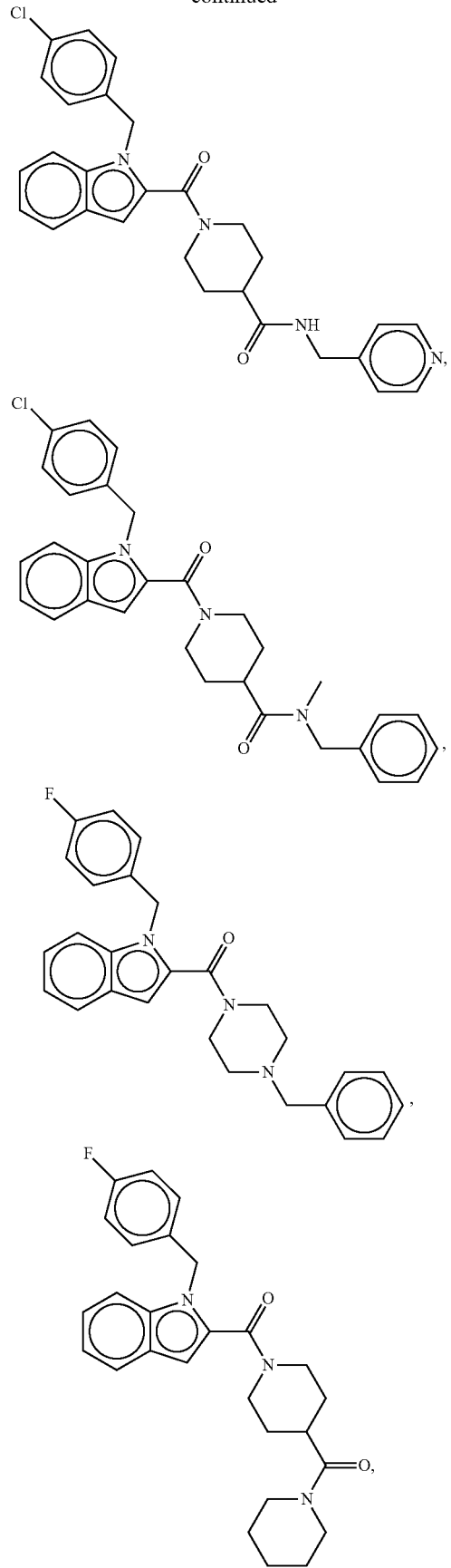

41
-continued
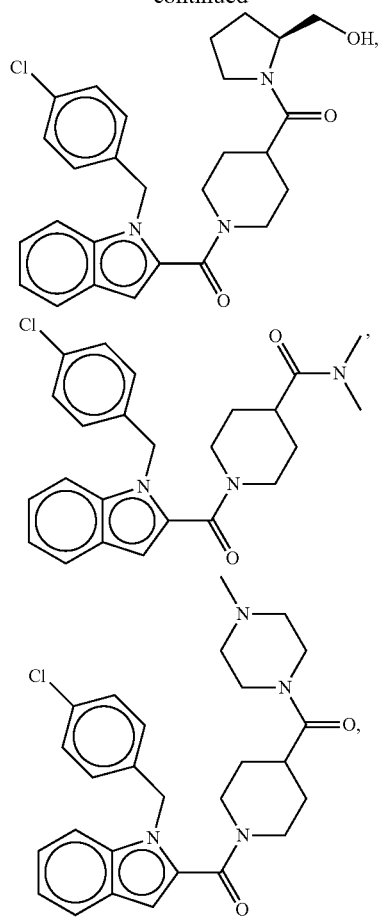
42
-continued
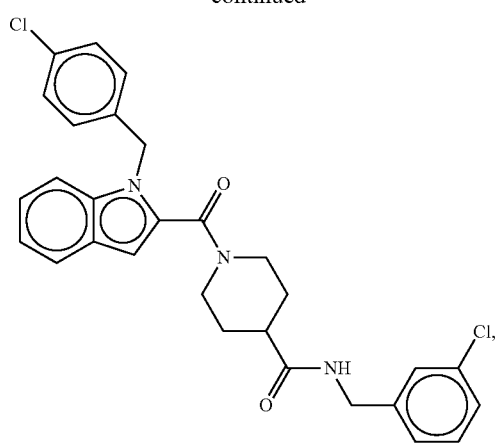
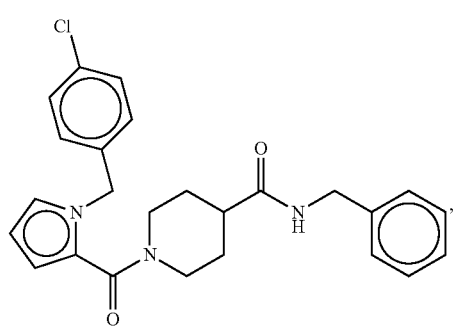
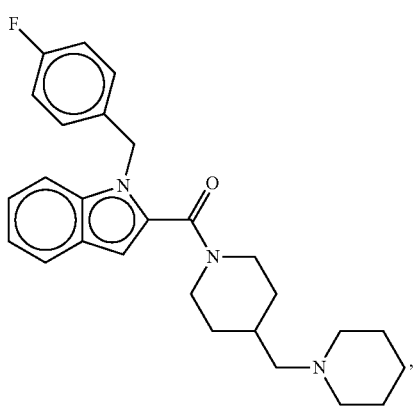
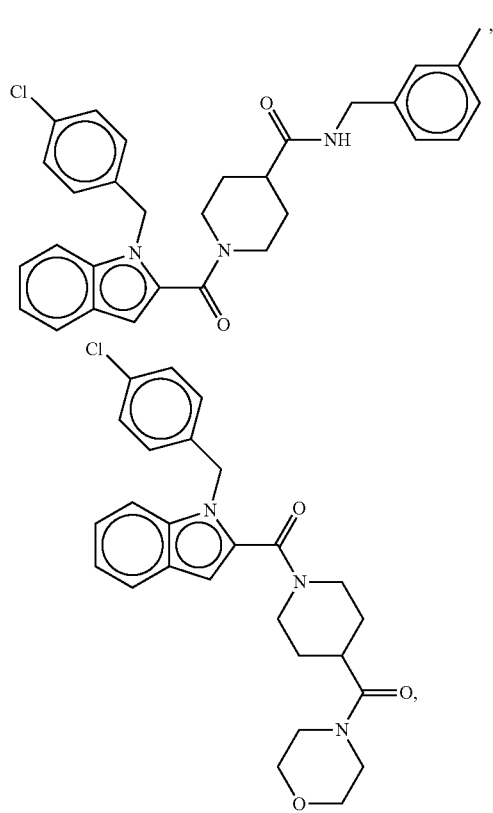

43
-continued
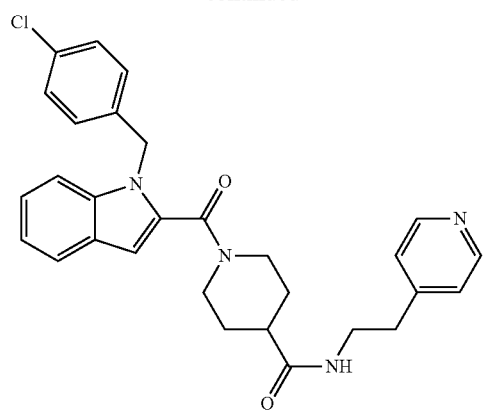
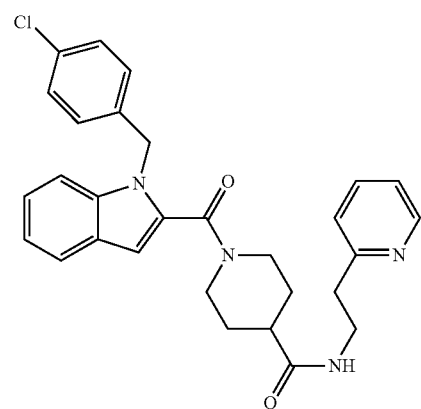
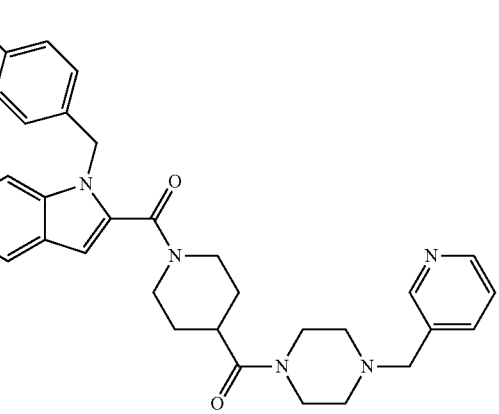
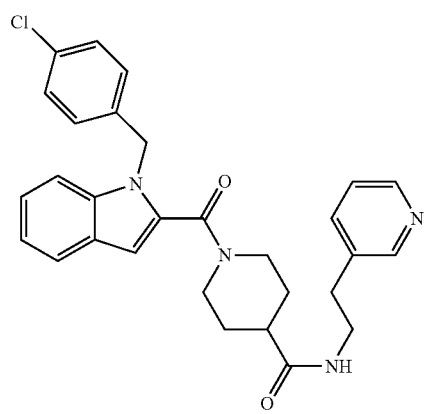
44
-continued
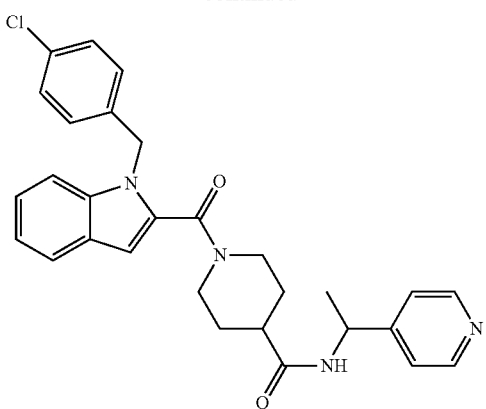
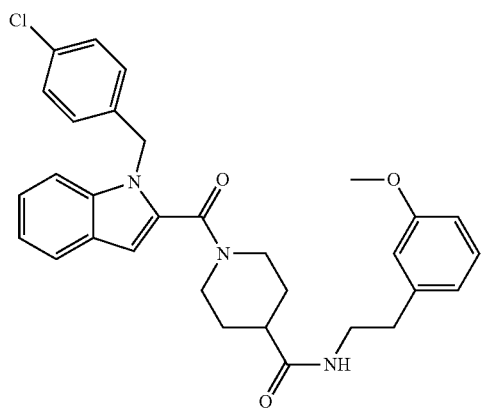
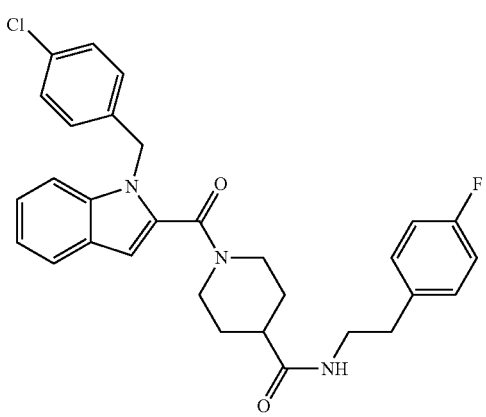
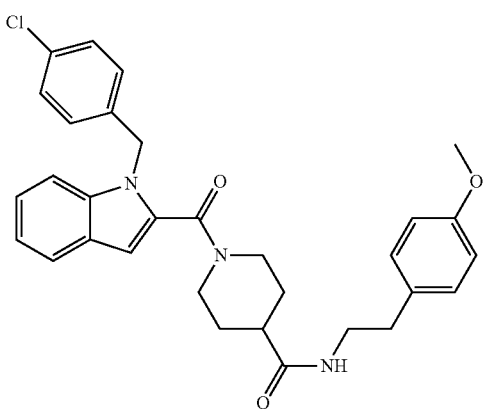

45
-continued
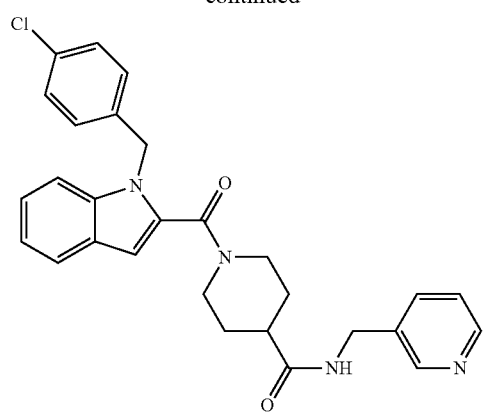
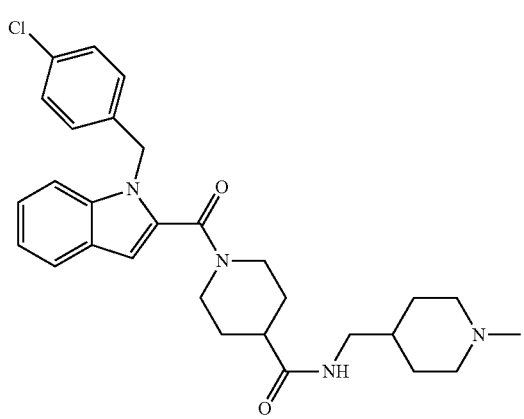
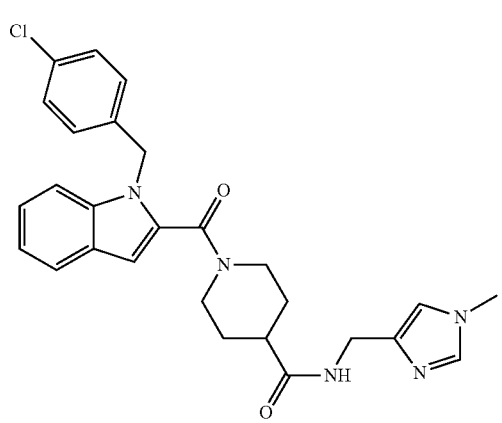
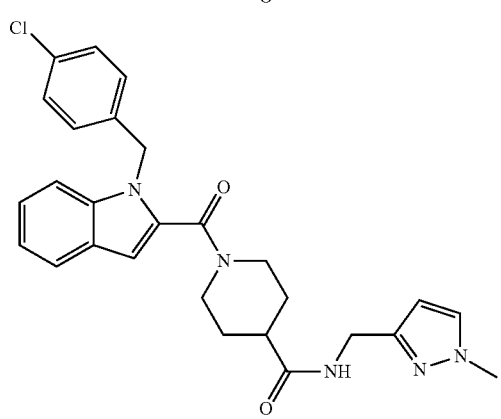
46
-continued
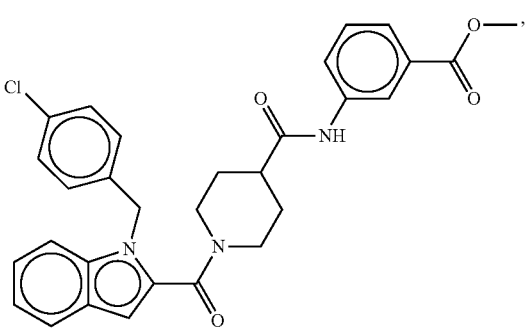
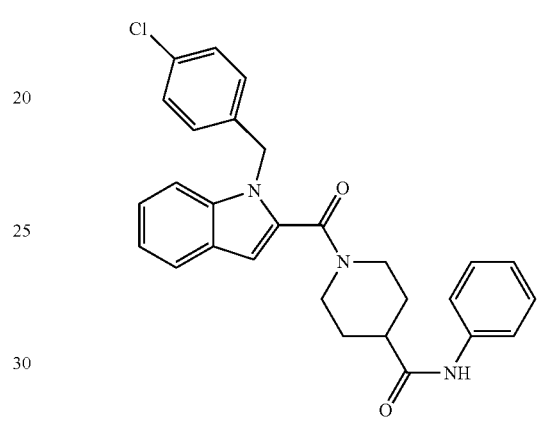
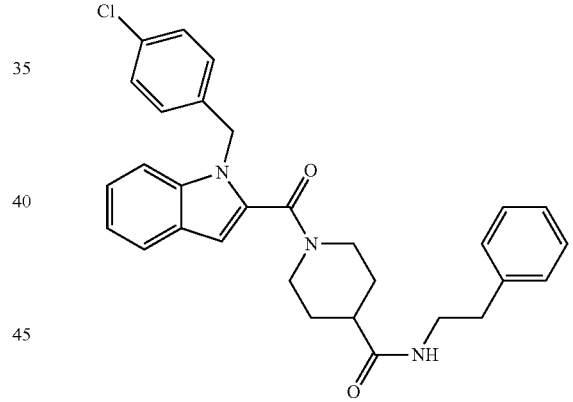
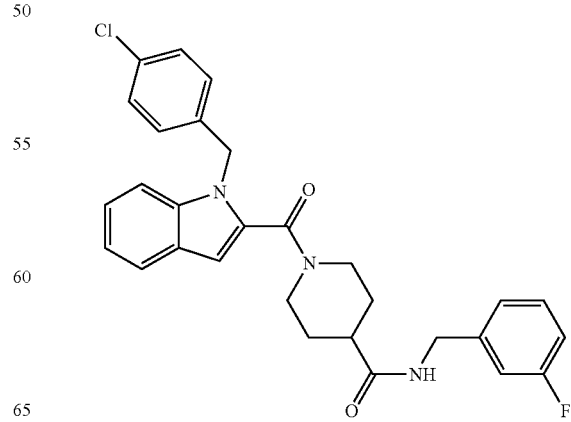

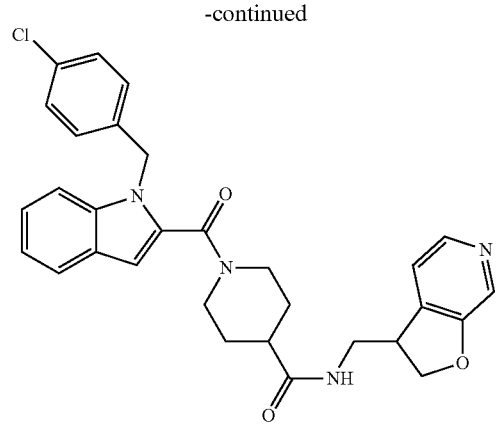
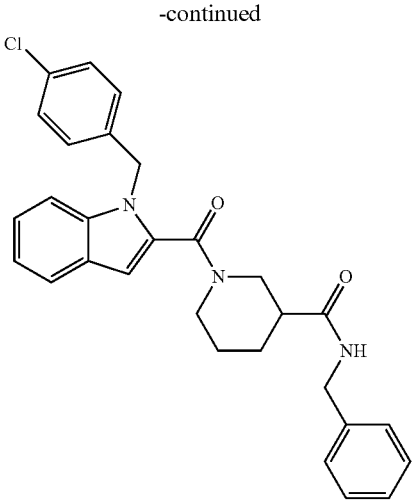
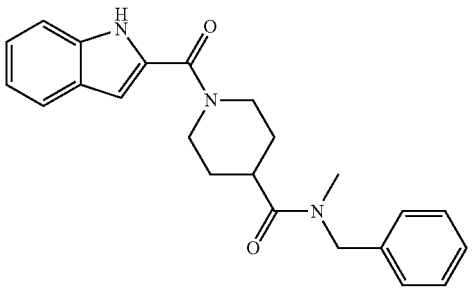
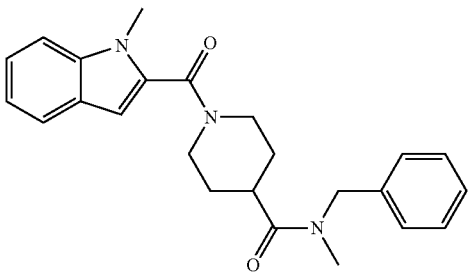
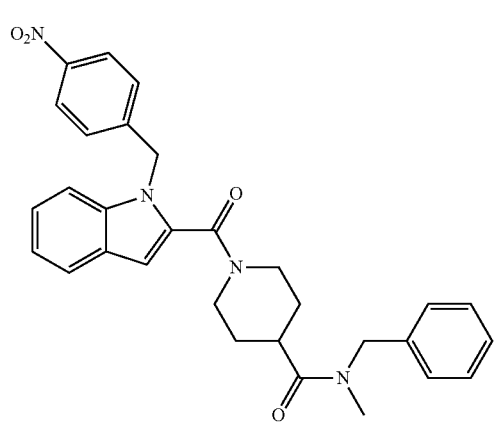

49
-continued
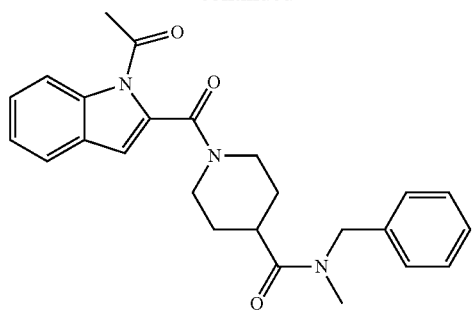
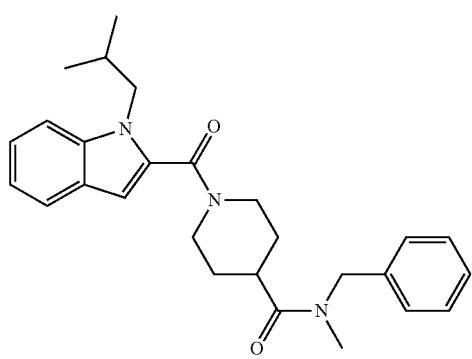
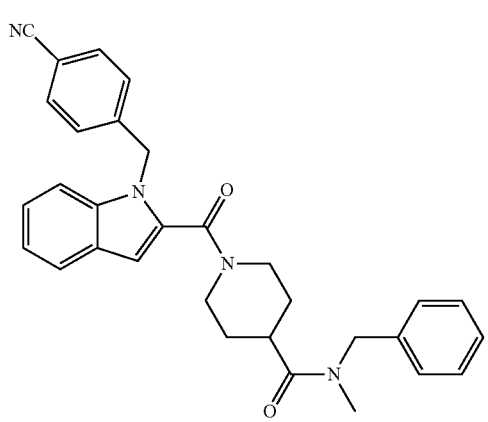
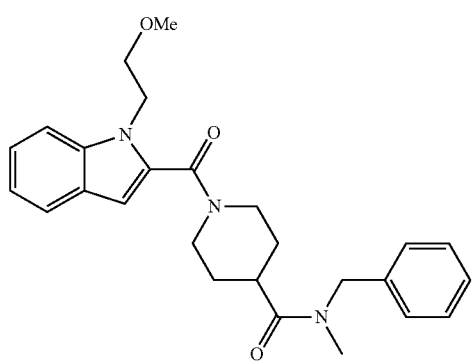
50
-continued
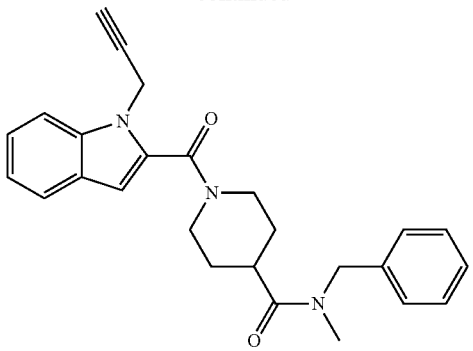
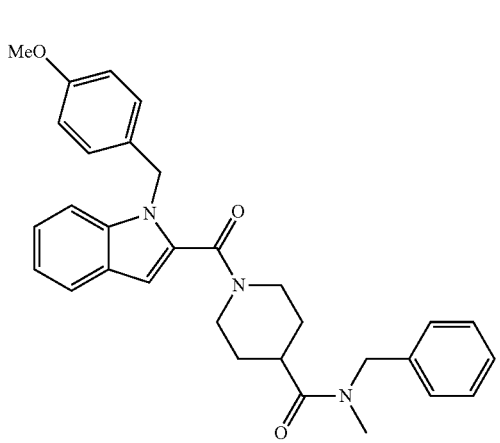
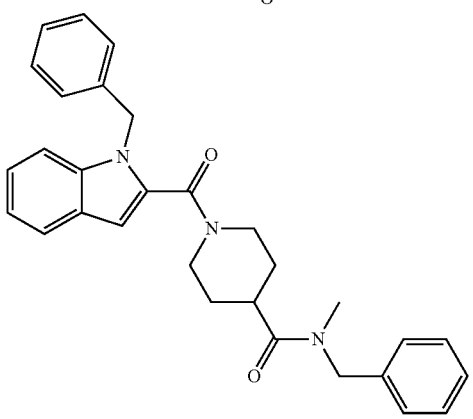
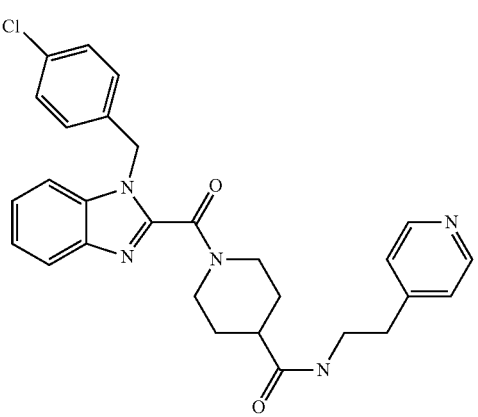

51
-continued
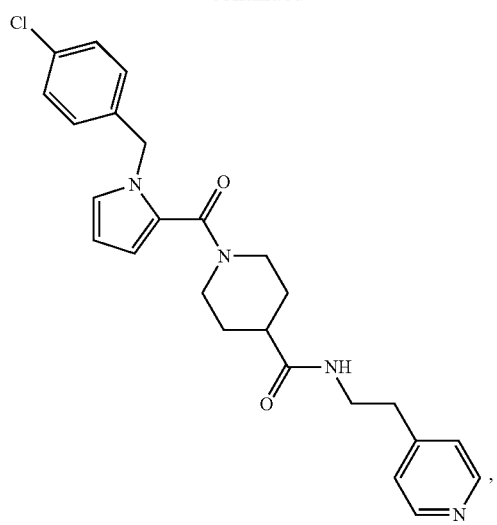
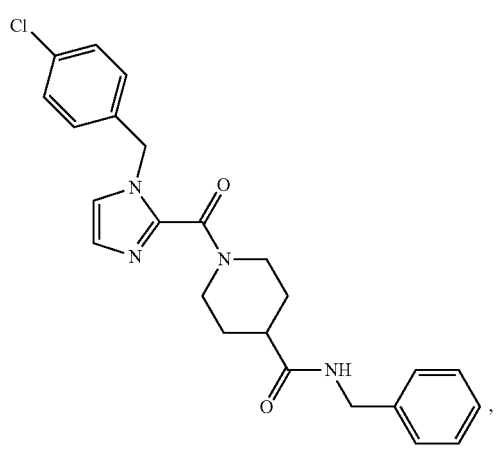
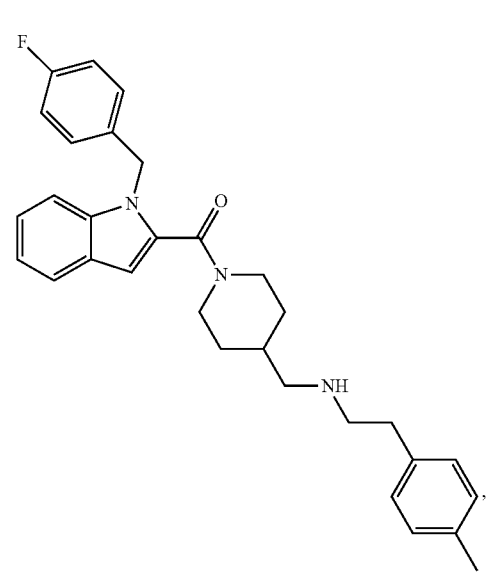
52
-continued
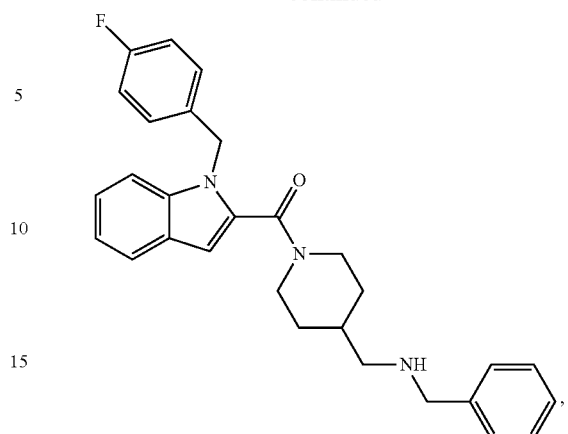
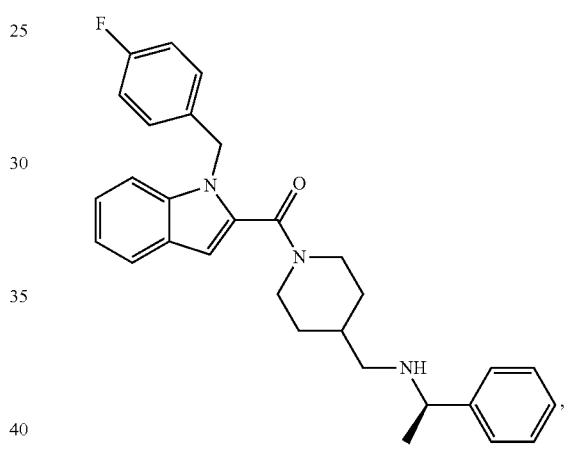
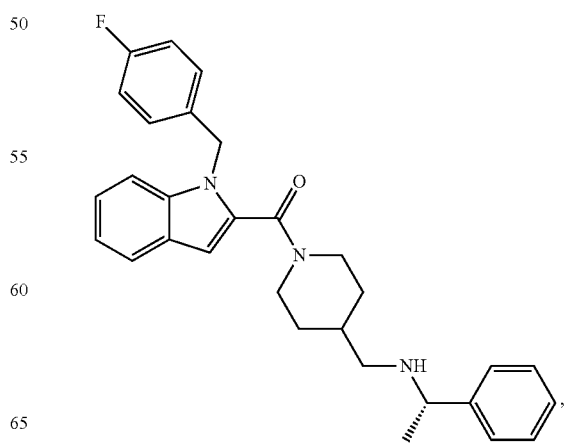

53
-continued
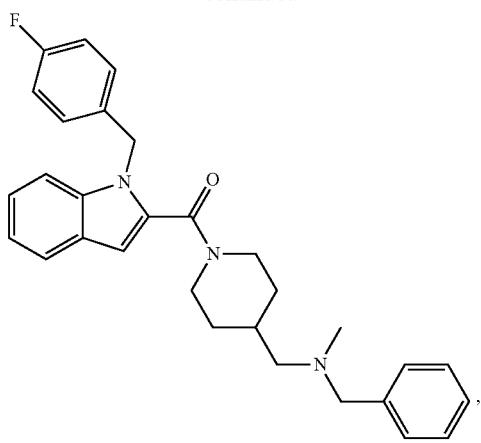
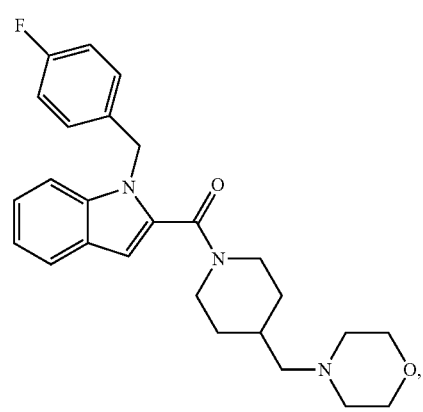
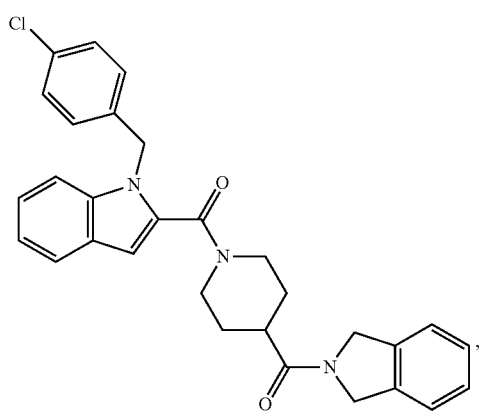
54
-continued
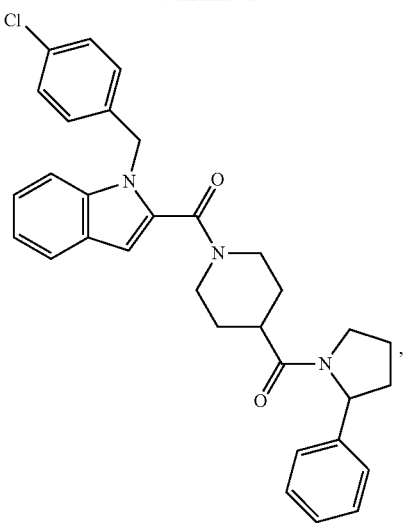
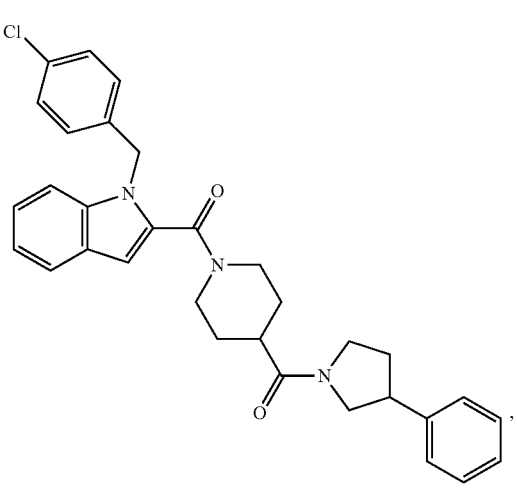
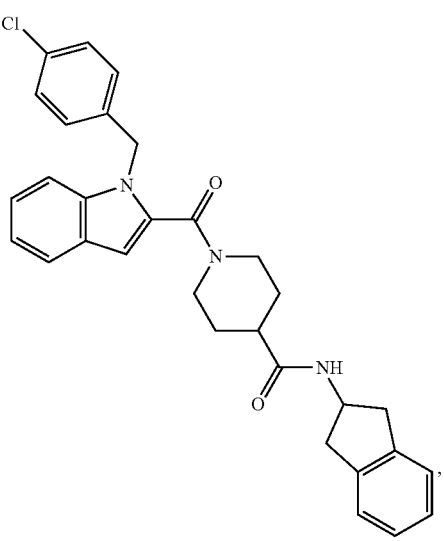

-continued
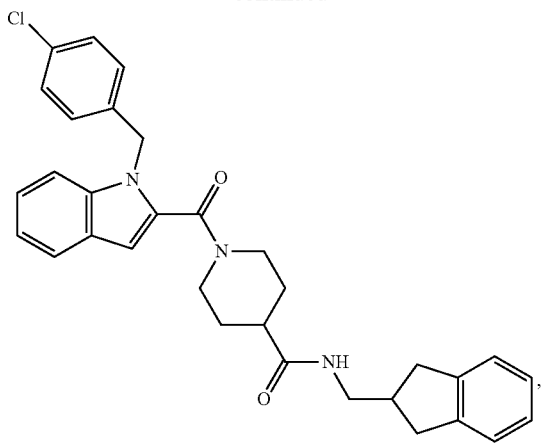
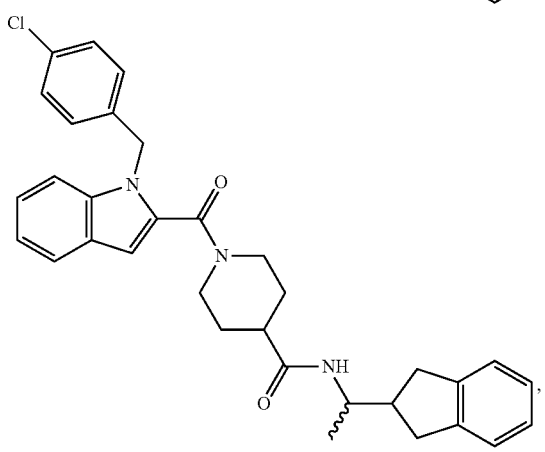
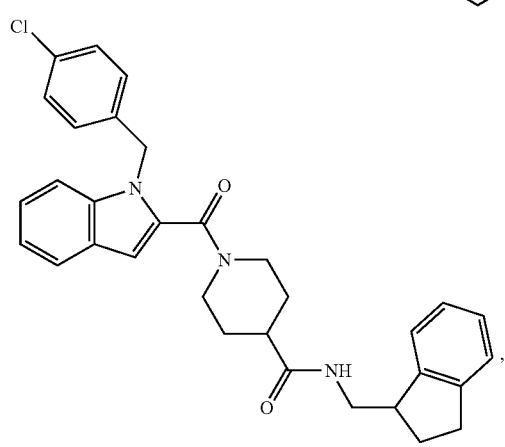
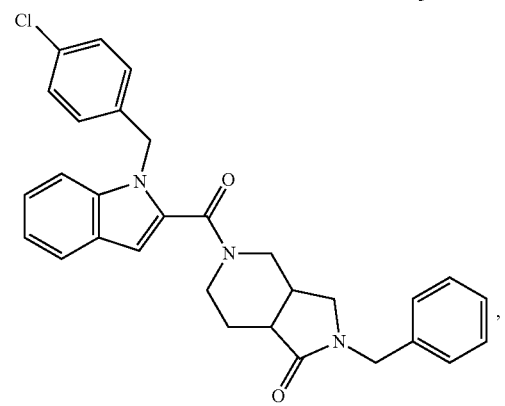
-continued
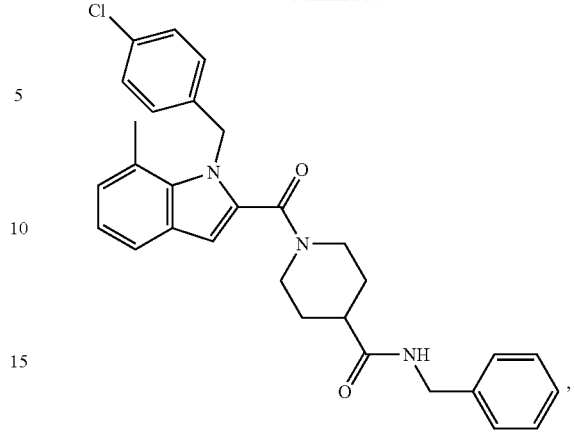
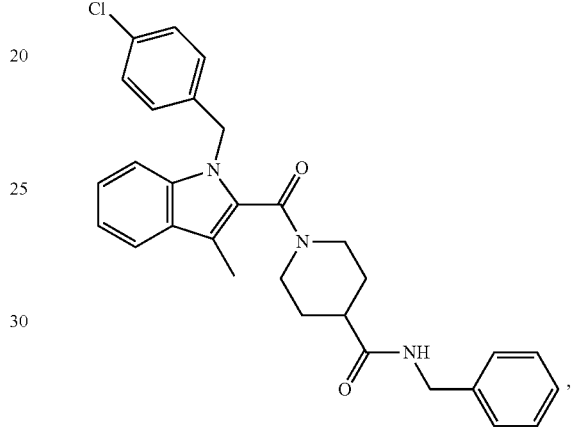
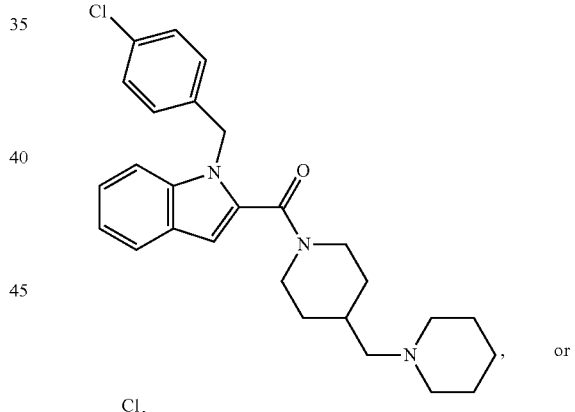
or
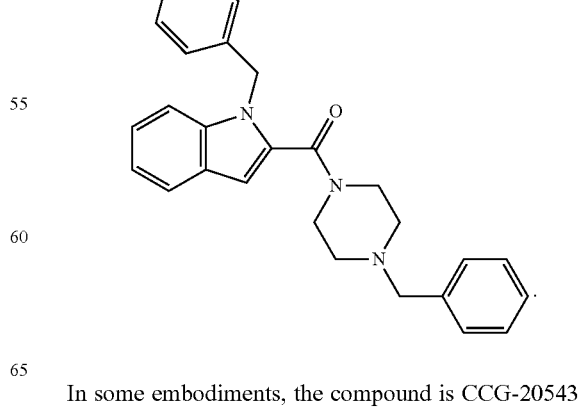
In some embodiments, the compound is CCG-205432 or CCG-206381.

Embodiments of the present invention further provide derivatives, mimetics, stereoisomers, salts, etc. of the above named compounds.

In some embodiments, the compound is, for example, selected from those described in Table 2 below.

In some embodiments, the compound is a mimetic, stereoisomer, salt or derivative of a compound described herein.

The present invention also provides methods of modifying and derivatizing the compositions of the present invention to increase desirable properties (e.g., binding affinity, activity, and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In some embodiments, rational design methods are used to predict and model in silico ligand-receptor interactions prior to confirming results by routine experimentation.

The compounds of embodiments of the invention (or derivatives, mimetics, variants, etc. thereof) can be prepared from readily available starting materials using known methods. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Third Edition, Wiley, New York, 1999, and references cited therein.

If the compounds of embodiments of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

II. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat or prevent arbovirus infection. The methods and techniques for preparing medicaments of a compound are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent (e.g., arbovirus inhibitor), as defined above, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In some embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose)surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in an known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer a therapeutic agent (e.g., arbovirus inhibitor) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified herein as effective for their intended purpose can be administered to subjects or individuals susceptible to or at risk of arbovirus infection or disease. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or vaccines may each be administered using different modes or different formulations.

The agent or agents to be co-administered depends on the type of condition being treated. For example, when the condition being treated is arbovirus infection, the additional agent can be an antiviral agent or an agent that treats symptoms of arbovirus infection or an arbovirus vaccine. The additional agents to be co-administered can be any of the well-known agents in the art, including, but not limited to, those that are currently in clinical use. The determination of appropriate type and dosage of radiation treatment is also within the skill in the art or can be determined with relative ease.

III. Drug Screens

In some embodiments of the present invention, the compounds of the present invention, and other potentially useful compounds, are screened for their biological activity (e.g., ability to treat or prevent arbovirus infection). In some embodiments of the present invention, the compounds of the present invention, and other potentially useful compounds, are screened for their ability to treat or prevent arbovirus infection using one of the in vitro or in vivo assays described herein.

For example, in some embodiments, drug screening applications utilize a reporter gene assay comprising arbovirus genes linked to a reporter gene to assay for arbovirus genome replication.

In some embodiments, candidate compounds identified using the reporter gene assay are further screened using cellular toxicity assays (e.g., in vitro or in vivo) or live virus assays (e.g., in vitro or in an animal model). In some embodiments, compounds are screened for their ability to cross the BBB (e.g., using assays known in the art).

IV. Therapeutic Application

In some embodiments, the present invention provides compositions and methods for treating or preventing arbovirus infection. In some embodiments, the arbovirus is an arbovirus (e.g., Sindbis virus, Semliki forest virus, O'nyong'nyong virus, Chikungunya virus, Mayaro virus, Ross River virus, Barmah Forest virus, Eastern equine encephalitis virus, Western equine encephalitis virus, or Venezuelan equine encephalitis virus), flavivirus (e.g., West Nile virus, St. Louis encephalitis virus, Japanese encephalitis virus) or a bunyavirus (e.g., La Crosse encephalitis virus, California encephalitis virus).

In some embodiments, the compounds described herein (e.g., those described in Table 2) and section I above are utilized. In other embodiments, derivatives, mimetics, variants, etc. of the described compounds are utilized.

EXAMPLES

The following examples are provided to demonstrate and further illustrate certain embodiments of the present invention and are not to be construed as limiting the scope thereof.

Example 1

This example describes exemplary synthesis schemes and activity levels for compounds of embodiments of the present invention.

A. Synthesis Schemes and Synthesis of Intermediates

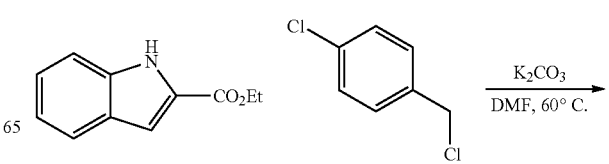

-continued

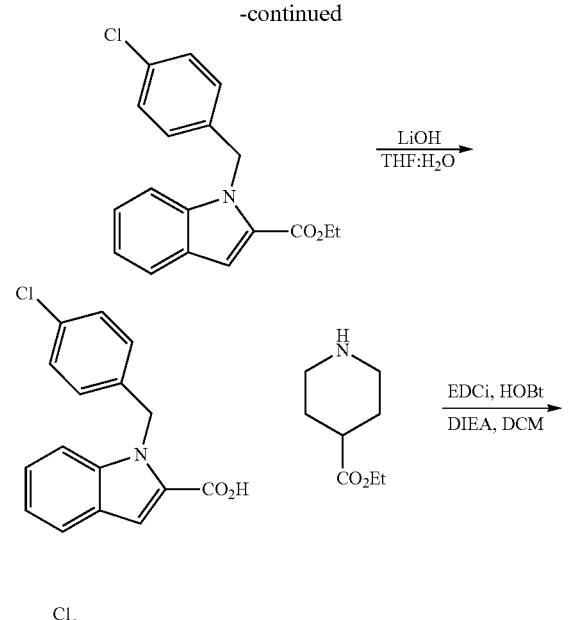

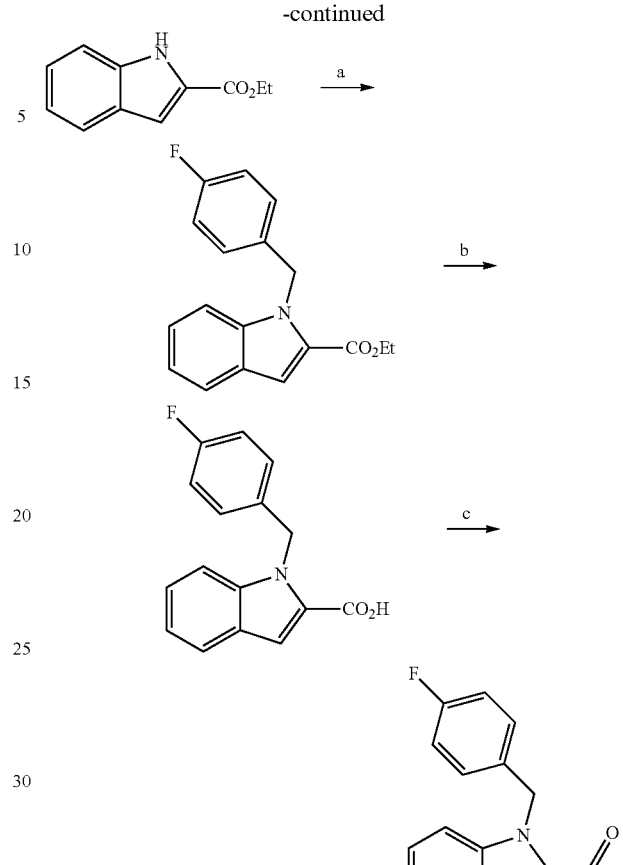

Reagents and conditions: (a) p-fluorobenzylchloride, K₂CO₃, DMF, 60° C., 20 h; (b) 7M NaOH, EtOH, 50° C., 3 h; (c) amine, EDC, HOBt, DIPEA, DMF, rt, ~24 h;

Ethyl 1-(4-fluorobenzyl)-1H-indole-2-carboxylate

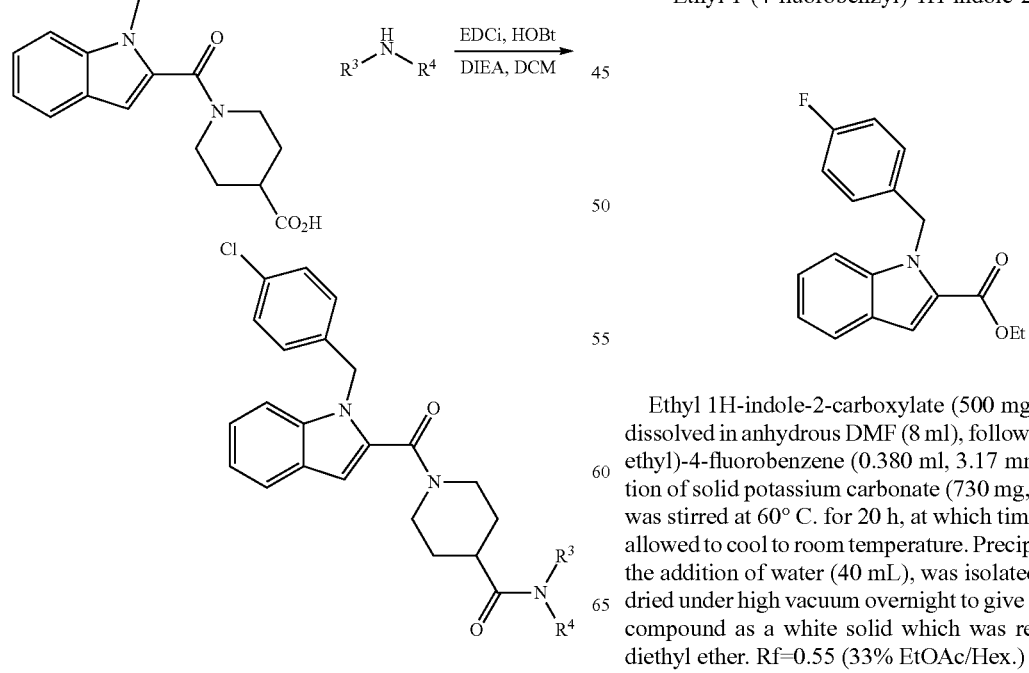

Ethyl 1H-indole-2-carboxylate (500 mg, 2.64 mmol) was dissolved in anhydrous DMF (8 ml), followed by 1-(chloromethyl)-4-fluorobenzene (0.380 ml, 3.17 mmol) and the addition of solid potassium carbonate (730 mg, 5.29 mmol). This was stirred at 60° C. for 20 h, at which time the reaction was allowed to cool to room temperature. Precipitate formed upon the addition of water (40 mL), was isolated over a filter, and dried under high vacuum overnight to give 550 mg of the title compound as a white solid which was recrystallized from diethyl ether. Rf=0.55 (33% EtOAc/Hex.)

¹H NMR (400 MHz, DMSO) δ 7.74, 7.60, 7.38, 7.32, 7.17-7.06, 5.84, 4.29, 1.29

1-(4-fluorobenzyl)-1H-indole-2-carboxylic acid

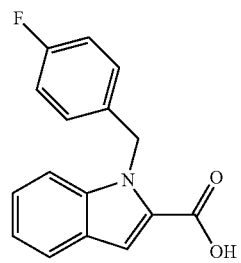 [SMILES: O=C(O)c1cc2ccccc2n1Cc1ccc(F)cc1]

Ethyl 1-(4-fluorobenzyl)-1H-indole-2-carboxylate (409 mg, 1.376 mmol) was suspended in ethanol (5 mL) and 7M NaOH (5 mL) and stirred at 50° C. for 3 h. Ethanol content was reduced in vacuo. The solution was then acidified to pH 2 and the precipitate was collected over a filter, washed with a small amount of ice cold-water, air dried on the filter, and then finally vacuum dried to give 360 mg of the title compound as a fine, white powder.

¹H NMR (400 MHz, DMSO) δ 13.00, 7.70, 7.56, 7.32, 7.29, 7.13, 7.09, 5.85

Methyl 1-(4-chlorobenzyl)-1H-pyrrole-2-carboxylate

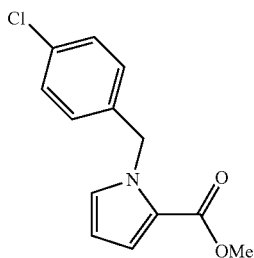 [SMILES: COC(=O)c1cccn1Cc1ccc(Cl)cc1]

Methyl 1H-pyrrole-2-carboxylate (330 mg, 2.64 mmol) was dissolved in anhydrous DMF (8 mL). Solid K2CO3 (547 mg, 3.96 mmol) was added, followed by the addition of 1-chloro-4-(chloromethyl)benzene (638 mg, 3.96 mmol). The reaction was permitted to stir at 60° C. for 36 h, at which time the reaction was allowed to cool to rt. Water was added and the resulting precipitate was isolated over a filter, and dried under high vacuum overnight to give 570 mg of the title compound.

¹H NMR (500 MHz, CDCl₃) δ 7.28, 7.03, 6.90, 6.22, 5.54, 3.78

1-(4-chlorobenzyl)-1H-pyrrole-2-carboxylic acid

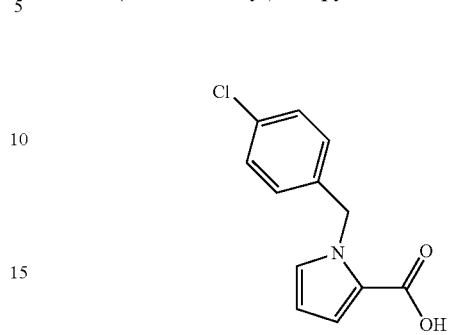

Methyl 1-(4-chlorobenzyl)-1H-pyrrole-2-carboxylate (550 mg, 2.203 mmol) was dissolved in ethanol (10 mL) and 7M aq. NaOH (8 mL). The reaction was stirred at 70° C. for 4 h and allowed to cool for 1 h. The ethanol was stripped by rotary evaporation until material began to precipitate, at which point the aqueous mixture was cooled in an ice bath and acidified with conc. HCl, which elicited further precipitation. The precipitate was collected over a filter and washed with a small amount of cold 1M HCl and dried under high vacuum to provide 375 mg of the title compound as a white, powdery solid.

¹H NMR (500 MHz, DMSO) δ 7.37, 7.20, 7.09, 6.83, 6.13, 5.56

Ethyl 1-(1-(4-chlorobenzyl)-1H-pyrrole-2-carbonyl) piperidine-4-carboxylate

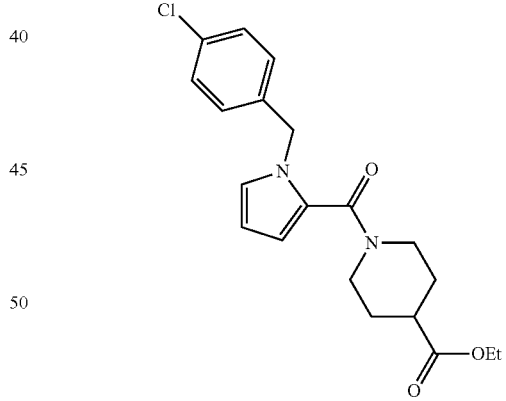

The following was added sequentially to anhydrous DMF (6 mL): 1-(4-chlorobenzyl)-1H-pyrrole-2-carboxylic acid (175 mg, 0.743 mmol), Hunig's Base (389 μl, 2.228 mmol), EDC (157 mg, 0.817 mmol), HOBT (125 mg, 0.817 mmol), and finally ethyl piperidine-4-carboxylate (172 μl, 1.114 mmol). The reaction was allowed to stir at room temperature for 24 h. At this time, a 1:1 solution of EtOAc:Et2O (100 mL) was added and washed with 10% Na2CO3 (2×50 mL) and brine (1×50 mL). The organic solution was then dried with anhydrous MgSO4 and concentrated in vacuo. Material was purified by column chromatography (20 g silica, 20% EtOAc/Hexanes) to provide 211 mg of the title compound.

¹H NMR (500 MHz, CDCl₃) δ 7.26, 7.05, 6.81, 6.33, 6.13, 5.29, 4.17, 2.95, 2.47, 1.80, 1.39, 1.27.

1-(1-(4-fluorobenzyl)-1H-pyrrole-2-carbonyl)piperidine-4-carboxylic acid

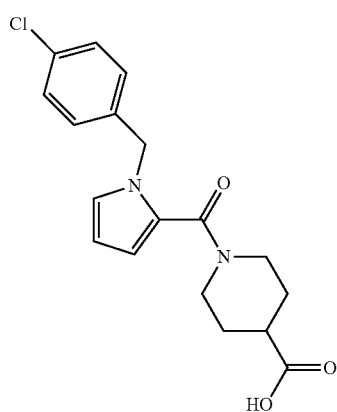 [SMILES: O=C(O)C1CCN(C(=O)c2cccn2Cc2ccc(Cl)cc2)CC1]

Ethyl 1-(1-(4-fluorobenzyl)-1H-pyrrole-2-carbonyl)piperidine-4-carboxylate (197 mg, 0.550 mmol) was dissolved in EtOH (6 mL), and 7M aq. NaOH was added (6 mL). The reaction was allowed to stir at 60° C. for 8 h. EtOH was then removed in vacuo, and the remaining aqueous solution was acidified (to ~pH 2) by conc. HCl. The precipitate was filtered over a scintered glass filter and collected as a viscous oil. This material was dried overnight under high-vacuum to afford 169 mg of the title compound.

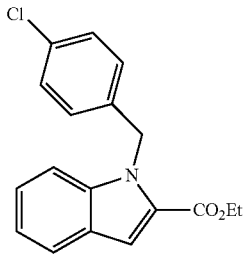 [SMILES: CCOC(=O)c1cc2ccccc2n1Cc1ccc(Cl)cc1]

1) Ethyl 1-(4-chlorobenzyl)-1H-indole-2-carboxylate
Ethyl 1H-indole-carboxylate (1.5 g, 7.93 mmol) was dissolved in DMF (15.0 mL). A DMF (4.8 mL) solution of 1-chloro-4-(chloromethyl)benzene (1.660 g, 10.31 mmol) was added. Solid potassium carbonate (1.424 g, 10.31 mmol) was added to the flask. The reaction was allowed to stir at 60° C. overnight. The reaction was cooled to room temperature where it was diluted with water followed by ethyl acetate. The layers were transferred into a separatory funnel and separated. An additional 100 mL of ethyl acetate was added to the separatory funnel. The organic layer was washed with saturated sodium chloride (3×100 mL) then dried over magnesium sulfate, filtered and concentrated. The crude material was triturated with methanol. The resulting white solid was filtered and dried under vacuum. Yield: 1.80 g, (White solid)

¹H-NMR (DMSO-d₆): 7.73, 7.58, 7.39, 7.32, 7.16, 7.03, 5.84, 4.28, 1.29

1-(4-chlorobenzyl)-1H-indole-2-carboxylic acid

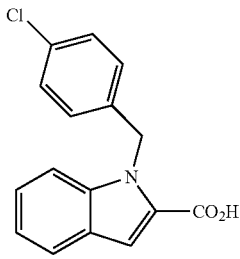 [SMILES: O=C(O)c1cc2ccccc2n1Cc1ccc(Cl)cc1]

Ethyl 1-(4-chlorobenzyl)-1H-indole-2-carboxylate (2.00 g, 6.37 mmol) and lithium hydroxide (1.53 g, 63.7 mmol) were dissolved in THF:water (10 mL: 20 mL). The reaction was heated at 60° C. overnight. The reaction was cooled and further diluted with water. The reaction was transferred into a separatory funnel and was washed with diethyl ether. The aqueous layer was acidified using 2N HCl to pH 2 where a white solid formed. The suspension was returned to the separatory funnel and was washed with ethyl acetate. The organic layer was dried over magnesium sulfate, filtered and concentrated to obtain pure product as a white solid. Yield: 1.47 g, (White solid).

¹H-NMR (DMSO-d₆): 12.99, 7.70, 7.53, 7.34-7.27, 7.13, 7.03, 5.49

Ethyl 1-(1-(4-chlorobenzyl)-1H-indole-2-carbonyl)piperidine-4-carboxylate

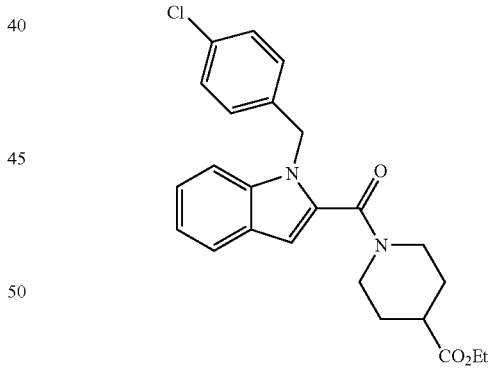

1-(4-chlorobenzyl)-1H-indole-2-carboxylic acid (2.4 g, 8.40 mmol), 1-ethyl-3-(3-dimethylaminopropyl) carbodiimide (2.4 g, 12.60 mmol), and 1-Hydroxybenzotriazole hydrate (1.9 g, 12.60 mmol) were dissolved in 20.0 mL of DCM. The resulting suspension was stirred for twenty minutes where it turned into a clear, yellow solution. N,N-Diisopropylethylamine (2.2 mL, 12.60 mmol) and ethyl piperidine-4-carboxylate (1.94 mL, 12.60 mmol) were added to the reaction. The reaction was stirred overnight. Water was added to the reaction followed by ethyl acetate. The layers were separated and the organic layer was washed sequentially with 1N HCl, saturated sodium bicarbonate, and saturated sodium chloride. The organic layer was dried over magnesium sulfate, filtered and concentrated. The resulting crude mixture was triturated with diethyl ether to obtain pure product as a white solid. Yield: 2.79 g, (White solid)

$^1$H-NMR (DMSO-$d_6$): 7.60, 7.31, 7.23, 7.13-7.05, 6.73, 4.25, 4.07, 3.88, 2.99, 2.67, 1.75, 1.33, 1.18, 1.07

1-(1-(4-chlorobenzyl)-1H-indole-2-carbonyl)piperidine-4-carboxylic acid

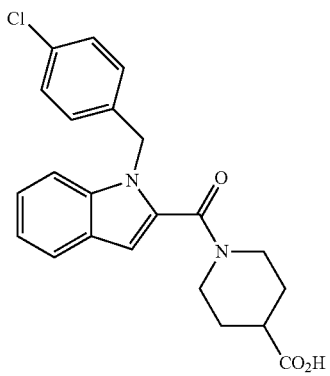 [SMILES: O=C(O)C1CCN(C(=O)c2cc3ccccc3n2Cc2ccc(Cl)cc2)CC1]

Ethyl 1-(1-(4-chlorobenzyl)-1H-indole-2-carbonyl)piperidine-4-carboxylate (692 mg, 1.62 mmol) was dissolved in 1.50 mL of THF and 3.0 mL of water. Solid lithium hydroxide (390 mg, 16.29 mmol) was added to the solution. The reaction was allowed to stir overnight. After 24 hours at room temperature, the reaction was diluted with water and extracted twice with diethyl ether. The aqueous layer was acidified to pH ~2 with 2N HCl. The resulting suspension was washed with ethyl acetate three times. The organic layers were combined and washed with saturated sodium chloride solution, dried over magnesium sulfate, filtered and concentrated to obtain product as a white solid. Yield: 458 mg (White solid)

$^1$H-NMR (DMSO-$d_6$) 12.29, 7.59, 7.33-7.07, 6.72, 5.49, 4.25, 3.91, 2.67, 3.00, 1.76, 1.24

B. Synthesis of Inhibitors (1-(4-chlorobenzyl)-1H-indol-2-yl)(4-(pyrrolidine-1-carbonyl)piperidin-1-yl)methanone (CCG 102514)

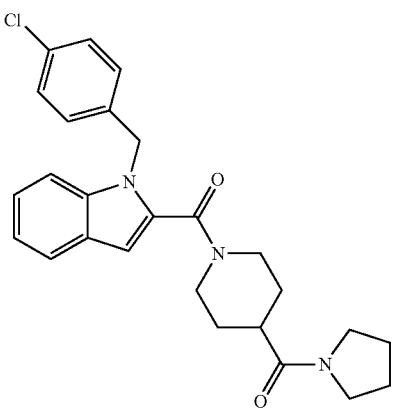 [SMILES: O=C(c1cc2ccccc2n1Cc1ccc(Cl)cc1)N1CCC(C(=O)N2CCCC2)CC1]

1-(1-(4-chlorobenzyl)-1H-indole-2-carbonyl)piperidine-4-carboxylic acid (100 mg, 0.252 mmol), 1-ethyl-3-(3-dimethylaminopropyl) carbodiimide (97 mg, 0.504 mmol), and 1-Hydroxybenzotriazole (68 mg, 0.504 mmol) were dissolved in 3.0 mL of DCM. The reaction was allowed to stir for 10 minutes before N,N-Diisopropylethylamine (88 μL, 0.504 mmol) and pyrrolidine (41.7 μL, 0.504 mmol) were added. The reaction was allowed to stir overnight. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was purified in silica gel using the gradient 100% DCM to 5% 7M NH$_3$ in methanol diluted with 95% DCM. After purification, pure white solid was obtained. Yield: 83 mg (White solid)

$^1$H-NMR (DMSO-$d_6$) 7.58, 7.35-7.08, 6.73, 5.50, 4.45-4.04, 3.47, 3.27, 3.04-2.91, 2.71, 1.87, 1.77-1.41

N-benzyl-1-(1-(4-chlorobenzyl)-1H-indole-2-carbonyl)piperidine-4-carboxamide (CCG 102516)

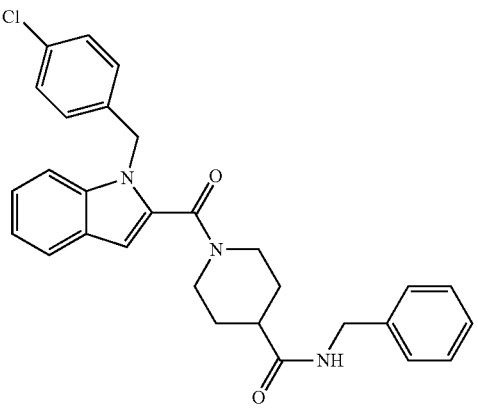

1-(1-(4-chlorobenzyl)-1H-indole-2-carbonyl)piperidine-4-carboxylic acid (200 mg, 0.500 mmol), 1-ethyl-3-(3-dimethylaminopropyl) carbodiimide (115 mg, 0.600 mmol), and 1-Hydroxybenzotriazole (81 mg, 0.600 mmol) were dissolved in 10.0 mL of DCM. The reaction was allowed to stir for 10 minutes before N,N-Diisopropylethylamine (131 μL, 0.750 mmol) and benzylamine (82 μL, 0.750 mmol) were added. The reaction was allowed to stir overnight. The reaction was diluted with water and dichloromethane. The layers were separated and the organic layer was washed with water, saturated ammonium chloride, and saturated sodium chloride. The organic layer was dried over magnesium sulfate, filtered and concentrated. The crude material was purified using 10 gram silica Biotage column, with the gradient 30% ethyl acetate: hexanes to 100% ethyl acetate. After purification, pure white solid was obtained. Yield: 105 mg (White solid)

¹H-NMR (DMSO-d₆) 8.34, 7.58, 7.35-7.08, 6.73, 5.49, 4.45-4.15, 2.95, 2.46, 1.75-1.45

1-(1-(4-chlorobenzyl)-1H-indole-2-carbonyl)-N-(4-methylphenethyl)piperidine-4-carboxamide (CCG102518)

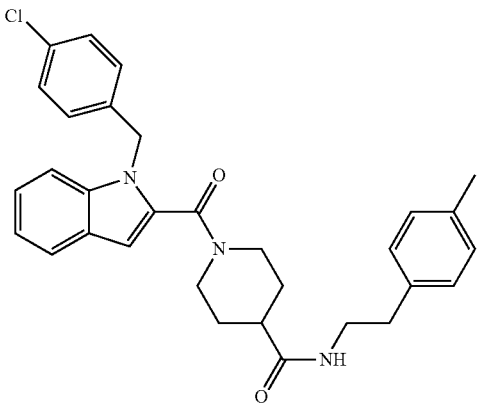 [SMILES: Cc1ccc(CCNC(=O)C2CCN(C(=O)c3cc4ccccc4n3Cc3ccc(Cl)cc3)CC2)cc1]

1-(1-(4-chlorobenzyl)-1H-indole-2-carbonyl)piperidine-4-carboxylic acid (100 mg, 0.252 mmol), 1-ethyl-3-(3-dimethylaminopropyl) carbodiimide (97 mg, 0.504 mmol), and 1-Hydroxybenzotriazole (68 mg, 0.504 mmol) were dissolved in 3.0 mL of DCM. The reaction was allowed to stir for 10 minutes before N,N-Diisopropylethylamine (88 µL, 0.504 mmol) and 2-(p-tolyl)ethanamine (73 µL, 0.504 mmol) were added. The reaction was allowed to stir overnight. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was purified in silica gel using the gradient 100% DCM to 5% 7M NH₃ in methanol diluted with 95% DCM. After purification, pure white solid was obtained. Yield: 24 mg (White solid)

¹H-NMR (DMSO-d₆) 7.85, 7.58, 7.35-7.05, 6.72, 5.49, 4.40-3.96, 3.23, 2.91, 2.65, 2.25, 1.63-1.36

N-benzyl-1-(1-(4-fluorobenzyl)-1H-indole-2-carbonyl)piperidine-4-carboxamide (CCG 203880)

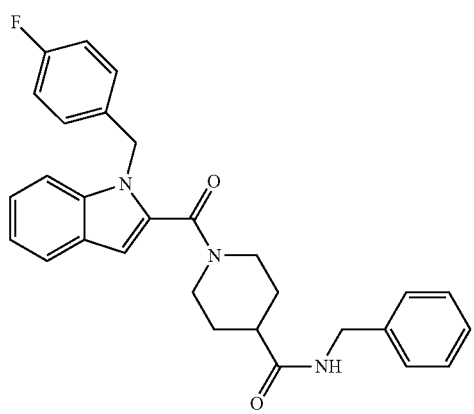 [SMILES: O=C(NCc1ccccc1)C1CCN(C(=O)c2cc3ccccc3n2Cc2ccc(F)cc2)CC1]

1-(1-(4-fluorobenzyl)-1H-indole-2-carbonyl)piperidine-4-carboxylic acid (100 mg, 0.263 mmol), 1-ethyl-3-(3-dimethylaminopropyl) carbodiimide (76 mg, 0.394 mmol), and 1-Hydroxybenzotriazole (53 mg, 0.394 mmol) were dissolved in 3.0 mL of DCM. The reaction was allowed to stir for 10 minutes before N,N-Diisopropylethylamine (68.9 µL, 0.504 mmol) and phenylmethanamine (43.1 µL, 0.394 mmol) were added. The reaction was allowed to stir for 48 hours. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was triturated in methanol, filtered and dried under vacuum to obtain pure product as a white solid. Yield: 60 mg (White solid)

¹H-NMR (DMSO-d₆) 8.33, 7.60, 7.33-7.08, 6.72, 5.48, 4.44-4.00, 2.91, 2.45, 1.68-1.45

(R)-1-(1-(4-chlorobenzyl)-1H-indole-2-carbonyl)-N-(1-phenylethyl)piperidine-4-carboxamide (CCG 203926)

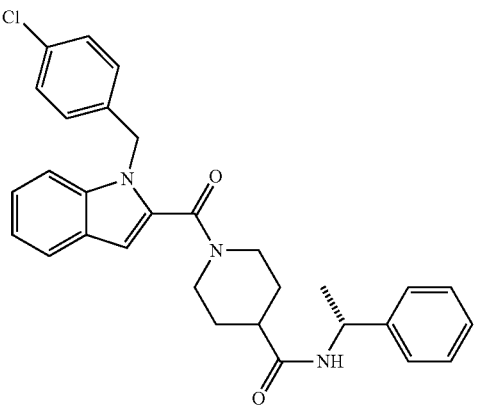 [SMILES: C[C@@H](NC(=O)C1CCN(C(=O)c2cc3ccccc3n2Cc2ccc(Cl)cc2)CC1)c1ccccc1]

1-(1-(4-fluorobenzyl)-1H-indole-2-carbonyl)piperidine-4-carboxylic acid (100 mg, 0.263 mmol), 1-ethyl-3-(3-dimethylaminopropyl) carbodiimide (76 mg, 0.394 mmol), and 1-Hydroxybenzotriazole (53 mg, 0.394 mmol) were dissolved in 3.0 mL of DCM. The reaction was allowed to stir for 10 minutes before N,N-Diisopropylethylamine (68.9 µL, 0.504 mmol) and (R)-1-phenylethanamine (64 µL, 0.504 mmol) were added. The reaction was allowed to stir for 48 hours. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was triturated in methanol, filtered and dried under vacuum to obtain pure product as a white solid. Yield: 32.9 mg (White solid)

¹H-NMR (DMSO-d₆) 8.18, 7.50, 7.27-7.00, 6.65, 5.41, 4.83, 4.39-3.95, 2.85, 2.38, 1.65-1.25

(1-(4-chlorobenzyl)-1H-indol-2-yl)(4-(piperidine-1-carbonyl)piperidin-1-yl)methanone (CCG 203928)

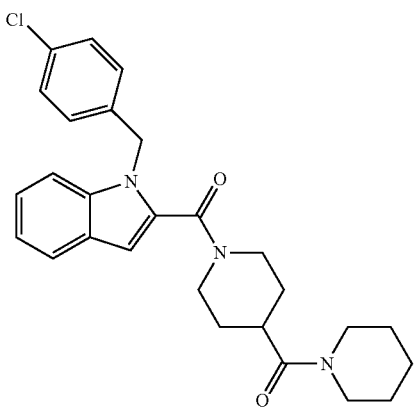 [SMILES: O=C(c1cc2ccccc2n1Cc1ccc(Cl)cc1)N1CCC(C(=O)N2CCCCC2)CC1]

1-(1-(4-chlorobenzyl)-1H-indole-2-carbonyl)piperidine-4-carboxylic acid (100 mg, 0.252 mmol), 1-ethyl-3-(3-dimethylaminopropyl) carbodiimide (97 mg, 0.504 mmol), and 1-Hydroxybenzotriazole (68 mg, 0.504 mmol) were dissolved in 3.0 mL of DCM. The reaction was allowed to stir for 10 minutes before N,N-Diisopropylethylamine (88 µL, 0.504 mmol) and piperidine (50 µL, 0.504 mmol) were added. The reaction was allowed to stir overnight. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was purified in silica gel using the gradient 100% hexanes to 50% ethyl acetate:hexanes. Yield: 86 mg (White solid)

¹H-NMR (DMSO-d₆) 7.58, 7.34-7.08, 6.73, 5.49, 4.59-3.89, 3.44, 3.15-2.91, 1.58-1.41

1-(1-(4-chlorobenzyl)-1H-indole-2-carbonyl)-N-(pyridin-4-ylmethyl)piperidine-4-carboxamide (CCG 203929)

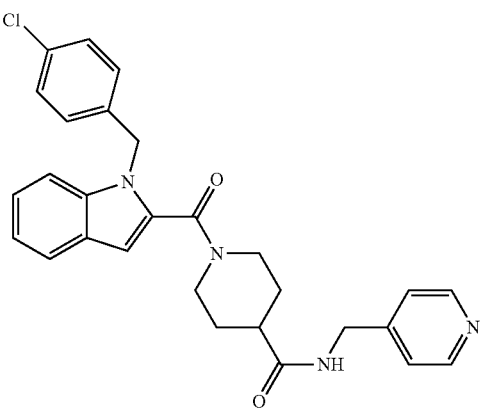 [SMILES: O=C(NCc1ccncc1)C1CCN(C(=O)c2cc3ccccc3n2Cc2ccc(Cl)cc2)CC1]

1-(1-(4-chlorobenzyl)-1H-indole-2-carbonyl)piperidine-4-carboxylic acid (100 mg, 0.252 mmol), 1-ethyl-3-(3-dimethylaminopropyl) carbodiimide (97 mg, 0.504 mmol), and 1-Hydroxybenzotriazole (68 mg, 0.504 mmol) were dissolved in 3.0 mL of DCM. The reaction was allowed to stir for 10 minutes before N,N-Diisopropylethylamine (88 µL, 0.504 mmol) and pyridin-4-ylmethanamine (0.051 ml, 0.504 mmol) were added. The reaction was allowed to stir overnight. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was purified in silica gel using the gradient 60% ethyl acetate:hexanes to 100% ethyl acetate. After purification, pure white solid was obtained. Yield: 79.5 mg (White solid)

¹H-NMR (DMSO-d₆) 8.46, 7.59, 7.35-7.10, 6.57, 5.49, 4.56-4.10, 2.94, 2.33, 1.75-1.44

N-benzyl-1-(1-(4-chlorobenzyl)-1H-indole-2-carbonyl)-N-methylpiperidine-4-carboxamide (CCG203930)

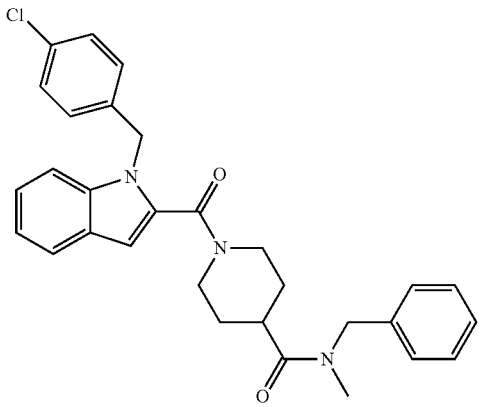 [SMILES: CN(Cc1ccccc1)C(=O)C1CCN(C(=O)c2cc3ccccc3n2Cc2ccc(Cl)cc2)CC1]

1-(1-(4-chlorobenzyl)-1H-indole-2-carbonyl)piperidine-4-carboxylic acid (150 mg, 0.378 mmol), 1-ethyl-3-(3-dimethylaminopropyl) carbodiimide (145 mg, 0.756 mmol), and 1-Hydroxybenzotriazole (102 mg, 0.756 mmol) were dissolved in 2.0 mL of DCM. The reaction was allowed to stir for 10 minutes before N,N-Diisopropylethylamine (132 µL, 0.756 mmol) and N-methyl-1-phenylmethanamine (45.8 mg, 0.378 mmol) were added as a 1.0 mL DCM solution. The reaction was allowed to stir overnight. The reaction was diluted with water and ethyl acetate. The layers were separated and the organic layer was washed with another aliquot of water. The ethyl acetate layer was washed with 1N HCl followed by saturated sodium bicarbonate then saturated sodium chloride. The organic layer was dried over magnesium sulfate, filtered and concentrated. The crude material was triturated with methanol and filtered under vacuum to obtain pure product as a white solid. Yield: 63.7 mg (White solid)

¹H-NMR (DMSO-d₆) 7.64-7.08, 6.73, 5.50, 4.65, 4.50-4.01, 2.99-2.78, 1.89-1.33

(4-benzylpiperazin-1-yl)(1-(4-fluorobenzyl)-1H-indol-2-yl)methanone (CCG-203942)

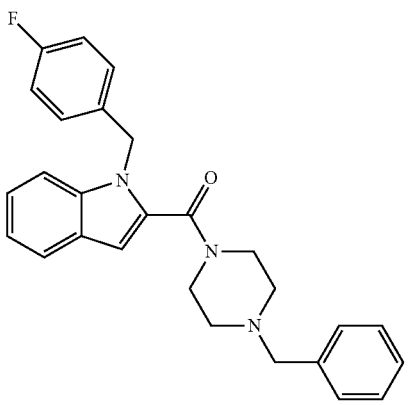 [SMILES: O=C(c1cc2ccccc2n1Cc1ccc(F)cc1)N1CCN(Cc2ccccc2)CC1]

The following was added sequentially to anhydrous DMF: 1-(4-fluorobenzyl)-1H-indole-2-carboxylic acid (50 mg, 0.186 mmol), Hunig's Base (0.065 ml, 0.371 mmol), EDC (46.3 mg, 0.241 mmol), HOBT (37.0 mg, 0.241 mmol), and 1-benzylpiperazine (32.7 mg, 0.186 mmol). The solution was allowed to stir at room temperature for 22 h. At this time, a 1:1 solution of diethylether/ethyl acetate (5 mL) was added, and this was washed with aqueous 10% Na₂CO₃ (3×2 mL). The extract was then dried with anhydrous MgSO₄, filtered, and the filtrate was concentrated in vacuo. The crude residue was purified by column chromatography (20 g silica, 80% EtOAC/Hexanes) to provide 57 mg of the title compound.

¹H NMR (500 MHz, CDCl₃) δ 7.69, 7.42, 7.38-7.29, 7.20, 7.12, 6.98, 6.66, 5.53, 3.75-3.62, 3.49, 2.44-2.09

(1-(4-fluorobenzyl)-1H-indol-2-yl)(4-(piperidine-1-carbonyl)piperidin-1-yl)methanone (CCG-203945)

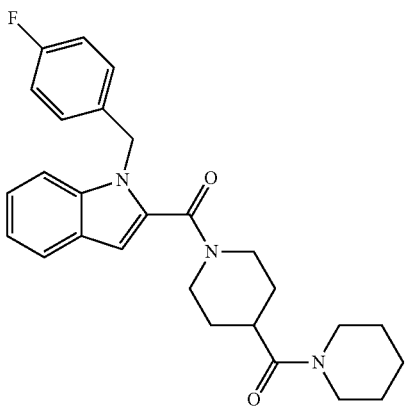 [SMILES: O=C(c1cc2ccccc2n1Cc1ccc(F)cc1)N1CCC(C(=O)N2CCCCC2)CC1]

The following was added sequentially to anhydrous DMF (2 mL): 1-(4-fluorobenzyl)-1H-indole-2-carboxylic acid (50 mg, 0.186 mmol), Hunig's Base (0.065 ml, 0.371 mmol), EDC (46.3 mg, 0.241 mmol), HOBT (37.0 mg, 0.241 mmol), and piperidin-1-yl(piperidin-4-yl)methanone (36.4 mg, 0.186 mmol). The solution was allowed to stir at room temperature for 24 h. At this time, a 1:1 solution of diethylether/ethyl acetate (5 mL) was added, and this was washed with aqueous 10% Na₂CO₃ (3×2 mL). The extract was then dried with anhydrous MgSO₄, filtered, and the filtrate was concentrated in vacuo. The crude residue was purified by column chromatography (20 g silica, 80% EtOAc/Hex) to provide 29 mg of the title compound.

¹H NMR (500 MHz, CDCl₃) δ 7.66, 7.37, 7.28, 7.17, 7.12, 6.96, 6.67, 5.49, 4.60-4.20, 3.58, 3.45, 2.93, 2.74, 1.67, 1.58, 1.28

(S)-(1-(4-chlorobenzyl)-1H-indol-2-yl)(4-(2-(hydroxymethyl)pyrrolidine-1-carbonyl)piperidin-1-yl)methanone (CCG 204021)

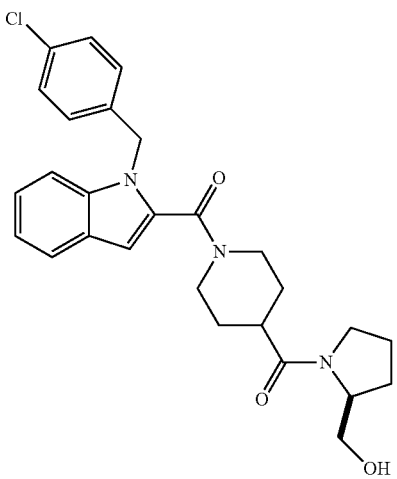 [SMILES: O=C(c1cc2ccccc2n1Cc1ccc(Cl)cc1)N1CCC(C(=O)N2CCC[C@H]2CO)CC1]

1-(1-(4-chlorobenzyl)-1H-indole-2-carbonyl)piperidine-4-carboxylic acid (100 mg, 0.252 mmol), 1-ethyl-3-(3-dimethylaminopropyl) carbodiimide (97 mg, 0.504 mmol), and 1-Hydroxybenzotriazole (68 mg, 0.504 mmol) were dissolved in 3.0 mL of DCM. The reaction was allowed to stir for 10 minutes before N,N-Diisopropylethylamine (88 μL, 0.504 mmol) and L-prolinol (49.5 μL, 0.504 mmol) were added. The reaction was allowed to stir overnight. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was purified in silica gel using the gradient 100% DCM to 5% 7M NH₃ in methanol diluted with 95% DCM. After purification, pure white solid was obtained. Yield: 118 mg (White solid)

$^1$H-NMR (DMSO-d$_6$) 7.57, 7.36-7.08, 6.73, 5.49, 4.43-3.93, 3.48, 3.24-2.67, 1.94-1.39

1-(1-(4-chlorobenzyl)-1H-indole-2-carbonyl)-N,N-dimethylpiperidine-4-carboxamide (CCG 204022)

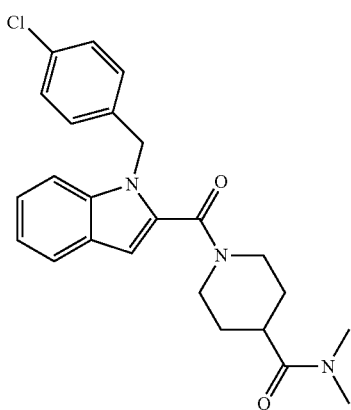 [SMILES: CN(C)C(=O)C1CCN(C(=O)c2cc3ccccc3n2Cc2ccc(Cl)cc2)CC1]

1-(1-(4-chlorobenzyl)-1H-indole-2-carbonyl)piperidine-4-carboxylic acid (100 mg, 0.252 mmol), 1-ethyl-3-(3-dimethylaminopropyl) carbodiimide (97 mg, 0.504 mmol), and 1-Hydroxybenzotriazole (68 mg, 0.504 mmol) were dissolved in 3.0 mL of DCM. The reaction was allowed to stir for 10 minutes before N,N-Diisopropylethylamine (88 µL, 0.504 mmol) and dimethylamine (2M in THF, 126 µL, 0.252 mmol) were added. The reaction was allowed to stir overnight. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was purified in silica gel using the gradient 100% DCM to 5% 7M NH$_3$ in methanol diluted with 95% DCM. After purification, pure white solid was obtained. Yield: 73 mg (White solid)

$^1$H-NMR (DMSO-d$_6$) 7.58, 7.35-7.08, 6.73, 5.50, 4.45-4.04, 3.02-2.81, 1.61-1.36

(1-(4-chlorobenzyl)-1H-indol-2-yl)(4-(4-methylpiperazine-1-carbonyl)piperidin-1-yl)methanone (CCG 204023)

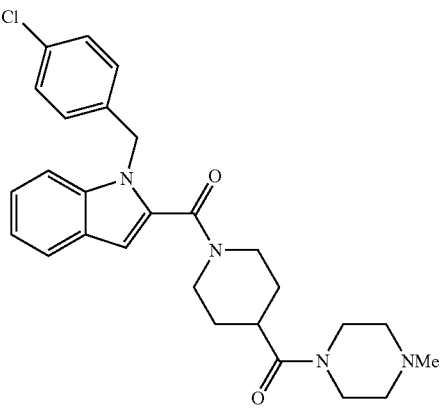 [SMILES: CN1CCN(C(=O)C2CCN(C(=O)c3cc4ccccc4n3Cc3ccc(Cl)cc3)CC2)CC1]

1-(1-(4-chlorobenzyl)-1H-indole-2-carbonyl)piperidine-4-carboxylic acid (100 mg, 0.252 mmol), 1-ethyl-3-(3-dimethylaminopropyl) carbodiimide (97 mg, 0.504 mmol), and 1-Hydroxybenzotriazole (68 mg, 0.504 mmol) were dissolved in 3.0 mL of DCM. The reaction was allowed to stir for 10 minutes before N,N-Diisopropylethylamine (88 µL, 0.504 mmol) and morpholine (44 µL, 0.504 mmol) were added. The reaction was allowed to stir overnight. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was purified in silica gel using the gradient 100% DCM to 5% 7M NH$_3$ in methanol diluted with 95% DCM. After purification, pure white solid was obtained. Yield: 69 mg (White solid)

$^1$H-NMR (DMSO-d$_6$) 7.58, 7.34-7.08, 6.73, 5.49, 4.43-3.99, 3.49-3.39, 3.04-2.92, 2.29-2.18, 1.78-1.36

(1-(4-chlorobenzyl)-1H-indol-2-yl)(4-(morpholine-4-carbonyl)piperidin-1-yl)methanone (CCG 204024)

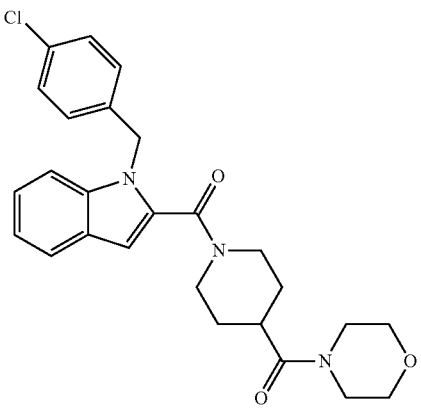 [SMILES: O=C(c1cc2ccccc2n1Cc1ccc(Cl)cc1)N1CCC(C(=O)N2CCOCC2)CC1]

1-(1-(4-chlorobenzyl)-1H-indole-2-carbonyl)piperidine-4-carboxylic acid (100 mg, 0.252 mmol), 1-ethyl-3-(3-dimethylaminopropyl) carbodiimide (97 mg, 0.504 mmol), and 1-Hydroxybenzotriazole (68 mg, 0.504 mmol) were dissolved in 3.0 mL of DCM. The reaction was allowed to stir for 10 minutes before N,N-Diisopropylethylamine (88 µL, 0.504 mmol) and morpholine (44 µL, 0.504 mmol) were added. The reaction was allowed to stir overnight. The reaction was diluted with water and ethyl acetate. The layers were separated and the organic layer was washed with another aliquot of water. The ethyl acetate layer was washed with saturated citric acid, saturated sodium bicarbonate, and saturated sodium chloride. The organic layer was dried over magnesium sulfate, filtered and concentrated. The crude material was purified in silica gel using the gradient 100% DCM to 5% 7M NH$_3$ in methanol diluted with 95% DCM. After purification, pure white solid was obtained. Yield: 47.6 mg (White solid)

¹H-NMR (DMSO-d₆) 7.55, 7.308-7.05, 6.70, 5.46, 4.40-3.97, 3.51-3.40, 2.99-2.87, 1.79-1.24

1-(1-(4-chlorobenzyl)-1H-indole-2-carbonyl)-N-(3-methylbenzyl)piperidine-4-carboxamide (CCG 204042)

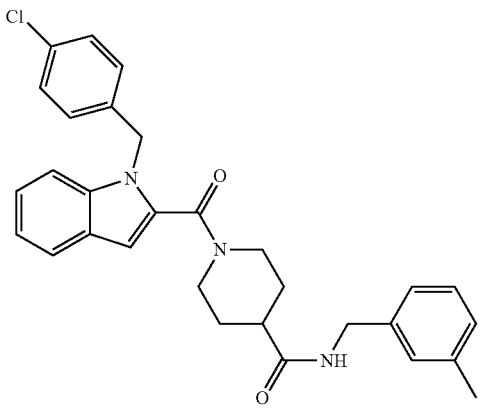 [SMILES: Cc1cccc(CNC(=O)C2CCN(C(=O)c3cc4ccccc4n3Cc3ccc(Cl)cc3)CC2)c1]

1-(1-(4-chlorobenzyl)-1H-indole-2-carbonyl)piperidine-4-carboxylic acid (393 mg, 0.990 mmol), 1-ethyl-3-(3-dimethylaminopropyl) carbodiimide (237 mg, 1.23 mmol), and 1-Hydroxybenzotriazole (167 mg, 1.23 mmol) were dissolved in 2.0 mL of DCM. The reaction was allowed to stir for 10 minutes before N,N-Diisopropylethylamine (216 µL, 1.059 mmol) and m-tolylmethanamine (100 mg, 0.83 mmol) were added as a 1.0 mL DCM solution. The reaction was allowed to stir overnight. The reaction was diluted with water and ethyl acetate. The layers were separated and the organic layer was washed with another aliquot of water. The ethyl acetate layer was washed with 1N HCl followed by saturated sodium bicarbonate then saturated sodium chloride. The organic layer was dried over magnesium sulfate, filtered and concentrated. The crude material was triturated with methanol and filtered under vacuum to obtain pure product as a white solid. Yield: 190 mg (White solid)

¹H-NMR (DMSO-d₆) 8.31, 7.58, 7.34, 7.23-7.00, 6.73, 5.49, 4.43-4.12, 2.45, 2.28, 1.75-1.43

N-(3-chlorobenzyl)-1-(1-(4-chlorobenzyl)-1H-indole-2-carbonyl)piperidine-4-carboxamide (CCG 204043)

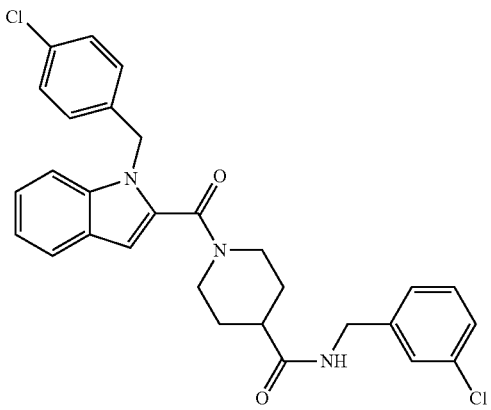 [SMILES: O=C(NCc1cccc(Cl)c1)C1CCN(C(=O)c2cc3ccccc3n2Cc2ccc(Cl)cc2)CC1]

1-(1-(4-chlorobenzyl)-1H-indole-2-carbonyl)piperidine-4-carboxylic acid (336 mg, 0.847 mmol), 1-ethyl-3-(3-dimethylaminopropyl) carbodiimide (203 mg, 1.509 mmol), and 1-Hydroxybenzotriazole (143 mg, 1.059 mmol) were dissolved in 2.0 mL of DCM. The reaction was allowed to stir for 10 minutes before N,N-Diisopropylethylamine (185 µL, 1.059 mmol) and (3-chlorophenyl)methanamine (100 mg, 0.706 mmol) were added as a 1.0 mL DCM solution. The reaction was allowed to stir overnight. The reaction was diluted with water and ethyl acetate. The layers were separated and the organic layer was washed with another aliquot of water. The ethyl acetate layer was washed with 1N HCl followed by saturated sodium bicarbonate then saturated sodium chloride. The organic layer was dried over magnesium sulfate, filtered and concentrated. The crude material was triturated with methanol and filtered under vacuum to obtain pure product as a white solid. Yield: 179 mg (White solid)

¹H-NMR (DMSO-d₆) 8.29, 7.59, 7.35-7.08, 6.73, 5.49, 4.50-4.16, 2.99, 2.45, 2.79-1.44

N-benzyl-1-(1-(4-chlorobenzyl)-1H-pyrrole-2-carbonyl)piperidine-4-carboxamide (CCG-204054)

Synthesis scheme for compound:

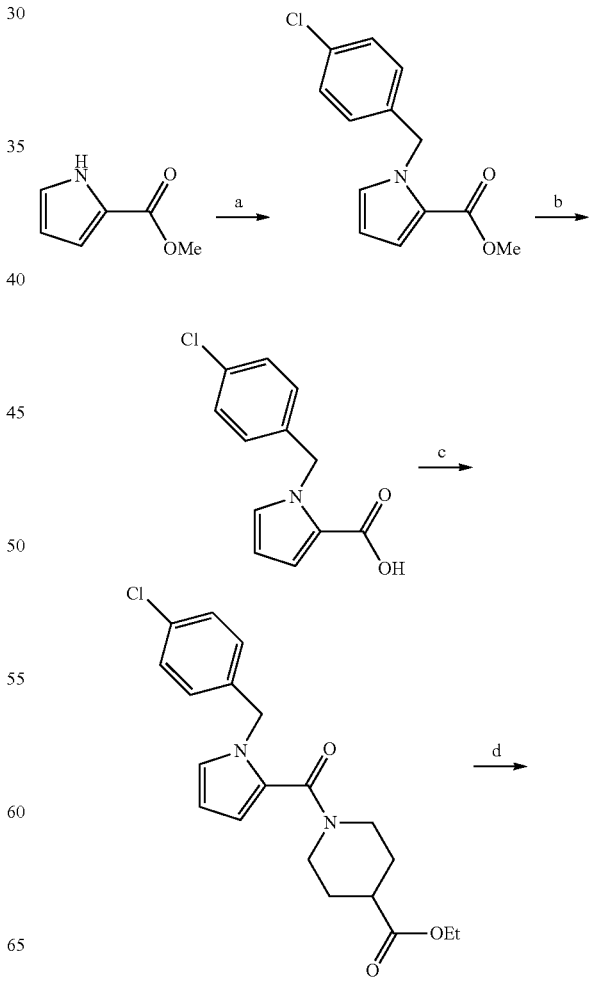

-continued

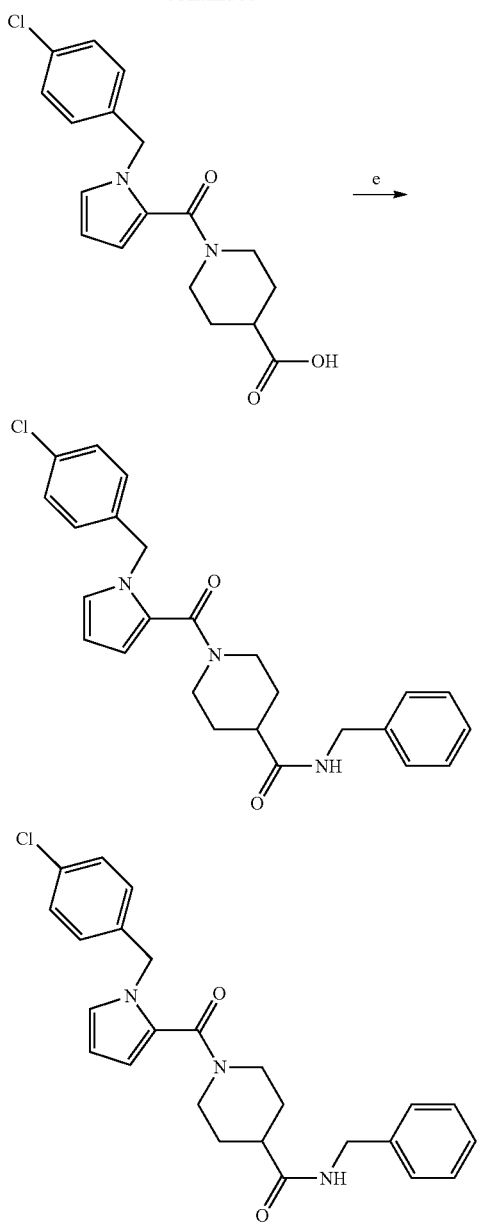

Reagents and conditions: (a) p-chlorobenzylchloride, K₂CO₃, DMF, 60° C., 36 h; (b) 7M NaOH, EtOH, 70° C., 4 h; (c) ethyl isonipecotate, EDC, HOBt, DIPEA, DMF, rt, 24 h; (d) 7M NaOH, EtOH, 60° C., 8 h; (e) benzylamine, EDC, HOBt, DIPEA, DMF, rt, 24 h.

The following was dissolved in anhydrous DMF (3 mL): 1-(1-(4-chlorobenzyl)-1H-pyrrole-2-carbonyl)piperidine-4-carboxylic acid (115 mg, 0.332 mmol), Hunig's Base (0.174 ml, 0.995 mmol), EDC (76 mg, 0.398 mmol), HOBt (60.9 mg, 0.398 mmol), and benzylamine (0.040 ml, 0.365 mmol). This was stirred at room temperature for 1 day with 3 Å molecular sieves. At this time, a 1:1 solution of EtOAc:Et2O (20 mL) was added and the organic layer was washed with 10% aq. Na₂CO₃ (2×10 mL) and brine (1×10 mL). The organic solution was then dried (anhydrous MgSO4) and concentrated in vacuo. Trituration in Et2O provided 101 mg of the title compound as a fine, ruddy brown solid.

¹H NMR (500 MHz, CDCl₃) δ 7.37, 7.29, 7.06, 6.82, 6.35, 6.15, 5.76, 5.30, 4.47, 4.39, 2.86, 2.32, 2.07, 1.81, 1.67, 1.50.

(1-(4-fluorobenzyl)-1H-indol-2-yl)(4-(piperidin-1-ylmethyl)piperidin-1-yl)methanone (CCG-204055)

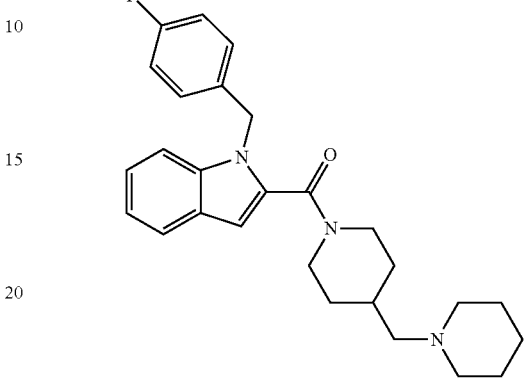

The following was added to anhydrous DMF (2 mL) sequentially: 1-(4-fluorobenzyl)-1H-indole-2-carboxylic acid (66.8 mg, 0.248 mmol), Hunig's Base (0.217 ml, 1.240 mmol), EDC (52.3 mg, 0.273 mmol), HOBT (41.8 mg, 0.273 mmol), and 1-(piperidin-4-ylmethyl)piperidine (45.2 mg, 0.248 mmol) (from SJB-2-083.) This was stirred at room temperature for 24 h with 3 Å MS. At this time, a 1:1 solution of EtOAc:Et2O was added and the solution was washed with 10% aq. Na2CO3. The organic phase was dried with MgSO4 and concentrated in vacuo. The residue was then purified by silica gel chromatography (20 g silica, 80% EtOAc/Hexanes) to give 58 mg of the title compound as an oil.

¹H NMR (500 MHz, CDCl₃) δ 7.66, 7.40, 7.28, 7.18, 7.12, 6.95, 6.63, 5.50, 4.66, 4.11, 2.9-2.73, 2.34, 2.08, 1.82-1.44, 1.05, 0.66

(1-(4-fluorobenzyl)-1H-indol-2-yl)(4-(hydroxy(phenyl)methyl)piperidin-1-yl)methanone (CCG-204056)

The following was added sequentially to anhydrous DMF (5 mL): 1-(4-fluorobenzyl)-1H-indole-2-carboxylic acid (0.119 g, 0.443 mmol), Hunig's Base (0.232 ml, 1.329 mmol), EDC (0.093 g, 0.487 mmol), HOBT (0.075 g, 0.487 mmol), and phenyl(piperidin-4-yl)methanol (0.085 g, 0.443 mmol). The solution was stirred at room temperature for 30 h, at which time a 1:1 solution of EtOAc:Et2O was added and washed with 10% aq. Na2CO3. The organic solution was dried with MgSO4 and concentrated in vacuo to give a residue that was purified by silica gel chromatography (45 g silica, 80% EtOAc/Hexanes) to give 67 mg of the title compound.

$^1$H NMR (500 MHz, CDCl$_3$) δ 7.98, 7.65, 7.41-7.27, 7.17, 7.09, 6.95, 6.61, 5.47, 4.66, 4.34, 4.15-4.03, 2.95-2.43, 2.10-1.75, 1.29-0.92

Methyl 3-(1-(1-(4-chlorobenzyl)-1H-indole-2-carbonyl)piperidine-4-carboxamido)benzoate (CCG 204057)

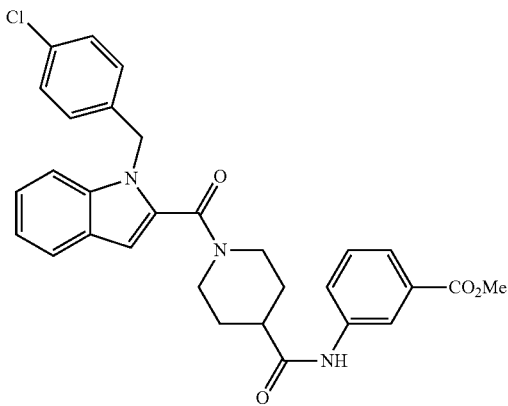 [SMILES: COC(=O)c1cccc(NC(=O)C2CCN(C(=O)c3cc4ccccc4n3Cc3ccc(Cl)cc3)CC2)c1]

1-(1-(4-chlorobenzyl)-1H-indole-2-carbonyl)piperidine-4-carboxylic acid (315 mg, 0.794 mmol), 1-ethyl-3-(3-dimethylaminopropyl) carbodiimide (254 mg, 1.32 mmol), and 1-Hydroxybenzotriazole (179 mg, 1.32 mmol) were dissolved in 2.0 mL of DCM. The reaction was allowed to stir for 10 minutes before N,N-Diisopropylethylamine (232 μL, 1.32 mmol) and methyl 3-aminobenzoate (100 mg, 0.662 mmol) were added as a 1.0 mL DCM solution. The reaction was allowed to stir overnight. The reaction was diluted with water and ethyl acetate.

The layers were separated and the organic layer was washed with another aliquot of water. The ethyl acetate layer was washed with 1N HCl followed by saturated sodium bicarbonate then saturated sodium chloride. The organic layer was dried over magnesium sulfate, filtered and concentrated. The crude material was triturated with methanol and filtered under vacuum to obtain pure product as a white solid. Yield: 190 mg (White solid)

$^1$H-NMR (DMSO-d$_6$) 8.29, 7.85, 7.65-7.61, 7.55, 7.45, 7.35, 7.23, 7.20-7.08, 6.75, 5.51, 4.49-4.07, 3.85, 2.95, 2.61, 1.80-1.44

C. Results

Table 2 shows activity and IC$_{50}$ of exemplary compounds of embodiments of the present invention. Activity was determined as described (Peng et al, J Infec Diseases 2009, 199, 950; incorporated herein by reference).

TABLE 2

| CCG # | Structure | Activity (% control LUC) | | | Activity IC$_{50}$ |
| | | 50 μM | 10 μM | 2 μM | (μM) |
|---|---|---|---|---|---|
| 102514 | | 10.5 | 66.4 | 83.1 | 23.8 |

TABLE 2-continued
| CCG # | Structure | Activity (% control LUC) | | | Activity IC$_{50}$ (μM) |
|---|---|---|---|---|---|
| | | 50 μM | 10 μM | 2 μM | |
| 102516 | 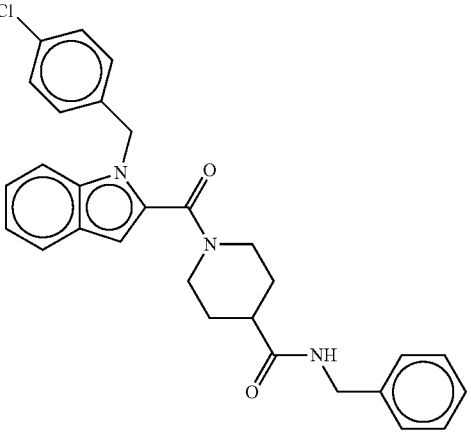 | 59.7 | 76.9 | 88.0 | 18.6 |
| 102518 | 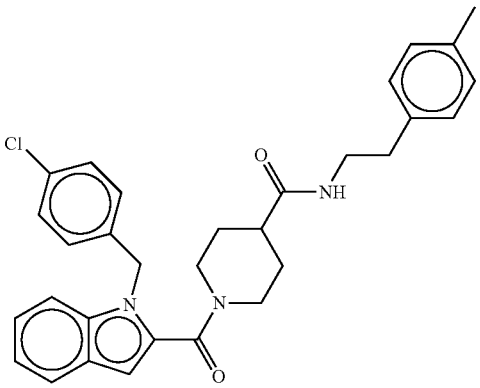 | 32.2 | 33.8 | 83.0 | 4.2 |
| 203880 | 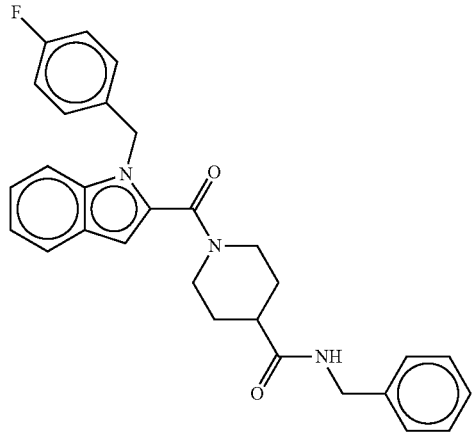 | 67.0 | 121.0 | 133.5 | 25.0 |

TABLE 2-continued

| CCG # | Structure | Activity (% control LUC) | | | Activity IC$_{50}$ |
|---|---|---|---|---|---|
| | | 50 μM | 10 μM | 2 μM | (μM) |
| 203926 | 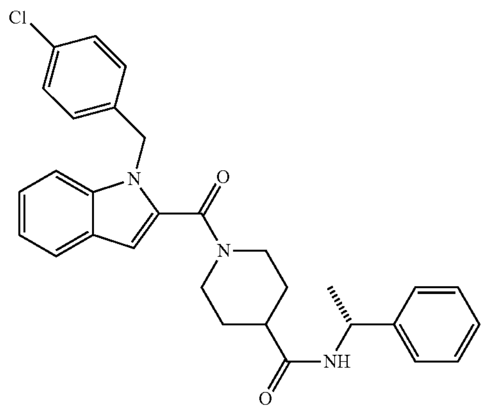 [SMILES: C[C@@H](NC(=O)C1CCN(C(=O)c2cc3ccccc3n2Cc2ccc(Cl)cc2)CC1)c1ccccc1] | 17.0 | 55.0 | 100.3 | 8.7 |
| 203928 | 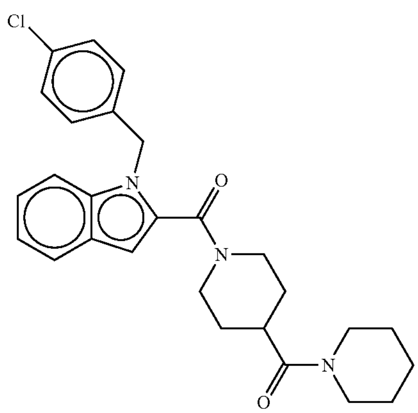 | 3.4 | 65.4 | 95.1 | 8.1 |
| 203929 | 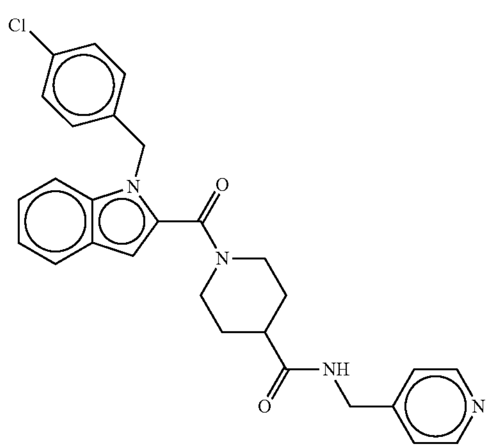 | 36.4 | 51.8 | 99.5 | 6.6 |

TABLE 2-continued
| CCG # | Structure | Activity (% control LUC) | | | Activity IC$_{50}$ (μM) |
|---|---|---|---|---|---|
| | | 50 μM | 10 μM | 2 μM | |
| 203930 | 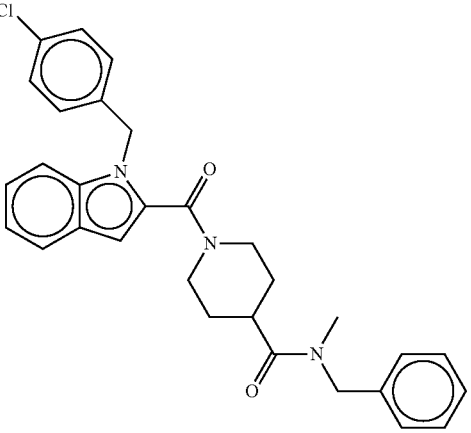 | 38.0 | 59.5 | 109.7 | 18.6 |
| 203942 | 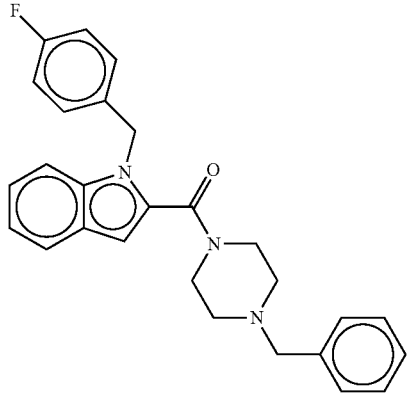 | 48.9 | 73.8 | 115.6 | 12.8 |
| 203945 | 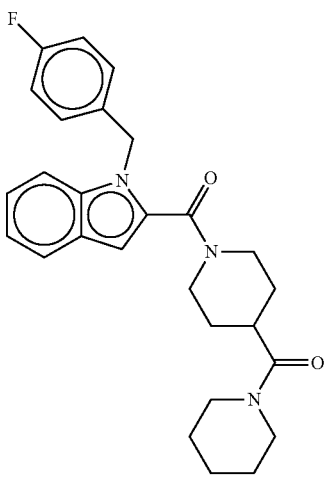 | 21.3 | 64.4 | 85.0 | 20.0 |

TABLE 2-continued

| CCG # | Structure | Activity (% control LUC) | | | Activity IC$_{50}$ |
|---|---|---|---|---|---|
| | | 50 μM | 10 μM | 2 μM | (μM) |
| 204021 | 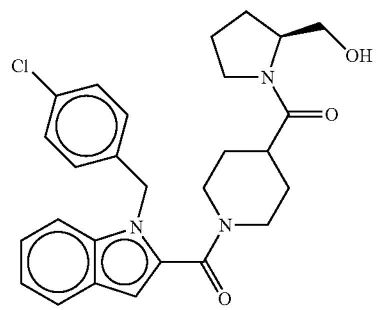 | 21.1 | 77.9 | 87.8 | 32.1 |
| 204022 | 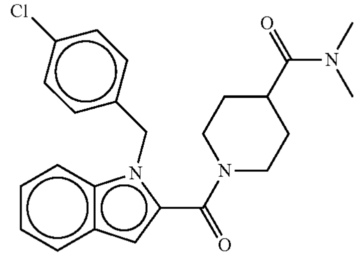 | 5.8 | 51.9 | 87.3 | 10.4 |
| 204023 | 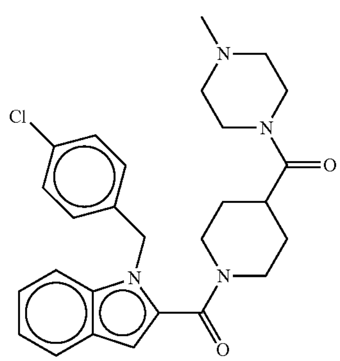 | 6.0 | 67.4 | 99.0 | 21.4 |
| 204024 | 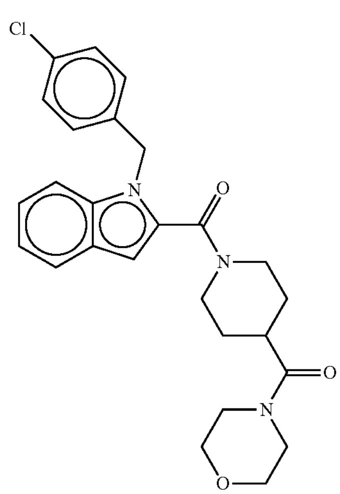 | 8.3 | 47.4 | 74.9 | 12.3 |

TABLE 2-continued

| CCG # | Structure | Activity (% control LUC) | | | Activity IC$_{50}$ |
|---|---|---|---|---|---|
| | | 50 μM | 10 μM | 2 μM | (μM) |
| 204042 | 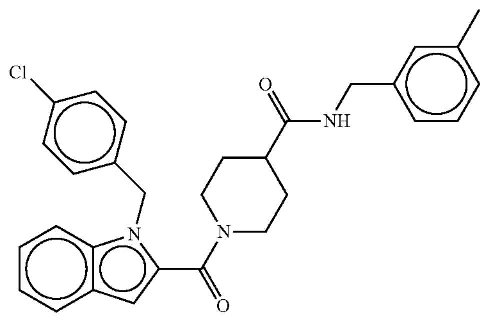 | 64.4 | 59.5 | 93.7 | 9.8 |
| 204043 | 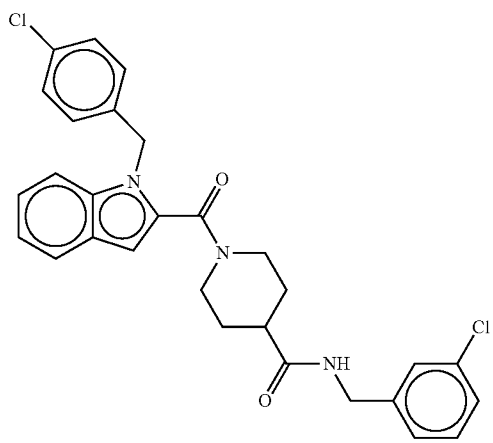 | 53.6 | 60.9 | 78.6 | 28.5 |
| 204054 | 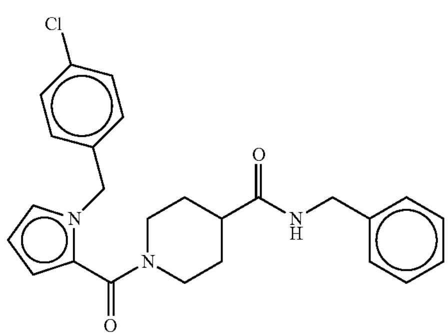 | 74.5 | 107.7 | 110.4 | 54.6 |
| 204055 | 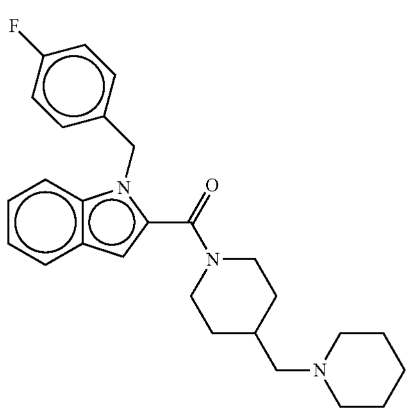 | 40.0 | 69.9 | 89.7 | 13.3 |

TABLE 2-continued

| CCG # | Structure | Activity (% control LUC) | | | Activity IC$_{50}$ ($\mu$M) |
|---|---|---|---|---|---|
| | | 50 $\mu$M | 10 $\mu$M | 2 $\mu$M | |
| 204056 | 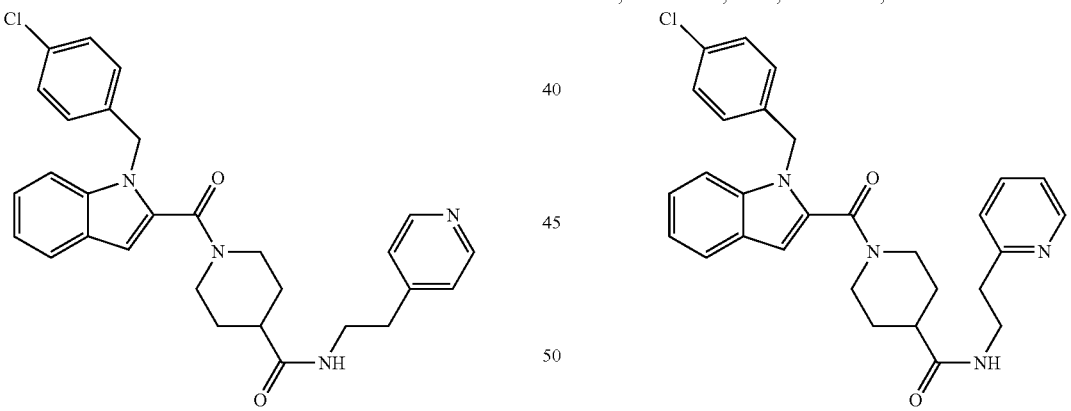 | 8.3 | 71.7 | 99.3 | 16.0 |
| 204057 | 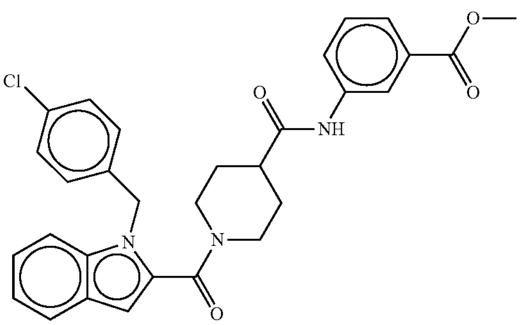 | 50.9 | 54.0 | 87.9 | 35.6 |

Example 2

This example describes further compounds useful in the inhibition of arboviruses.

1-(1-(4-chlorobenzyl)-1H-indole-2-carbonyl)-N-(2-(pyridin-4-yl)ethyl)piperidine-4-carboxamide (CCG 205432)

1-(1-(4-chlorobenzyl)-1H-indole-2-carbonyl)piperidine-4-carboxylic acid (390 mg, 0.982 mmol), 1-hydroxybenzotriazole (221 mg, 1.637 mmol) and EDCI (314 mg, 1.637 mmol) were dissolved in DCM (Volume: 4.0 ml). The suspension was stirred at room temperature for 10 minutes where it turned clear. Hunig's Base (0.286 ml, 1.637 mmol) and 2-(pyridin-4-yl)ethanamine (0.098 ml, 0.819 mmol) were added. The reaction was stirred at room temperature overnight. The reaction was concentrated and triturated with ethyl acetate to afford the product as a white solid. Yield: 328 mg (White solid) $^1$H-NMR (500 MHz, DMSO-d$_6$) 8.46, 7.91, 7.63, 7.55, 7.34, 7.25-7.18, 7.14-7.06, 6.72, 5.49, 4.54-3.80, 3.32, 3.07-2.77, 2.73, 2.37-2.28, 1.77-1.18.

1-(1-(4-chlorobenzyl)-1H-indole-2-carbonyl)-N-(2-(pyridin-2-yl)ethyl)piperidine-4-carboxamide (CCG 205456)

N1-((ethylimino)methylene)-N3,N3-dimethylpropane-1,3-diamine hydrochloride (235 mg, 1.228 mmol), 1H-benzo[d][1,2,3]triazol-1-ol (166 mg, 1.228 mmol), and 1-(1-(4-chlorobenzyl)-1H-indole-2-carbonyl)piperidine-4-carboxylic acid (390 mg, 0.982 mmol) were dissolved in 4.0 mL of DCM. The reaction was stirred for ten minutes before adding N-ethyl-N-isopropylpropan-2-amine (0.214 ml, 1.228 mmol) and 2-(pyridin-2-yl)ethanamine (100 mg, 0.819 mmol) as a 1.0 mL DCM solution. The reaction was stirred overnight at room temperature. It was diluted with water and ethyl acetate. The organic phase was washed with water, saturated sodium bicarbonate (twice), and saturated sodium chloride. The organic phase was dried over magnesium sulfate, filtered and concentrated. The crude material was triturated with ether and ethyl acetate and filtered to obtain white solid as a product. $^1$H-NMR (400 MHz, DMSO-d$_6$) 8.46, 7.84, 7.66, 7.60, 7.51, 7.37-7.27, 7.24-7.14, 7.12-7.03, 6.69, 5.46, 4.58-3.75, 3.37, 3.12-2.67, 2.34-2.25, 1.59, 1.33

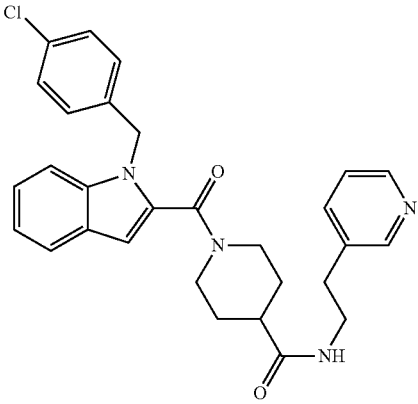 [SMILES: O=C(NCCc1cccnc1)C1CCN(C(=O)c2cc3ccccc3n2Cc2ccc(Cl)cc2)CC1]

1-(1-(4-chlorobenzyl)-1H-indole-2-carbonyl)-N-(2-(pyridin-3-yl)ethyl)piperidine-4-carboxamide (CCG 205433)

1-(1-(4-chlorobenzyl)-1H-indole-2-carbonyl)piperidine-4-carboxylic acid (300 mg, 0.756 mmol), 1-hydroxybenzotriazole (170 mg, 1.261 mmol), EDCI (242 mg, 1.261 mmol) were dissolved in DCM (Ratio: 4.00, Volume: 4.0 ml). the reaction was allowed to stir at room temperature for 10 minutes before adding Hunig'sBase (0.330 ml, 1.891 mmol) and a DMF (Ratio: 1.000, Volume: 1 ml) solution of 2-(pyridin-3-yl)ethanamine, HCl (100 mg, 0.630 mmol). The reaction was stirred overnight. The reaction was diluted with water and ethyl acetate. The organic layer was washed with saturated sodium bicarbonate, 10% aqeuous citric acid solution, followed by saturated sodium chloride solution. The organic layer was dried over magnesium sulfate, filtered and concentrated. The resulting solid was triturated with ethyl acetate to obtain white solid as a product. $^1$H-NMR (400 MHz, DMSO-d$_6$) 8.40, 7.88, 7.66-7.57, 7.54, 7.36-7.27, 7.20, 7.16-7.04, 6.71, 5.48, 4.56-3.80, 3.32-3.25, 2.89, 2.73, 2.38-2.27, 1.47

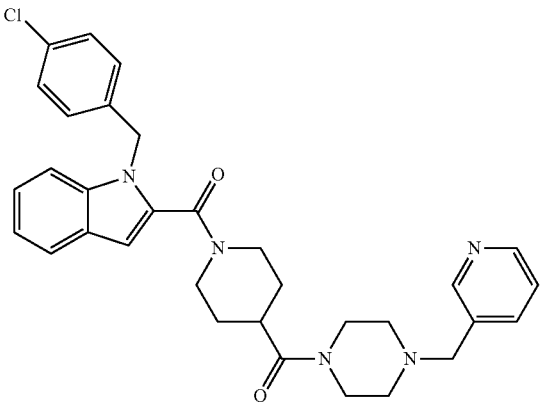 [SMILES: O=C(c1cc2ccccc2n1Cc1ccc(Cl)cc1)N1CCC(C(=O)N2CCN(Cc3cccnc3)CC2)CC1]

(1-(4-chlorobenzyl)-1H-indol-2-yl)(4-(4-(pyridin-3-ylmethyl)piperazine-1-carbonyl)piperidin-1-yl)methanone (CCG 205430)

1-(1-(4-chlorobenzyl)-1H-indole-2-carbonyl)piperidine-4-carboxylic acid (100 mg, 0.252 mmol), 1-hydroxybenzotriazole (68.1 mg, 0.504 mmol) and EDCI (97 mg, 0.504 mmol) were dissolved in DCM (Volume: 4.0 ml). The suspension was stirred at room temperature for 10 minutes where it turned clear. Hunig'sBase (0.088 ml, 0.504 mmol) and 1-(pyridin-3-ylmethyl)piperazine (100 mg, 0.564 mmol) were added. The reaction was stirred at room temperature overnight. It was diluted with water and ethyl acetate. The water layer was washed with another portion of ethyl acetate. The combined organic layer was washed with saturated sodium bicarbonate and saturated sodium chloride. The organic layer was dried over magnesium sulfate, filtered, and concentrated. The dark brown oil crude material was purified using 5% Methanolic ammonia/DCM resulting in a white solid as a product. (Yield: 105 mg, white solid) $^1$H-NMR (400 MHz, DMSO-d$_6$) 8.51-8.45, 7.74-7.68, 7.62, 7.53, 7.39-7.30, 7.24-7.18, 7.13-7.07, 6.73, 5.49, 4.58-3.85, 3.55-3.42, 3.13-2.80, 2.40-2.27, 1.60, 1.36

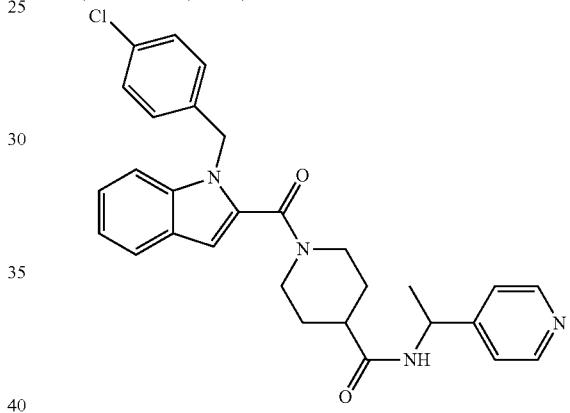

1-(1-(4-chlorobenzyl)-1H-indole-2-carbonyl)-N-(1-(pyridin-4-yl)ethyl)piperidine-4-carboxamide (CCG 206329)

N1-((ethylimino)methylene)-N3,N3-dimethylpropane-1,3-diamine hydrochloride (259 mg, 1.350 mmol), 1-(1-(4-chlorobenzyl)-1H-indole-2-carbonyl)piperidine-4-carboxylic acid (428 mg, 1.080 mmol), and 1H-benzo[d][1,2,3]triazol-1-ol (182 mg, 1.350 mmol) were dissolved in 4.0 mL of DCM. The reaction was stirred at room temperature for ten minutes before Hunig's Base (0.236 ml, 1.350 mmol) and 1-(4-pyridinyl)ethanamine as a 1.0 mL DCM solution was added. The reaction was allowed to stir at room temperature overnight. The reaction was diluted with water and ethyl acetate. The organic phase was washed with water, saturated sodium bicarbonate (twice), and saturated sodium chloride. The organic phase was dried over magnesium sulfate, filtered and concentrated. The crude material was triturated with ether and ethyl acetate and filtered to obtain white solid as a product. (Yield: 37.9 mg, white solid) $^1$H-NMR (400 MHz, DMSO-d$_6$) 8.52-8.45, 8.35, 7.62, 7.53, 7.36-7.30, 7.30-7.25, 7.24-7.18, 7.13-7.06, 6.72, 5.48, 4.87, 4.57-3.84, 2.93, 2.48-2.42, 1.71, 1.58-1.26

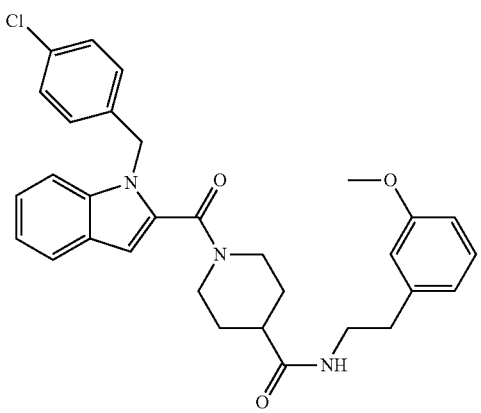 [SMILES: COc1cccc(CCNC(=O)C2CCN(C(=O)c3cc4ccccc4n3Cc3ccc(Cl)cc3)CC2)c1]

1-(1-(4-chlorobenzyl)-1H-indole-2-carbonyl)-N-(3-methoxyphenethyl)piperidine-4-carboxamide (CCG 206395)

1-(1-(4-chlorobenzyl)-1H-indole-2-carbonyl)piperidine-4-carboxylic acid (100 mg, 0.252 mmol), 1-hydroxybenzotriazole (51.1 mg, 0.378 mmol), and EDCI (72.5 mg, 0.378 mmol) were dissolved in 2.0 mL of DCM. The reaction was allowed to stir at room temperature for 10 minutes before 2-(3-methoxyphenyl)ethanamine (0.056 ml, 0.378 mmol) and Hunig's Base (0.066 ml, 0.378 mmol) were added as a 1.0 mL DCM solution. The reaction was allowed to stir overnight. The reaction was diluted with water and ethyl acetate. The organic phase was washed with 1N HCl, saturated sodium bicarbonate, and brine. The organic phase was dried over magnesium sulfate, filtered, and concentrated. The crude material was triturated with ethyl acetate to obtain product as a white solid. (Yield: 89 mg, white solid)
$^1$H-NMR (400 MHz, DMSO-$d_6$) 7.85, 7.63, 7.54, 7.37-7.31, 7.25-7.16, 7.13-7.07, 6.79-6.73, 6.71, 5.49, 4.49-3.84, 3.72, 3.26, 2.91, 2.67, 2.36-2.29, 1.64, 1.37

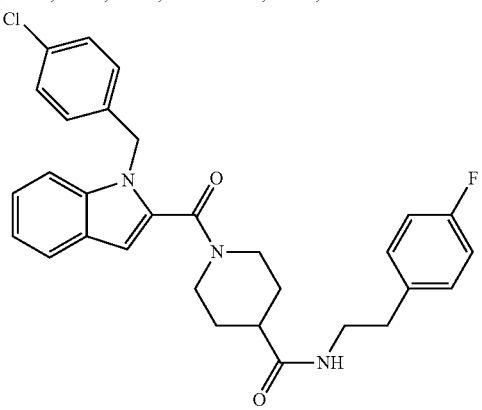

1-(1-(4-chlorobenzyl)-1H-indole-2-carbonyl)-N-(4-fluorophenethyl)piperidine-4-carboxamide (CCG 206396)

1-(1-(4-chlorobenzyl)-1H-indole-2-carbonyl)piperidine-4-carboxylic acid (100 mg, 0.252 mmol), EDCI (72.5 mg, 0.378 mmol), and 1-hydroxybenzotriazole (51.1 mg, 0.378 mmol) were dissolved in DCM (Volume: 3.0 ml). The reaction was stirred at room temperature for 10 minutes before Hunig's Base (0.066 ml, 0.378 mmol) and 2-(4-fluorophenyl)ethanamine (0.050 ml, 0.378 mmol) were added. The reaction was allowed to stir overnight at room temperature. The reaction was diluted with water and ethyl acetate. The organic phase was washed with 1N HCl, saturated sodium bicarbonate, and brine. The organic phase was dried over magnesium sulfate, filtered, and concentrated. The crude material was triturated with ethyl acetate to obtain product as a white solid. (Yield: 111 mg, white solid) $^1$H-NMR (400 MHz, DMSO-$d_6$) 7.84, 7.62, 7.54, 7.36-7.30, 7.26-7.17, 7.14-7.04, 6.71, 5.49, 4.58-3.71, 3.25, 2.91, 2.69, 2.37-2.29, 1.61, 1.36

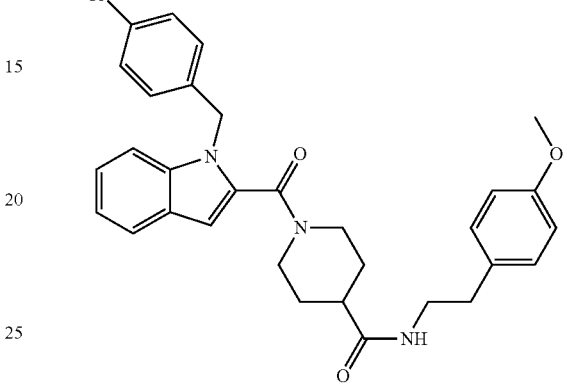

1-(1-(4-chlorobenzyl)-1H-indole-2-carbonyl)-N-(4-methoxyphenethyl)piperidine-4-carboxamide (CCG 206398)

1-(1-(4-chlorobenzyl)-1H-indole-2-carbonyl)piperidine-4-carboxylic acid (100 mg, 0.252 mmol), EDCI (72.5 mg, 0.378 mmol), and 1-hydroxybenzotriazole (51.1 mg, 0.378 mmol) were dissolved in DCM (Volume: 3.0 ml). The reaction was stirred at room temperature for 10 minutes before Hunig'sBase (0.066 ml, 0.378 mmol) and 2-(4-methoxyphenyl)ethanamine (0.055 ml, 0.378 mmol) were added. The reaction was allowed to stir overnight at room temperature. The reaction was diluted with water and ethyl acetate. The organic phase was washed with 1N HCl, saturated sodium bicarbonate, and brine. The organic phase was dried over magnesium sulfate, filtered, and concentrated. The crude material was triturated with ethyl acetate to obtain product as a white solid. (Yield: 84 mg, white solid) $^1$H-NMR (400 MHz, DMSO-$d_6$) 7.80, 7.59, 7.51, 7.34-7.27, 7.23-7.14, 7.12-7.02, 6.84-6.78, 6.68, 5.45, 4.48-3.82, 3.67, 3.18, 2.89, 2.60, 2.34-2.26, 1.59, 1.31

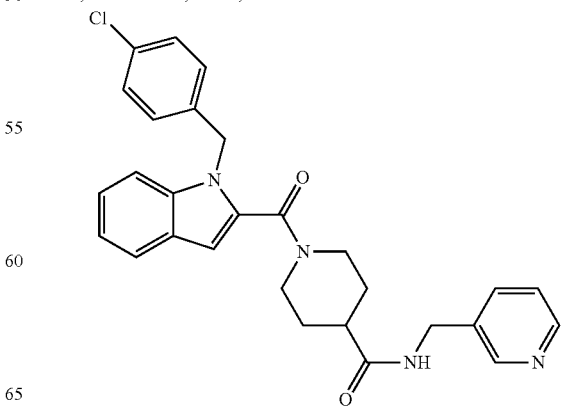

1-(1-(4-chlorobenzyl)-1H-indole-2-carbonyl)-N-(pyridin-3-ylmethyl)piperidine-4-carboxamide (CCG 205422)

1-(1-(4-chlorobenzyl)-1H-indole-2-carbonyl)piperidine-4-carboxylic acid (365 mg, 0.920 mmol), 1-hydroxybenzotriazole (249 mg, 1.839 mmol) and EDCI (353 mg, 1.839 mmol) were dissolved in DCM (Volume: 3.0 ml). The suspension was stirred at room temperature for 10 minutes where it turned clear. Hunig'sBase (0.321 ml, 1.839 mmol) and pyridin-3-ylmethanamine (199 mg, 1.839 mmol) were added. The reaction was stirred at room temperature overnight. Solid precipitate formed overnight. The reaction was concentrated and triturated with ethyl acetate to afford product as a white solid. (Yield: 315 mg, white solid) $^1$H-NMR (400 MHz, DMSO-$d_6$) 8.46, 8.40, 7.70-7.60, 7.54, 7.40-7.29, 7.21, 7.13-7.05, 6.73, 5.49, 4.38, 4.30, 4.04, 2.95, 2.47-2.39, 1.71, 1.42

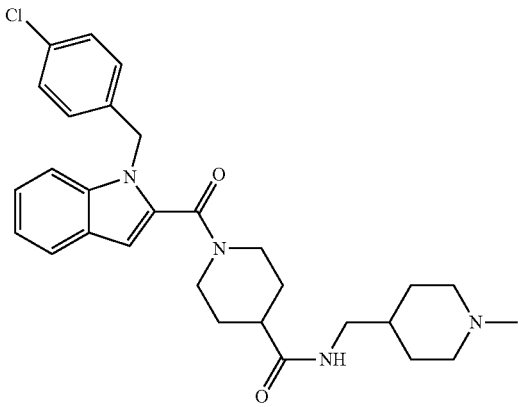 [SMILES: CN1CCC(CNC(=O)C2CCN(C(=O)c3cc4ccccc4n3Cc3ccc(Cl)cc3)CC2)CC1]

1-(1-(4-chlorobenzyl)-1H-indole-2-carbonyl)-N-((1-methylpiperidin-4-yl)methyl)piperidine-4-carboxamide (CCG 205429)

1-(1-(4-chlorobenzyl)-1H-indole-2-carbonyl)piperidine-4-carboxylic acid (100 mg, 0.252 mmol), 1-hydroxybenzotriazole (68.1 mg, 0.504 mmol) and EDCI (97 mg, 0.504 mmol) were dissolved in DCM (Volume: 4.0 ml). The suspension was stirred at room temperature for 10 minutes where it turned clear. Hunig'sBase (0.132 ml, 0.756 mmol) and (1-methylpiperidin-4-yl)methanamine (100 mg, 0.780 mmol) were added. The reaction was stirred at room temperature overnight. It was diluted with water and ethyl acetate. The water layer was washed with another portion of ethyl acetate. The combined organic layer was washed with saturated sodium bicarbonate and saturated sodium chloride. The organic layer was dried over magnesium sulfate, filtered, and concentrated. The resulting crude material was triturated with diethyl ether/ethyl acetate to afford the product as a white solid. (Yield: 83 mg, white solid) $^1$H-NMR (400 MHz, DMSO-$d_6$) 7.77, 7.62, 7.54, 7.35-7.30, 7.21, 7.13-7.06, 6.72, 5.49, 4.38, 4.02, 2.93, 2.78, 2.42-2.30, 2.17, 1.77, 1.57, 1.45-1.02

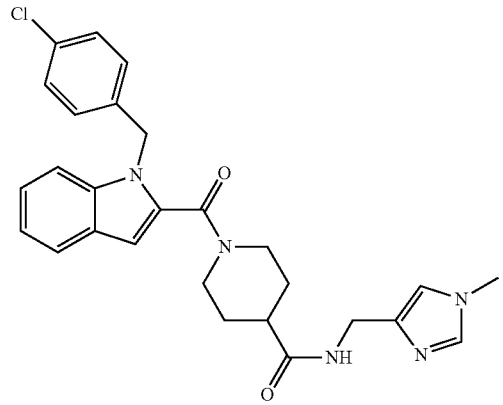 [SMILES: Cn1cnc(CNC(=O)C2CCN(C(=O)c3cc4ccccc4n3Cc3ccc(Cl)cc3)CC2)c1]

1-(1-(4-chlorobenzyl)-1H-indole-2-carbonyl)-N-((1-methyl-1H-imidazol-4-yl)methyl)piperidine-4-carboxamide (CCG 205455)

N1-((ethylimino)methylene)-N3,N3-dimethylpropane-1,3-diamine hydrochloride (259 mg, 1.350 mmol), 1-(1-(4-chlorobenzyl)-1H-indole-2-carbonyl)piperidine-4-carboxylic acid (428 mg, 1.080 mmol), and 1H-benzo[d][1,2,3]triazol-1-ol (182 mg, 1.350 mmol) were dissolved in 4.0 mL of DCM. The reaction was stirred at room temperature for ten minutes before Hunig's Base (0.236 ml, 1.350 mmol) and (1-methyl-1H-imidazol-4-yl)methanamine (100 mg, 0.900 mmol) as a 1.0 mL DCM solution was added. The reaction was allowed to stir at room temperature overnight. The reaction was diluted with water and ethyl acetate. The organic phase was washed with water, saturated sodium bicarbonate (twice), and saturated sodium chloride. The organic phase was dried over magnesium sulfate, filtered and concentrated. The crude material was triturated with ether and ethyl acetate and filtered to obtain white solid as a product. $^1$H-NMR (400 MHz, DMSO-$d_6$) 8.07, 7.62, 7.53, 7.46, 7.34, 7.21, 7.14-7.08, 6.87, 6.72, 5.49, 4.40, 4.09, 3.93, 3.59, 2.91, 2.47-2.37, 1.68, 1.43

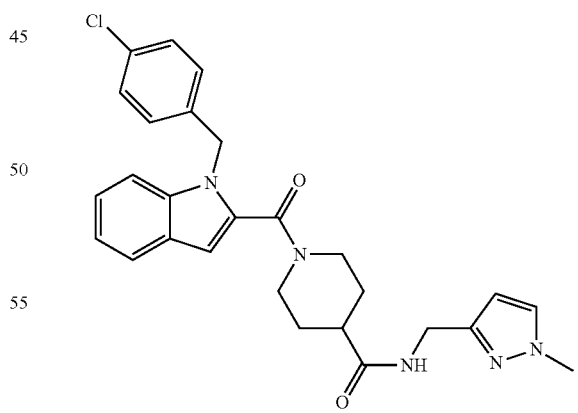

1-(1-(4-chlorobenzyl)-1H-indole-2-carbonyl)-N-((1-methyl-1H-pyrazol-3-yl)methyl)piperidine-4-carboxamide (CCG 205454)

N1-((ethylimino)methylene)-N3,N3-dimethylpropane-1,3-diamine hydrochloride (259 mg, 1.350 mmol), 1-(1-(4- chlorobenzyl)-1H-indole-2-carbonyl)piperidine-4-carboxylic acid (428 mg, 1.080 mmol), and 1H-benzo[d][1,2,3]triazol-1-ol (182 mg, 1.350 mmol) were dissolved in 4.0 mL of DCM. The reaction was stirred at room temperature for ten minutes before Hunig's Base (0.236 ml, 1.350 mmol) and (1-methyl-1H-pyrazol-3-yl)methanamine (100 mg, 0.900 mmol) as a 1.0 mL DCM solution was added. The reaction was allowed to stir at room temperature overnight. The reaction was diluted with water and ethyl acetate. The organic layer was washed with water, saturated sodium bicarbonate (twice), and saturated sodium chloride. The organic phase was dried over magnesium sulfate, filtered and concentrated. The resulting material was triturated with ethyl acetate to obtain white solid as the product. $^1$H-NMR (400 MHz, DMSO-$d_6$) 8.18, 7.66-7.51, 7.35, 7.22, 7.12, 6.73, 6.05, 5.49, 4.40, 4.18, 3.96, 3.77, 2.93, 2.41, 1.69, 1.44

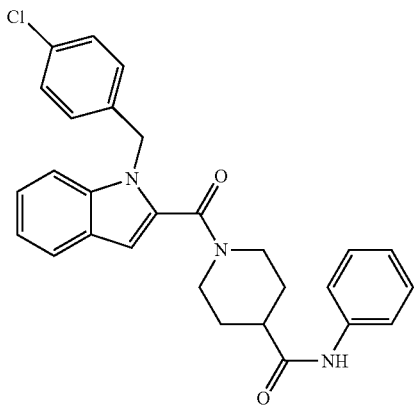 [SMILES: O=C(Nc1ccccc1)C1CCN(C(=O)c2cc3ccccc3n2Cc2ccc(Cl)cc2)CC1]

1-(1-(4-chlorobenzyl)-1H-indole-2-carbonyl)-N-phenylpiperidine-4-carboxamide (CCG 206334)

1-(1-(4-chlorobenzyl)-1H-indole-2-carbonyl)piperidine-4-carboxylic acid (100 mg, 0.252 mmol), N1-((ethylimino)methylene)-N3,N3-dimethylpropane-1,3-diamine hydrochloride (97 mg, 0.504 mmol), and 1H-benzo[d][1,2,3]triazol-1-ol (68.1 mg, 0.504 mmol) were dissolved 2.0 mL of DCM. The reaction was stirred at room temperature for ten minutes before N-ethyl-N-isopropylpropan-2-amine (0.088 mL, 0.504 mmol) and aniline, HCl (65.3 mg, 0.504 mmol) as a 1.0 mL DCM solution was added. The reaction was allowed to stir at room temperature overnight. The reaction was diluted with water and ethyl acetate. The organic phase was washed with water, saturated sodium bicarbonate (twice), and saturated sodium chloride. The organic phase was dried over magnesium sulfate, filtered and concentrated. The crude material was recrystallized with ether and ethyl acetate and filtered to obtain white solid as a product. (Yield: 77 mg, white solid) $^1$H-NMR (400 MHz, DMSO-$d_6$) 9.89, 7.66-7.52, 7.37-7.18, 7.13-7.07, 7.02, 6.75, 5.51, 4.44, 4.03, 2.95, 2.64-2.55, 1.79, 1.47

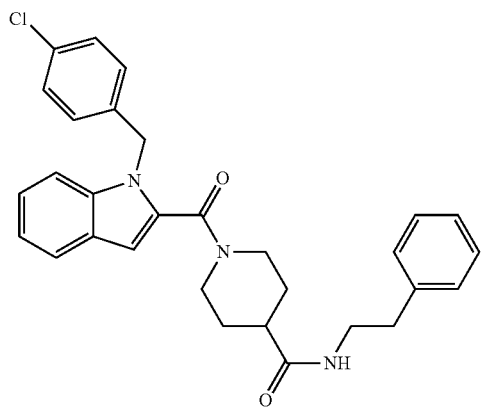

1-(1-(4-chlorobenzyl)-1H-indole-2-carbonyl)-N-phenethylpiperidine-4-carboxamide (CCG 206397)

1-(1-(4-chlorobenzyl)-1H-indole-2-carbonyl)piperidine-4-carboxylic acid (100 mg, 0.252 mmol), EDCI (97 mg, 0.504 mmol), and 1-hydroxybenzotriazole (68.1 mg, 0.504 mmol) were dissolved in DCM (Volume: 3.0 ml). The reaction was stirred at room temperature for 10 minutes before Hunig's Base (0.088 ml, 0.504 mmol) and 2-phenylethanamine (0.063 ml, 0.504 mmol) were added. The reaction was allowed to stir overnight at room temperature. The reaction was diluted with water and ethyl acetate. The organic phase was washed with 1N HCl, saturated sodium bicarbonate, and brine. The organic phase was dried over magnesium sulfate, filtered, and concentrated. The crude material was recrystallized in ether and ethyl acetate to obtain product as a white solid. (Yield: 76 mg, white solid) $^1$H-NMR (400 MHz, DMSO-$d_6$) 7.85, 7.62, 7.53, 7.36-7.05, 6.71, 5.48, 4.38, 4.01, 3.26, 2.90, 2.69, 2.39-2.28, 1.61, 1.36

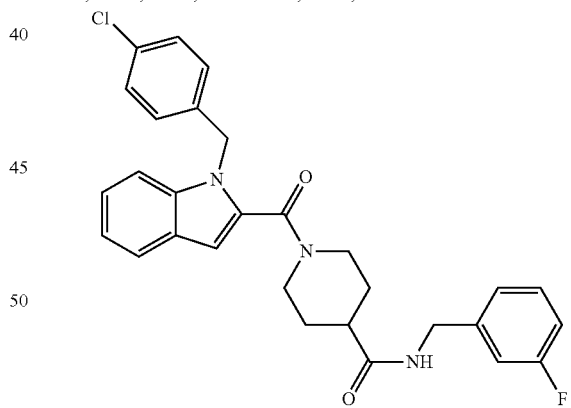

1-(1-(4-chlorobenzyl)-1H-indole-2-carbonyl)-N-(3-fluorobenzyl)piperidine-4-carboxamide (CCG 206399)

1-(1-(4-chlorobenzyl)-1H-indole-2-carbonyl)piperidine-4-carboxylic acid (100 mg, 0.252 mmol), EDCI (72.5 mg, 0.378 mmol), and 1-hydroxybenzotriazole (51.1 mg, 0.378 mmol) were dissolved in DCM (Volume: 3.0 ml). The reaction was stirred at room temperature for 10 minutes before Hunig's Base (0.066 ml, 0.378 mmol) and (3-fluorophenyl)methanamine (0.043 ml, 0.378 mmol) were added. The reaction was allowed to stir overnight at room temperature. The reaction was diluted with water and ethyl acetate. The organic phase was washed with 1N HCl, saturated sodium bicarbonate, and brine. The organic phase was dried over magnesium sulfate, filtered, and concentrated. The crude material was triturated with ethyl acetate to obtain product as a white solid. (Yield: 57 mg, white solid) $^1$H-NMR (400 MHz, DMSO-$d_6$) 8.38, 7.63, 7.54, 7.35, 7.21, 7.13-7.00, 6.73, 5.49, 4.44, 4.28, 4.13-3.91, 2.94, 1.72, 1.44

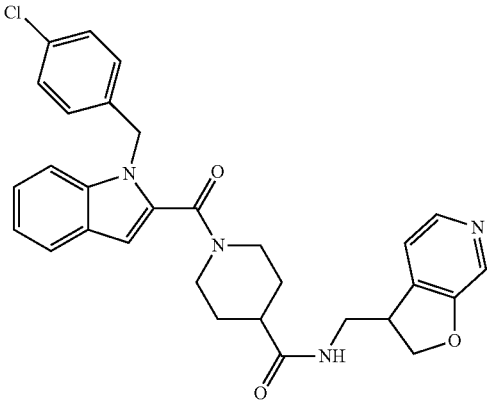 [SMILES: O=C(NCC1COc2cnccc21)C1CCN(C(=O)c2cc3ccccc3n2Cc2ccc(Cl)cc2)CC1]

1-(1-(4-chlorobenzyl)-1H-indole-2-carbonyl)-N-((2,3-dihydrofuro[2,3-c]pyridin-3-yl)methyl)piperidine-4-carboxamide (CCG 206581)

1-(1-(4-chlorobenzyl)-1H-indole-2-carbonyl)piperidine-4-carboxylic acid (317 mg, 0.799 mmol), 1-hydroxybenzotriazole (135 mg, 0.999 mmol), and EDC (191 mg, 0.999 mmol) were dissolved in 2.0 mL of DCM. The reaction was allowed to stir at room temperature for 10 minutes before adding (2,3-dihydrofuro[2,3-c]pyridin-3-yl)methanamine (100 mg, 0.666 mmol) as a DCM solution and Hunig'sBase (0.174 mL, 0.999 mmol). The reaction was allowed to stir at room temperature overnight. The reaction was diluted with water and ethyl acetate. The organic layer was washed with saturated sodium bicarbonate and saturated sodium chloride solution. It was dried over magnesium sulfate, filtered and concentrated. The crude material was triturated in ethyl acetate, filtered and concentrated to obtain white solid. (Yield: 176 mg, white solid) $^1$H-NMR (500 MHz, DMSO-$d_6$) 8.13-8.04, 7.63, 7.55, 7.37-7.28, 7.22, 7.13-7.02, 6.72, 5.47, 4.59, 4.47-4.28, 4.13-3.85, 3.73-3.62, 3.17, 3.07-2.76, 2.41-2.31, 1.79-1.20

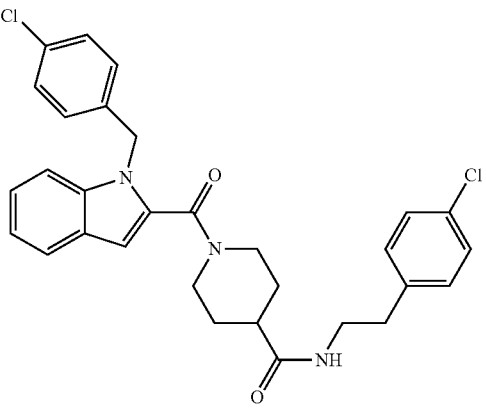 [SMILES: O=C(NCCc1ccc(Cl)cc1)C1CCN(C(=O)c2cc3ccccc3n2Cc2ccc(Cl)cc2)CC1]

1-(1-(4-chlorobenzyl)-1H-indole-2-carbonyl)-N-(4-chlorophenethyl)piperidine-4-carboxamide (CCG 206400)

1-(1-(4-chlorobenzyl)-1H-indole-2-carbonyl)piperidine-4-carboxylic acid (100 mg, 0.252 mmol), N1-((ethylimino)methylene)-N3,N3-dimethylpropane-1,3-diamine hydrochloride (72.5 mg, 0.378 mmol), and 1H-benzo[d][1,2,3]triazol-1-ol (51.1 mg, 0.378 mmol) were dissolved in DCM (Volume: 3.0 mL). The reaction was stirred for 10 minutes before 2-(4-chlorophenyl)ethanamine (0.053 mL, 0.378 mmol) and N-ethyl-N-isopropylpropan-2-amine (0.066 mL, 0.378 mmol). The reaction was stirred overnight at room temperature. The reaction was diluted with water and ethyl acetate. The organic layer was washed with 1N HCl, saturated sodium bicarbonate solution, and finally saturated sodium chloride. the organic layer was then dried over magnesium sulfate, filtered and concentrated. The crude material was triturated in ethyl acetate to give the product as a white solid. (Yield: 60 mg, white solid) $^1$H-NMR (400 MHz, DMSO-$d_6$) 7.85, 7.63, 7.54, 7.38-7.31, 7.24-7.18, 7.14-7.06, 6.71, 5.49, 4.37, 4.00, 3.26, 2.92, 2.69, 2.37-2.27, 1.76-1.22

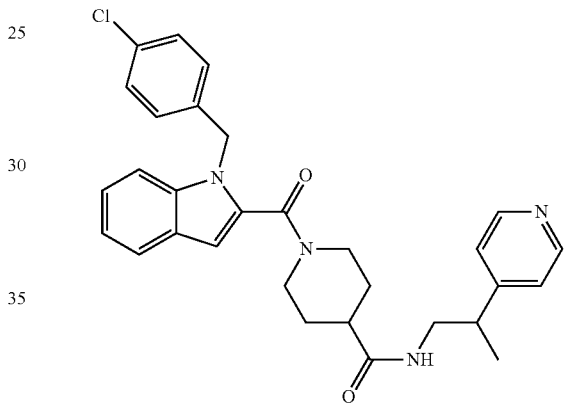

1-(1-(4-chlorobenzyl)-1H-indole-2-carbonyl)-N-(2-(pyridin-4-yl)propyl)piperidine-4-carboxamide (CCG 206580)

1-(1-(4-chlorobenzyl)-1H-indole-2-carbonyl)piperidine-4-carboxylic acid (0.350 g, 0.882 mmol), 1-hydroxybenzotriazole (0.149 g, 1.103 mmol), and EDC (0.211 g, 1.103 mmol) were dissolved in 3.0 mL of DCM. The reaction was allowed to stir at room temperature for 15 minutes before adding Hunig's Base (0.321 mL, 1.838 mmol) and 2-(pyridin-4-yl)propan-1-amine (0.100 g, 0.735 mmol) as a 2 mL DCM solution. The reaction was allowed to stir overnight. The reaction was dissolved in water and ethyl acetate. The organic phase was washed with saturated sodium bicarbonate and saturated sodium chloride. It was then dried over magnesium sulfate, filtered and concentrated. The crude material was triturated in ethyl acetate to obtain product. (Yield: 151 mg) $^1$H-NMR (500 MHz, CDCl$_3$) 8.59-8.51, 7.65, 7.34, 7.22-7.12, 7.06-6.99, 6.62, 5.46, 5.31, 4.69-4.03, 3.64-3.53, 3.36-3.27, 3.06-2.95, 2.89-2.78, 2.23-2.13, 1.87-1.25

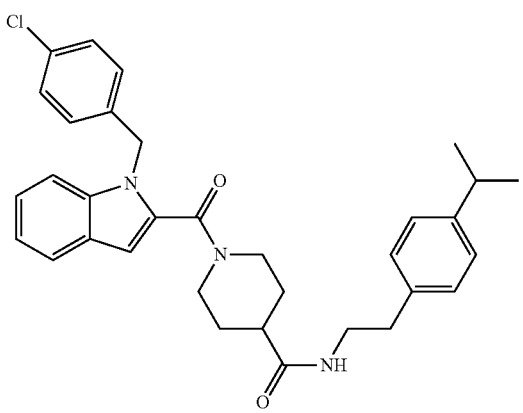 [SMILES: CC(C)c1ccc(CCNC(=O)C2CCN(C(=O)c3cc4ccccc4n3Cc3ccc(Cl)cc3)CC2)cc1]

1-(1-(4-chlorobenzyl)-1H-indole-2-carbonyl)-N-(4-isopropylphenethyl)piperidine-4-carboxamide (CCG 206461)

1-(1-(4-chlorobenzyl)-1H-indole-2-carbonyl)piperidine-4-carboxylic acid (100 mg, 0.252 mmol), N1-((ethylimino)methylene)-N3,N3-dimethylpropane-1,3-diamine hydrochloride (72.5 mg, 0.378 mmol), and 1H-benzo[d][1,2,3]triazol-1-ol (51.1 mg, 0.378 mmol) were dissolved in 2.0 mL of DCM and stirred for 10 minutes before the addition of a 2-(4-isopropylphenyl)ethanamine, HCl (75 mg, 0.378 mmol) and N-ethyl-N-isopropylpropan-2-amine (0.132 mL, 0.756 mmol) as a 1.0 mL DCM solution. The reaction was allowed to stir overnight. The reaction was diluted with water and ethyl acetate. The organic layer was washed with 1N HCl, saturated sodium bicarbonate solution, and finally saturated sodium chloride solution. The organic layer was dried over magnesium sulfate, filtered and concentrated. The crude material purified using silica gel chromatography 0-60% ethyl acetate/hexanes. (Yield: 50 mg, white solid) ¹H-NMR (500 MHz, DMSO-d₆) 7.88, 7.62, 7.55, 7.34, 7.22, 7.18-7.06, 6.71, 5.49, 4.40, 3.97, 3.24, 3.13-2.73, 2.66, 2.40-2.29, 1.79-1.23, 1.16

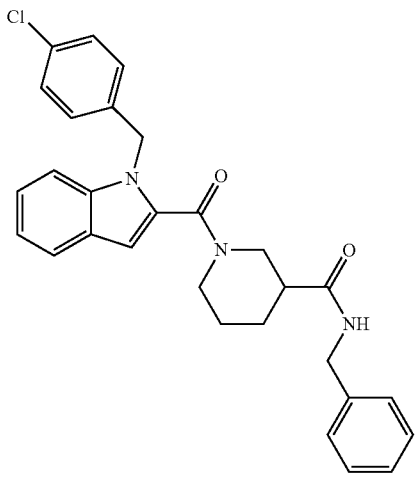 [SMILES: O=C(NCc1ccccc1)C1CCCN(C(=O)c2cc3ccccc3n2Cc2ccc(Cl)cc2)C1]

N-benzyl-1-(1-(4-chlorobenzyl)-1H-indole-2-carbonyl)piperidine-3-carboxamide (CCG 205483)

1-(1-(4-chlorobenzyl)-1H-indole-2-carbonyl)piperidine-3-carboxylic acid (50 mg, 0.126 mmol), 1-hydroxybenzotriazole (34.0 mg, 0.252 mmol), and EDCI (48.3 mg, 0.252 mmol) were dissolved in DCM (Volume: 3 ml). The reaction was stirred at room temperature for 15 minutes before the addition of Hunig's Base (0.044 ml, 0.252 mmol) and benzylamine (0.028 ml, 0.252 mmol). The reaction was stirred at room temperature overnight. It was diluted with water and ethyl acetate. The water layer was washed with another portion of ethyl acetate. The combined organic layer was washed with 1N HCl, saturated sodium bicarbonate, and saturated sodium chloride. The organic layer was dried over magnesium sulfate, filtered, and concentrated. Flash chromatography with 0-5% methanolic ammonia: DCM afforded the product as a white solid (Yield: 38 mg, white solid) ¹H-NMR (400 MHz, DMSO-d₆) 8.44, 7.60, 7.49, 7.36-7.03, 6.72, 5.46, 4.58-3.74, 2.93, 2.30, 1.93-1.48,

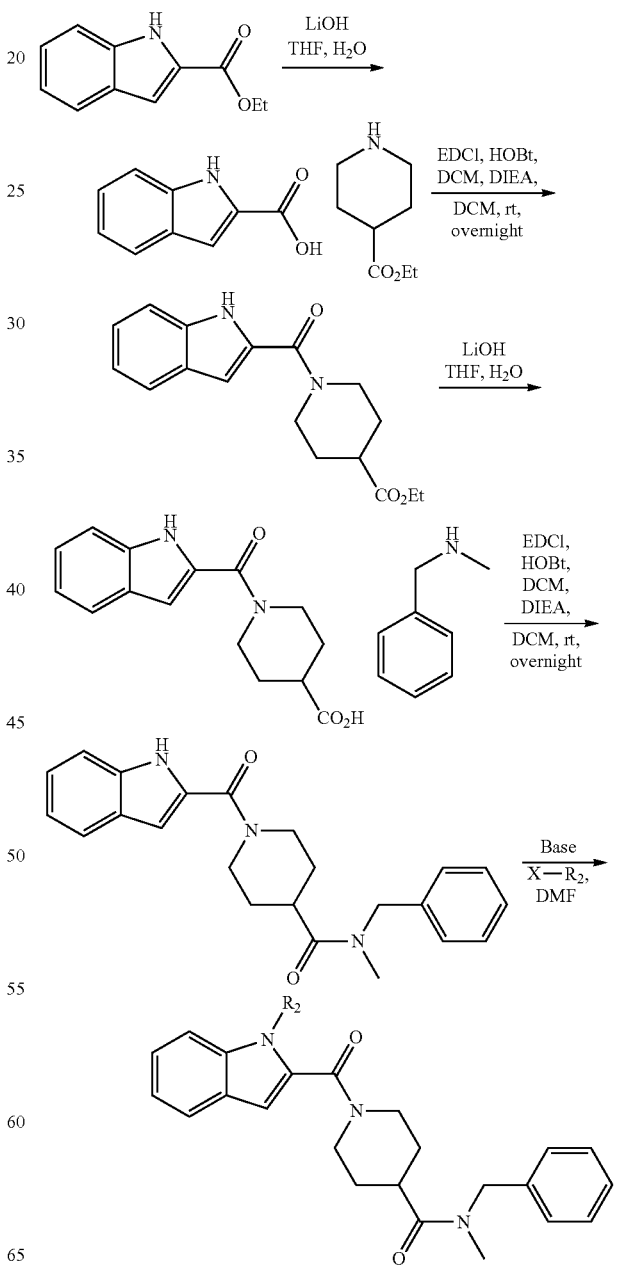

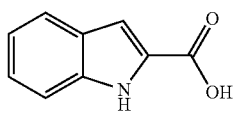 [SMILES: O=C(O)c1cc2ccccc2[nH]1]

1H-indole-2-carboxylic acid

Ethyl 1H-indole-2-carboxylate (3.0 g, 15.86 mmol) and lithium hydroxide, H$_2$O (3.33 g, 79 mmol) were dissolved in THF (Ratio: 1.000, Volume: 10 ml) and Water (Ratio: 2, Volume: 20.00 ml). The reaction was stirred overnight. The reaction was diluted with water and diethyl ether. The water layer was washed with diethyl ether twice. The aqueous layer was acidified to pH 2 using 2N HCl. The suspension was extracted using ethyl acetate. The organic layer was washed with saturated sodium chloride solution, dried over magnesium sulfate, filtered and concentrated to obtain product. (Yield: 2.39 g, white solid) $^1$H-NMR (400 MHz, DMSO-d$_6$) 12.90, 11.70, 7.60, 7.40, 7.24-7.14, 7.07-6.98

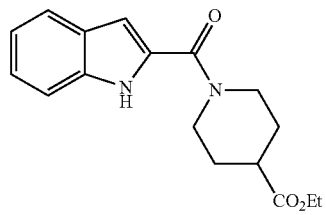 [SMILES: CCOC(=O)C1CCN(C(=O)c2cc3ccccc3[nH]2)CC1]

ethyl 1-(1H-indole-2-carbonyl)piperidine-4-carboxylate 1H-indole-2-carboxylic acid (2.49 g, 15.45 mmol), EDCI (4.44 g, 23.18 mmol), and HOBT (3.55 g, 23.18 mmol) were dissolved in THF (Volume: 30.0 ml). The reaction was allowed to stir for 15 minutes before DIEA (4.05 ml, 23.18 mmol) and ethyl piperidine-4-carboxylate (3.57 ml, 23.18 mmol) were added to the reaction. The reaction was diluted with water and ethyl acetate. The organic layer was washed with saturated sodium bicarbonate, 1H HCl, and saturated sodium chloride. The organic layer was then dried over magnesium sulfate, filtered and concentrated. the resulting solid is then triturated with ethyl acetate. (Yield: 3.27 g, white solid) $^1$H-NMR (400 MHz, DMSO-d$_6$) 11.55, 7.60, 7.41, 7.18, 7.04, 6.77, 4.40-4.27, 4.09, 3.18, 2.76-2.63, 1.97-1.88, 1.65-1.51, 1.20

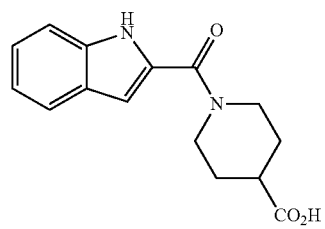 [SMILES: O=C(O)C1CCN(C(=O)c2cc3ccccc3[nH]2)CC1]

1-(1H-indole-2-carbonyl)piperidine-4-carboxylic acid ethyl 1-(1H-indole-2-carbonyl)piperidine-4-carboxylate (3.0 g, 9.99 mmol) and lithium hydroxide, H2O (4.19 g, 100 mmol)) were dissolved in THF (Ratio: 1, Volume: 20 ml) and Water (Ratio: 2, Volume: 40.0 ml) and allowed to stir overnight at room temperature. The reaction was diluted with water, and extracted with diethyl ether. The aqueous layer was acidified using 2N HCl to pH ~2. A fine, white suspension resulted. The aqueous layer was extracted with ethyl acetate twice. The combined ethyl acetate layers were dried over magnesium sulfate, filtered and concentrated to afford the product as a white solid. (Yield: 678 mg, white solid) $^1$H-NMR (400 MHz, DMSO-d$_6$) 12.33, 11.53, 7.60, 7.41, 7.21-6.94, 6.76, 4.40-4.21, 3.17, 2.66-2.53, 1.97-1.82, 1.63-1.47

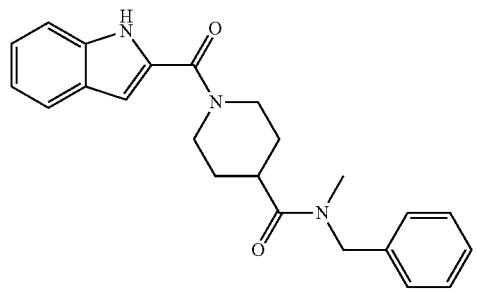 [SMILES: CN(Cc1ccccc1)C(=O)C1CCN(C(=O)c2cc3ccccc3[nH]2)CC1]

N-benzyl-1-(1H-indole-2-carbonyl)-N-methylpiperidine-4-carboxamide (CCG 205400)

1-(1H-indole-2-carbonyl)piperidine-4-carboxylic acid (1.00 g, 3.67 mmol), N1-((ethylimino)methylene)-N3,N3-dimethylpropane-1,3-diamine hydrochloride (1.408 g, 7.34 mmol), and 1H-benzo[d][1,2,3]triazol-1-ol hydrate (1.125 g, 7.34 mmol) were dissolved in DCM (Volume: 10 ml). The reaction was allowed to stir for 10 minutes before adding DIEA (1.283 ml, 7.34 mmol) and N-methyl-1-phenylmethanamine (0.836 ml, 7.34 mmol). The reaction was allowed to stir overnight at room temperature. The reaction was diluted with water and ethyl acetate. The organic phase was washed with saturated sodium bicarbonate, 1N HCl, and saturated sodium chloride solution. The organic layer was dried over magnesium sulfate, filtered and concentrated. The crude material was purified by silica gel chromatography using 30% to 60% ethyl acetate:hexanes to obtain product. (Yield: 1.03 g, white solid) 11.53, 7.59-7.54, 7.41-7.11, 7.01, 6.76-6.70, 4.66, 4.52-4.35, 3.22-2.93, 2.76, 1.84-1.51

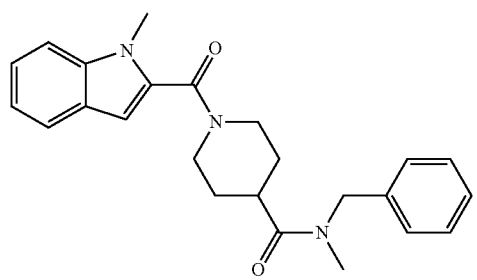 [SMILES: CN(Cc1ccccc1)C(=O)C1CCN(C(=O)c2cc3ccccc3n2C)CC1]

N-benzyl-N-methyl-1-(1-methyl-1H-indole-2-carbonyl)piperidine-4-carboxamide (CCG 205428)

N-benzyl-1-(1H-indole-2-carbonyl)-N-methylpiperidine-4-carboxamide (100 mg, 0.266 mmol) was added to a suspension of sodium hydride (12.78 mg, 0.320 mmol) in THF (Volume: 1.5 mL) at 0° C. The reaction was stirred for 10 minutes before iodomethane (0.200 mL, 3.20 mmol) was added. The reaction was allowed to stir at room temperature overnight. The reaction was diluted with water and extracted with ethyl acetate. The organic layer was washed with water and saturated sodium chloride solution. It was dried over magnesium sulfate, filtered and concentrated. The crude material was purified using 50%-100% ethyl acetate in hexanes. (Yield: 41.5 mg, white solid) To obtain white solid as a product. $^1$H-NMR (400 MHz, DMSO-$d_6$) 7.63-7.57, 7.53-7.47, 7.43-7.16, 7.13-7.05, 6.63, 4.67, 4.58-4.00, 3.78-3.71, 3.21-2.91, 2.79, 1.87-1.52

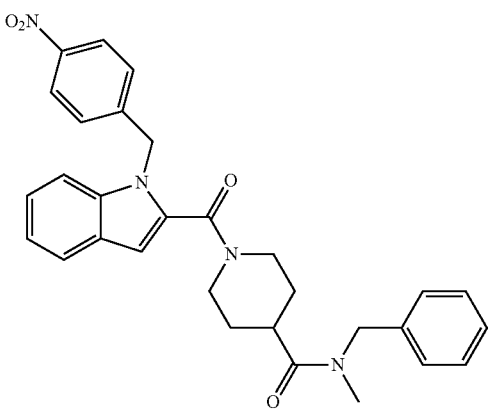 [SMILES: CN(Cc1ccccc1)C(=O)C1CCN(C(=O)c2cc3ccccc3n2Cc2ccc([N+](=O)[O-])cc2)CC1]

N-benzyl-N-methyl-1-(1-(4-nitrobenzyl)-1H-indole-2-carbonyl)piperidine-4-carboxamide (CCG 205484)

N-benzyl-1-(1H-indole-2-carbonyl)-N-methylpiperidine-4-carboxamide (50 mg, 0.133 mmol) was added to a suspension of sodium hydride (7.99 mg, 0.200 mmol) in DMF (Volume: 2 ml). The reaction was allowed to stir for 10 minutes at 60° C. 1-(chloromethyl)-4-nitrobenzene (45.7 mg, 0.266 mmol) and potassium iodide (44.2 mg, 0.266 mmol) were added and the reaction was stirred overnight at 60° C. The reaction was diluted with water and ethyl acetate. The organic layer was washed with water and saturated sodium chloride solution. It was dried over magnesium sulfate, filtered and concentrated. The crude material was purified using 40-100% ethyl acetate:hexanes to afford the product as a white solid. (Yield: 11 mg, white solid) $^1$H-NMR (400 MHz, DMSO-$d_6$) 8.20-8.12, 7.70-7.62, 7.55, 7.43-7.08, 6.81-6.75, 5.71-5.61, 4.62, 4.56-3.95, 3.21-2.85, 2.74, 1.81-1.13

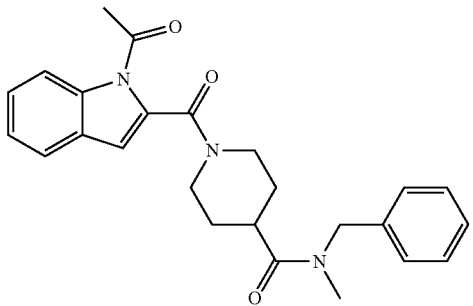 [SMILES: CC(=O)n1c(C(=O)N2CCC(C(=O)N(C)Cc3ccccc3)CC2)cc2ccccc21]

1-(1-acetyl-1H-indole-2-carbonyl)-N-benzyl-N-methylpiperidine-4-carboxamide (CCG 206333)

A solution of N-benzyl-1-(1H-indole-2-carbonyl)-N-methylpiperidine-4-carboxamide (100 mg, 0.266 mmol) in 1 mL of DMF was added to a suspension of sodium hydride (11.72 mg, 0.293 mmol) in 2.0 mL DMF. The reaction was stirred at 80° C. for 10 minutes before adding acetic anhydride (0.050 ml, 0.533 mmol). The reaction was allowed to stir for 5 hours before it was cooled to room temperature and diluted with ammonium chloride and ethyl acetate. The organic phase was washed with saturated ammonium chloride twice, followed by saturated sodium chloride, dried over magnesium sulfate, filtered and concentrated. The crude material was purified via silica gel chromatography for 50% ethyl acetate/hexanes to 100% ethyl acetate. Purification afforded white solid as the product. (Yield: 13 mg, white solid) $^1$H-NMR (400 MHz, DMSO-$d_6$) 8.12-8.06, 7.65-7.59, 7.41-7.13, 6.91-6.84, 4.65, 4.49, 3.96-3.83, 3.06-2.94, 2.76, 2.61-2.55, 1.87-1.49

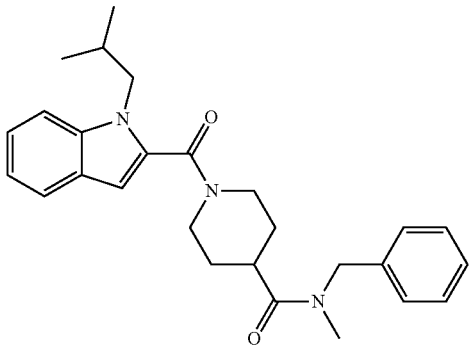 [SMILES: CC(C)Cn1c(C(=O)N2CCC(C(=O)N(C)Cc3ccccc3)CC2)cc2ccccc21]

N-benzyl-1-(1-isobutyl-1H-indole-2-carbonyl)-N-methylpiperidine-4-carboxamide (CCG 206332)

N-benzyl-1-(1H-indole-2-carbonyl)-N-methylpiperidine-4-carboxamide (100 mg, 0.266 mmol) was dissolved in 1.0 mL of DMF and added to a suspension of sodium hydride (12.78 mg, 0.320 mmol) in 2.0 mL of DMF. The reaction was stirred at 80° C. for 10 minutes before adding 1-iodo-2-methylpropane (0.061 mL, 0.533 mmol). The reaction was allowed to stir overnight. After 18 hours, the reaction was cooled to room temperature before diluting with water and ethyl acetate. The organic phase was washed with water followed by saturated sodium chloride, dried over magnesium sulfate, filtered and concentrated. The crude material was purified via column chromatography using 50% ethyl acetate/hexanes to 100% ethyl acetate. The purification provided product as a white solid. (Yield: 28 mg, white solid) $^1$H-NMR (400 MHz, DMSO-$d_6$) 7.64-7.51, 7.43-7.16, 7.11-7.03, 6.71-6.61, 4.67, 4.51, 4.19-4.07, 3.13-2.91, 2.79, 2.06-1.93, 1.88-1.50, 0.84-0.73

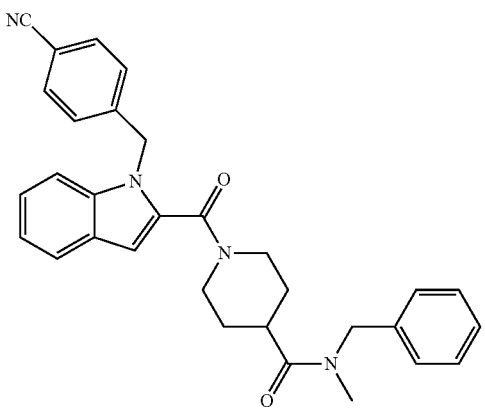 [SMILES: CN(Cc1ccccc1)C(=O)C1CCN(C(=O)c2cc3ccccc3n2Cc2ccc(C#N)cc2)CC1]

N-benzyl-1-(1-(4-cyanobenzyl)-1H-indole-2-carbo-
nyl)-N-methylpiperidine-4-carboxamide (CCG
206330)

Sodium iodide (99 mg, 0.660 mmol) and 4-(chloromethyl) benzonitrile (100 mg, 0.660 mmol) were dissolved in Acetone (Volume: 2.199 mL) and allowed to stir at room temperature for 4 hours. The resulting solid was filtered and the filtrate concentrated to obtain 4-(iodomethyl)benzonitrile (130 mg, 0.535 mmol, 81% yield) as an orange oil. It was taken directly to the next step without characterization and purification. N-benzyl-1-(1H-indole-2-carbonyl)-N-methylpiperidine-4-carboxamide (100 mg, 0.266 mmol) was dissolved in 1.0 mL of DMF and added to a suspension of sodium hydride (12.78 mg, 0.320 mmol) in 2.0 of DMF. The reaction was stirred at 80° C. for 10 minutes before adding 4-(iodomethyl)benzonitrile (129 mg, 0.533 mmol) dissolved in 2.0 mL of DMF. The reaction was allowed to stir overnight. After 18 hours, the reaction was cooled to room temperature before diluting with water and ethyl acetate. The organic phase was washed with water followed by saturated sodium chloride, dried over magnesium sulfate, filtered and concentrated. The crude material was purified via column chromatography using 50% ethyl acetate/hexanes to 100% ethyl acetate. The purification provided product as a white solid. (Yield: 50 mg, white solid) $^1$H-NMR (400 MHz, DMSO-$d_6$) 7.78-7.67, 7.66-7.57, 7.49, 7.43-7.01, 6.80-6.68, 5.65-5.51, 4.62, 4.54-3.83, 3.16-2.83, 2.75, 2.35-2.26, 1.80-1.24

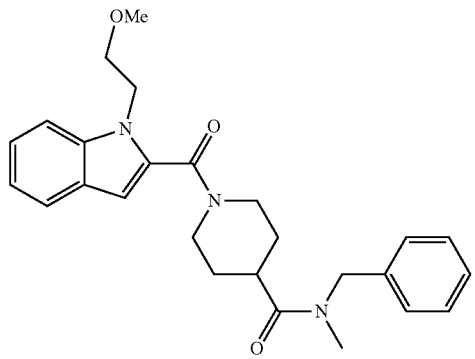 [SMILES: COCCn1c(C(=O)N2CCC(C(=O)N(C)Cc3ccccc3)CC2)cc2ccccc21]

N-benzyl-1-(1-(2-methoxyethyl)-1H-indole-2-carbo-
nyl)-N-methylpiperidine-4-carboxamide (CCG
206331)

N-benzyl-1-(1H-indole-2-carbonyl)-N-methylpiperidine-4-carboxamide (50 mg, 0.133 mmol) dissolved in 0.5 mL of DMF was added to a suspension of sodium hydride (7.99 mg, 0.200 mmol) in 1.0 mL of DMF. The reaction was heated at 70° C. for ten minutes before adding 2-methoxyethyl 4-methylbenzenesulfonate (0.144 mL, 0.266 mmol). The reaction was allowed to stir overnight. After 18 hours, the reaction was cooled to room temperature before diluting with water and ethyl acetate. The organic phase was washed with water followed by saturated sodium chloride, dried over magnesium sulfate, filtered and concentrated. The crude material was purified via column chromatography using 50-80% ethyl acetate/hexanes. The purification provided product as a white solid $^1$H-NMR (400 MHz, DMSO-$d_6$) 7.63-7.49, 7.43-7.14, 7.12-7.03, 6.67-6.58, 4.68, 4.63-4.06, 3.53, 3.20-3.13, 3.10-2.92, 2.79, 1.92-1.50

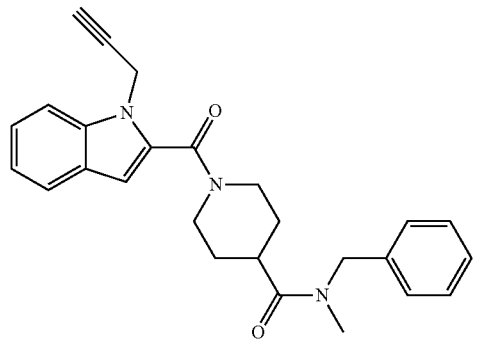 [SMILES: C#CCn1c(C(=O)N2CCC(C(=O)N(C)Cc3ccccc3)CC2)cc2ccccc21]

N-benzyl-N-methyl-1-(1-(prop-2-yn-1-yl)-1H-in-
dole-2-carbonyl)piperidine-4-carboxamide (CCG
206401)

sodium hydride (12.78 mg, 0.320 mmol) was added to an oven dried flask and placed under nitrogen. It was then suspended in 1.0 mL of DMF. The suspension was placed in a 70° C. oil bath before adding N-benzyl-1-(1H-indole-2-carbonyl)-N-methylpiperidine-4-carboxamide (100 mg, 0.266 mmol) as a 0.5 mL DMF solution. The reaction was allowed to stir for 20 minutes before the addition of 3-bromoprop-1-yne (0.047 ml, 0.533 mmol) dropwise. The reaction was allowed to stir overnight. The reaction was cooled and diluted with saturated ammonium chloride and ethyl acetate. The organic layer was washed with saturated ammonium chloride followed by saturated sodium chloride. The organic layer was dried over magnesium sulfate, filtered, and concentrated. The yellow crude material was purified via Biotage column 30-70% ethyl acetate:hexanes 4 gram silicycle column to obtain white solid. (Yield: 50 mg, white solid) $^1$H-NMR (400 MHz, DMSO-$d_6$) 7.64-7.53, 7.40-7.05, 6.75-6.65, 5.16-5.04, 4.65, 4.58-3.99, 3.23, 3.10-2.93, 2.76, 1.85-1.52

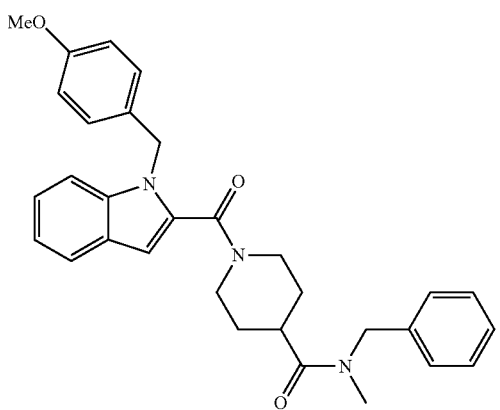 [SMILES: COc1ccc(Cn2c(C(=O)N3CCC(C(=O)N(C)Cc4ccccc4)CC3)cc3ccccc32)cc1]

N-benzyl-1-(1-(4-methoxybenzyl)-1H-indole-2-carbonyl)-N-methylpiperidine-4-carboxamide (CCG 205477)

N-benzyl-1-(1H-indole-2-carbonyl)-N-methylpiperidine-4-carboxamide (100 mg, 0.266 mmol) was added to a suspension of sodium hydride (12.78 mg, 0.320 mmol) in THF (Volume: 1.5 mL). The reaction was stirred for 10 minutes before 1-(bromomethyl)-4-methoxybenzene (0.039 mL, 0.266 mmol) was added. The reaction was allowed to stir at room temperature overnight. The reaction was diluted with water and extracted with ethyl acetate. The organic layer was washed with water and saturated sodium chloride solution. It was dried over magnesium sulfate, filtered and concentrated. The crude material was purified using 50%-100% ethyl acetate in hexanes to obtain white solid as a product. (Yield: 42 mg, white solid) $^1$H-NMR (400 MHz, DMSO-$d_6$) 7.64-7.58, 7.41-7.15, 7.10-7.05, 6.85-6.81, 6.70-6.64, 5.48-5.38, 4.64, 4.56-4.45, 3.70-3.66, 3.01-2.92, 2.78, 1.54

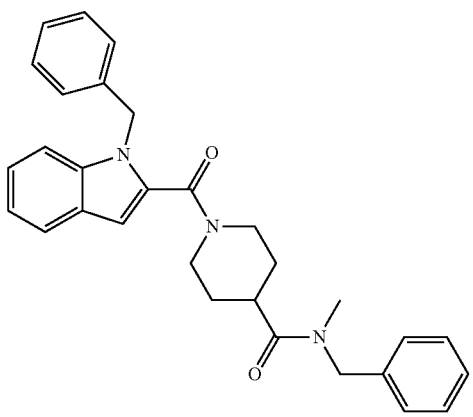 [SMILES: CN(Cc1ccccc1)C(=O)C1CCN(C(=O)c2cc3ccccc3n2Cc2ccccc2)CC1]

N-benzyl-1-(1-benzyl-1H-indole-2-carbonyl)-N-methylpiperidine-4-carboxamide (CCG 205404)

N-benzyl-1-(1H-indole-2-carbonyl)-N-methylpiperidine-4-carboxamide (50 mg, 0.133 mmol) was dissolved in 0.5 mL of DMF and cooled to 0° C. Lithium bis(trimethylsilyl)amide (0.146 ml, 0.146 mmol) was added dropwise and the reaction was allowed to stir for 10 minutes. (bromomethyl)benzene (0.024 ml, 0.200 mmol) was added to the reaction, and was allowed to stir overnight at room temperature. The reaction showed disappearance of the majority of the starting material. The reaction was quenched with water. It was then extracted with ethyl acetate. The organic layer was washed with saturated sodium chloride solution three times and dried over magnesium sulfate, filtered and concentrated. The crude material was purified through silica gel chromatography using 25% EtOAc:DCM. $^1$H-NMR (400 MHz, DMSO -$d_6$) 7.64-7.55, 7.42-7.15, 7.13-7.06, 6.75-6.68, 5.56-5.47, 4.64, 4.57-3.91, 3.21-2.89, 2.78, 1.92-1.20

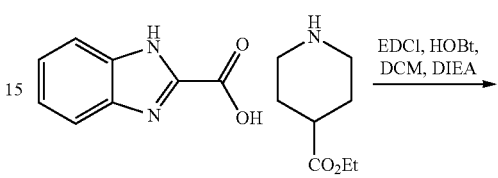

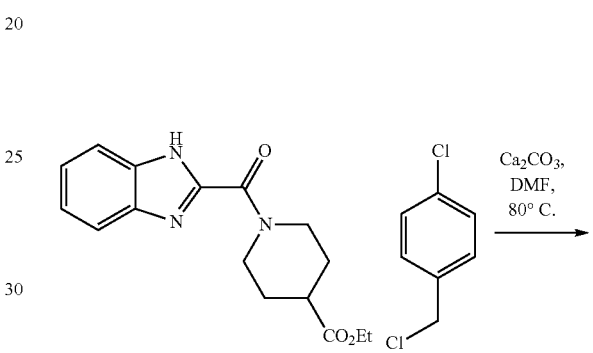

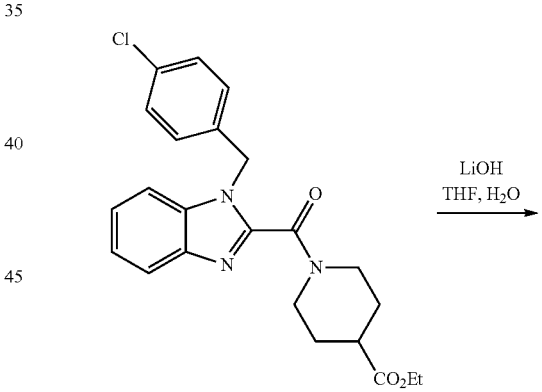

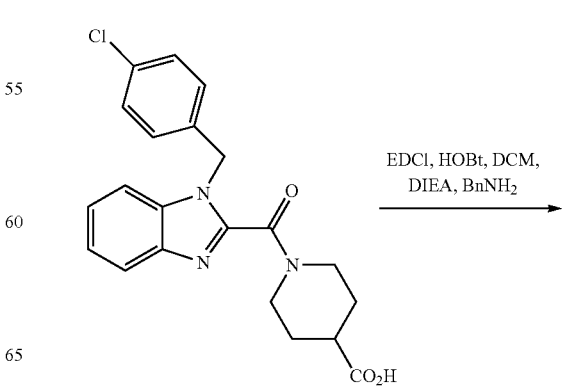

-continued

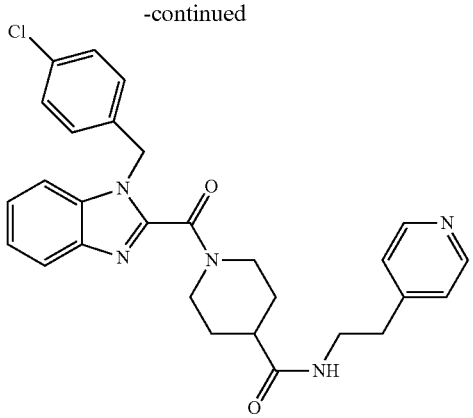

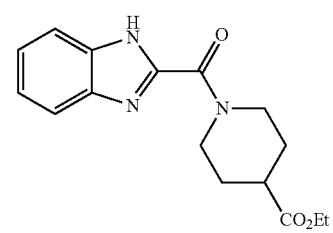 [SMILES: CCOC(=O)C1CCN(C(=O)c2nc3ccccc3[nH]2)CC1]

ethyl 1-(1H-benzo[d]imidazole-2-carbonyl)piperidine-4-carboxylate 1H-benzo[d]imidazole-2-carboxylic acid, H2O (500 mg, 2.78 mmol), EDCI (1170 mg, 6.11 mmol), and 1-HYDROXYBENZOTRIAZOLE (825 mg, 6.11 mmol) were dissolved in DCM. The reaction was allowed to stir for 10 minutes before Hunig's Base (1.066 mL, 6.11 mmol) and ethyl piperidine-4-carboxylate (0.941 mL, 6.11 mmol) were added. The reaction was allowed to stir overnight at room temperature. The reaction was diluted with water and ethyl acetate. The organic phase was washed with 1N HCl, saturated sodium bicarbonate, and saturated sodium chloride solution. The ethyl acetate layer was dried over magnesium sulfate, filtered and concentrated. The resulting crude material was triturated with ethyl acetate to obtain white solid as a product. (Yield: 113 mg, white solid) $^1$H-NMR (400 MHz, DMSO-$d_6$) 13.09, 7.74, 7.53, 7.36-7.20, 5.31, 4.42, 4.09, 3.48, 3.05, 2.77-2.66, 1.97, 1.69-1.50, 1.20

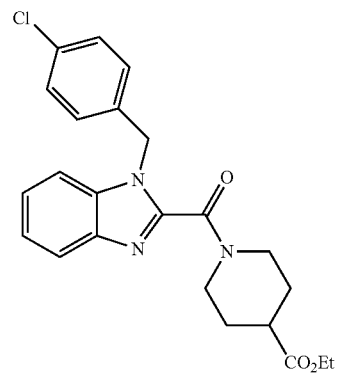 [SMILES: CCOC(=O)C1CCN(C(=O)c2nc3ccccc3n2Cc2ccc(Cl)cc2)CC1]

ethyl 1-(1-(4-chlorobenzyl)-1H-benzo[d]imidazole-2-carbonyl)piperidine-4-carboxylate ethyl 1-(1H-benzo[d]imidazole-2-carbonyl)piperidine-4-carboxylate (80 mg, 0.265 mmol) and cesium carbonate (130 mg, 0.398 mmol) were dissolved in DMF (Volume: 2.0 ml). 1-chloro-4-(chloromethyl)benzene (0.051 ml, 0.398 mmol) was added and the reaction was heated at 80° C. overnight. After 18 hours, the reaction was cooled to room temperature and diluted with water and ethyl acetate. The organic phase was washed with saturated sodium chloride four times before it was dried over magnesium sulfate, filtered and concentrated. The crude material was taken directly to the next step without purification. (Yield: 85 mg, beige solid). $^1$H-NMR (400 MHz, DMSO-$d_6$) 7.74, 7.66, 7.47-7.21, 5.51, 5.15, 4.48, 4.43-4.32, 4.08, 3.96-3.85, 3.16, 2.99, 2.69-2.55, 1.98-1.87, 1.76-1.66, 1.52-1.38, 1.26-1.12

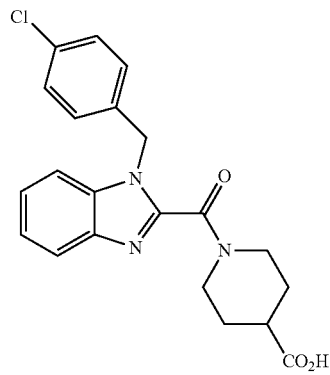 [SMILES: O=C(O)C1CCN(C(=O)c2nc3ccccc3n2Cc2ccc(Cl)cc2)CC1]

1-(1-(4-chlorobenzyl)-1H-benzo[d]imidazole-2-carbonyl)piperidine-4-carboxylic acid ethyl 1-(1-(4-chlorobenzyl)-1H-benzo[d]imidazole-2-carbonyl)piperidine-4-carboxylate (60 mg, 0.141 mmol) and lithium hydroxide, H2O (23.65 mg, 0.564 mmol) were dissolved in THF (Ratio: 1.000, Volume: 0.25 ml) and Water (Ratio: 2, Volume: 0.500 ml). The reaction was stirred for two hours before it was diluted with water and diethyl ether. The aqueous phase was washed with diethyl ether twice. It was then acidified to pH ~2 and extracted with ethyl acetate. The organic phase was washed with saturated sodium chloride, dried over magnesium sulfate, filtered and concentrated to obtain crude acid. No further purification was performed. (Yield: 54 mg, white solid). $^1$H-NMR (400 MHz, DMSO-$d_6$) 12.28, 7.65, 7.36-7.18, 5.51, 4.36-4.27, 3.91-3.82, 3.12, 2.96, 1.92-1.83, 1.74-1.63, 1.50-1.17

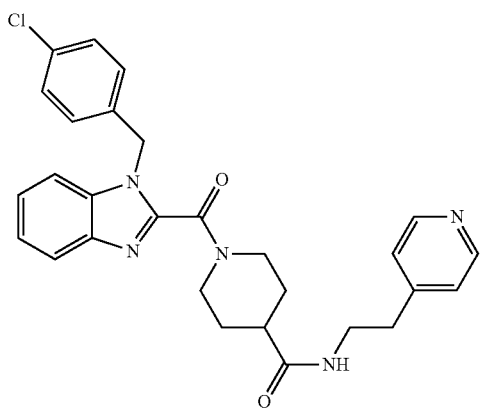 [SMILES: O=C(NCCc1ccncc1)C1CCN(C(=O)c2nc3ccccc3n2Cc2ccc(Cl)cc2)CC1]

1-(1-(4-chlorobenzyl)-1H-benzo[d]imidazole-2-carbonyl)-N-(2-(pyridin-4-yl)ethyl)piperidine-4-carboxamide (CCG 206565)

1-(1-(4-chlorobenzyl)-1H-benzo[d]imidazole-2-carbonyl)piperidine-4-carboxylic acid (50 mg, 0.126 mmol), EDC (48.2 mg, 0.251 mmol), and 1-hydroxybenzotriazole (34.0 mg, 0.251 mmol) were dissolved in DCM (Volume: 2.0 mL). The reaction was allowed to stir for 10 minutes before the addition of Hunig's Base (0.044 mL, 0.251 mmol) and 2-(pyridin-4-yl)ethanamine (0.030 mL, 0.251 mmol). The reaction was allowed to stir overnight. The reaction was diluted with water and ethyl acetate. The organic layer was washed with saturated sodium bicarbonate and saturated sodium chloride. The ethyl acetate layer was dried over magnesium sulfate, filtered and concentrated. The crude material was triturated in diethyl ether/ethyl acetate to obtain white solid. $^1$H-NMR (500 MHz, DMSO-$d_6$) 8.47-8.43, 7.93, 7.74, 7.61, 7.39, 7.35-7.24, 7.21, 5.55, 4.45, 3.98, 3.33-3.28, 3.04, 2.87, 2.73, 2.40-2.31, 1.74, 1.58-1.32

TABLE 3

| | Activity of compounds | |
|---|---|---|
| CCG Number | 50 μM (% control) Luc | IC$_{50}$ (μM) |
| 205432 | 3.75 | 0.53 |
| 205456 | 24.1 | 22.35 |
| 205433 | 1.9 | 5.34 |
| 205430 | 3.55 | 13.05 |
| 206329 | 12.7 | 2.39 |
| 206395 | 38.35 | 11.7 |
| 206396 | 34.85 | 10.55 |
| 206398 | 12.95 | 7.1 |
| 205422 | 7.05 | 11.43 |
| 205429 | 26.8 | ND |
| 205455 | 50.8 | ND |
| 205454 | 46.6 | 76.85 |
| 206334 | 77.35 | ND |
| 206397 | 40.25 | 15.18 |
| 206399 | 50.35 | ND |
| 206581 | 8.6 | 3.58 |
| 206400 | 28.55 | 7.45 |
| 206580 | 13.4 | 1.66 |
| 206461 | 32.65 | 2.9 |
| 205483 | 44.1 | 30.55 |
| 206565 | 12 | 4.07 |
| 205400 | 29.05 | 27.7 |
| 205428 | 77.15 | ND |
| 205484 | 53.95 | 41.9 |
| 206333 | 58.45 | ND |
| 206332 | 1.7 | 27.93 |
| 206330 | 45.25 | 79.3 |
| 206331 | 74.45 | ND |
| 206401 | 57.4 | ND |
| 205477 | 33.3 | 16.48 |
| 205404 | 20.5 | 16.95 |

Example 3

This example describes further compounds useful in the inhibition of arboviruses.

TABLE 4

| | Activity of Compounds | |
|---|---|---|
| CCG Number | 50 μM (% control) Luc | IC$_{50}$ (μM) |
| 205431 | 48.4 | >100 |
| 205470 | 51.8 | ND |
| 205471 | 60.9 | ND |
| 205473 | 33.9 | ND |
| 205474 | 57.1 | ND |
| 206382 | 25.8 | 0.53 |
| 206549 | 36.9 | 1.7 |
| 206550 | 47.4 | 7.1 |
| 206447 | 46.8 | 60.7 |
| 206485 | 39.4 | 17.1 |
| 206500 | 0 | 6.5 |
| 206501 | 0 | 8.9 |
| 206499 | 0 | ND |
| 206502 | 39.1 | 40.6 |
| 206503 | 28.2 | 25.1 |
| 206486 | 0 | 6.1 |
| 206381 | 9.9 | 0.68 |
| 206586 | 69.5 | ND |
| 205476 | 6.5 | 9.8 |
| 206327 | 33.3 | 11.5 |

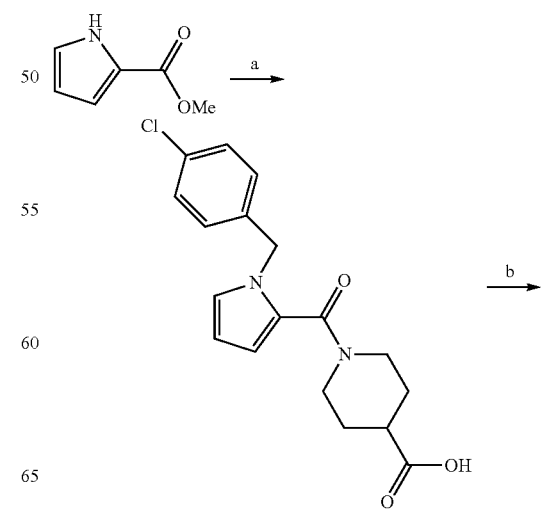

121

-continued

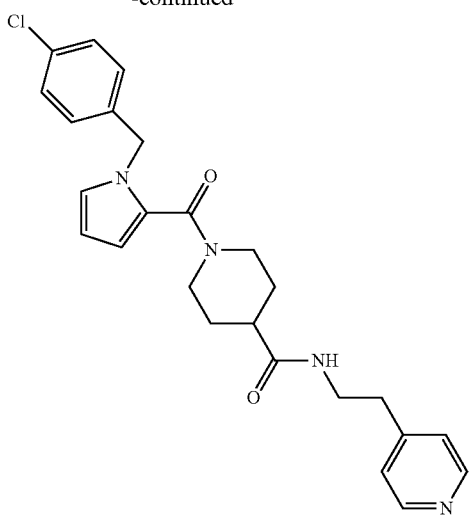

Reagents and conditions: (a) see example 1 (b) piperidinylethylamine, EDC, HOBt, DIPEA, DMF, rt, 18.5 h.

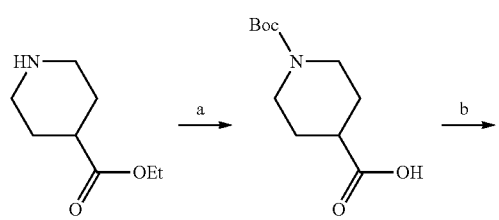

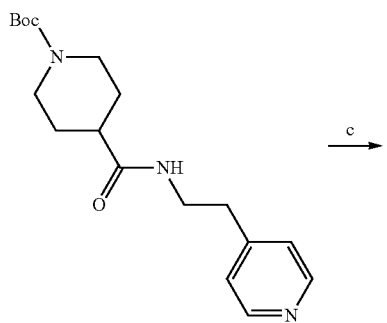

Reagents and conditions: (a) From PCT Int. Appl., 2010027236, 11 Mar. 2010; (b) pyridylethylamine, DIPEA, EDC, HOBT, DCM, rt, 17 h; (c) HCl/dioxane, Et₂O, rt, 30 min.

122

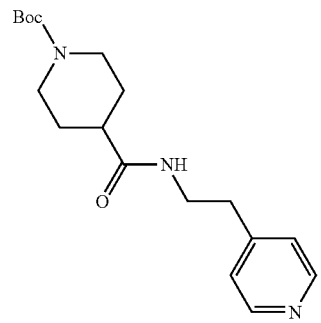 [SMILES: CC(C)(C)OC(=O)N1CCC(C(=O)NCCc2ccncc2)CC1]

tert-butyl 4-((2-(pyridin-4-yl)ethyl)carbamoyl)piperidine-1-carboxylate

The following was added to DCM: 1-(tert-butoxycarbonyl)piperidine-4-carboxylic acid (600 mg, 2.62 mmol), DIPEA (1.37 mL, 7.85 mmol), EDC (552 mg, 2.88 mmol), HOBT (441 mg, 2.88 mmol), and pyridylethylamine (0.34 mL, 2.88 mL). The solution was stirred at rt for 17 h, at which time the DCM was stripped off and 10% aq. sodium carbonate was added. Material was extracted out with EtOAc (3×). The organic extractions were pooled, dried over magnesium sulfate, and concentrated in vacuo. The residue was taken up in a small amount of EtOAc and diethyl ether was added. The precipitate was collected over a filter and washed with diethyl ether to give the title compound as an off-white solid. (Yield: 634 mg, 1.9 mmol, 73%) $^1$H NMR (400 MHz, CDCl$_3$) 8.49, 7.09, 5.67-5.54, 4.10, 3.52, 2.81, 2.68, 2.14, 1.81-1.66, 1.56, 1.43

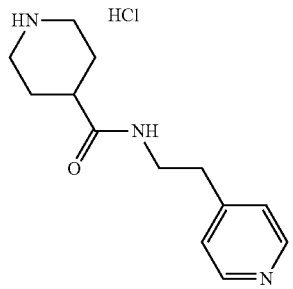 [SMILES: Cl ; O=C(NCCc1ccncc1)C1CCNCC1]

N-(2-(pyridin-4-yl)ethyl)piperidine-4-carboxamide hydrochloride

The boc-protected amine tert-butyl 4-((2-(pyridin-4-yl)ethyl)carbamoyl)piperidine-1-carboxylate (575 mg, 1.72 mmol) was suspended in diethyl ether at rt, and 4M HCl in dioxane (6 mL, 24 mmol) was added. The mixture was stirred at rt for 30 min, at which time the organic solution was decanted off and the solid material collected and dried in vacuo. The title compound was thus obtained as a tan hydrochloride powder. (Yield: 448 mg, 1.6 mmol, 97%) $^1$H NMR (400 MHz, DMSO-d$_6$) 8.79, 7.89, 3.40, 3.15, 3.00, 2.85-2.70, 2.40-2.28, 1.82-1.58

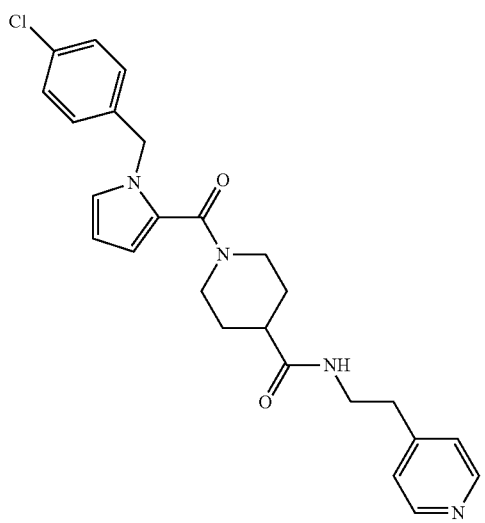 [SMILES: O=C(NCCc1ccncc1)C1CCN(C(=O)c2cccn2Cc2ccc(Cl)cc2)CC1]

1-(1-(4-chlorobenzyl)-1H-pyrrole-2-carbonyl)-N-(2-(pyridin-4-yl)ethyl)piperidine-4-carboxamide (CCG-206381)

The following was added sequentially to DCM: 1-(1-(4-chlorobenzyl)-1H-pyrrole-2-carbonyl)piperidine-4-carboxylic acid (600 mg, 1.73 mmol), TEA (0.725 mL, 5.19 mmol), EDC (365 mg, 1.903 mmol), and HOBt (291 mqg, 1.903 mmol). This was allowed to stir at rt for 30 min, at which time pyridylethylamine (0.227 mL, 1.903 mmol) was added. Stirring continued for 18 h. At this time, the DCM and TEA were stripped off, and the residue was taken up in EtOAc and washed with 10% aqueous sodium carbonate (3×). The organic phase was collected, dried over magnesium sulfate, and concentrated in vacuo. The resulting solid/oil mixture was recrystallized from EtOAc to afford the title compound as small, white crystals. (Yield: 586 mg, 1.29 mmol, 75%) $^1$H NMR (400 MHz, CDCl$_3$) 8.50, 7.21, 7.09, 7.02, 6.78, 6.30, 6.11, 5.55-5.42, 5.25, 4.32, 3.52, 2.87-2.71, 2.28-2.10, 1.72-1.65, 1.42-1.25

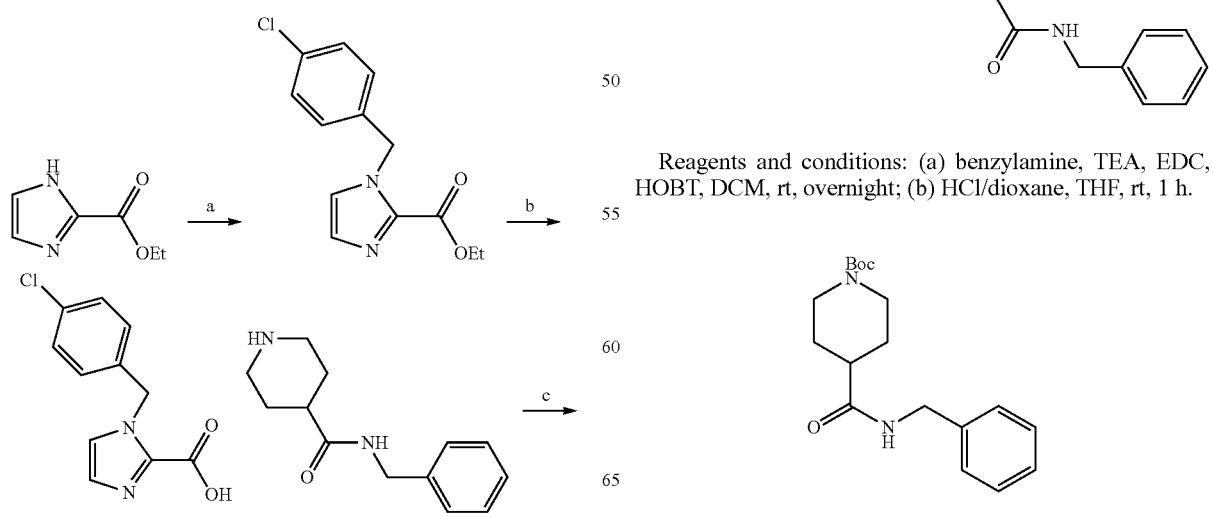

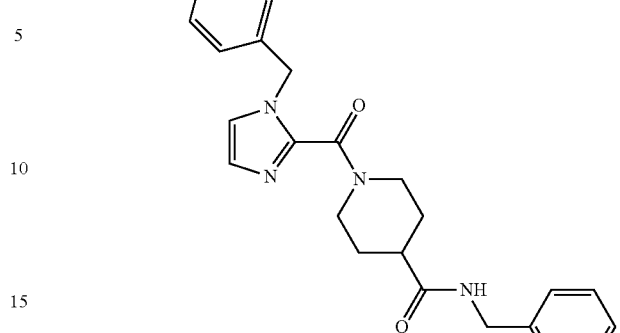

Reagents and conditions: (a) p-chlorobenzylchloride, Na$_2$CO$_3$, DMF, rt, 24 h; (b) 10% aq. NaOH, EtOH, rt, 15 h; (c) N-benzylpiperidine-4-carboxamide, DIPEA, EDC, HOBt, DCM, rt, 24 h.

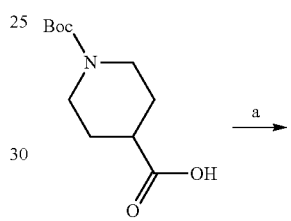

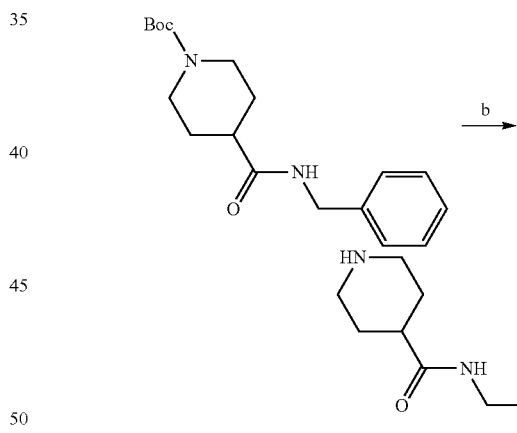

Reagents and conditions: (a) benzylamine, TEA, EDC, HOBT, DCM, rt, overnight; (b) HCl/dioxane, THF, rt, 1 h.

tert-butyl 4-(benzylcarbamoyl)piperidine-1-carboxylate 1-(tert-butoxycarbonyl)piperidine-4-carboxylic acid (10.41 g, 45.4 mmol), HOBT (13.91 g, 91 mmol), and EDCI (17.41 g, 91 mmol) were dissolved in DCM (Volume: 150 ml). The reaction was stirred for twenty minutes before benzylamine (9.92 ml, 91 mmol) and triethylamine (18.99 ml, 136 mmol) were added. The reaction was allowed to overnight. The reaction was diluted with water and ethyl acetate. The organic layer was washed with saturated sodium bicarbonate solution, dried over magnesium sulfate, filtered and concentrated. The crude material was purified via column chromatography using 0-50% ethyl acetate:hexanes to obtain a white solid. (Yield: 6.9 g, white solid) $^1$H-NMR (400 MHz, DMSO-$d_6$) 8.32, 7.329-7.207, 4.25, 3.96-3.93, 2.72, 2.38-2.32, 1.70-1.67, 1.48-1.37

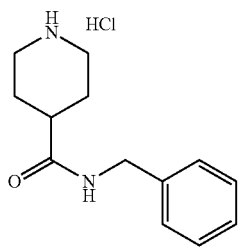 [SMILES: Cl ; O=C(NCc1ccccc1)C1CCNCC1]

N-benzylpiperidine-4-carboxamide hydrochloride tert-butyl 4-(benzylcarbamoyl)piperidine-1-carboxylate (95 mg, 0.298 mmol) was dissolved in anhydrous THF (3 mL), and 4M HCl/dioxane (1 mL, 4.0 mmol) was added at rt. The solution was allowed to stir for 1 h, at which time the resulting precipitate was collected over a filter. Residual mineral acid was removed in vacuo, and the material was used directly in the next reaction without further characterization. (Yield: 76 mg, 0.298 mmol, 100%)

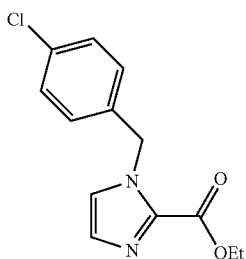 [SMILES: CCOC(=O)c1nccn1Cc1ccc(Cl)cc1]

ethyl 1-(4-chlorobenzyl)-1H-imidazole-2-carboxylate

Ethyl 1H-imidazole-2-carboxylate (4 g, 28.5 mmol), p-chlorobenzylchloride (4.38 mL, 34.3 mmol), and sodium carbonate (3.63 g, 34.3 mmol), was dissolved in DMF (8 mL). The solution was stirred at rt for 24 h, at which time water was added and material was extracted with EtOAc. The organic phase was collected, dried over magnesium sulfate, and decanted. Purification accomplished via silica gel flash chromatography (150 g silica, 10% EtOAc/Hexanes to 80% EtOAc/Hexanes.) The title compound was obtained as a clear, yellow-tinted oil. (Yield: 7.28 g, 27.5 mmol, 96%) $^1$H NMR (400 MHz, CDCl$_3$) 7.25, 7.15, 7.10-7.00, 5.55, 4.34, 1.36

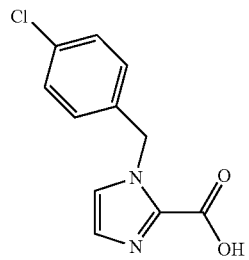 [SMILES: O=C(O)c1nccn1Cc1ccc(Cl)cc1]

1-(4-chlorobenzyl)-1H-imidazole-2-carboxylic acid

Ethyl 1-(4-chlorobenzyl)-1H-imidazole-2-carboxylate (7.28 g, 27.5 mmol), was dissolved in EtOH (10 mL) and 10% aq. NaOH (20 mL) and stirred at rt for 15 h. The solvent was then stripped off, water was added, and the solution acidified with HCl. The resulting precipitate was collected over a filter and washed with 1M HCl and dried to afford the title compound as a white powder without further characterization. (Yield: 6.506 g, 27.5 mmol, 100%)

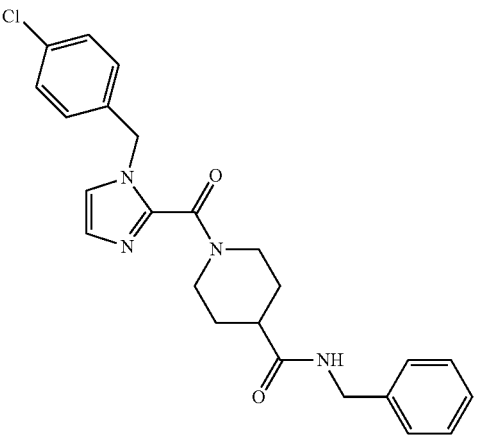 [SMILES: O=C(NCc1ccccc1)C1CCN(C(=O)c2nccn2Cc2ccc(Cl)cc2)CC1]

N-benzyl-1-(1-(4-chlorobenzyl)-1H-imidazole-2-carbonyl)piperidine-4-carboxamide (CCG-206586)

The following was added sequentially to DMF: 1-(4-chlorobenzyl)-1H-imidazole-2-carboxylic acid (71 mg, 0.298 mmol), DIPEA (0.16 mL, 0.894 mmol), EDC (69 mg, 0.358 mmol), and HOBT (55 mg, 0.358 mmol). This was allowed to stir at rt for 30 min, at which time N-benzylpiperidine-4-carboxamide hydrochloride (76 mg, 0.298 mmol) was added and stirring continued at rt for 14 h. Addition of water caused precipitation, which was collected over a filter and washed with water and small amount of diethyl ether and EtOAc to give the title compound as a white solid. (Yield: 37 mg, 0.085 mmol, 28%) $^1$H NMR (400 MHz, CDCl$_3$) 7.34-7.23, 7.13, 7.11, 7.04, 6.93, 5.79-5.65, 5.36, 4.63, 4.43, 3.14, 2.82, 2.42-2.32, 1.95, 1.83, 1.70-1.59

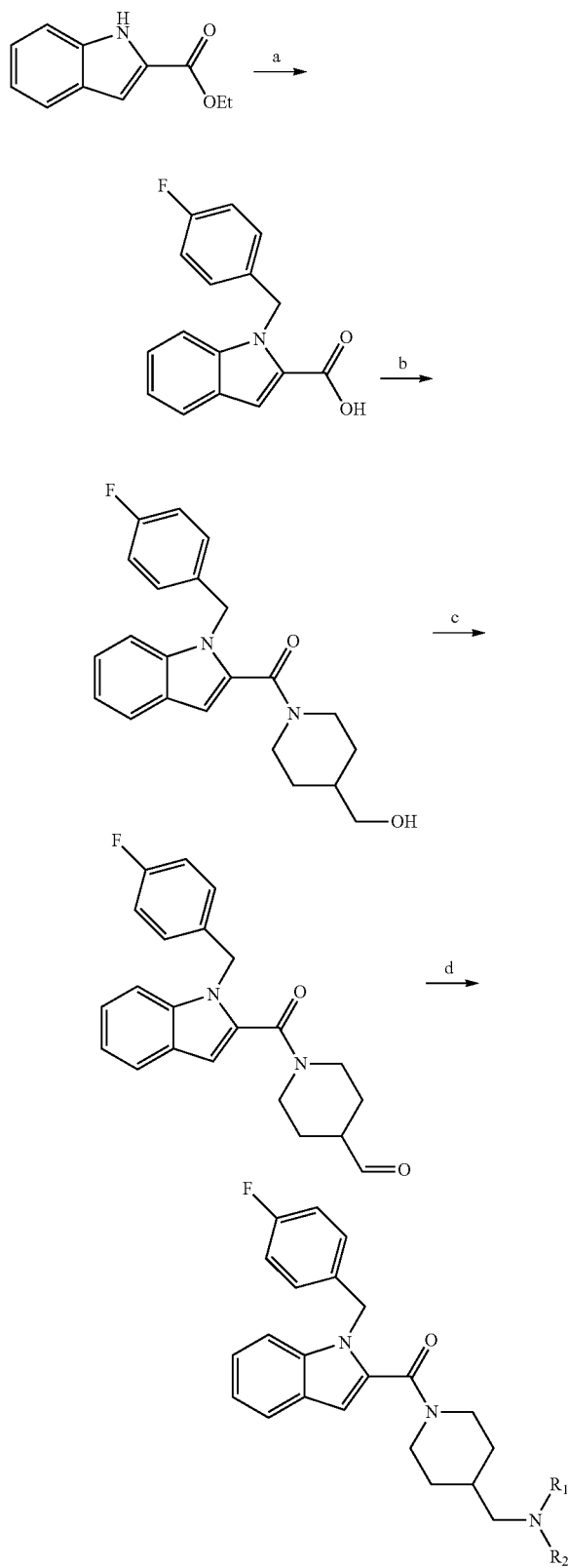
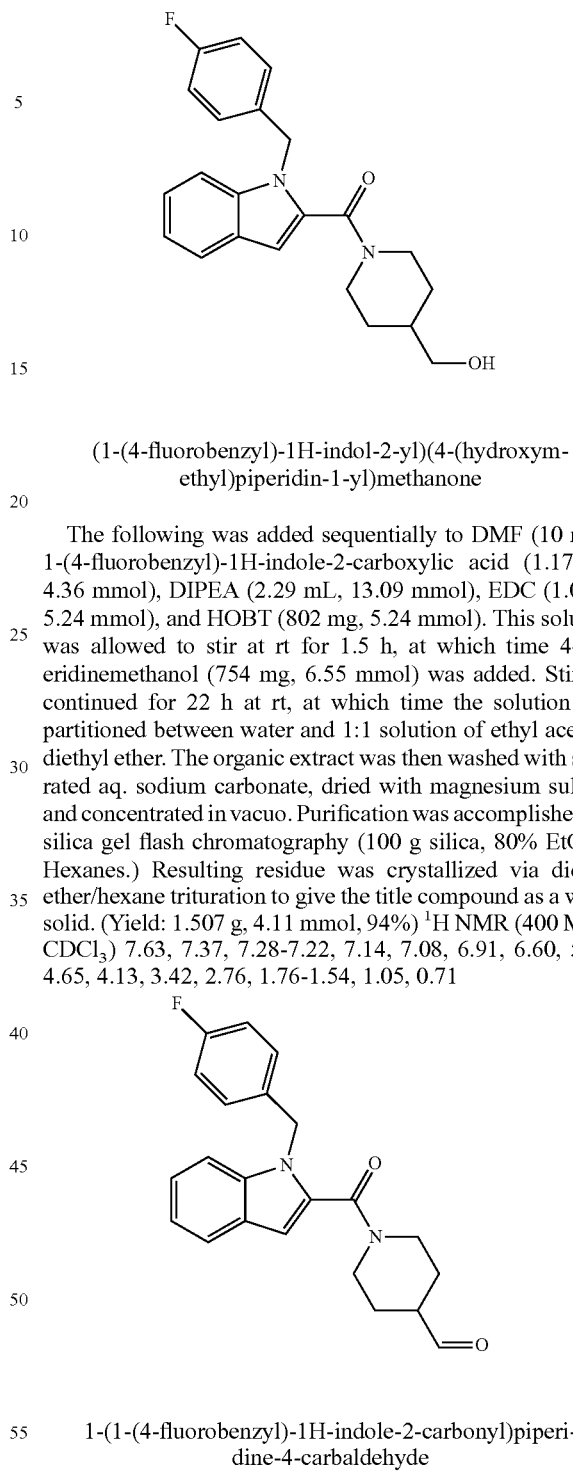

Reagents and conditions: (a) see example 1 (b) 4-(hydroxymethyl)piperidine, EDC, HOBt, DIPEA, DMF, rt, ~24 h; (c) (COCl)$_2$, DMSO, TEA, DCM, −78° C. to 0° C., 2 h; (d) amine, Na(CN)BH$_3$, EtOH, AcOH, rt, ~24 h.

(1-(4-fluorobenzyl)-1H-indol-2-yl)(4-(hydroxymethyl)piperidin-1-yl)methanone

The following was added sequentially to DMF (10 mL): 1-(4-fluorobenzyl)-1H-indole-2-carboxylic acid (1.175 g, 4.36 mmol), DIPEA (2.29 mL, 13.09 mmol), EDC (1.00 g, 5.24 mmol), and HOBT (802 mg, 5.24 mmol). This solution was allowed to stir at rt for 1.5 h, at which time 4-piperidinemethanol (754 mg, 6.55 mmol) was added. Stirring continued for 22 h at rt, at which time the solution was partitioned between water and 1:1 solution of ethyl acetate: diethyl ether. The organic extract was then washed with saturated aq. sodium carbonate, dried with magnesium sulfate, and concentrated in vacuo. Purification was accomplished via silica gel flash chromatography (100 g silica, 80% EtOAc/Hexanes.) Resulting residue was crystallized via diethyl ether/hexane trituration to give the title compound as a white solid. (Yield: 1.507 g, 4.11 mmol, 94%) $^1$H NMR (400 MHz, CDCl$_3$) 7.63, 7.37, 7.28-7.22, 7.14, 7.08, 6.91, 6.60, 5.46, 4.65, 4.13, 3.42, 2.76, 1.76-1.54, 1.05, 0.71

1-(1-(4-fluorobenzyl)-1H-indole-2-carbonyl)piperidine-4-carbaldehyde

The alcohol (1-(4-fluorobenzyl)-1H-indol-2-yl)(4-(hydroxymethyl)piperidin-1-yl)methanone (100 mg, 0.273 mmol) was dissolved in DCM (2 mL) at rt. The solution was chilled in an acetone/dry ice bath under nitrogen, and DMSO (48 μL, 0.682 mmol) and oxalylchloride (48 μL, 0.546 mmol) were added. The solution was stirred under these conditions for 30 min, at which time TEA (190 μL, 1.365 mmol) was slowly added dropwise, and stirring continued for 30 min. At this time, EtOAC and 0.1 M HCl was added to the cold solution. The organic phase was collected and washed again with 0.1 M HCl, dried over magnesium sulfate, and concentrated. Purification accomplished via silica gel flash chromatography (30 g silica, 90% EtOAc/Hexanes.) Crystallized from DCM. (Yield: 66 mg, 0.181 mmol, 66%) $^1$H NMR (400 MHz, CDCl$_3$) 9.60, 7.63, 7.38, 7.28, 7.14, 7.10-7.05, 6.95-6.89, 6.61, 5.46, 5.38-5.25, 4.17, 3.08, 2.79-2.44, 1.97-1.56

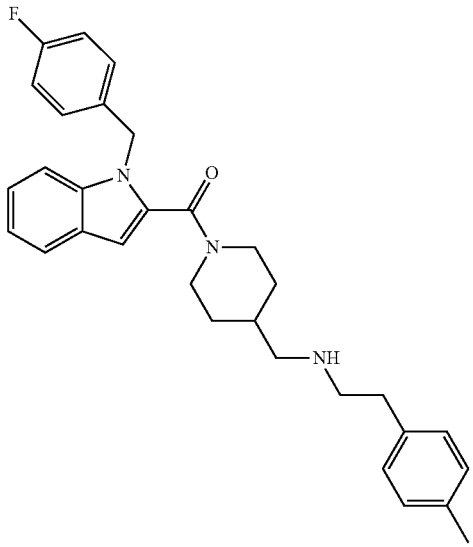 [SMILES: Cc1ccc(CCNCC2CCN(C(=O)c3cc4ccccc4n3Cc3ccc(F)cc3)CC2)cc1]

(1-(4-fluorobenzyl)-1H-indol-2-yl)(4-(((4-methylphenethyl)amino)methyl)piperidin-1-yl)methanone (CCG-206486)

1-(1-(4-fluorobenzyl)-1H-indole-2-carbonyl)piperidine-4-carbaldehyde (46 mg, 0.126 mmol) was dissolved in THF (2 mL) and 2-(p-tolyl)ethanamine (0.030 mL, 0.189 mmol) was added. The solution was stirred at rt for 10 h, at which time the THF was removed in vacuo and the residue dissolved in EtOH (5 mL), and sodium cyanoborohydride (24 mg, 0.349 mmol) and a catalytic drop of glacial acetic acid were added. Stirring was permitted for 14 h, at which time the solvent was removed in vacuo, the residue was taken up in EtOAc. The organic phase was washed with 10% aq. sodium carbonate, dried over magnesium sulfate, and concentrated. Purification was accomplished via silica gel flash chromatography (30 g silica gel, 5:95 7M methanolic ammonia:ethyl acetate.) The title compound was obtained as a yellow oil. (Yield: 26 mg, 0.054 mmol, 43%) $^1$H NMR (400 MHz, CDCl$_3$) 7.62, 7.36, 7.29-7.20, 7.17-7.07, 6.90, 6.58, 5.46, 4.62, 4.08, 2.89-2.65, 2.42, 2.31, 1.60, 1.01, 0.64

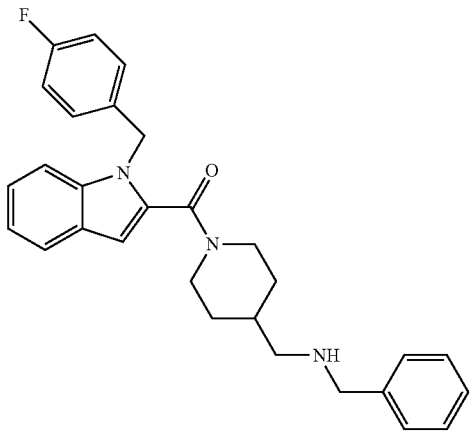 [SMILES: O=C(c1cc2ccccc2n1Cc1ccc(F)cc1)N1CCC(CNCc2ccccc2)CC1]

(4-((benzylamino)methyl)piperidin-1-yl)(1-(4-fluorobenzyl)-1H-indol-2-yl)methanone (CCG-206500)

1-(1-(4-fluorobenzyl)-1H-indole-2-carbonyl)piperidine-4-carbaldehyde (52 mg, 0.143 mmol) was dissolved in THF (2 mL) and benzylamine (0.025 mL, 0.285 mmol) was added. The solution was stirred at rt for 10 h, at which time the THF was removed in vacuo and the residue dissolved in EtOH (5 mL), and sodium cyanoborohydride (18 mg, 0.285 mmol) and a catalytic drop of glacial acetic acid were added. Stirring was permitted for 14 h, at which time the solvent was removed in vacuo, the residue was taken up in EtOAc. The organic phase was washed with 10% aq. sodium carbonate, dried over magnesium sulfate, and concentrated. Purification was accomplished via silica gel flash chromatography (30 g silica gel, 5:95 7M methanolic ammonia:ethyl acetate.) The title compound was obtained as a yellow oil. (Yield: 23 mg, 0.050 mmol, 40%) $^1$H NMR (400 MHz, CDCl$_3$) 7.63, 7.37-7.23, 7.14, 7.12-7.02, 6.89, 6.59, 5.46, 4.62, 4.09, 3.76, 2.75, 2.44, 1.98-0.49

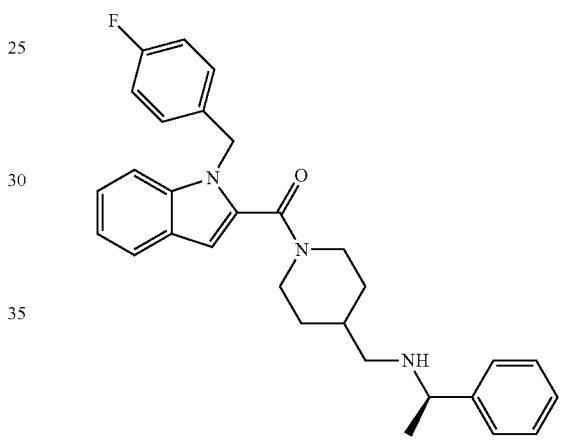

(R)-(1-(4-fluorobenzyl)-1H-indol-2-yl)(4-(((1-phenylethyl)amino)methyl)piperidin-1-yl)methanone (CCG-206499)

1-(1-(4-fluorobenzyl)-1H-indole-2-carbonyl)piperidine-4-carbaldehyde (91 mg, 0.250 mmol) was dissolved in THF (4 mL) and (R)-α-methylbenzylamine (0.048 mL, 0.375 mmol) was added. The solution was stirred at rt for 10 h, at which time the THF was removed in vacuo and the residue dissolved in EtOH (5 mL), and sodium cyanoborohydride (47 mg, 0.749 mmol) and a catalytic drop of glacial acetic acid were added. Stirring was permitted for 15 h, at which time the solvent was removed in vacuo, the residue was taken up in EtOAc. The organic phase was washed with 10% aq. sodium carbonate, dried over magnesium sulfate, and concentrated. Purification was accomplished via silica gel flash chromatography (30 g silica gel, 5:95 7M methanolic ammonia:ethyl acetate.) The title compound was obtained as a yellow oil. (Yield: 52 mg, 0.111 mmol, 44%) $^1$H NMR (400 MHz, CDCl$_3$) 7.62, 7.39-7.22, 7.14, 7.07-6.99, 6.89-6.80, 6.57, 5.41, 4.56, 4.02, 3.76, 2.73, 2.36-2.18, 1.60, 1.39, 0.97, 0.52

(4-((benzyl(methyl)amino)methyl)piperidin-1-yl)(1-(4-fluorobenzyl)-1H-indol-2-yl)methanone (CCG-206503)

1-(1-(4-fluorobenzyl)-1H-indole-2-carbonyl)piperidine-4-carbaldehyde (86 mg, 0.236 mmol) was dissolved in EtOH (5 mL) and N-methylbenzylamine (0.027 mL, 0.283 mmol), sodium cyanoborohydride (30 mg, 0.472 mmol), and a catalytic drop of glacial acetic acid were added. Stirring was permitted for 14 h, at which time the solvent was removed in vacuo, the residue was taken up in EtOAc. The organic phase was washed with 10% aq. sodium carbonate, dried over magnesium sulfate, and concentrated. Purification was accomplished via silica gel flash chromatography (30 g silica gel, 100% EtOAc.) The title compound was obtained as an oil. (Yield: 23 mg, 0.049 mmol, 20%) $^1$H NMR (400 MHz, CDCl$_3$) 7.62, 7.37-7.23, 7.14, 7.08-7.02, 6.82, 6.57, 5.45, 4.60, 4.04, 3.44, 2.75, 2.16, 2.10, 1.83-1.59, 0.91, 0.51

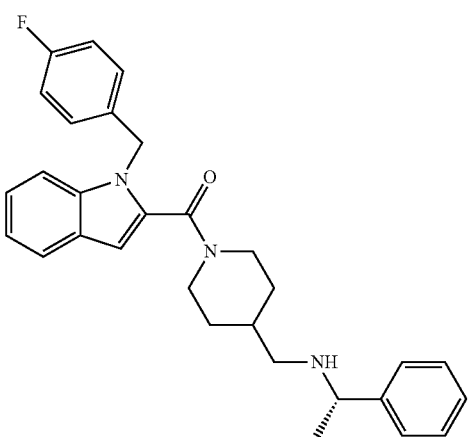 [SMILES: C[C@H](NCC1CCN(C(=O)c2cc3ccccc3n2Cc2ccc(F)cc2)CC1)c1ccccc1]

(S)-(1-(4-fluorobenzyl)-1H-indol-2-yl)(4-(((1-phenylethyl)amino)methyl)piperidin-1-yl)methanone (CCG-206501)

1-(1-(4-fluorobenzyl)-1H-indole-2-carbonyl)piperidine-4-carbaldehyde (35 mg, 0.096 mmol) was dissolved in THF (2 mL) and (S)-α-methylbenzylamine (0.013 mL, 0.115 mmol) was added. The solution was stirred at rt for 10 h, at which time the THF was removed in vacuo and the residue dissolved in EtOH (5 mL), and sodium cyanoborohydride (13 mg, 0.192 mmol) and a catalytic drop of glacial acetic acid were added. Stirring was permitted for 14 h, at which time the solvent was removed in vacuo, the residue was taken up in EtOAc. The organic phase was washed with 10% aq. sodium carbonate, dried over magnesium sulfate, and concentrated. Purification was accomplished via silica gel flash chromatography (30 g silica gel, 5:95 7M methanolic ammonia:ethyl acetate.) The title compound was obtained as a yellow oil. (Yield: 21 mg, 0.045 mmol, 47%) $^1$H NMR (400 MHz, CDCl$_3$) 7.62, 7.39-7.23, 7.14, 7.09-7.02, 6.86, 6.57, 5.45, 4.59, 4.06, 3.76-3.63, 2.74, 2.39-2.15, 1.76-1.52, 1.33, 0.98, 0.63

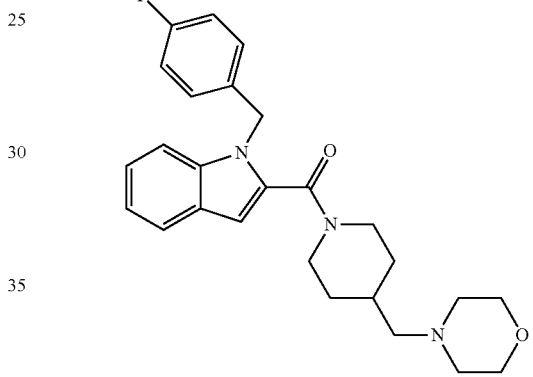

(1-(4-fluorobenzyl)-1H-indol-2-yl)(4-(morpholinomethyl)piperidin-1-yl)methanone (CCG-206502)

1-(1-(4-fluorobenzyl)-1H-indole-2-carbonyl)piperidine-4-carbaldehyde (52 mg, 0.143 mmol) was dissolved in EtOH (5 mL) and morpholine (0.025 mL, 0.285 mmol), sodium cyanoborohydride (18 mg, 0.285 mmol), and a catalytic drop of glacial acetic acid were added. Stirring was permitted for 13 h, at which time the solvent was removed in vacuo, the residue was taken up in EtOAc. The organic phase was washed with 10% aq. sodium carbonate, dried over magnesium sulfate, and concentrated. Purification was accomplished via silica gel flash chromatography (30 g silica gel, 100% EtOAc.) The title compound was obtained as an oil. (Yield: 15 mg, 0.034 mmol, 24%) $^1$H NMR (400 MHz, CDCl$_3$) 7.63, 7.37, 7.27-7.24, 7.14, 7.11-7.04, 6.91, 6.59, 5.47, 4.62, 4.09, 3.67, 2.74, 2.36, 2.08, 1.63, 0.96, 0.61

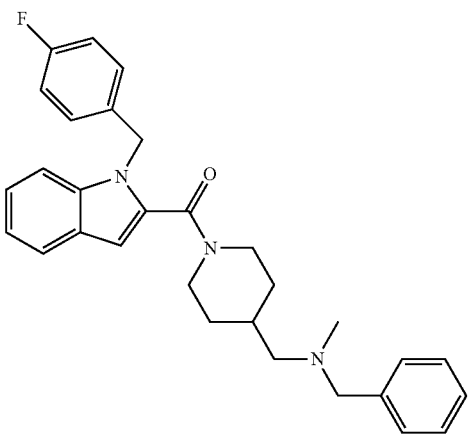 [SMILES: CN(Cc1ccccc1)CC1CCN(C(=O)c2cc3ccccc3n2Cc2ccc(F)cc2)CC1]

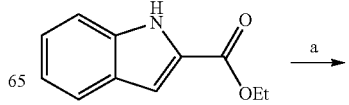

-continued

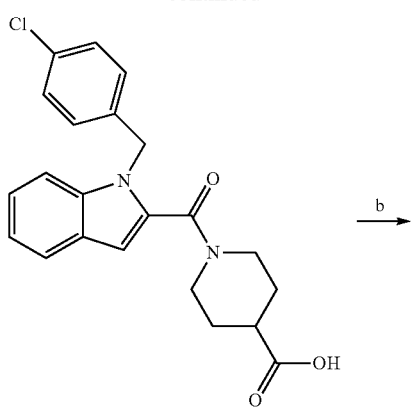

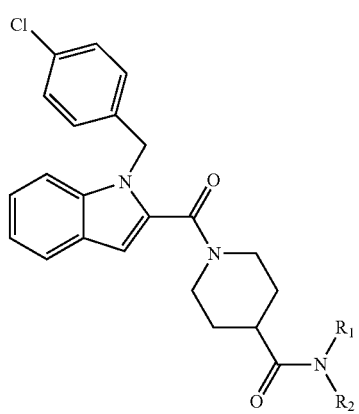

Reagents and conditions: (a) see example 1 (b) amine, EDC, HOBt, DIPEA, DMF, rt, ~24 h.

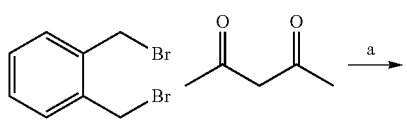

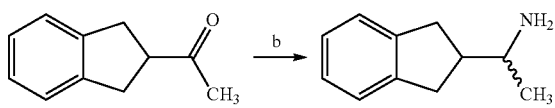

Reagents and conditions: (a) From Synthesis (1995), (2), 139-40; (b) 7M NH₃/MeOH, NaBH₄, rt, 16 h.

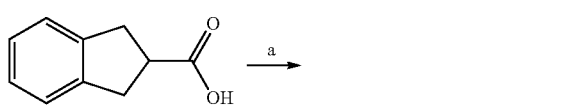

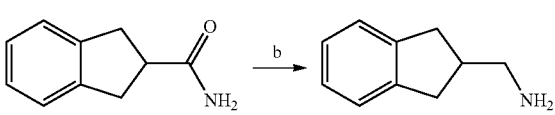

Reagents and conditions: (a) HMDS, HATU, DIPEA, DMF, rt, 20 h. (b) LAH, THF, rt, 8 h.

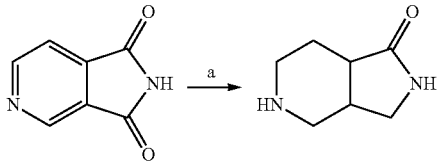 [SMILES: O=C1NC(=O)c2cnccc21 ; O=C1NCC2CNCCC12]

Reagents and conditions: (a) From Patent WO 2005/103003.

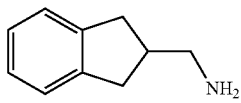

2,3-dihydro-1H-indene-2-carboxamide 2-indancarboxylic acid (1.4 g, 8.63 mmol) was dissolved in anhydrous DMF (20 mL), and the following was added sequentially: DIPEA (3.02 mL, 17.26 mmol), HATU (3.94 g, 10.36 mmol), and HMDS (2.17 mL, 10.36 mmol) after 30 min of stirring at rt. After stirring for 20 h at rt, the solution was taken up in EtOAc and washed with 0.5M HCl (3×), water (3×), and 10% aq. sodium carbonate (3×). The organic phase was collected and dried over magnesium sulfate, and concentrated in vacuo. The solid residue was recrystallized from EtOH to afford the title compound as sharp, colorless crystals. (Yield: 861 mg, 5.06 mmol, 59%) $^1$H NMR (400 MHz, CDCl₃) 7.34-7.12, 5.52, 3.41-3.08

(2,3-dihydro-1H-inden-2-yl)methanamine 2,3-dihydro-1H-indene-2-carboxamide (55 mg, 0.341 mmol) was added to anhydrous THF (8 mL), and cooled in an ice bath under nitrogen. LAH (0.34 mL, 0.341 mmol, 1M THF soln) was added under nitrogen, and the reaction was allowed to warm to rt and stir for 7 h. At this time, the reaction was quenched by the Fieser method and the precipitate removed over a filter. The filtrate was collected and concentrated in vacuo, and then taken up in a small amount of THF. 4M HCl/dioxane was added, the solvent removed in vacuo, and the residue sonicated in diethyl ether to afford the hydrochloride salt. Title compound was not purified, but taken directly into subsequent reactions without characterization.

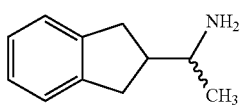

1-(2,3-dihydro-1H-inden-2-yl)ethanamine 1-(2,3-dihydro-1H-inden-2-yl)ethanone (44 mg, 0.275 mmol) was dissolved in methanol (2 mL), and 7 M methanolic ammonia was added (1 mL, 7 mmol). This was allowed to stir at rt for 4 h, at which time sodium borohydride (31 mg, 0.824 mmol) and a catalytic drop of glacial acetic acid was added. Stirring continued for 14 h at rt, after which time the solvent was removed in vacuo. The residue was taken up in ethyl acetate and washed with a small amount of 10% aqueous sodium carbonate, dried with magnesium sulfate, and concentrated. The residue was then taken on in subsequent reactions without further purification or characterization.

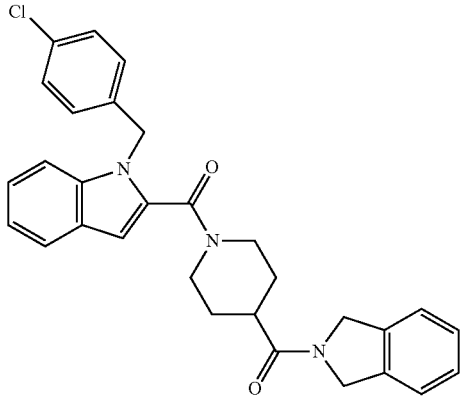 [SMILES: O=C(c1cc2ccccc2n1Cc1ccc(Cl)cc1)N1CCC(C(=O)N2Cc3ccccc3C2)CC1]

(1-(4-chlorobenzyl)-1H-indol-2-yl)(4-(isoindoline-2-carbonyl)piperidin-1-yl)methanone (CCG-205470)

The following was added sequentially to DCM (2 mL): 1-(1-(4-chlorobenzyl)-1H-indole-2-carbonyl)piperidine-4-carboxylic acid (50 mg, 0.126 mmol), DIPEA (0.07 mL, 0.378 mmol), EDC (30 mg, 0.151 mmol), HOBT (24 mg, 0.151 mmol), and isoindoline (0.018 mL, 0.151 mmol). The mixture was stirred for 18 h at rt, at which time the solution diluted with a 1:1 solution of ethyl acetate:diethyl ether and washed with 1M HCl (1×), 10% aq. sodium carbonate (1×) and brine (1×). The organic phase was dried with magnesium sulfate and concentrated in vacuo. The resulting residue was dissolved in EtOAc and precipitated out hexanes, and then collected over a filter and washed with a 10:1 solution of hexanes:ethyl acetate. (Yield: 22 mg, 0.044 mmol, 35%) $^1$H NMR (400 MHz, CDCl$_3$) 7.65, 7.35-7.21, 7.15, 7.05, 6.68, 5.47, 4.77-4.17, 2.97, 2.76-2.64, 1.78, 1.47-1.34, 1.37-1.24, 0.95-0.83

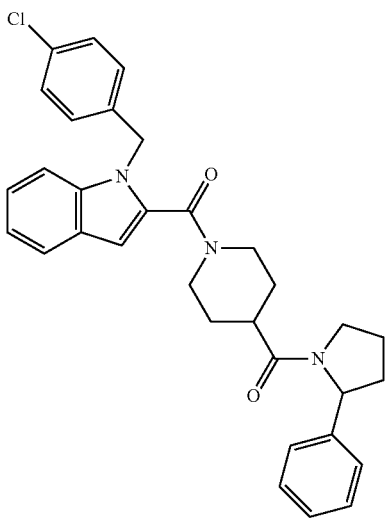 [SMILES: O=C(c1cc2ccccc2n1Cc1ccc(Cl)cc1)N1CCC(C(=O)N2CCCC2c2ccccc2)CC1]

(1-(4-chlorobenzyl)-1H-indol-2-yl)(4-(2-phenylpyrrolidine-1-carbonyl)piperidin-1-yl)methanone (CCG-205473)

The following was added sequentially to DCM (2 mL): 1-(1-(4-chlorobenzyl)-1H-indole-2-carbonyl)piperidine-4-carboxylic acid (50 mg, 0.126 mmol), DIPEA (0.07 mL, 0.378 mmol), EDC (30 mg, 0.151 mmol), HOBT (24 mg, 0.151 mmol), and 2-phenylpyrrolidine (0.023 mL, 0.151 mmol). The mixture was stirred for 18 h at rt, at which time the solution diluted with a 1:1 solution of ethyl acetate:diethyl ether and washed with 1M HCl (1×), 10% aq. sodium carbonate (1×) and brine (1×). The organic phase was dried with magnesium sulfate and concentrated in vacuo. The resulting residue was dissolved in EtOAc and precipitated out hexanes, and then collected over a filter and washed with diethyl ether to give the title compound as a white solid. (Yield: 20 mg, 0.038 mmol, 30%) $^1$H NMR (400 MHz, CDCl$_3$) 7.61, 7.43-7.05, 7.09-6.94, 6.58, 5.41, 5.06-4.82, 4.33, 3.83-3.60, 3.11-2.88, 2.50-2.22, 2.06-1.58, 1.16-0.82

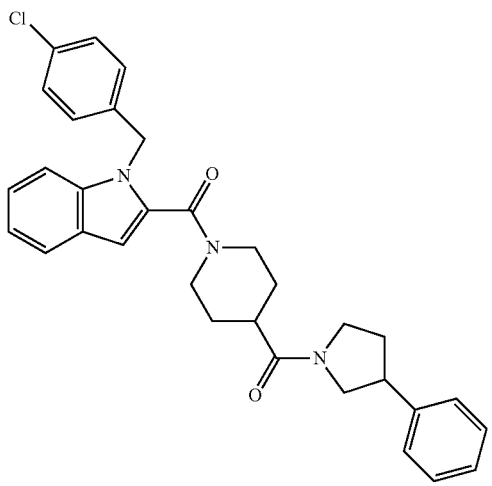 [SMILES: O=C(c1cc2ccccc2n1Cc1ccc(Cl)cc1)N1CCC(C(=O)N2CCC(c3ccccc3)C2)CC1]

(1-(4-chlorobenzyl)-1H-indol-2-yl)(4-(3-phenylpyrrolidine-1-carbonyl)piperidin-1-yl)methanone (CCG-205474)

The following was added sequentially to DCM (2 mL): 1-(1-(4-chlorobenzyl)-1H-indole-2-carbonyl)piperidine-4-carboxylic acid (50 mg, 0.126 mmol), DIPEA (0.07 mL, 0.378 mmol), EDC (30 mg, 0.151 mmol), HOBT (24 mg, 0.151 mmol), and 3-phenylpyrrolidine (0.023 mL, 0.151 mmol). The mixture was stirred for 36 h at rt, at which time the solution diluted with a 1:1 solution of ethyl acetate:diethyl ether and washed with 1M HCl (1×), 10% aq. sodium carbonate (1×) and brine (1×). The organic phase was dried with magnesium sulfate and concentrated in vacuo. The resulting residue was dissolved in EtOAc and precipitated out hexanes, and then collected over a filter and washed with diethyl ether to give the title compound as a slightly yellow solid. (Yield: 21 mg, 0.040 mmol, 32%) $^1$H NMR (400 MHz, CDCl$_3$) 7.66, 7.41-7.17, 7.06, 6.70, 5.50, 4.41, 4.10-3.39, 2.64, 2.36-0.90

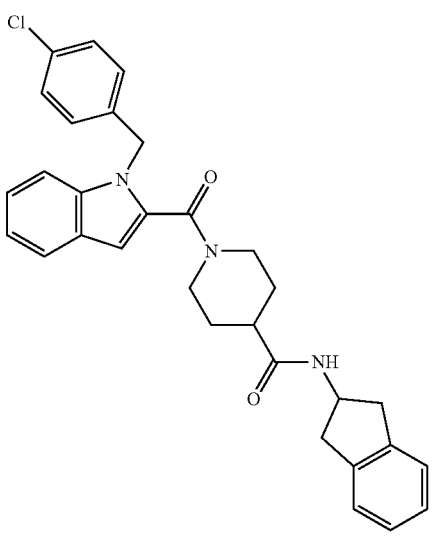 [SMILES: O=C(NC1Cc2ccccc2C1)C1CCN(C(=O)c2cc3ccccc3n2Cc2ccc(Cl)cc2)CC1]

1-(1-(4-chlorobenzyl)-1H-indole-2-carbonyl)-N-(2,
3-dihydro-1H-inden-2-yl)piperidine-4-carboxamide
(CCG-205471)

The following was added sequentially to DCM (2 mL): 1-(1-(4-chlorobenzyl)-1H-indole-2-carbonyl)piperidine-4-carboxylic acid (50 mg, 0.126 mmol), DIPEA (0.07 mL, 0.378 mmol), EDC (30 mg, 0.151 mmol), HOBT (24 mg, 0.151 mmol), and 2-aminoindane (0.020 mL, 0.151 mmol). The mixture was stirred for 36 h at rt, at which time the solution diluted with a 1:1 solution of ethyl acetate:diethyl ether and washed with 1M HCl (1×), 10% aq. sodium carbonate (1×) and brine (1×), which resulted in a precipitate that failed to go into either phase. The precipitate was collected and washed with water and diethyl ether to afford the title compound as a white solid. (Yield: 52 mg, 0.102 mmol, 81%) $^1$H NMR (400 MHz, CDCl$_3$) 7.64, 7.33-7.14, 7.03, 6.64, 5.62, 5.51, 4.76, 4.4, 3.33, 2.84-2.75, 2.21, 1.75

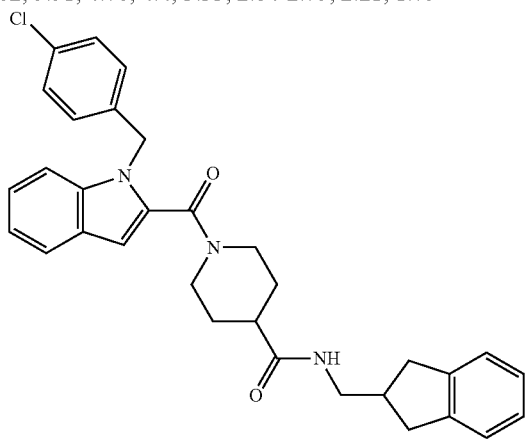

1-(1-(4-chlorobenzyl)-1H-indole-2-carbonyl)-N-((2,
3-dihydro-1H-inden-2-yl)methyl)piperidine-4-carboxamide (CCG-206382)

The following was added sequentially to DCM (8 mL): 1-(1-(4-chlorobenzyl)-1H-indole-2-carbonyl)piperidine-4-carboxylic acid (180 mg, 0.454 mmol), DIPEA (0.317 mL, 1.814 mmol), EDC (96 mg, 0.499 mmol), HOBT (76 mg, 0.499 mmol), and crude (2,3-dihydro-1H-inden-2-yl)methanamine (~105 mg, 0.713 mmol). The mixture was stirred for 18 h at rt, at which time the solution diluted with a 1:1 solution of ethyl acetate:diethyl ether and washed with 1M HCl (1×), 10% aq. sodium carbonate (1×). The organic phase was dried with magnesium sulfate and concentrated in vacuo. Purification was accomplished via silica gel flash chromatography (60 g silica, 50% EtOAc/Hexanes), followed by EtOAc/hexane trituration to give the title compound as a white powder. (Yield: 137 mg, 0.260 mmol, 57%) $^1$H NMR (400 MHz, CDCl$_3$) 7.66, 7.36-7.14, 7.04, 6.65, 5.55-5.40, 4.35, 3.39, 3.15-3.03, 2.88, 2.71-2.65, 2.31-2.19, 1.74, 1.49

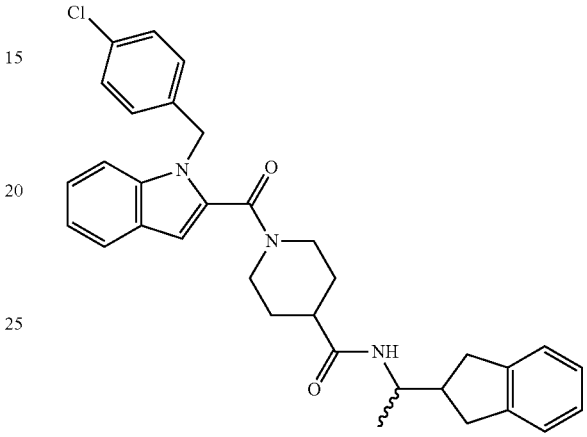

1-(1-(4-chlorobenzyl)-1H-indole-2-carbonyl)-N-(1-
(2,3-dihydro-1H-inden-2-yl)ethyl)piperidine-4-carboxamide (CCG-206549)

The following was added sequentially to DCM (5 mL): 1-(1-(4-chlorobenzyl)-1H-indole-2-carbonyl)piperidine-4-carboxylic acid (109 mg, 0.275 mmol), DIPEA (0.144 mL, 0.825 mmol), EDC (63 mg, 0.330 mmol), HOBT (51 mg, 0.330 mmol), and crude 2-(1-aminoethyl)indane (~44 mg, 0.275 mmol). The mixture was stirred for 16 h at rt, at which time the solution diluted with a 1:1 solution of ethyl acetate:diethyl ether and washed with 1M HCl (1×), 10% aq. sodium carbonate (1×) and brine (1×). The organic phase was dried with magnesium sulfate and concentrated in vacuo. The resulting residue was dissolved in EtOAc and precipitated out hexanes, and then collected over a filter and washed with diethyl ether to give the title compound as a white solid. (Yield: 59 mg, 0.109 mmol, 40%) $^1$H NMR (400 MHz, CDCl$_3$) 7.64, 7.31, 7.27-7.09, 7.02, 6.63, 5.45, 5.24, 4.33, 4.17, 3.00, 2.90-2.58, 2.49, 2.29-2.11, 1.83-1.34, 1.18

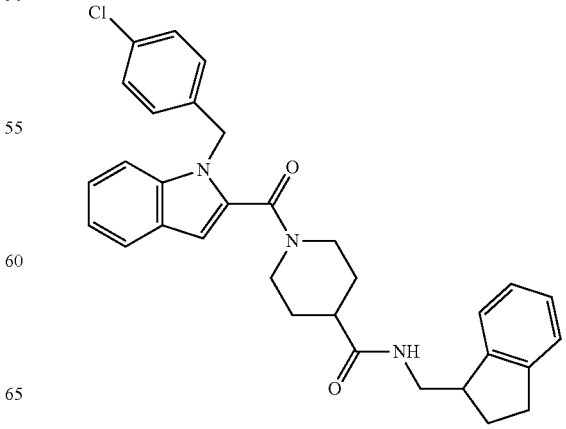

1-(1-(4-chlorobenzyl)-1H-indole-2-carbonyl)-N-((2, 3-dihydro-1H-inden-1-yl)methyl)piperidine-4-carboxamide (CCG-206550)

The following was added sequentially to DCM (6 mL): 1-(1-(4-chlorobenzyl)-1H-indole-2-carbonyl)piperidine-4-carboxylic acid (134 mg, 0.340 mmol), DIPEA (0.178 mL, 1.019 mmol), EDC (78 mg, 0.408 mmol), HOBT (62.4 mg, 0.408 mmol), and 2-indanmethanamine hydrochloride (62 mg, 0.340 mmol). The mixture was stirred for 18 h at rt, at which time the solution diluted with a 1:1 solution of ethyl acetate:diethyl ether and washed with 1M HCl (1×), 10% aq. sodium carbonate (1×) and brine (1×). The organic phase was dried with magnesium sulfate and concentrated in vacuo. The resulting residue was dissolved in EtOAc and precipitated out hexanes, and then collected over a filter and washed with diethyl ether to give the title compound as a white solid. (Yield: 72 mg, 0.137 mmol, 41%) $^1$H NMR (400 MHz, CDCl$_3$) 7.63, 7.32, 7.28-7.11, 7.01, 6.62, 5.45, 5.38, 4.36, 3.70-3.52, 3.51-3.07, 3.06-2.76, 2.30-2.19, 1.86-1.61, 1.49

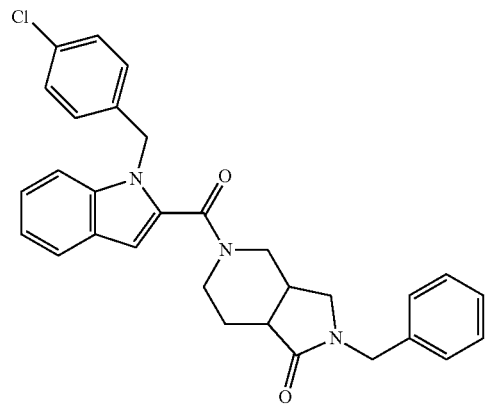

2-benzyl-5-(1-(4-chlorobenzyl)-1H-indole-2-carbonyl)octahydro-1H-pyrrolo[3,4-c]pyridin-1-one (CCG-206485)

5-(1-(4-chlorobenzyl)-1H-indole-2-carbonyl)octahydro-1H-pyrrolo[3,4-c]pyridin-1-one (64 mg, 0.245 mmol) was dissolved in anhydrous DMF (5 mL). NaH (60% oil suspension, 29 mg, 0.735 mmol) was added at rt under nitrogen and stirred for 1 h. Benzylbromide (0.035 mL, 0.294 mmol) was added and stirring continued for 18 h under the same conditions. After this time, the solution was diluted with ethyl acetate and washed with 10% aq. sodium carbonate (2×), dried with magnesium sulfate, and concentrated in vacuo. Purification was done via silica gel flash chromatography (25 g silica, 80% EtOAc/hexanes.) The residue was dissolved in DCM, and rapid solvent removal afforded the title compound as a white powder. (Yield: 56 mg, 0.112 mmol, 72%) $^1$H NMR (400 MHz, CDCl$_3$) 7.69, 7.33-6.99, 5.47, 4.56, 4.38, 4.11, 3.39-3.36, 2.94-2.82, 2.53-2.47, 1.75, 1.39

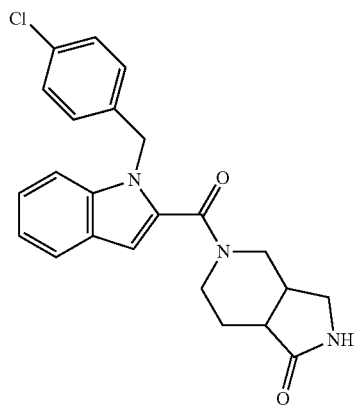 [SMILES: O=C1NCC2CN(C(=O)c3cc4ccccc4n3Cc3ccc(Cl)cc3)CCC12]

5-(1-(4-chlorobenzyl)-1H-indole-2-carbonyl)octahydro-1H-pyrrolo[3,4-c]pyridin-1-one The following was added sequentially to DMF (10 mL): 1-(4-chlorobenzyl)-1H-indole-2-carboxylic acid (250 mg, 0.875 mmol), DIPEA (0.46 mL, 2.64 mmol), EDC (202 mg, 1.050 mmol), and HOBT (162 mg, 1.050 mmol). This solution was allowed to stir at rt for 1 h, at which time crude octahydro-1H-pyrrolo[3,4-c]pyridin-1-one (~123 mg, 0.875 mmol) was added. Stirring continued for 12 h at rt, at which time the solution was partitioned between water and 1:1 solution of ethyl acetate:diethyl ether. The organic extract was then washed with water (1×) and saturated aq. sodium carbonate (1×), dried with magnesium sulfate, and concentrated in vacuo. Purification was accomplished via silica gel flash chromatography (100 g silica, 100% EtOAc.) Resulting residue was crystallized from the in vacuo removal of DCM to give the title compound as a slightly pink solid. (Yield: 200 mg, 0.49 mmol, 56%) $^1$H NMR (400 MHz, CDCl$_3$) 7.72, 7.40-7.24, 7.20, 7.17-7.11, 6.94, 6.31, 5.51, 4.57, 4.30-4.08, 3.59-3.46, 3.39, 3.17-3.02, 2.63, 2.51, 2.02-1.77

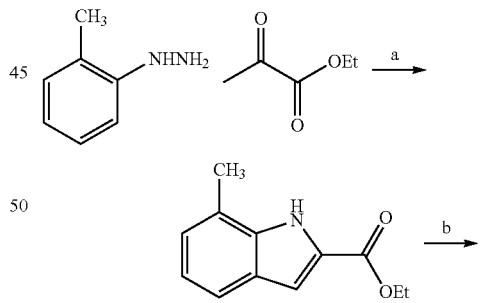

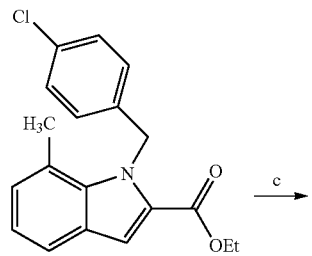

141

-continued

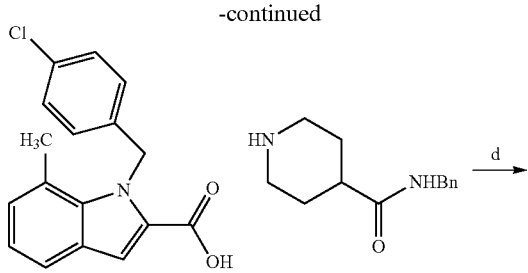 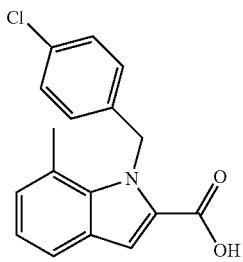

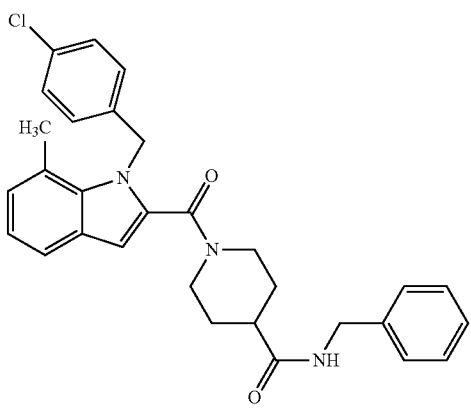

Reagents and conditions: (a) From Medicinal Chemistry (2005), (5), 501-17. (b) $_p$-chlorobenzylchloride, K$_2$CO$_3$, DMF, 60° C., 3 d; (c) 10% KOH, EtOH, 70° C., 4 h; (d) piperidinylbenzylamide, EDC, HOBt, DIPEA, DMF, rt, 18 h.

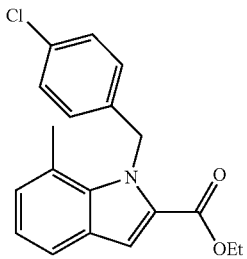 [SMILES: CCOC(=O)c1cc2cccc(C)c2n1Cc1ccc(Cl)cc1]

ethyl 1-(4-chlorobenzyl)-7-methyl-1H-indole-2-carboxylate ethyl 7-methyl-1H-indole-2-carboxylate (500 mg, 2.46 mmol) was dissolved in DMF (20 mL) and granular potassium carbonate (425 mg, 3.08 mmol) and p-chlorobenzylchloride (0.39 mL, 3.08 mmol) were added The mixture was stirred for 3 d at 60° C., after which time the incomplete reaction was terminated by dilution with ethyl acetate and subsequent washing with brine (3×). The organic phase was dried over magnesium sulfate, concentrated, and purified vial silica gel flash chromatography (80 g silica, 40% EtOAc/hexanes.) The title compound was obtained as white crystals. (Yield: 390 mg, 1.19 mmol, 46%) $^1$H NMR (400 MHz, CDCl$_3$) 7.56, 7.41, 7.32-6.96, 6.78, 6.08, 4.31-4.25, 2.54, 1.34

142

1-(4-chlorobenzyl)-7-methyl-1H-indole-2-carboxylic acid ethyl 1-(4-chlorobenzyl)-7-methyl-1H-indole-2-carboxylate (212 mg, 0.647 mmol) was dissolved in EtOH (10 mL) and 10% aq. KOH (10 mL) was added. The reaction stirred for 4 h at 70° C., after which time as much solvent was stripped off as possible. The mostly aqueous mixture was cooled in an ice bath and acidified with concentrate HCl to obtain a precipitate that was collected over a filter and washed with 1M HCl and water. The title compound was not purified or characterized further. (Yield: 182 mg, 0.607 mmol, 94%).

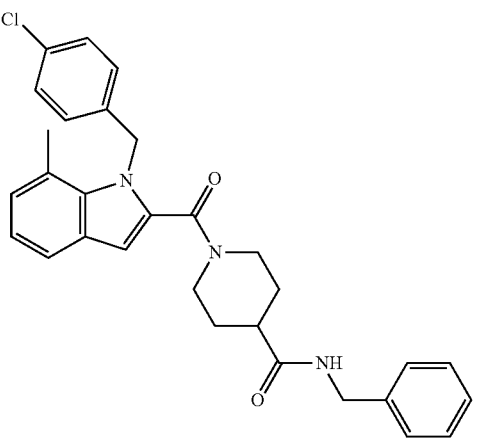 [SMILES: Cc1cccc2cc(C(=O)N3CCC(C(=O)NCc4ccccc4)CC3)n(Cc3ccc(Cl)cc3)c12]

N-benzyl-1-(1-(4-chlorobenzyl)-7-methyl-1H-indole-2-carbonyl)piperidine-4-carboxamide (CCG-206447)

The following was added to sequentially to DMF (2 mL): 1-(4-chlorobenzyl)-7-methyl-1H-indole-2-carboxylic acid (50 mg, 0.167 mmol), DIPEA (0.10 mL, 0.584 mmol), EDC (38 mg, 0.200 mmol), and HOBT (31 mg, 0.200 mmol). This was allowed to stir for 30 min at rt, after which time the crude N-benzylpiperidine-4-carboxamide (~36 mg, 0.20 mmol) was added. The reaction was stirred at rt for 18 h, at which time the reaction was diluted with 1:1 EtOAc:diethyl ether and washed with 10% aq. sodium carbonate (2×), dried over magnesium sulfate, and concentrated. The residue was purified via silica gel flash chromatography (20 g silica, 50% EtOAc/Hexanes) to afford the title compound as a white powder. (Yield: 39 mg, 0.078 mmol, 47%) $^1$H NMR (400 MHz, CDCl$_3$) 7.50, 7.38-7.26, 7.18, 7.05-6.97, 6.81, 6.63, 5.72, 5.66-5.57, 4.70-3.89, 4.44, 2.86-2.66, 2.57, 2.32-2.23, 1.77

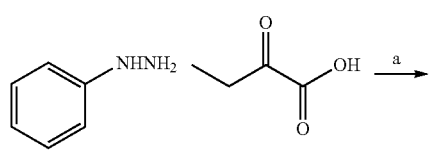

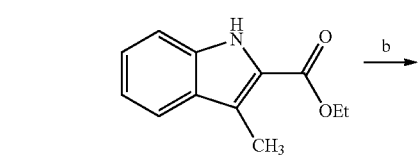

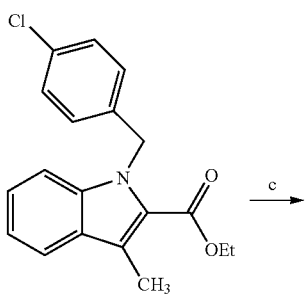

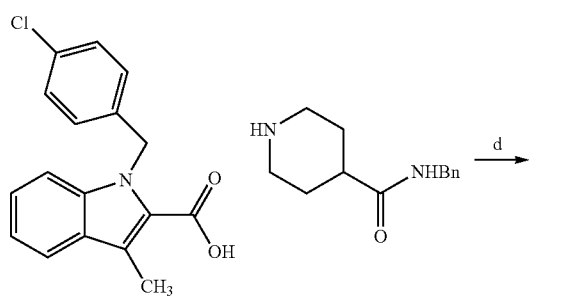

Reagents and conditions: (a) From Patent WO 2007/115315. (b) p-chlorobenzylchloride, K₂CO₃, DMF, 60° C., 14 h; (c) 5M aq. NaOH, THF, 55° C., 18 h; (d) piperidinylbenzylamide, EDC, HOBt, DIPEA, DMF, rt, 18 h.

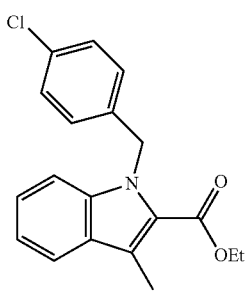 [SMILES: CCOC(=O)c1c(C)c2ccccc2n1Cc1ccc(Cl)cc1]

ethyl 1-(4-chlorobenzyl)-3-methyl-1H-indole-2-carboxylate

Ethyl 3-methyl-1H-indole-2-carboxylate (480 mg, 2.362 mmol) was dissolved in anhydrous DMF (5 mL), followed by the addition of granular potassium carbonate (408 mg, 2.95 mmol) and p-chlorobenzylchloride (0.38 mL, 2.95 mmol). The reaction was allowed to stir at 60° C. for 24 h, after which time the solution was diluted with a 1:1 solution of ethyl acetate:diethyl ether. The organic phase was washed with 10% aqueous sodium carbonate, dried with magnesium sulfate, and concentrated in vacuo. Purification was accomplished via silica gel flash chromatography (60 g silica, 10% EtOAc/hexanes) to give the title compound as a white powder. (Yield: 510 mg, 1.60 mmol, 66%) ¹H NMR (400 MHz, CDCl₃) 7.71, 7.34-7.15, 6.95, 5.73, 4.34, 2.63, 1.36

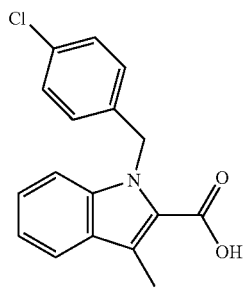 [SMILES: Cc1c(C(=O)O)n(Cc2ccc(Cl)cc2)c2ccccc12]

1-(4-chlorobenzyl)-3-methyl-1H-indole-2-carboxylic acid ethyl 1-(4-chlorobenzyl)-3-methyl-1H-indole-2-carboxylate (480 mg, 1.46 mmol) was dissolved in EtOH (15 mL) and 10% aq. NaOH was added (6 mL). The reaction was allowed to stir at rt for 32 h, at which time as much solvent was stripped off as possible, water was added, and the mixture cooled in an ice bath. The mixture was acidified with concentrated HCl and the precipitate collected over a filter. The title compound was obtained as a white powder that was not purified or characterized further. (Yield: 430 mg, 1.435 mmol, 98%)

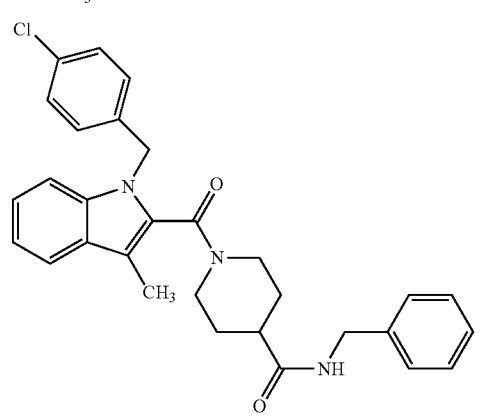

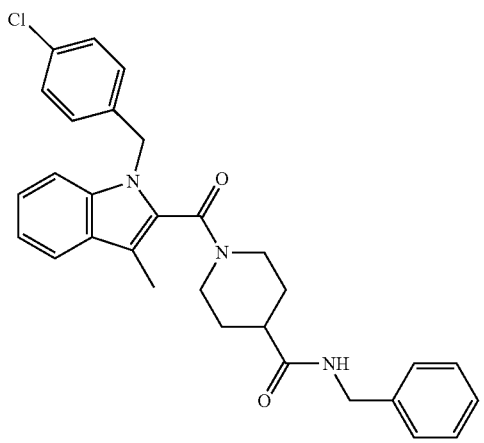 [SMILES: Cc1c(C(=O)N2CCC(C(=O)NCc3ccccc3)CC2)n(Cc2ccc(Cl)cc2)c2ccccc12]

N-benzyl-1-(1-(4-chlorobenzyl)-3-methyl-1H-indole-2-carbonyl)piperidine-4-carboxamide (CCG-205431)

The following was added to sequentially to DMF (3 mL): 1-(4-chlorobenzyl)-3-methyl-1H-indole-2-carboxylic acid (90 mg, 0.315 mmol), DIPEA (0.170 mL, 0.945 mmol), and HATU (144 mg, 0.378 mmol). This was allowed to stir for 30 min at rt, after which time the crude N-benzylpiperidine-4-carboxamide (~70 mg, 0.315 mmol) was added. The reaction was stirred at rt for 17 h, at which time the reaction was diluted with 1:1 EtOAc:diethyl ether and washed with 10% aq. sodium carbonate (2×), dried over magnesium sulfate, and concentrated. The residue was purified via silica gel flash chromatography (20 g silica, 50% EtOAc/Hexanes) to afford the title compound as an oil. Yield: (77 mg, 0.153 mmol, 51%) $^1$H NMR (400 MHz, CDCl$_3$) 7.59, 7.34-7.14, 7.03, 5.73, 5.57, 5.43-5.32, 4.76, 4.43, 3.77-3.64, 3.10, 2.80, 2.19-1.52

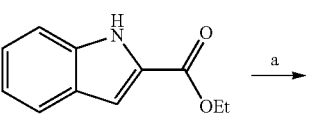

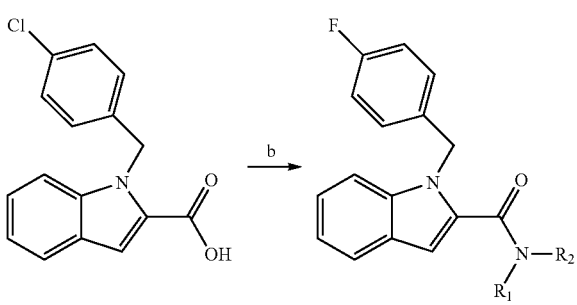

Reagents and conditions: (a) see example 1 (b) amine, EDC, HOBt, DIPEA, DMF, rt, 15-16 h.

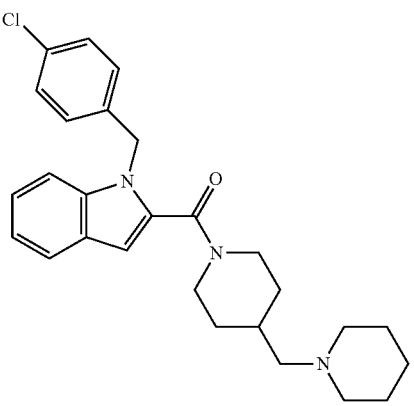 [SMILES: O=C(c1cc2ccccc2n1Cc1ccc(Cl)cc1)N1CCC(CN2CCCCC2)CC1]

(1-(4-chlorobenzyl)-1H-indol-2-yl)(4-(piperidin-1-ylmethyl)piperidin-1-yl)methanone (CCG-205476)

The following was added to DCM (6 mL): 1-(4-chlorobenzyl)-1H-indole-2-carboxylic acid (110 mg, 0.380 mmol), DIPEA (0.5 mL, 2.95 mmol), EDC (100 mg, 0.506 mmol), HOBT (80 mg, 0.506 mmol), and 1-(piperidin-4-ylmethyl)piperidine (150 mg, 0.843 mmol). The solution was stirred at rt for 15 h, at which time the solution was diluted with a 1:1 solution of ethyl acetate:diethyl ether and washed with water (1×), 10% aq. sodium carbonate (1×), and brine (1×). The organic phase was then dried over magnesium sulfate and concentrated in vacuo. The resulting residue was purified via silica gel flash chromatography (40 g silica, 10% EtOAc/hexanes) and triturated with ethyl acetate and hexanes to afford the title compound as a white powder. (Yield: 109 mg, 0.242 mmol, 70%) $^1$H NMR (400 MHz, CDCl$_3$) δ 7.63, 7.35, 7.23-7.12, 7.03, 6.59, 5.46, 4.59, 4.09, 2.75, 2.34, 2.08, 1.71-1.46, 1.46-1.36

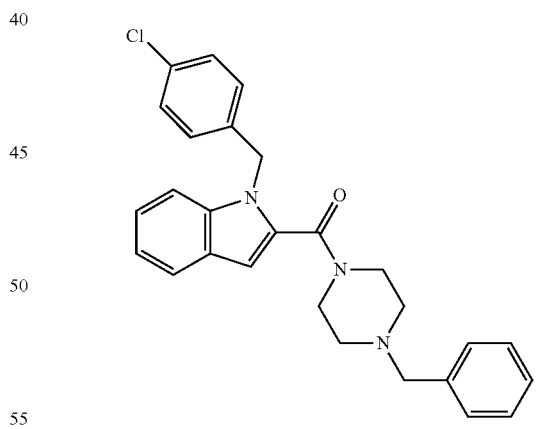

(4-benzylpiperazin-1-yl)(1-(4-chlorobenzyl)-1H-indol-2-yl)methanone (CCG-206327)

The following was added to DCM (5 mL): 1-(4-chlorobenzyl)-1H-indole-2-carboxylic acid (70 mg, 0.245 mmol), DIPEA (0.130 mL, 0.735 mmol), EDC (57 mg, 0.294 mmol), HOBT (45 mg, 0.294 mmol), and 1-benzylpiperazine (0.085 mL, 0.490 mmol). The solution was stirred at rt for 16 h, at which time the solution was diluted with a 1:1 solution of ethyl acetate:diethyl ether and washed with water (1×), 10% aq. sodium carbonate (1×), and brine (1×). The organic phase was then dried over magnesium sulfate and concentrated in vacuo. The resulting residue was purified via silica gel flash chromatography (30 g silica, 10% EtOAc/hexanes) and triturated with ethyl acetate and hexanes to afford the title compound as a white powder. (Yield: 52 mg, 0.117 mmol, 48%) $^1$H NMR (400 MHz, CDCl$_3$) δ 7.62, 7.36-7.19, 7.14, 7.02, 6.60, 5.48, 3.62, 3.42, 2.32, 2.03

Example 4

This Example describes further characterization of the activity of compounds of embodiments of the present invention.

Materials and Methods

In Vitro Antiviral and Cytotoxicity Assays.

The WEEV replicon assay was done as previously described (Peng et al., J Infect Dis 2009, 199 (7), 950-957) with the following modifications. A clonal derivative of the original BSR-T7 cell line was obtained by limiting dilution and used for all replicon assays. The BSR-T7/C3 clone was cultured in Dulbecco's Modified Eagle Medium containing 5% heat inactivated fetal bovine serum, 1% sodium pyruvate, 0.1 mM non-essential amino acids, 10 U/ml penicillin, and 10 µg/ml streptomycin. Cells were cultured in the above media with 0.5 mg/ml G418 every third passage to maintain selection. Cells were transfected in 10-cm tissue culture plates for 2 h, detached by trypsinization, and transferred to 96-well plates preloaded with compound dilutions. Final cell concentrations were ~2×10$^6$ cells/ml, and plates were harvested 18-20 h later for luciferase and MTT assays as previously described.[12] BE(2)-C cell culture, virus infections, and plaque assays were done as previously described.[23] Cells were infected with WEEV or NSV at a multiplicities of infection of 0.1 or 10, respectively, to obtain approximately 20-25% residual cell viability at 24 h post infection.

Induction of Experimental Viral Encephalitis.

Female C57BL/6 mice were purchased from The Jackson Laboratory (Bar Harbor, Me.). All animals were housed and used on-site under specific pathogen-free conditions in strict accordance with guidelines set by the National Institutes of Health and protocols approved by the University Committee on the Use and Care of Animals. Mice were housed on a 10/14-hour light/dark cycle in ventilated cages containing no more than 5 animals per cage. Food and water were available ad libitum.

To induce encephalomyelitis, 5-6 week-old mice were anesthetized with isoflurane (Abbott Laboratories, Chicago, Ill.) and 1000 plaque-forming units (PFU) of the prototype alphavirus, neuroadapted Sindbis virus (NSV), suspended in 10 µl of phosphate-buffered saline (PBS) were inoculated directly into the right cerebral hemisphere of each animal. Experimental antiviral compounds were solubilized in dimethyl sulfoxide (DMSO) as stock solutions (100 µM), then diluted in PBS to generate working solutions for intraperitoneal injection into infected mice on a twice-daily dosing schedule. For those experiments where clinical outcome was the primary endpoint, each infected mouse was scored daily into one of the following categories: 1) normal, 2) mild paralysis (some weakness of one or both hind limbs), 2) moderate paralysis (weakness of one hind limb, paralysis of the other hind limb), 3) severe paralysis (complete paralysis of both hind limbs), or 5) dead. Other groups of animals were sacrificed at defined intervals post-infection in order to collect brain and spinal cord tissue for ex vivo analysis. Following intra-cardiac perfusion with ice-cold PBS, the left cerebral hemisphere and lower spinal cord was isolated from some animals, snap-frozen on dry ice, and stored at −80° C. for virus titration assays. Alternatively, naïve or NSV-infected mice were sequentially perfused with ice-cold PBS and then chilled 4% paraformaldehyde (PFA) in PBS so that the brains and spinal cords could be removed intact for histopathological analyses.

Virus Titration Assays.

Ten percent (w/v) homogenates of each tissue sample were prepared in PBS, and serial 10-fold dilutions of each homogenate were assayed for plaque formation on monolayers of BHK-21 cells, as previously described (Irani et al., J Neuropathol Exp Neurol 2007, 66 (6), 533-544). Results are presented as the geometric mean±standard error of the mean (SEM) of the log$_{10}$ number of PFU per gram of tissue derived from 4 animals at each time point.

Histopathology Analyses.

Nervous system tissues were post-fixed overnight at 4° C. in 4% PFA. The axonal processes of motor neurons (MN) in the lumbar spinal cord that innervate the hind limb musculature were quantified in cross sections of ventral spinal nerve roots as a correlate of hind limb paralysis according to published methods (Havert et al., J Virol 2000, 74 (11), 5352-5356; Prow et al., Exp Neurol 2007, 205 (2), 461-470). All experimental samples were collected from mice 14 days post-infection, since the loss of MN axons is delayed following destruction of the cell body within the spinal cord itself. Sections of the lumbar spinal column at the L4-L5 level were decalcified (Immunocal, Decal Corporation, Tallman, N.Y.) and embedded in paraffin. Sections were then stained using a modified Bielchowsky silver staining method to label the neurofilament proteins of each nerve axon (Havert et al., supra; Prow et al., 2007 supra; Kerr et al., J Virol 2002, 76 (20), 10393-10400; Nargi-Aizenman et al., Ann Neurol 2004, 55 (4), 541-549; Prow et al., J Neurochem 2008, 105 (4), 1276-1286). Axonal density (the number of intact axons per cross-sectional area of each nerve root) was determined for the right and left L4 and L5 ventral nerve roots from a minimum of 4 animals in each experimental group.

Neuronal damage in the brain was assessed in cryosections through the hippocampal formations of naïve and day 14 NSV-infected mice. Virus consistently and prominently infects this brain region (Jackson et al., Lab Invest 1988, 58 (5), 503-509). Before staining, each section was incubated in 0.1% Triton X-100 for 15 minutes to expose intracellular antigens. Slides were then incubated with NisslRed (NeuroTrace 530/615 fluorescent Nissl stain, Invitrogen, Grand Island, N.Y.) diluted 1:100 for 20 minutes, washed, incubated in a 0.06% potassium permanganate solution, washed again, and stained in 0.0001% Fluoro-Jade C compound (Millipore, Billerica, Mass.) in 1% acetic acid for 10 minutes. After further washing, slides were dried, dehydrated in xylene and coverslipped using VectaMount permanent mounting media (Vector Labs, Burlingame, Calif.). The right and left hippocampi from each animal were imaged at 20× magnification using a Nikon Ti-U inverted fluorescence microscope supported by the NIS-Elements Basic Research acquisition and analysis software (Nikon Instruments Inc., Melville, N.Y.). The total number of Fluoro-Jade-positive/NisslRed-positive cells (degenerating neurons) and NisslRed-positive cells (all neurons) was counted in duplicate slides from each hippocampus of triplicate mice for each experimental condition to determine the proportion of Fluoro-Jade-positive neurons.

Statistical Analyses.

The Prism 5.0 software package (GraphPad Software, La Jolla, Calif.) was used for all statistical analyses. Differences in severity of paralysis and survival among cohorts of infected mice were measured using a log-rank (Mantel-Cox) test.

Unpaired Student's t test was used to assess differences between tissue viral titers or neuronal counts between two experimental groups at single time points. In all cases, differences at a $p<0.05$ level were considered significant.

Results

In Vitro Antiviral Assays.

Four analogs were selected for advancement to in vitro infection studies: the prototype thieno[3,2-b]pyrrole 5b (CCG-203881) and indole 9b (CCG-102516) analogs, along with the indole enantiomers 9g (CCG-203927) and 9h (CCG-203926).

Figure 1:
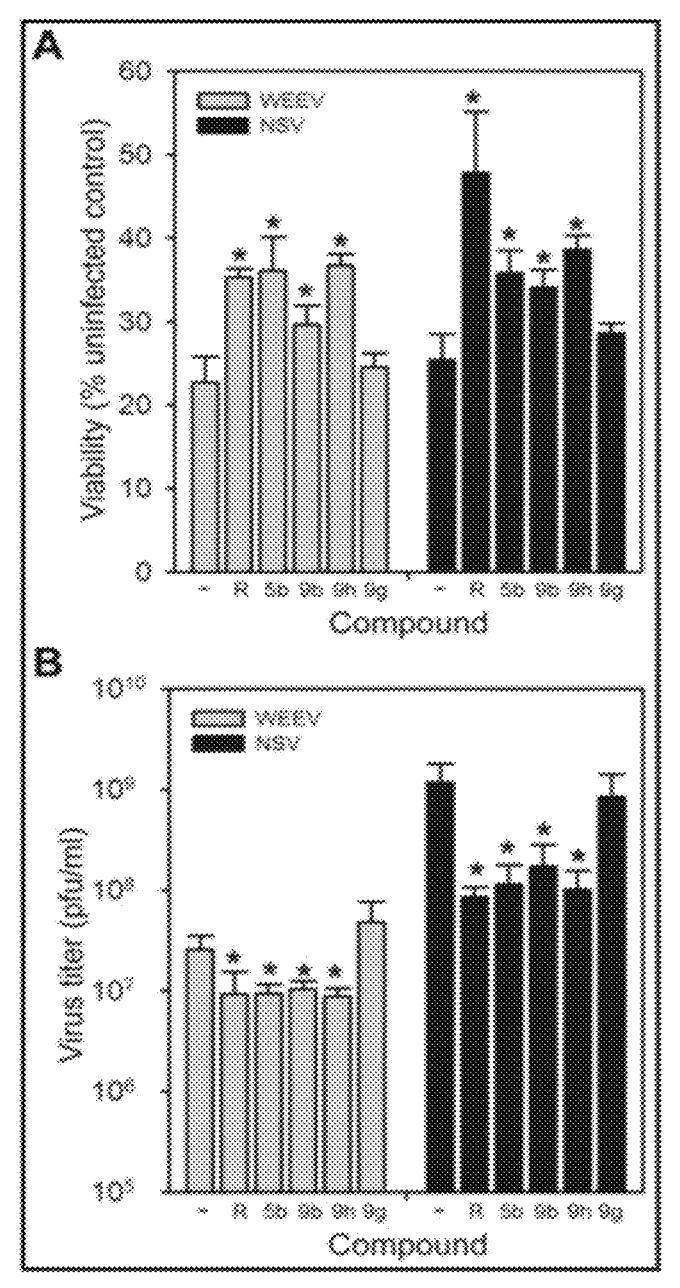

Antiviral activity was measured using two complementary assays in cultured neuronal cells: reduction in cytopathic effect (CPE) and extracellular virus titers (FIG. 1). Alphaviruses such as WEEV and the related neuroadapted Sindbis virus (NSV) are highly cytolytic to cultured cells, due in part to vigorous replication and virion production, such that antiviral compounds are predicted to increase cell viability and decrease virus titers after infection. Both the thieno[3,2-b]pyrrole 5b and indole 9b analog, as well as the indole enantiomer 9h that was active in the replicon inhibition assay (see above examples), increased cell viability by 1.5- to 2-fold after either WEEV or NSV infection (FIG. 1A). In contrast, the indole enantiomer 9g, which was inactive in the replicon inhibition assay, was unable to rescue virus-induced CPE. Consistent results were obtained when virion production was assayed via plaque assays, where the thieno[3,2-b]pyrrole 5b, the indole 9b analog, and the indole enantiomer 9h all significantly reduced both WEEV and NSV titers, whereas the indole enantiomer 9g was inactive in this assay (FIG. 1B). These antiviral assay results correlated with the replicon inhibition studies (see above examples), and support the conclusion that chirality at the benzylamide position is a major determinant of compound activity. Moreover, the antiviral effects of 5b, 9b and 9h were comparable to those of ribavirin, an established broad spectrum antiviral agent used as a positive control.

In Vivo Infection Studies.

The indole enantiomers were selected 9g and 9h for initial in vivo testing. Compound 9h offered favorable antiviral activity, relatively low cytotoxicity and good stability to microsomal metabolism, while 9g provided an ideal negative control as a closely related but inactive enantiomer. Without treatment, direct intracerebral injection of NSV causes hind limb paralysis and death in weanling mice. Pilot survival assays using 9h at doses of 10 mg/kg and 30 mg/kg indicated that the higher concentration was more effective. In larger experimental cohorts, mice treated with 9h at a dose of 30 mg/kg twice daily beginning 12 hours after viral challenge and continuing for a 7-day period (that reflects the interval of peak viral replication and clearance) were significantly protected from lethal NSV infection compared to animals that were otherwise untreated, that received a vehicle control, or that were given 9g at the identical concentration (FIG. 2A). Treatment with 9h also conferred benefit against the development of severe hind limb paralysis prior to death (FIG. 2B), a characteristic feature of NSV-induced disease that follows intracerebral challenge.

Figure 3:
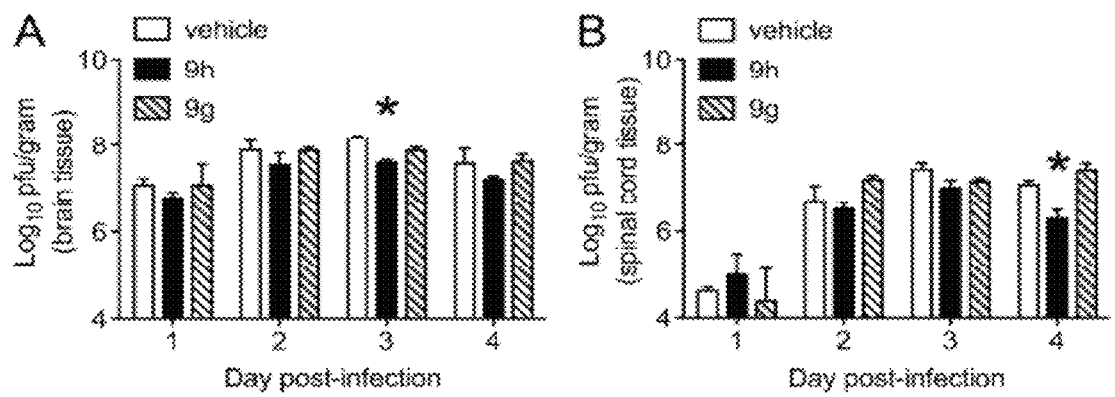
FIG. 3 shows virological effects of indole enantiomers in mice with acute NSV encephalomyelitis. At 24-hour intervals, viral titers were measured in quadruplicate brain (A) and spinal cord (B) tissue samples from each group by plaque titration assay.

To investigate the effects of 9g and 9h on virus replication in vivo, the amount of infectious NSV present directly in the CNS was measured early (1-4 days) after infection, when titers peak and then begin to wane as antiviral host immunity is activated. Plaque titration assays showed that viral titers were lower in the brains of mice receiving 9h compared to 9g or a vehicle control, achieving statistical significance on Day 3 (FIG. 3A). A similar extent of viral inhibition was also observed in the spinal cords of NSV-infected mice (FIG. 3B). Prior studies have shown that reducing CNS viral titers by a log are associated with improved disease outcome after NSV infection (Jackson et al., Lab Invest 1987, 56 (4), 418-423; Jackson et al., Lab Invest 1988, 58 (5), 503-509).

Figure 4:
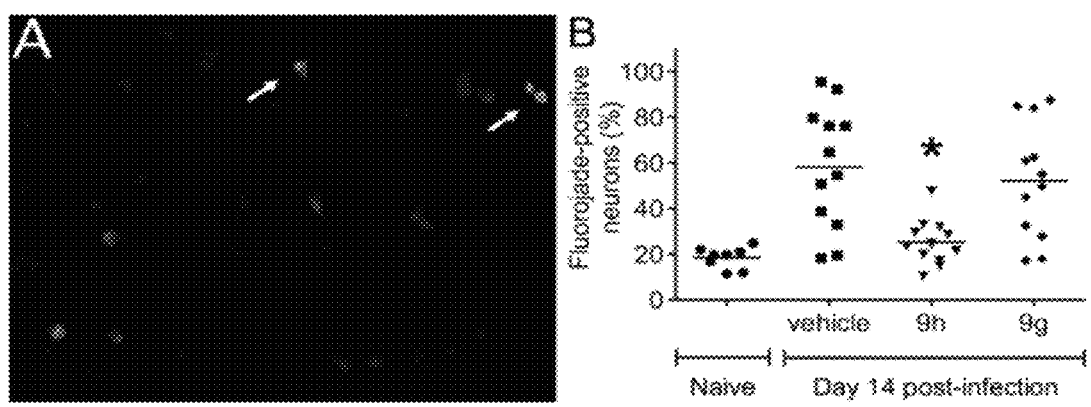
FIG. 4 shows effects of indole enantiomers on neuronal survival in the brains of NSV-infected mice. (A) Representative fluorojade staining of damaged hippocampal neurons in the brains of NSV-infected mice. (B) The proportion of fluorojade-positive hippocampal neurons was determined in quadruplicate slides prepared from 3 mice in each group.
Figure 5:
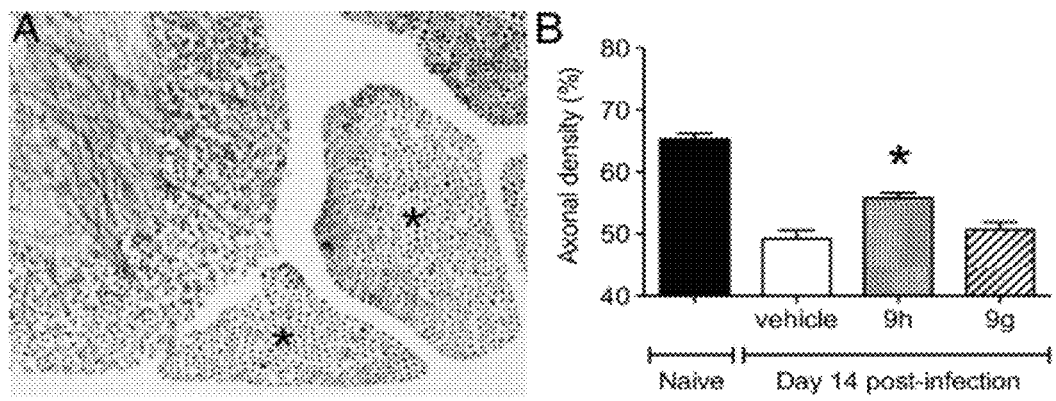
FIG. 5 shows effects of indole enantiomers on neuronal survival in the spinal cords of NSV-infected mice. (A) A representative specimen from an uninfected animal is shown, with the L4 and L5 ventral nerve roots identified (marked with an *). (B) Quantification of axonal density in these lumbar ventral nerve roots shows relative neuronal sparing in treated animals compared to vehicle- or treated controls.

To determine the extent to which clinical protection correlated with enhanced neuronal survival, an established fluorojade labeling method was employed. In the hippocampus, where many neurons are infected by NSV, treatment with 9h led to reduced neuronal injury compared to mice that were given either 9g or a vehicle control (FIG. 4B). In these assays, the Nissl substance was stained to enumerate hippocampal neurons and the proportion of these cells that were also fluorojade-positive was counted by fluorescence microscopy (example shown in FIG. 4A). In the spinal cord, silver staining was used to label motor neuron axons in lumbar ventral nerve roots (FIG. 5A), and the density of preserved axons following treatment with 9h showed enhanced cell survival compared to mice given 9g or a vehicle control (FIG. 5B). Taken together, these data show that 9h exerts an antiviral effect within the CNS of NSV-infected mice, causing enhanced neuronal survival that leads to improved disease outcome.

Successful antiviral therapy in animal models of acute alphavirus encephalitis has only been accomplished in a few settings. In newborn mice, seco-pregnane steroids delayed mortality when given within 4 hours of viral challenge but did not alter overall survival (Li et al., Proc Natl Acad Sci USA 2007, 104 (19), 8083-8088). In weanling mice infected intranasally with a vaccine strain of Venezuelan equine encephalitis virus (VEEV), (−)-carbodine improved outcome when initiated up to 4 days after viral challenge while lowering peak CNS viral titers by a half-log (Julander et al., Antiviral Res 2008, 80 (3), 309-315). The same drug showed no benefit following wild-type VEEV challenge.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising a compound having the Formula

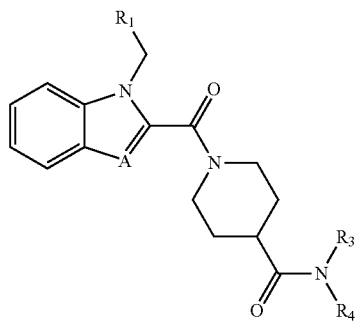

including pharmaceutically acceptable salts;

wherein $R^1$ is selected from the group consisting of H, phenyl,

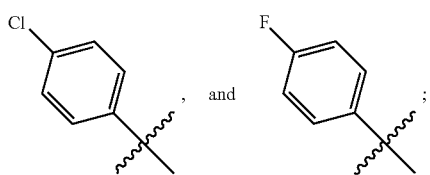

wherein R3 and R4 are the same or different, and are selected from the group consisting of H, $C_1$-$C_8$ alkyl, $C_0$-$C_6$ alkyl-aryl, $C_0$-$C_6$ cycloalkyl-aryl, $C_0$-$C_6$-alkyl-heteroaryl, or together form a substituted cyclic alkyl amine of 4-8 atoms; wherein alkyl, cycloalkyl, aryl and heteroaryl may be optionally substituted;

and wherein A is selected from the group consisting of CH and C—$CH_3$.

2. The composition of claim 1, wherein said compound is selected from the group consisting of

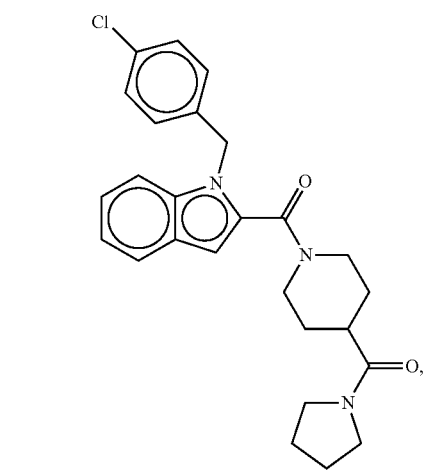

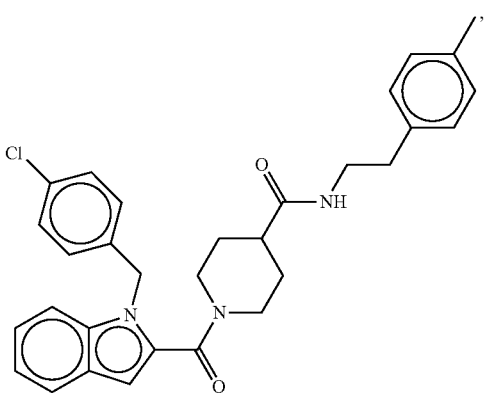

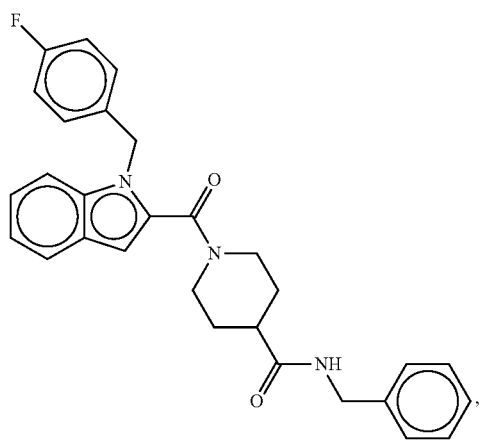

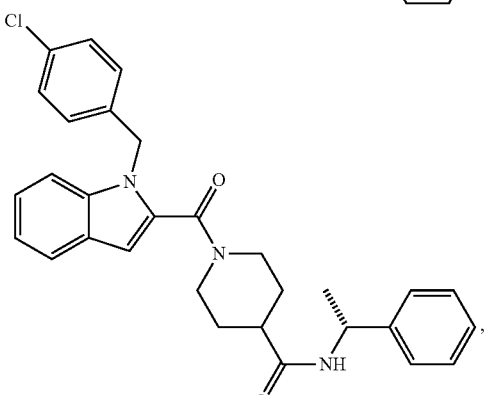

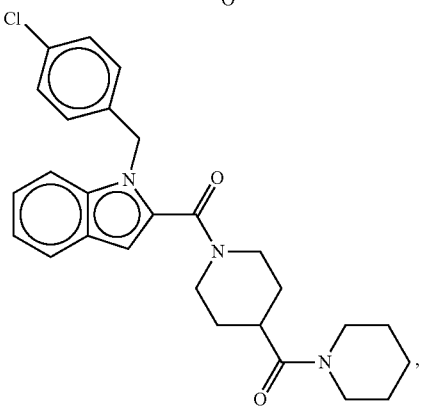

153
-continued
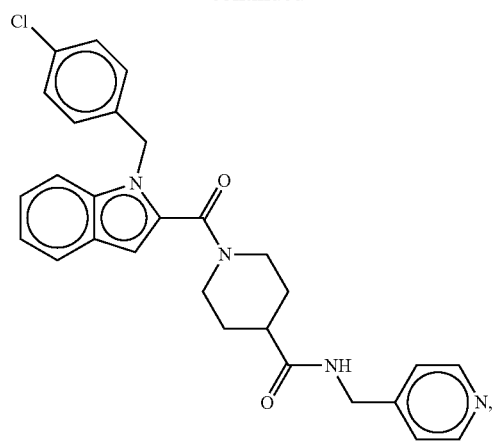
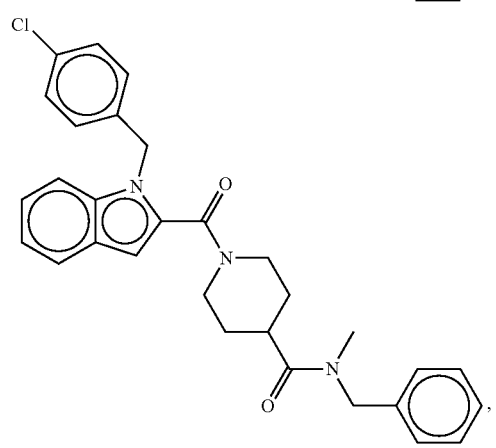
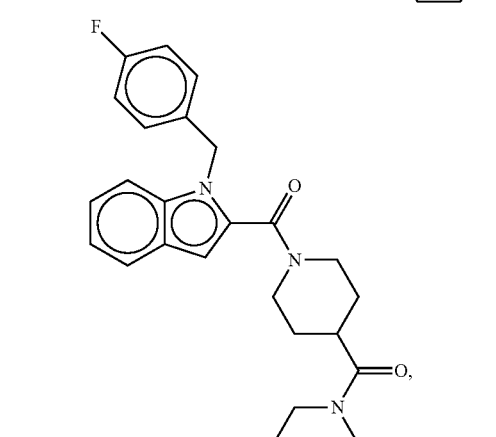
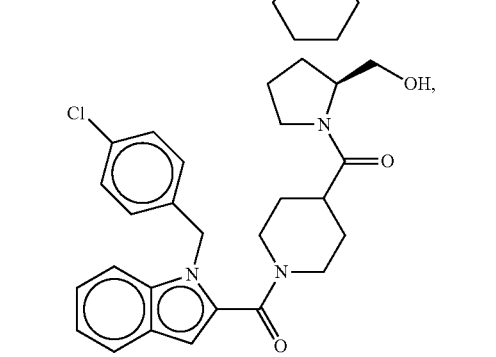
154
-continued
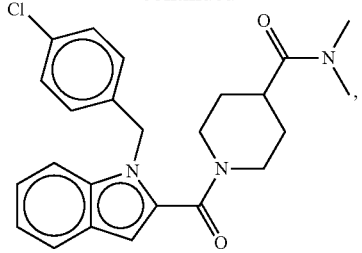
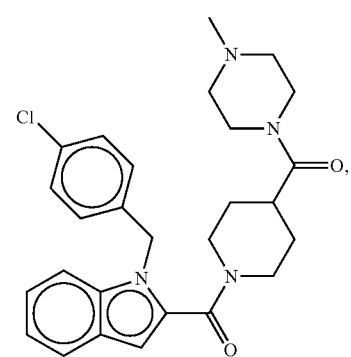
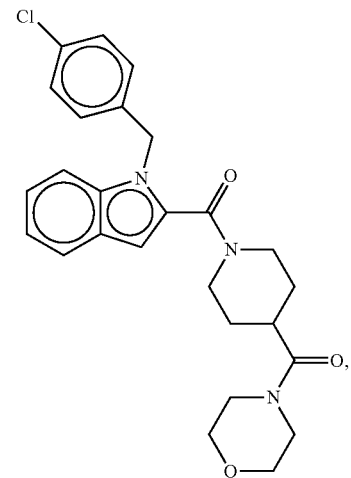
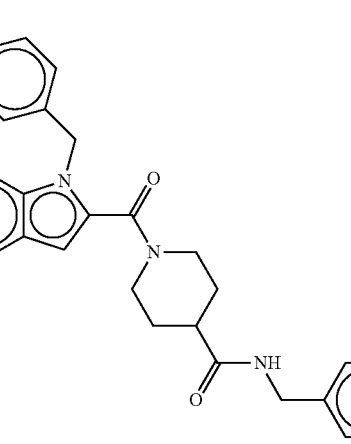

155
-continued
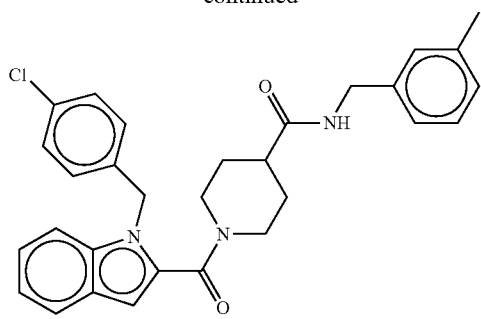
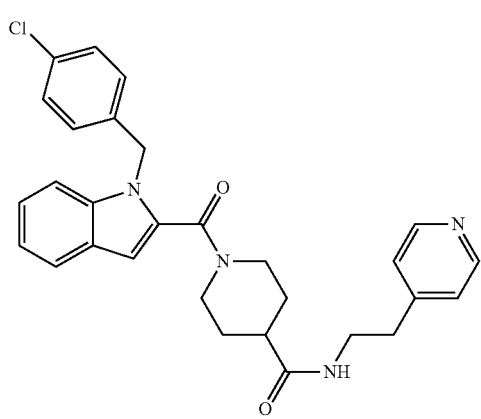
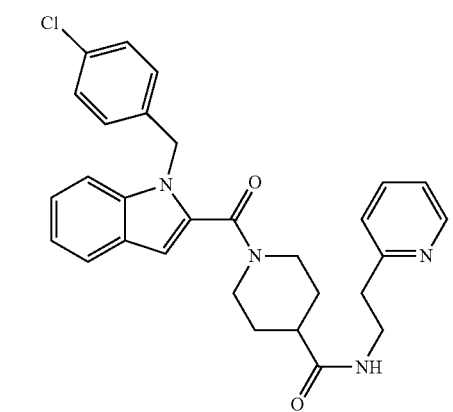
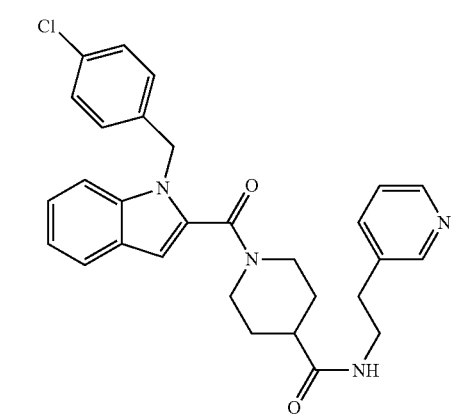
156
-continued
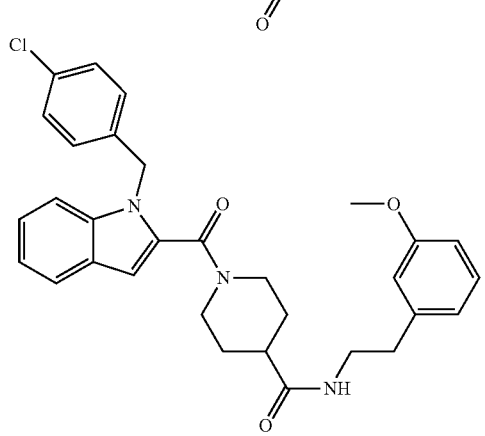
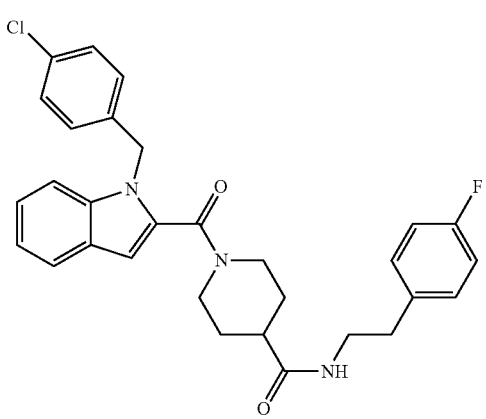
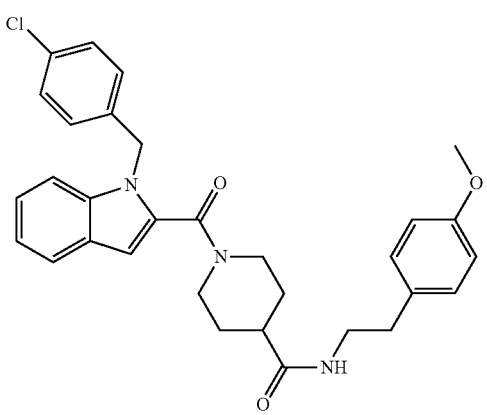

157
-continued
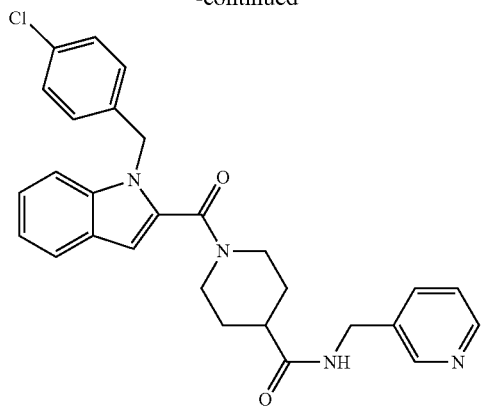
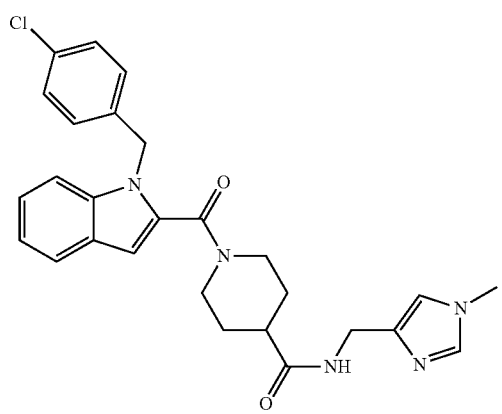
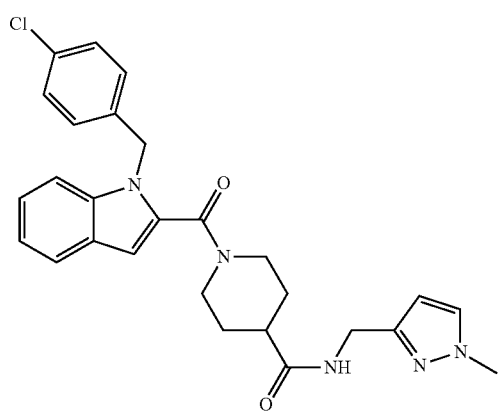
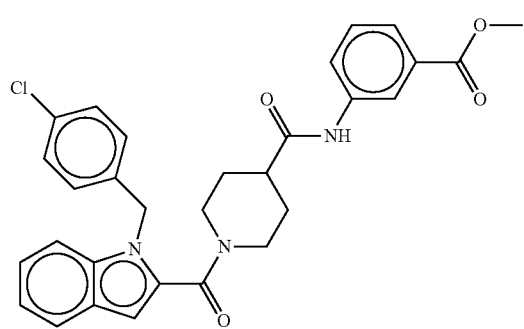
158
-continued
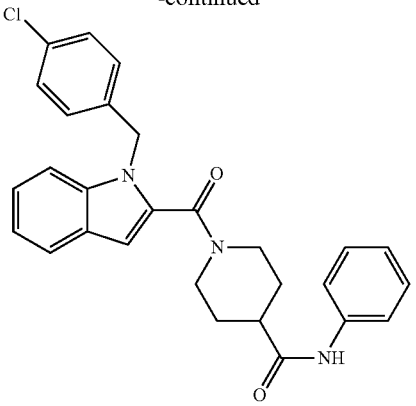
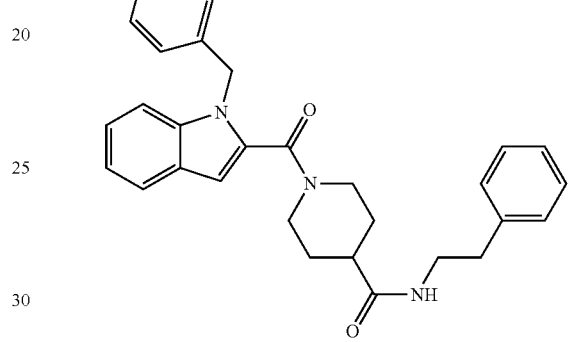
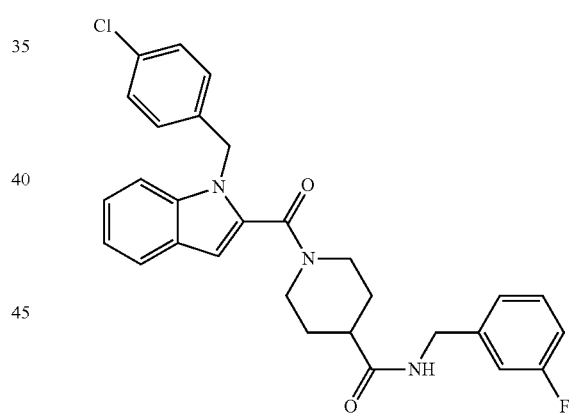
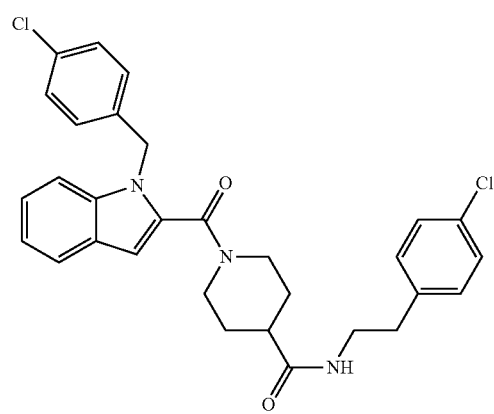

159
-continued
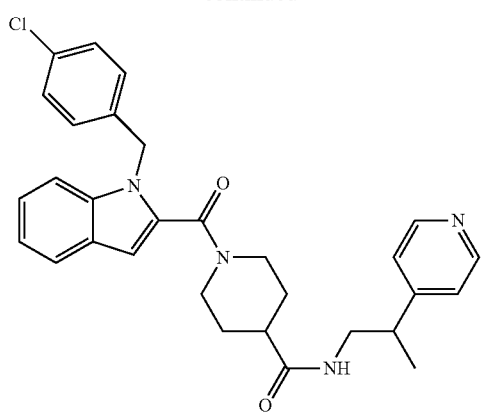
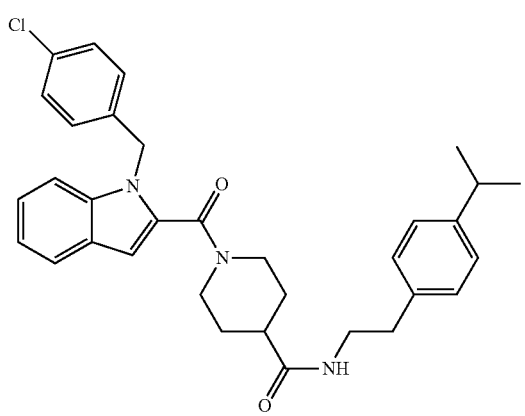
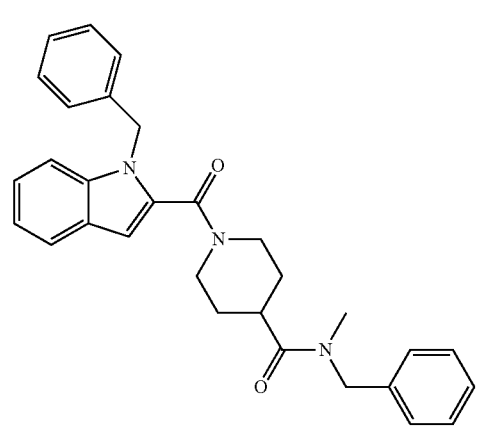
160
-continued
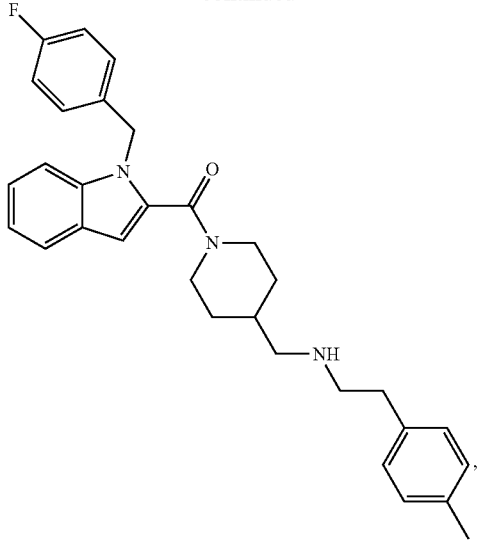
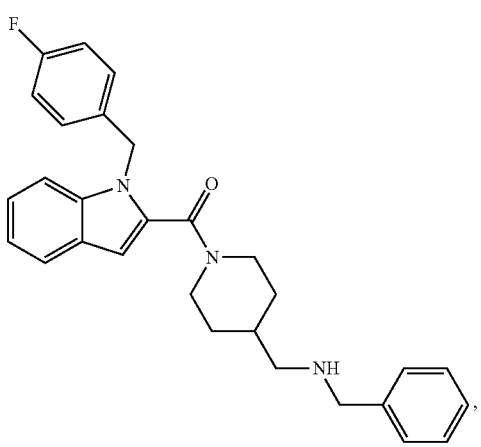
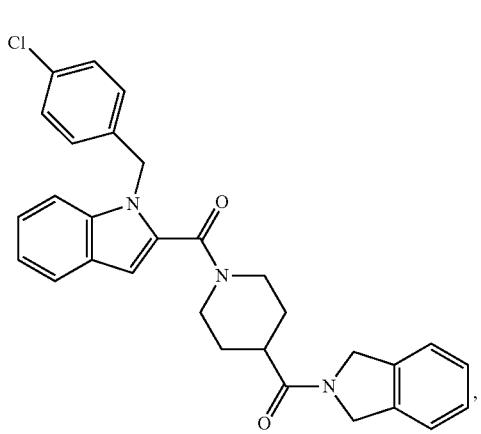

161
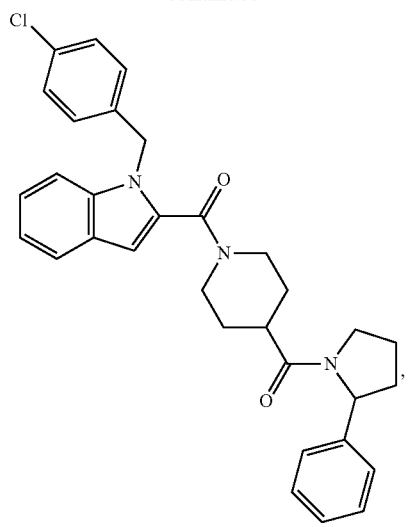
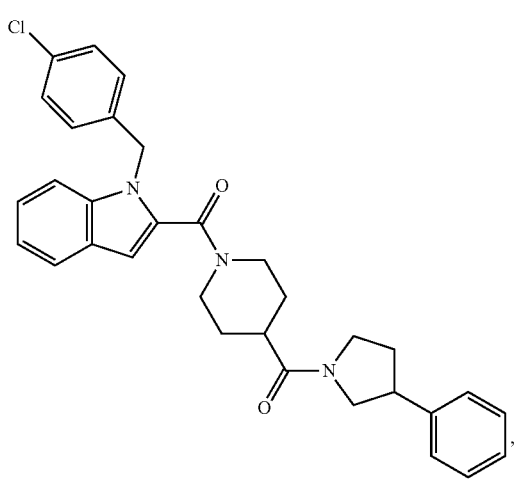
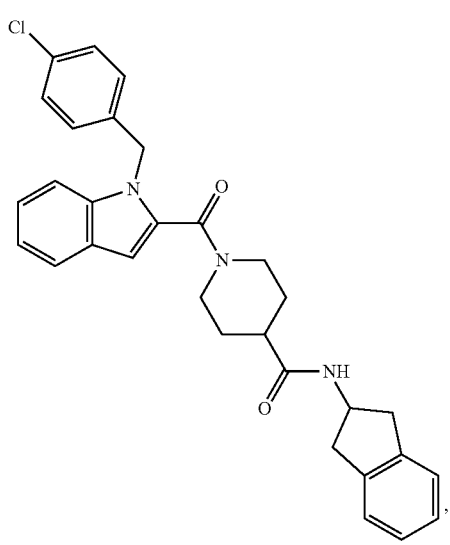
162
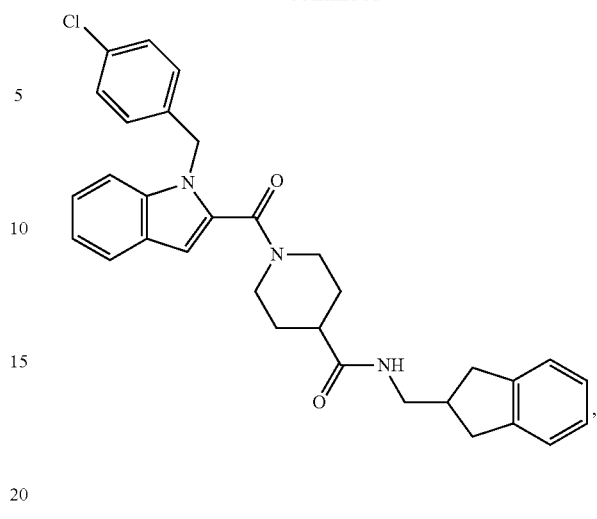
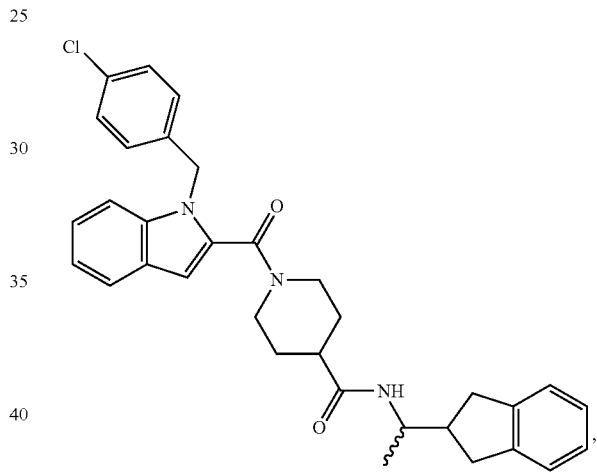
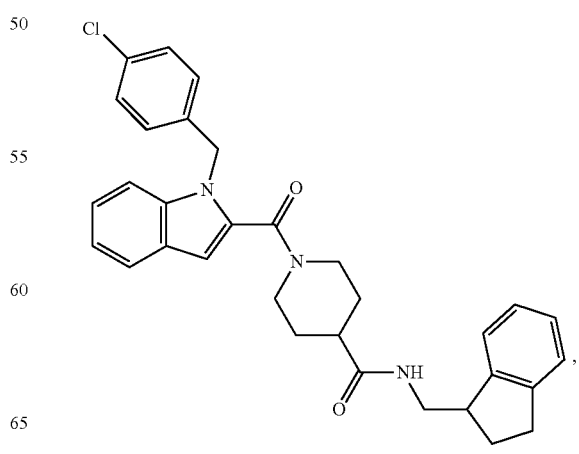

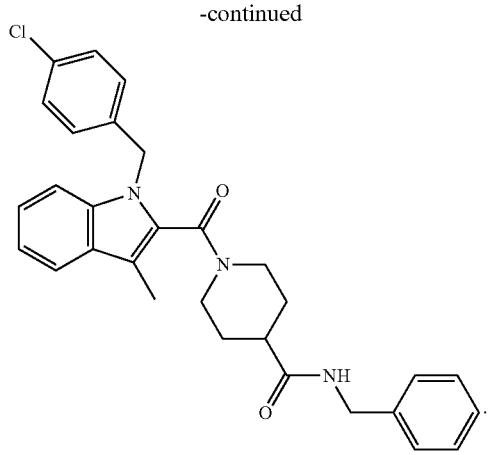

3. A pharmaceutical composition, comprising:
a) a compound as recited in claim 1; and
b) a pharmaceutically acceptable carrier.

4. A method of inhibiting the growth of an arbovirus, comprising contacting an arbovirus with a compound under conditions such that said compound inhibits the growth of said arbovirus, wherein the arbovirus is an alphavirus, wherein said compound is shown in the following structure:

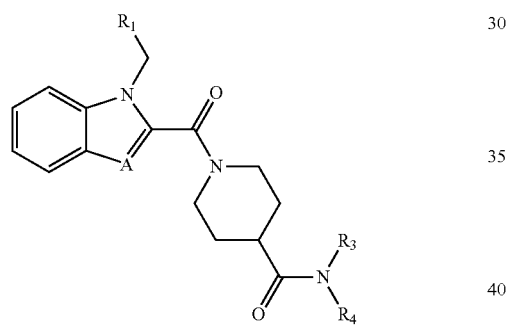

including pharmaceutically acceptable salts;
wherein $R^1$ is selected from the group consisting of H, phenyl,

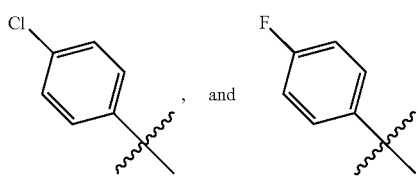

wherein R3 and R4 are the same or different, and are selected from the group consisting of H, $C_1$-$C_8$ alkyl, $C_0$-$C_6$ alkyl-aryl, $C_0$-$C_6$ cycloalkyl-aryl, $C_0$-$C_6$-alkyl-heteroaryl, or together form a substituted cyclic alkyl amine of 4-8 atoms; wherein alkyl, cycloalkyl, aryl and heteroaryl may be optionally substituted;
and
wherein A is selected from the group consisting of CH and C—$CH_3$.

5. The method of claim 4, wherein said compound is selected from the group consisting of

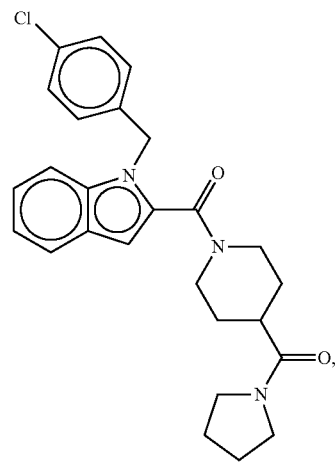

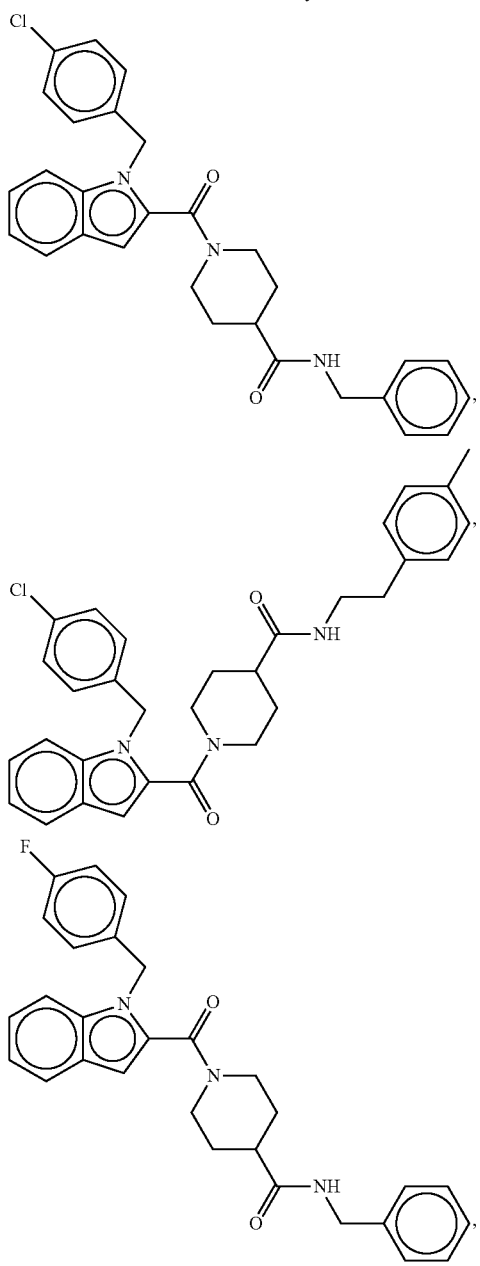

165
-continued
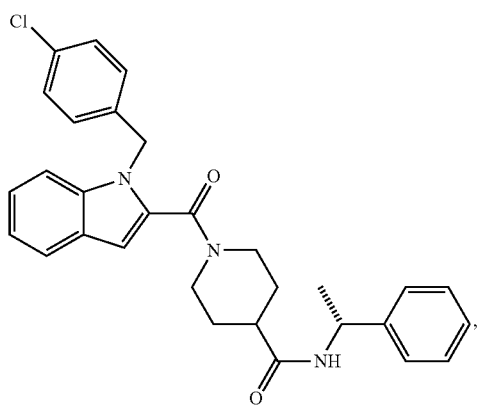
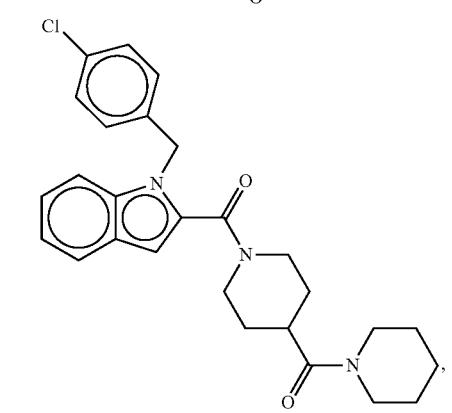
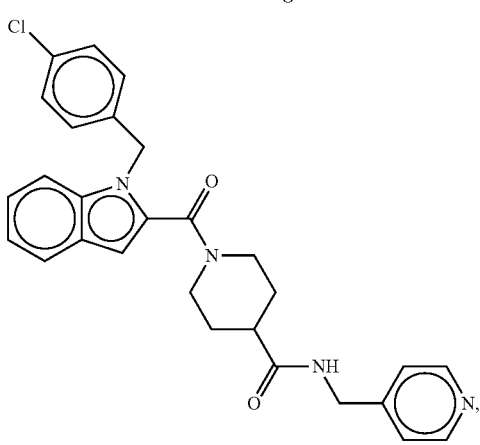
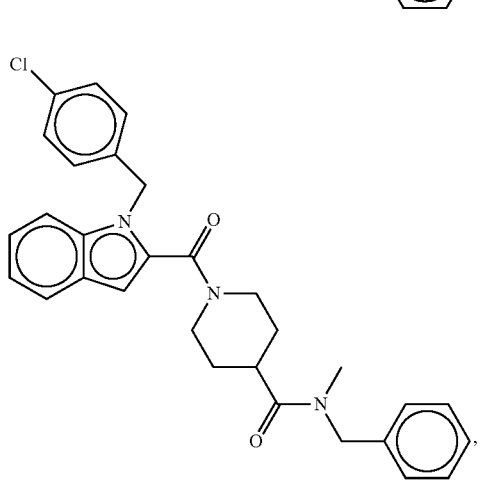
166
-continued
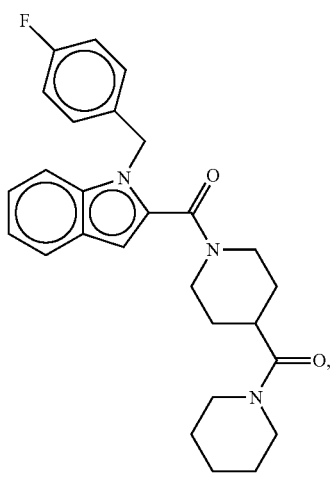
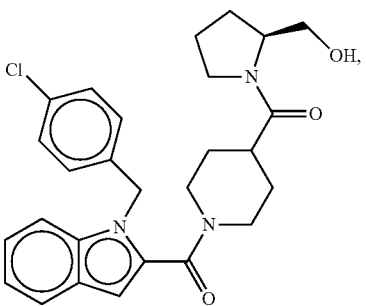
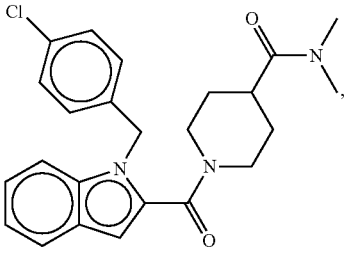
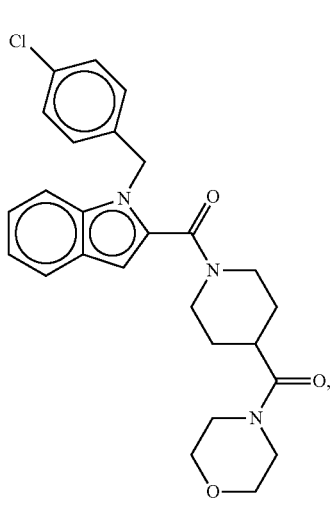

167
-continued
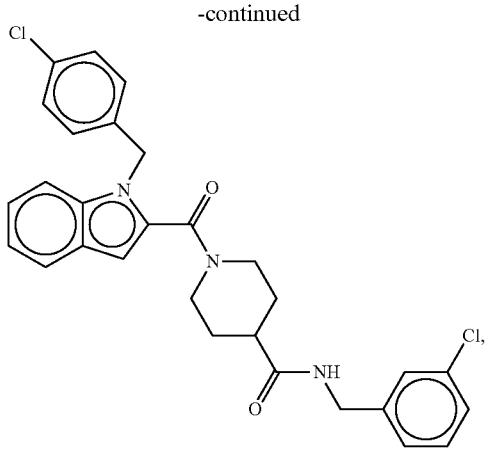
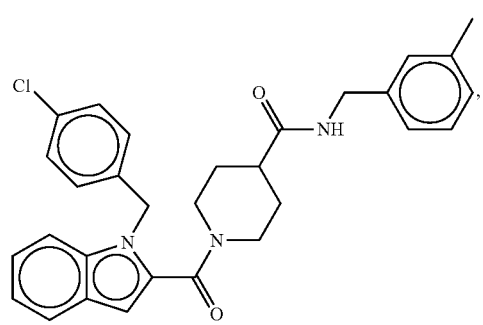
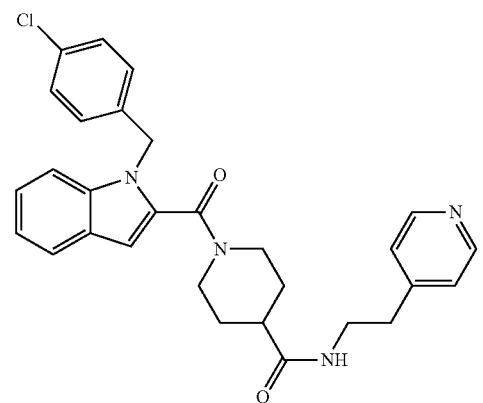
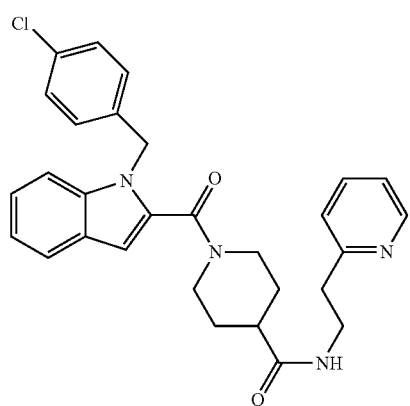
168
-continued
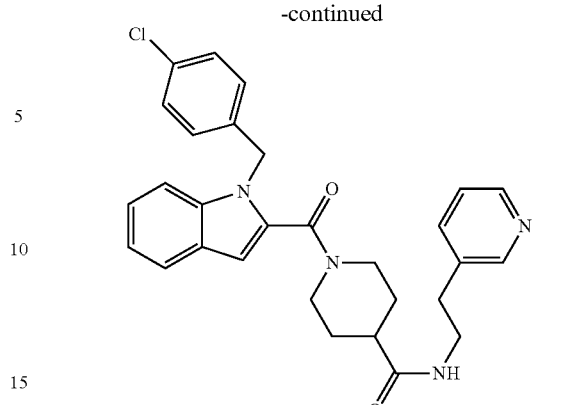
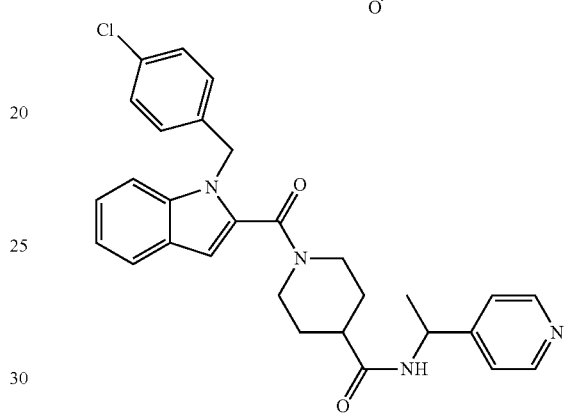
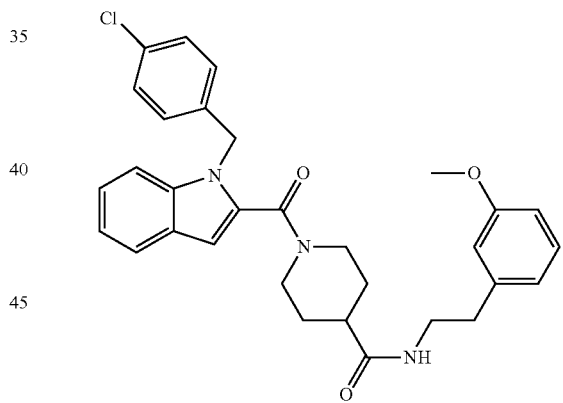
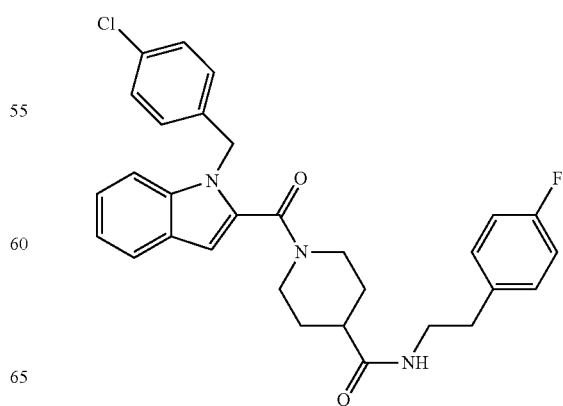

169
-continued
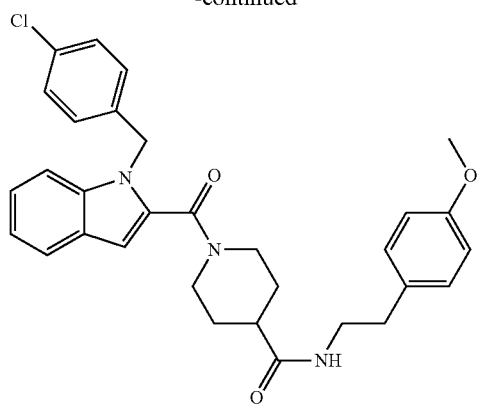
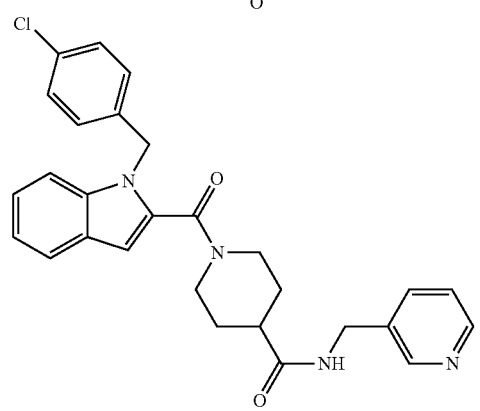
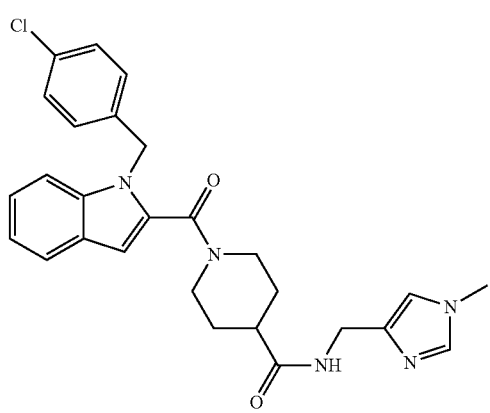
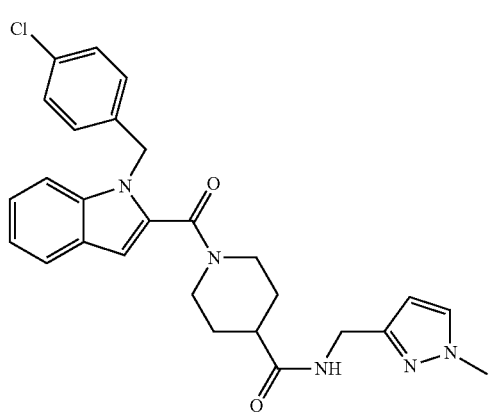
170
-continued
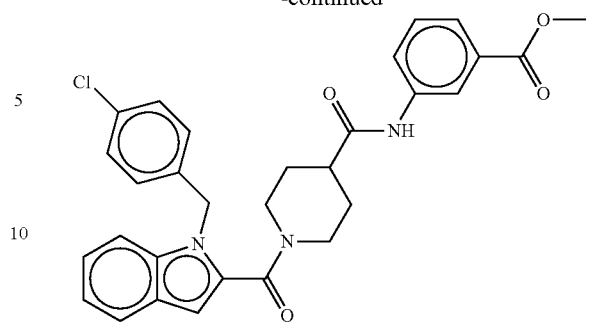
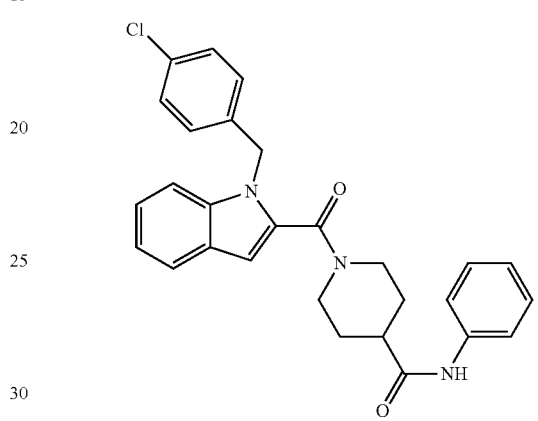
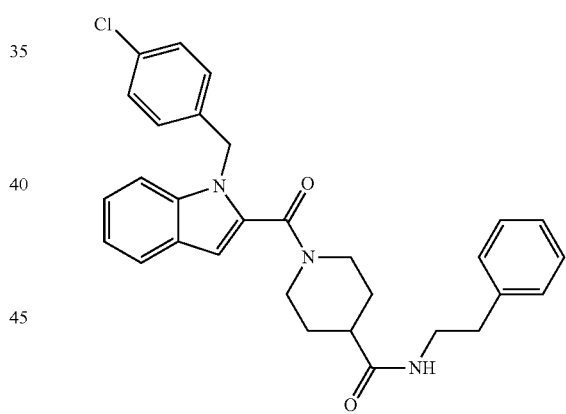
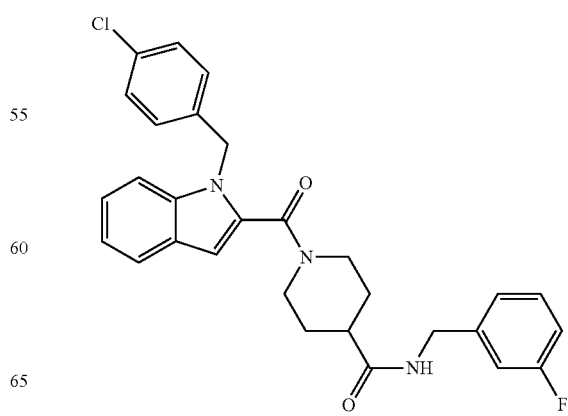

-continued
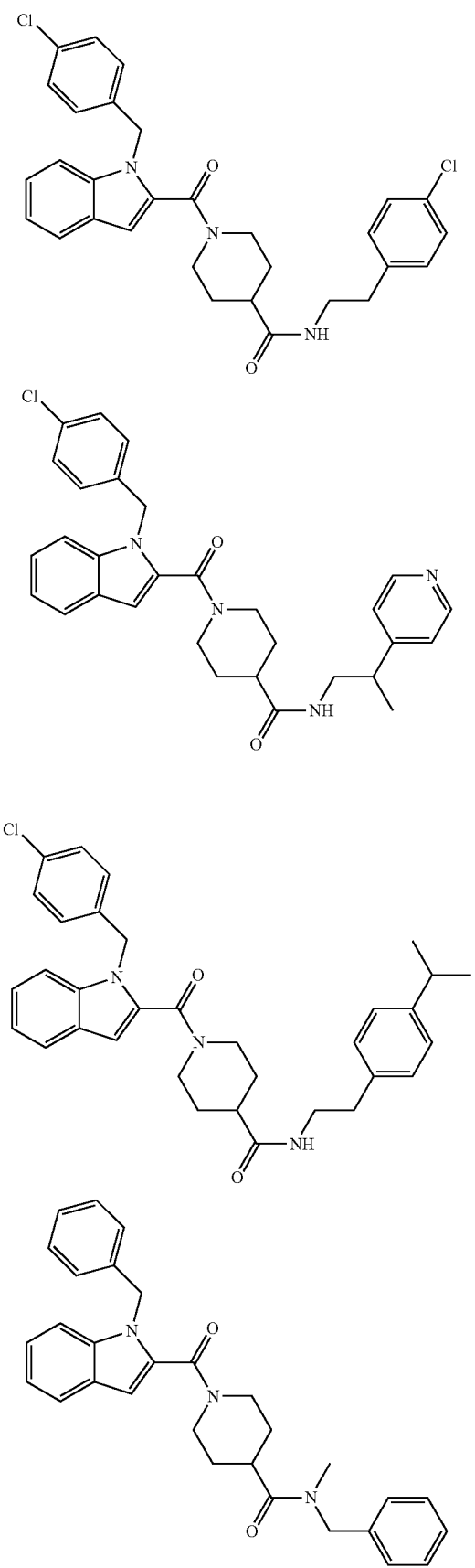
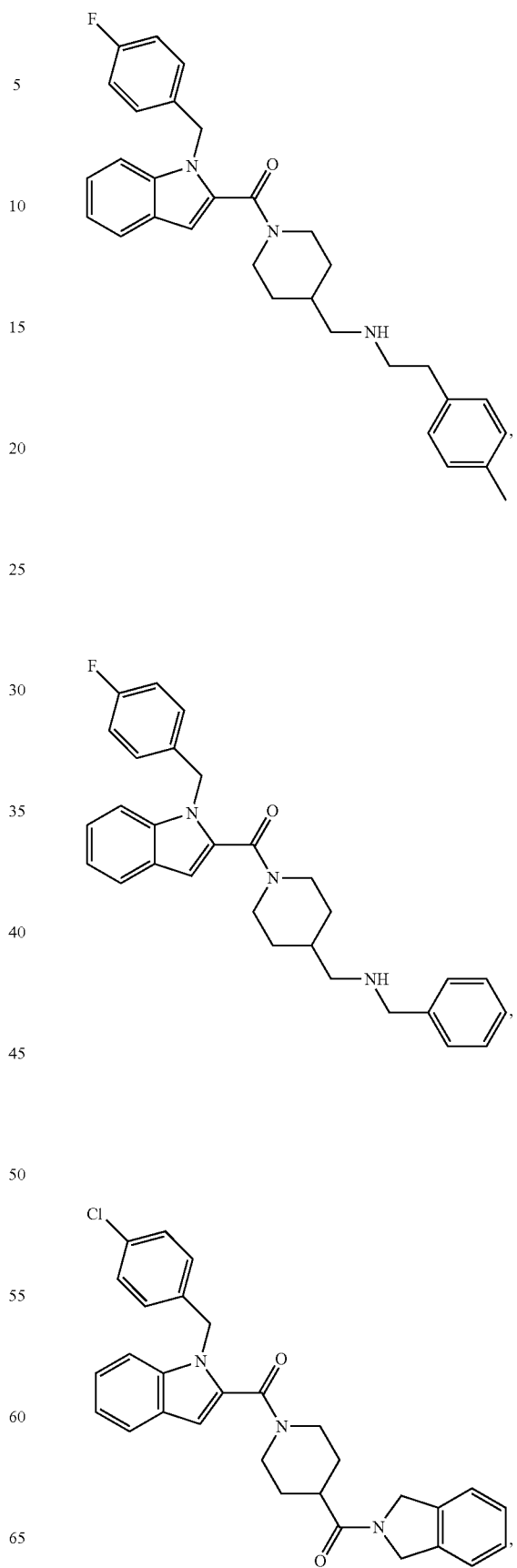

173
-continued
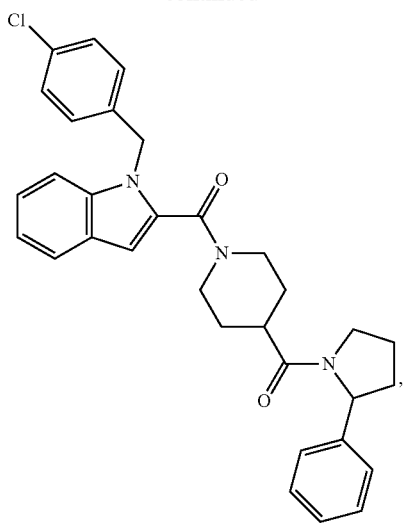
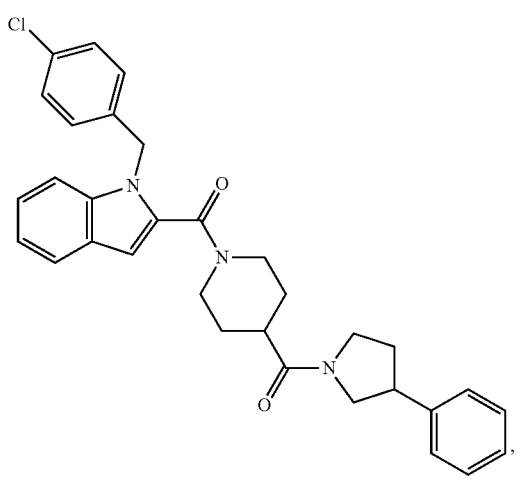
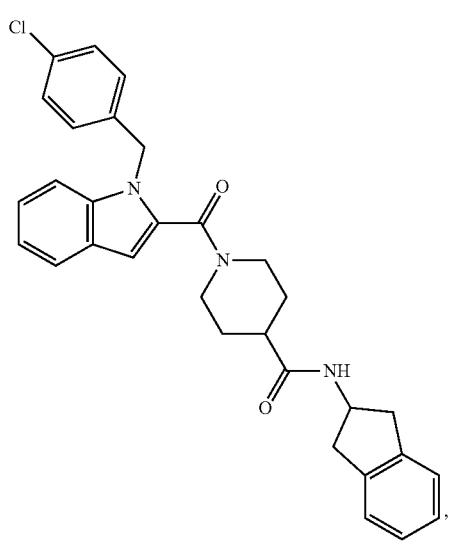
174
-continued
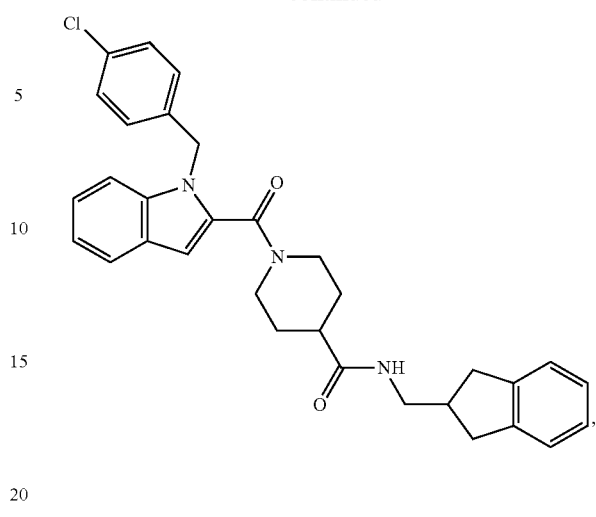
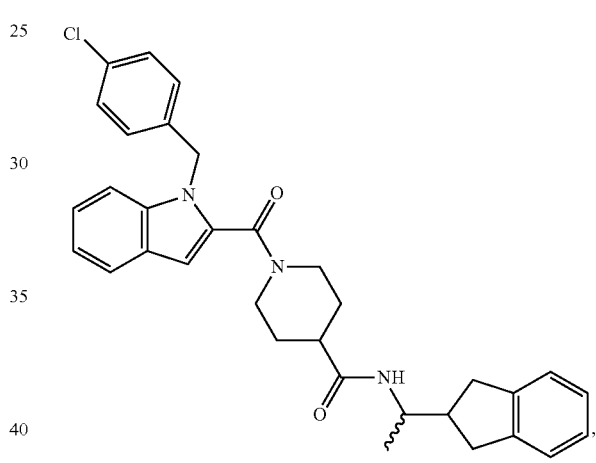
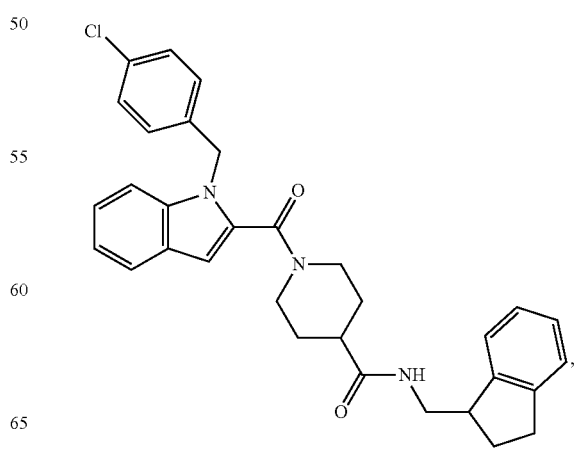

-continued

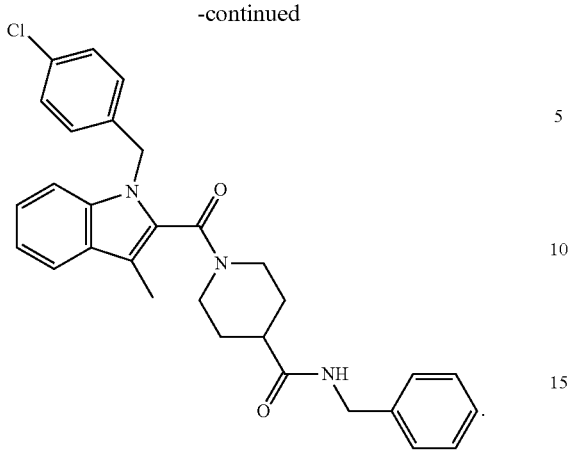

6. The method of claim 4, wherein said arbovirus is in a cell.

7. The method of claim 6, wherein said cell is in an animal.

8. The method of claim 7, wherein said animal exhibits symptoms of an arbovirus infection and said contacting with said compound results in a decrease or elimination of said symptoms of an arbovirus infection.

9. The method of claim 4, wherein said alphavirus is selected from the group consisting of Sindbis virus, Semliki forest virus, O'nyong'nyong virus, Chikungunya virus, Mayaro virus, Ross River virus, Barmah Forest virus, Eastern equine encephalitis virus, Western equine encephalitis virus, and Venezuelan equine encephalitis virus.

* * * * *